United States Patent
Bagley et al.

(10) Patent No.: US 7,199,243 B2
(45) Date of Patent: Apr. 3, 2007

(54) PIPERIDINE COMPOUNDS USEFUL AS PPAR ACTIVATORS

(75) Inventors: Scott W. Bagley, Mystic, CT (US); Thomas A. Brandt, North Stonington, CT (US); Robert W. Dugger, Stonington, CT (US); William A. Hada, Waterford, CT (US); Cheryl M. Hayward, Old Lyme, CT (US); Zhengyu Liu, Carlsbad, CA (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 340 days.

(21) Appl. No.: 10/720,942

(22) Filed: Nov. 24, 2003

(65) Prior Publication Data

US 2004/0157885 A1    Aug. 12, 2004

Related U.S. Application Data

(60) Provisional application No. 60/429,506, filed on Nov. 26, 2002.

(51) Int. Cl.
*C07D 211/08* (2006.01)
*C07D 211/02* (2006.01)
*A61K 31/445* (2006.01)

(52) U.S. Cl. .................. 546/191; 546/184; 514/330

(58) Field of Classification Search .............. 546/191, 546/184; 514/330
See application file for complete search history.

(56) References Cited

U.S. PATENT DOCUMENTS

| | | | |
|---|---|---|---|
| 3,801,581 A | 4/1974 | Rossi et al. | 260/293.72 |
| 4,460,594 A * | 7/1984 | Markwell | 514/323 |
| 4,476,311 A | 10/1984 | Shetty et al. | 548/531 |
| 4,618,614 A * | 10/1986 | Hausberg et al. | 514/321 |
| 5,411,972 A | 5/1995 | Komoto et al. | 514/330 |
| 5,420,305 A | 5/1995 | Ramig et al. | 549/292 |
| 5,658,944 A | 8/1997 | Chapman, Jr. et al. | 514/748 |
| 5,994,356 A | 11/1999 | Pieper et al. | 514/252 |
| 6,153,758 A | 11/2000 | Sannicolo et al. | 548/111 |
| 6,303,637 B1 | 10/2001 | Bao et al. | 514/331 |
| 6,323,229 B1 | 11/2001 | Howard | 514/373 |
| 6,362,203 B1 | 3/2002 | Mogi et al. | 514/327 |
| 6,376,494 B1 | 4/2002 | Childers et al. | 514/252.14 |

FOREIGN PATENT DOCUMENTS

| | | | |
|---|---|---|---|
| EP | 0548798 | * | 6/1993 |
| JP | 02173426 | | 6/2002 |
| WO | WO 9210468 | | 6/1992 |
| WO | WO 9219594 | | 11/1992 |
| WO | WO 9307141 | | 4/1993 |
| WO | WO 9312086 | | 6/1993 |
| WO | WO 96/02250 | * | 2/1996 |
| WO | WO 9602250 | | 2/1996 |
| WO | WO 9736579 | | 10/1997 |
| WO | WO 9805331 | | 2/1998 |
| WO | WO 0014066 | | 3/2000 |
| WO | WO 0023407 | | 4/2000 |
| WO | WO 01/90101 | * | 11/2001 |
| WO | WO 0181310 | | 11/2001 |
| WO | WO 0185716 | | 11/2001 |
| WO | WO 0190101 | | 11/2001 |
| WO | WO 0228834 | | 4/2002 |
| WO | WO 0230896 | | 4/2002 |
| WO | WO 02064139 | | 8/2002 |
| WO | WO 02064549 | | 8/2002 |

OTHER PUBLICATIONS

Palani et al., Journal of Medicinal Chemistry, 2005, 48, 4746.*
Heinone, T. Currect Atherosclerosis Reports, 2002, 4(1), Summary.*
Thomas et al., Archives des Maladies du Coeur et des Vaisseaux, 1992, 85, Summary.*
Narayanaswamy et al., J. Vas. Intervent. Radiol., 11(1), 2000, Summary.□□*
Archives des Maladies du Coeur et des Vaisseaux, 1991, 84/11, Summary.*
Human and Ecological Risk Assessment, 1999, 84/11, Summary.*
Patani et al., Chem. Rev., 1996, 96,3147-3176.*
Komoto, T., et al., New Strong Fibrates with Piperidne Moiety, Chem. Pharm. Bull., vol. 48, No. 12, pp. 1878-1985 (2000).

* cited by examiner

*Primary Examiner*—D. Margaret Seaman
(74) *Attorney, Agent, or Firm*—Lisa A. Samuels; Charles W. Ashbrook; Rosanne Goodman

(57) ABSTRACT

PPAR alpha activators, pharmaceutical compositions containing such compounds and the use of such compounds to elevate certain plasma lipid levels, including high density lipoprotein-cholesterol and to lower certain other plasma lipid levels, such as LDL-cholesterol and triglycerides and accordingly to treat diseases which are exacerbated by low levels of HDL cholesterol and/or high levels of LDL-cholesterol and triglycerides, such as atherosclerosis and cardiovascular diseases, in mammals, including humans.

12 Claims, No Drawings

PIPERIDINE COMPOUNDS USEFUL AS PPAR ACTIVATORS

CROSS-REFERENCE TO RELATED APPLICATION

This application Ser. No. 10/720,942 claims the benefit of U.S. provisional application No. 60/429,506, filed Nov. 26, 2002.

BACKGROUND OF INVENTION

The present invention relates to peroxisome proliferator activator receptor (PPAR) agonists, in particular, PPARα agonists, pharmaceutical compositions containing such agonists and the use of such agonists to treat atherosclerosis, hypercholesterolemia, hypertriglyceridemia, diabetes, obesity, osteoporosis and Syndrome X (also known as metabolic syndrome) in mammals, including humans.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Additional independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes could be improved. The use of insulin typically requires multiple daily doses. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and in more severe cases, insulin. However, the clinically available hypoglycemic agents can have side effects that limit their use. In the case of insulin dependent diabetes mellitus (Type I), insulin is usually the primary course of therapy.

U.S. Pat. No. 5,658,944, WO92/10468, WO97/36579, WO98/05331 and WO 00/23407 disclose agents for the treatment of atherosclerosis, obesity and diabetes.

T. Komoto et al., Chem. Pharm. Bull., 48 (12) 1978–1985 (2000), and JP14173426A disclose certain fibrate compounds containing piperidine moieties. International Publication No. WO 93/12086 discloses arylamide derivatives useful for treating and preventing various thromboses, embolisms, arterioscleroses, hypertensions and so forth. International Publication No. WO 02/30896 discloses 2,2-diphenylbutanamide derivatives useful as peripherally acting analgesic and neurogenic pain controller. U.S. Pat. No. 5,411,972 discloses arylamide derivatives for treating hyperlipemia. U.S. Pat. No. 6,362,203 discloses 4-hydroxy-4-phenylpiperidine derivatives having peripheral analgesic action. U.S. Pat. No. 5,994,356 discloses carboxylic acid derivatives having aggregation-inhibiting activity.

International Publication Nos. WO 02/064549 and 02/064139 disclose certain compounds which are PPARα activators.

U.S. Pat. No. 3,801,581 discloses certain α-phenyl-fatty acids substituted by azacycloalkyl residues and their derivatives which are useful as anti-inflammatory and antiphlogistic agents. International Publication No. WO 01/81310 discloses certain 1-aroyl-piperidinyl benzamidines which inhibit Factor Xa or tryptase.

International Publication No. WO 01/90101 discloses arylmethylamine derivatives for use as tryptase inhibitors. International Publication No. WO 01/85716 discloses nitro-substituted 2-piperidone compounds for the treatment of cancer. International Publication No. WO 00/14066 discloses 4,4-biarylpiperidine derivatives with opiod receptor activity. U.S. Pat. No. 6,153,755 discloses a process for preparing piperidine compounds and intermediates therefore.

International Publication No. WO 96/02250A1 discloses haloperidol analogs and their uses. International Publication No. WO 02/28834 discloses processes for the preparation of aryl-piperidine carbinols and intermediates thereof.

U.S. Pat. No. 6,376,494 discloses cycloalkyl-substituted aryl-piperazines, piperidines and tetrahydropyridines as serotonergic agents, which may be useful for the treatment of anxiety, depression, cognitive deficits and prostate cancer. U.S. Pat. No. 6,303,637 discloses heterocyclic potassium channel inhibitors to treat autoimmune disorders, cardiac arrhythmias and the like. U.S. Pat. No. 6,323,229 discloses N-acyl and N-aroyl aralkylamides useful in treating or preventing migraine, depression and other disorders for which a 5-HT$_1$ agonist or antagonist is indicated. U.S. Pat. No. 6,153,758 discloses heteroarylic-arylic diphosphines as chiral catalysts for stereocontrolled reactions.

Published European patent application 0 548 798 discloses a variety of heterocyclic-containing antiviral agents. International Publication No. WO 93/07141 discloses heterocyclic 3-phenylpyrrolidin-2-ones useful for inhibiting tumor necrosis factor production. International Publication No. WO 92/19594 discloses pyrrolidinone derivatives which inhibit phosphodiesterase IV and tumor necrosis factor (TNF). U.S. Pat. No. 5,420,154 relates to 4-(substituted phenyl)-2-pyrrolidinone derivatives which inhibit the production of tumor necrosis factor (TNF). U.S. Pat. No. 4,476,311 provides analgesic and anti-inflammatory 4-carboxy-pyrrolidin-2-one compounds.

Thus, although there are a variety of anti-atherosclerosis and diabetes therapies, there is a continuing need and a continuing search in this field of art for alternative therapies.

SUMMARY OF THE INVENTION

The present invention provides compounds of Formula I

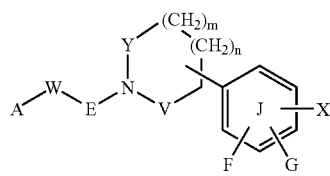

I isomers thereof, prodrugs of said compounds or isomers, or pharmaceutically acceptable salts of said compounds, isomers or prodrugs;

wherein m and n are each independently one or two;

V and Y are each independently a) methylene, or b) carbonyl;

F and G are each independently a) hydrogen, b) halo, c) $(C_1-C_4)$alkyl optionally substituted with one to nine fluoro, d) $(C_3-C_6)$cycloalkyl, e) hydroxy, f) $(C_1-C_4)$alkoxy or g) $(C_1-C_4)$alkylthio;

X is a)-Z or b) —B—C($R^1R^2$)-Z;

B is a) oxy, b) thio, c) sulfinyl, d) sulfonyl, e) methylene, or f) —N(H)—;

Z is a) —C(O)OH, b) —C(O)O—$(C_1-C_4)$alkyl, c) —C(O)O—$(C_0-C_4)$alkyl-aryl, d) —C(O)—$NH_2$, e) hydroxyaminocarbonyl, f) tetrazolyl, g) tetrazolylaminocarbonyl, h) 4,5-dihydro-5-oxo-1,2,4-oxadiazol-3-yl, i) 3-oxoisoxazolidin-4-yl-aminocarbonyl, j) —C(O)N(H)$SO_2R^4$, or k) —NH$SO_2R^4$; wherein $R^4$ is a) $(C_1-C_6)$alkyl, b) amino or c) mono-N- or di-N,N-$(C_1-C_6)$alkylamino, wherein the $(C_1-C_6)$alkyl substituents in $R^4$ are optionally independently substituted with one to nine fluoro;

$R^1$ is a) H, b) $(C_1-C_4)$alkyl, or c) $(C_3-C_6)$cycloalkyl;

$R^2$ is a) H, b) $(C_3-C_6)$cycloalkyl or c) a fully or partially saturated or fully unsaturated one to four membered straight or branched carbon chain; wherein the carbon(s) in the carbon chain may optionally be replaced with one or two heteroatoms selected independently from oxygen and sulfur; and wherein the sulfur is optionally mono- or di-substituted with oxo;

wherein the carbon(s) in the carbon chain in $R^2$ is optionally independently substituted as follows: a) the carbon(s) is optionally mono-, di- or tri-substituted independently with halo, b) the carbon(s) is optionally mono-substituted with hydroxy or $(C_1-C_4)$alkoxy, and c) the carbon(s) is optionally mono-substituted with oxo; and wherein the carbon(s) in the carbon chain in $R^2$ is optionally mono-substituted with Q;

wherein Q is a partially or fully saturated or fully unsaturated three to eight membered ring optionally having one to four heteroatoms selected independently from oxygen, sulfur and nitrogen, or is a bicyclic ring consisting of two fused partially or fully saturated or fully unsaturated three to six membered rings, taken independently; wherein the bicyclic ring optionally has one to four heteroatoms selected independently from oxygen, sulfur and nitrogen;

wherein the Q ring is optionally mono-, di- or tri-substituted independently with a) halo, b) $(C_2-C_6)$alkenyl, c) $(C_1-C_6)$ alkyl, d) hydroxy, e) $(C_1-C_6)$alkoxy, f) $(C_1-C_4)$alkylthio, g) amino, h) nitro, i) cyano, j) oxo, k) carboxy, l) $(C_1-C_6)$alkyloxycarbonyl, or m) mono-N- or di-N,N-$(C_1-C_6)$alkylamino; wherein the $(C_1-C_6)$alkyl and $(C_1-C_6)$ alkoxy substituents on the Q ring is optionally mono-, di- or tri-substituted independently with a) halo, b) hydroxy, c) $(C_1-C_6)$alkoxy, d) $(C_1-C_4)$alkylthio, e) amino, f) nitro, g) cyano, h) oxo, i) carboxy, j) $(C_1-C_6)$alkyloxycarbonyl, or k) mono-N- or di-N,N-$(C_1-C_6)$alkylamino; wherein the $(C_1-C_6)$alkyl substituent is on the Q ring is also optionally substituted with one to nine fluoro;

or wherein $R^1$ and $R^2$ are linked together to form a three to six membered fully saturated carbocyclic ring, optionally having one heteroatom selected from oxygen, sulfur and nitrogen to form a heterocyclic ring;

E is a) carbonyl, b) sulfonyl, or c) methylene;

W is a) a bond, b) carbonyl, c) —N(H)—, d) —N(($C_1-C_4$)alkyl)-, e) $(C_2-C_8)$alkenyl, f) oxy, g) —$(C_1-C_4)$alkyl-O—, h) —NH—$(C_1-C_4)$alkyl-, or i) —$(C_1-C_6)$alkyl-; wherein the $(C_1-C_6)$alkyl and the $(C_2-C_8)$alkenyl groups in W may optionally be mono- or di-substituted independently with a) oxo, b) halo, c) $(C_1-C_6)$alkoxycarbonyl, d) $(C_1-C_6)$alkyl, e) $(C_2-C_6)$alkenyl, f) $(C_3-C_7)$cycloalkyl, g) hydroxy, h) $(C_1-C_6)$alkoxy, i) $(C_1-C_4)$alkylthio, j) amino, k) cyano, l) nitro, m) mono-N- or di-N,N-$(C_1-C_6)$alkylamino, or n) —NH—$(C_1-C)$alkylamino;

or wherein W is $CR^7R^8$ wherein $R^7$ and $R^8$ are linked together to form a three to six membered fully saturated carbocyclic ring;

A is a) mono-N- or di-N,N-$(C_1-C_6)$alkylamino, b) $(C_2-C_6)$alkanoylamino, c) $(C_1-C_6)$alkoxy, d) a partially or fully saturated or fully unsaturated three to eight membered ring optionally having one to four heteroatoms selected independently from oxygen, sulfur and nitrogen, or e) a bicyclic ring consisting of two fused partially or fully saturated or fully unsaturated three to six membered rings, taken independently; wherein the bicyclic ring optionally has one to four heteroatoms selected independently from oxygen, sulfur and nitrogen; and wherein the A ring is optionally mono-, di- or tri-substituted independently with a) oxo, b) carboxy, c) halo, d) $(C_1-C_6)$alkoxycarbonyl, e) $(C_1-C_6)$alkyl, f) $(C_2-C_6)$alkenyl, g) $(C_3-C_7)$cycloalkyl, h) $(C_3-C_7)$cycloalkyl$(C_1-C_6)$alkyl, i) hydroxy, j) $(C_1-C_6)$alkoxy, k) $(C_1-C_4)$alkylthio, l) $(C_1-C_4)$alkylsulfonyl, m) amino, n) cyano, o) nitro, or p) mono-N- or di-N,N-$(C_1-C_6)$alkylamino; wherein the $(C_1-C_6)$alkyl and $(C_1-C_6)$alkoxy substituents on the A ring are also optionally mono-, di- or tri-substituted independently with a) halo, b) hydroxy, c) $(C_1-C_4)$alkyl optionally substituted with one to nine fluoro, d) $(C_3-C_6)$cycloalkyl, e) $(C_1-C_6)$ alkoxy, f) amino, or g) mono-N- or di-N,N-$(C_1-C_6)$alkylamino;

or wherein the A ring is optionally mono-substituted with a partially or fully saturated or fully unsaturated three to eight membered ring, optionally having one to four heteroatoms selected independently from oxygen, sulfur and nitrogen; also wherein this three to eight membered ring is optionally mono-, di- or tri-substituted independently with a) halo, b) hydroxy, c) $(C_1-C_4)$alkyl optionally substituted with one to nine fluoro, d) $(C_3-C_6)$cycloalkyl, e) $(C_1-C_6)$ alkoxy, f) amino, g) mono-N- or di-N,N-($C_1$–$C_6$)alkylamino, or h) ($C_1$–$C_4$)alkylthio;

provided that:

1) when V and Y are each methylene and m and n are each one forming a six-membered piperidinyl ring, this ring is substituted by the phenyl ring (designated as J) at other than the 4-position;

2) when E is carbonyl, W is a bond and X is —B—C($R^1R^2$)-Z wherein $R^1$ and $R^2$ are each hydrogen, B is —O— or —N(H)—, and Z is —C(O)OH or —C(O)O—($C_1$–$C_4$)alkyl, then one of F or G must be a) —($C_1$–$C_4$)alkyl, b) ($C_3$–$C_6$)cycloalkyl, c) ($C_1$–$C_4$)alkoxy or d) ($C_1$–$C_4$)alkylthio.

More particularly, the present invention provides compounds with the further proviso that:

3) when E is carbonyl, W is a bond, X is -Z, and Z is —C(O)OH, —C(O)O—($C_1$–$C_4$)alkyl, —C(O)NH$_2$, then one of F or G must be a) —($C_1$–$C_4$)alkyl, b) ($C_3$–$C_6$)cycloalkyl, c) ($C_1$–$C_4$)alkoxy or d) ($C_1$–$C_4$)alkylthio.

More particularly, the present invention provides compounds wherein V and Y are each methylene; or wherein one of V and Y is carbonyl and the other is methylene.

More particularly, the present invention provides compounds wherein

E is carbonyl;

W is a) a bond, b) oxy, c) —N(H)—, d) —N(H)—($C_1$–$C_4$)alkyl-, e) —($C_1$–$C_4$)alkyl-, f) —($C_1$–$C_4$)alkyl-O— or g) —$CR^7R^8$— wherein $R^7$ and $R^8$ are linked together to form a three-membered fully saturated carbocyclic ring; and A is a partially or fully saturated or fully unsaturated three to eight membered ring optionally having one to four heteroatoms selected independently from oxygen, sulfur and nitrogen;

wherein the A ring is optionally mono-, di- or tri-substituted independently with a) oxo, b) carboxy, c) halo, d) ($C_1$–$C_6$)alkoxycarbonyl, e) ($C_1$–$C_6$)alkyl, f) ($C_2$–$C_6$)alkenyl, g) ($C_3$–$C_7$)cycloalkyl, h) ($C_3$–$C_7$)cycloalkyl($C_1$–$C_6$)alkyl, i) hydroxy, j) ($C_1$–$C_6$)alkoxy, k) ($C_1$–$C_4$)alkylthio, l) ($C_1$–$C_4$)alkylsulfonyl, m) amino, n) cyano, o) nitro, or p) mono-N- or di-N,N-($C_1$–$C_6$)alkylamino; wherein the ($C_1$–$C_6$)alkyl and ($C_1$–$C_6$)alkoxy substituents on the A ring are also optionally mono-, di- or tri-substituted independently with a) halo, b) hydroxy, c) ($C_1$–$C_4$)alkyl optionally substituted with one to nine fluoro, d) ($C_3$–$C_6$)cycloalkyl, e) ($C_1$–$C_6$)alkoxy, f) amino, or g) mono-N- or di-N,N-($C_1$–$C_6$)alkylamino;

or wherein the A ring is optionally mono-substituted with a partially or fully saturated or fully unsaturated three to eight membered ring, optionally having one to four heteroatoms selected independently from oxygen, sulfur and nitrogen; also wherein this three to eight membered ring is optionally mono-, di- or tri-substituted independently with a) halo, b) hydroxy, c) ($C_1$–$C_6$)alkyl optionally substituted with one to nine fluoro, d) ($C_3$–$C_7$)cycloalkyl, e) ($C_1$–$C_6$)alkoxy optionally substituted with one to nine fluoro, f) amino, g) mono-N- or di-N,N-($C_1$–$C_6$)alkylamino, or h) ($C_1$–$C_4$)alkylthio;

More particularly, the present invention provides compounds wherein

A is a) phenyl optionally independently substituted with one or two 1) —($C_1$–$C_6$)alkyl, 2) —$CF_3$, 3) —$OCF_3$ 4) —($C_1$–$C_6$)alkoxy, 5) ($C_3$–$C_7$)cycloalkyl, 6) halo or 7) hydroxy; or b) thiazolyl optionally independently substituted with 1) one or two methyl or 2) phenyl optionally independently substituted with one or two a) —($C_1$–$C_6$)alkyl, b) —$CF_3$, c) —$OCF_3$, d) —($C_1$–$C_6$)alkoxy, e) ($C_3$–$C_7$)cycloalkyl, f) halo, g) —($C_1$–$C_4$)alkylthio or h) hydroxy.

More particularly, the present invention provides compounds wherein

F and G are each independently a) hydrogen, b) halo, c) ($C_1$–$C_4$)alkyl or d) ($C_1$–$C_4$)alkoxy;

X is a)-Z or b) —B—C($R^1R^2$)-Z;

B is a) oxy, b) thio or c) —N(H)—;

Z is a) —C(O)OH, b) —C(O)O—($C_1$–$C_4$)alkyl, c) —C(O)NH$_2$ or d) tetrazolyl;

$R^1$ is a) hydrogen or b) methyl; and $R^2$ is a) hydrogen or b) a fully or partially saturated or fully unsaturated one to four membered straight or branched carbon chain; wherein the carbon(s) in the carbon chain may optionally be replaced with one or two heteroatoms selected independently from oxygen and sulfur;

wherein the carbon(s) in the carbon chain in $R^2$ is optionally mono-substituted with Q;

wherein Q is a partially or fully saturated or fully unsaturated three to eight membered ring optionally having one to four heteroatoms selected independently from oxygen, sulfur and nitrogen.

More particularly, the present invention provides compounds wherein $R^1$ is a) hydrogen or b) methyl; and $R^2$ is a) hydrogen, b) methyl or c) —O—$CH_2$-phenyl.

More particularly, the present invention provides compounds wherein m is one, n is one and V and Y are each methylene to form a piperdinyl ring;

X is —B—C($R^1R^2$)-Z;

B is oxy; and the phenyl ring (designated as J) is attached at the 3-position of the piperidinyl ring.

In particular, the present invention provides compounds of formula I-A

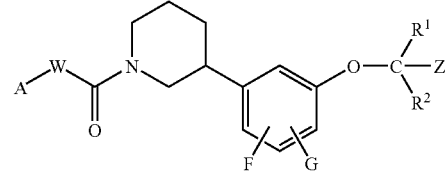

wherein $R^1$ and $R^2$ are each independently a) hydrogen or b) methyl;

F and G are each independently a) hydrogen or b) methyl; and

Z is —C(O)OH.

In particular, the present invention provides such compounds of formula I-A wherein W is a) oxy, b) —N(H)—, c) —N(H)—($C_1$–$C_4$)alkyl-, d) —($C_1$–$C_4$)alkyl- or e) —($C_1$–$C_4$)alkyl-O—; and A is phenyl optionally substituted with a) —($C_1$–$C_4$)alkyl, b) —$CF_3$, c) —$OCF_3$ d) —($C_1$–$C_4$)alkoxy, e) cyclopropyl, f) halo, g) —($C_1$–$C_4$)alkylthio or h) hydroxy.

In particular, the present invention also provides such compounds of formula I-A wherein W is a bond; and A is thiazolyl optionally substituted with a) one or two-methyl, or b)-phenyl optionally substituted with 1) —($C_1$–$C_4$)alkyl, 2) —$CF_3$, 3) —$OCF_3$ 4) —($C_1$–$C_4$)alkoxy, 5) cyclopropyl, 6) halo or 7) —($C_1$–$C_4$)alkylthio.

More particularly, the present invention provides compounds wherein m is one, n is one and V and Y are each methylene to form a piperidinyl ring;

X is -Z; and the phenyl ring (designated as J) is attached at the 3-position of the piperidinyl ring.

In particular, the present invention provides compounds of formula I-B

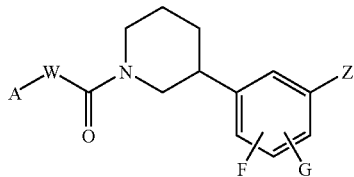

I-B wherein F and G are each a) hydrogen, b) methyl, c) fluoro or d) methoxy; and Z is a) —C(O)OH, b) —C(O)O—($C_1$–$C_4$)alkyl or c) —C(O)NH$_2$.

More particularly, the present invention provides compounds of formula I-B wherein W is a) —($C_1$–$C_4$)alkyl- or b) —($C_1$–$C_4$)alkyl-O—; and A is phenyl optionally substituted with a) —($C_1$–$C_4$)alkyl, b) —CF$_3$, c) —OCF$_3$, d) —($C_1$–$C_4$)alkoxy, e) cyclopropyl, f) halo or g) hydroxy.

More particularly, the present invention provides compounds of formula I-B wherein W is a bond; and A is thiazolyl optionally substituted with a) one or two-methyl or b)-phenyl optionally substituted with 1) —($C_1$–$C_4$)alkyl, 2) —CF$_3$, 3) —OCF$_3$ 4) —($C_1$–$C_4$)alkoxy, 5) cyclopropyl or 6) halo.

In particular, the present invention provides compounds of formula I-C

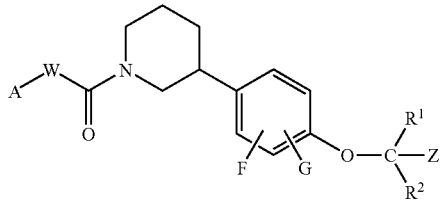

I-C wherein R$^1$ and R$^2$ are each independently a) hydrogen or b) methyl;

F and G are each independently a) hydrogen or b) methyl; and

Z is —C(O)OH.

More particularly, the present invention provides compounds of formula I-C wherein W is a) oxy, b) —N(H)—, c) —N(H)—($C_1$–$C_4$)alkyl, d) —($C_1$–$C_4$)alkyl- or e) —($C_1$–$C_4$)alkyl-O—; and A is phenyl optionally substituted with a) —($C_1$–$C_4$)alkyl, b) —CF$_3$, c) —OCF$_3$ d) —($C_1$–$C_4$)alkoxy, e) cyclopropyl, f) halo, g) —($C_1$–$C_4$)alkylthio or h) hydroxy.

More particularly, the present invention also provides compounds of formula I-C wherein W is a bond; and A is thiazolyl optionally substituted with a) one or two-methyl or b)-phenyl optionally substituted with 1) —($C_1$–$C_4$)alkyl, 2) —CF$_3$, 3) —OCF$_3$ 4) —($C_1$–$C_4$)alkoxy, 5) cyclopropyl, 6) halo or 7) —($C_1$–$C_4$)alkylthio.

In particular, the present invention provides compounds of formula I-D

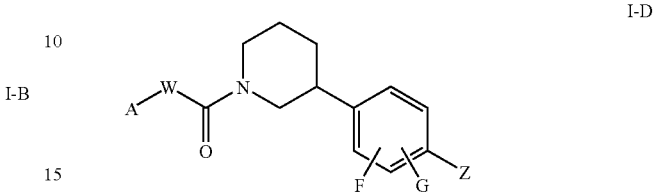

I-D wherein F and G are each independently a) hydrogen, b) methyl, c) fluoro or d) methoxy; and Z is a) —C(O)OH, b) —C(O)O—($C_1$–$C_4$)alkyl or c) —C(O)NH$_2$.

More particularly, the present invention provides such compounds of formula I-D wherein W is a) —($C_1$–$C_4$)alkyl- or b) —($C_1$–$C_4$)alkyl-O—; and A is phenyl optionally substituted with a) —($C_1$–$C_4$)alkyl, b) —CF$_3$, c) —OCF$_3$, d) —($C_1$–$C_4$)alkoxy, e) cyclopropyl, f) halo, g) —($C_1$–$C_4$)alkylthio or h) hydroxy.

More particularly, the present invention also provides such compounds of formula I-D wherein W is a bond; and A is a) thiazolyl optionally substituted with 1) one or two-methyl or 2)-phenyl optionally substituted with i) —($C_1$–$C_4$)alkyl, ii)-CF$_3$, iii)-OCF$_3$ iv)-($C_1$–$C_4$)alkoxy, v) cyclopropyl or vi) halo; or b) phenyl optionally substituted with 1) —($C_1$–$C_4$)alkyl, 2) —CF$_3$, 3) —OCF$_3$, 4) —($C_1$–$C_4$) alkoxy, 5) cyclopropyl, 6) halo or 7) —($C_1$–$C_4$)alkylthio.

More particularly, the present invention provides compounds, such as the following:

2-{3-[1-(4-Isopropyl-phenylcarbamoyl)-piperidin-3-yl]-phenoxy}-2-methyl-propionic acid;

(S)-2-{3-[1-(4-Isopropyl-phenylcarbamoyl)-piperidin-3-yl]-phenoxy}-2-methyl-propionic acid;

(R)-2-{3-[1-(4-Isopropyl-phenylcarbamoyl)-piperidin-3-yl]-phenoxy}-2-methyl-propionic acid;

2-Methyl-2-(3-{1-[(4-trifluoromethyl-phenyl)-acetyl]-piperidin-3-yl}-phenoxy)-propionic acid;

(S)-2-Methyl-2-(3-{1-[(4-trifluoromethyl-phenyl)-acetyl]-piperidin-3-yl}-phenoxy)-propionic acid;

(R)-2-Methyl-2-(3-{1-[(4-trifluoromethyl-phenyl)-acetyl]-piperidin-3-yl}-phenoxy)-propionic acid;

2-(3-{1-[(4-Isopropyl-phenyl)-acetyl]-piperidin-3-yl}-phenoxy)-2-methyl-propionic acid;

(S)-2-(3-{1-[(4-Isopropyl-phenyl)-acetyl]-piperidin-3-yl}-phenoxy)-2-methyl-propionic acid;

(R)-2-(3-{1-[(4-Isopropyl-phenyl)-acetyl]-piperidin-3-yl}-phenoxy)-2-methyl-propionic acid;

2-(3-{1-[3-(4-Isopropyl-phenyl)-propionyl]-piperidin-3-yl}-phenoxy)-2-methyl-propionic acid;

(S)-2-(3-{1-[3-(4-Isopropyl-phenyl)-propionyl]-piperidin-3-yl}-phenoxy)-2-methyl-propionic acid;

(R)-2-(3-{1-[3-(4-Isopropyl-phenyl)-propionyl]-piperidin-3-yl}-phenoxy)-2-methyl-propionic acid;

2-(3-{1-[(4-Isopropyl-phenoxy)-acetyl]-piperidin-3-yl}-phenoxy)-2-methyl-propionic acid;

(S)-2-(3-{1-[(4-Isopropyl-phenoxy)-acetyl]-piperidin-3-yl}-phenoxy)-2-methyl-propionic acid;

(R)-2-(3-{1-[(4-Isopropyl-phenoxy)-acetyl]-piperidin-3-yl}-phenoxy)-2-methyl-propionic acid;
2-(3-{1-[2-(4-Isopropyl-phenoxy)-2-methyl-propionyl]-piperidin-3-yl}-phenoxy)-2-methyl-propionic acid;
(S)-2-(3-{1-[2-(4-Isopropyl-phenoxy)-2-methyl-propionyl]-piperidin-3-yl}-phenoxy)-2-methyl-propionic acid;
(R)-2-(3-{1-[2-(4-Isopropyl-phenoxy)-2-methyl-propionyl]-piperidin-3-yl}-phenoxy)-2-methyl-propionic acid;
2-Methyl-2-(3-{1-[3-(4-trifluoromethyl-phenyl)-propionyl]-piperidin-3-yl}-phenoxy)-propionic acid;
(S)-2-Methyl-2-(3-{1-[3-(4-trifluoromethyl-phenyl)-propionyl]-piperidin-3-yl}-phenoxy)-propionic acid;
(R)-2-Methyl-2-(3-{1-[3-(4-trifluoromethyl-phenyl)-propionyl]-piperidin-3-yl}-phenoxy)-propionic acid;
2-Methyl-2-(3-{1-[(4-trifluoromethoxy-phenoxy)-acetyl]-piperidin-3-yl}-phenoxy)-propionic acid;
(S)-2-Methyl-2-(3-{1-[(4-trifluoromethoxy-phenoxy)-acetyl]-piperidin-3-yl}-phenoxy)-propionic acid;
(R)-2-Methyl-2-(3-{1-[(4-trifluoromethoxy-phenoxy)-acetyl]-piperidin-3-yl}-phenoxy)-propionic acid;
(3-{1-[(4-Isopropyl-phenyl)-acetyl]-piperidin-3-yl}-phenoxy)-acetic acid;
(S)-(3-{1-[(4-Isopropyl-phenyl)-acetyl]-piperidin-3-yl}-phenoxy)-acetic acid;
(R)-(3-{1-[(4-Isopropyl-phenyl)-acetyl]-piperidin-3-yl}-phenoxy)-acetic acid;
3-[3-(1-Carboxy-1-methyl-ethoxy)-phenyl]-piperidine-1-carboxylic acid 4-isopropyl-phenyl ester;
(S)-3-[3-(1-Carboxy-1-methyl-ethoxy)-phenyl]-piperidine-1-carboxylic acid 4-isopropyl-phenyl ester;
(R)-3-[3-(1-Carboxy-1-methyl-ethoxy)-phenyl]-piperidine-1-carboxylic acid 4-isopropyl-phenyl ester;
(S)-2-(3-{1-[(4-tert-Butyl-phenyl)-acetyl]-piperidin-3-yl}-phenoxy)-2-methyl-propionic acid;
(R)-2-(3-{1-[(4-tert-Butyl-phenyl)-acetyl]-piperidin-3-yl}-phenoxy)-2-methyl-propionic acid;
2-(3-{1-[(4-tert-Butyl-phenyl)-acetyl]-piperidin-3-yl}-phenoxy)-2-methyl-propionic acid;
(S)-2-Methyl-2-(3-{1-[(4-trifluoromethoxy-phenyl)-acetyl]-piperidin-3-yl}-phenoxy)-propionic acid;
(R)-2-Methyl-2-(3-{1-[(4-trifluoromethoxy-phenyl)-acetyl]-piperidin-3-yl}-phenoxy)-propionic acid;
2-Methyl-2-(3-{1-[(4-trifluoromethoxy-phenyl)-acetyl]-piperidin-3-yl}-phenoxy)-propionic acid;
(S)-3-[3-(1-Carboxy-1-methyl-ethoxy)-phenyl]-piperidine-1-carboxylic acid 4-isopropyl-benzyl ester;
(R)-3-[3-(1-Carboxy-1-methyl-ethoxy)-phenyl]-piperidine-1-carboxylic acid 4-isopropyl-benzyl ester;
3-[3-(1-Carboxy-1-methyl-ethoxy)-phenyl]-piperidine-1-carboxylic acid 4-isopropyl-benzyl ester;
(S)-3-[3-(1-Carboxy-1-methyl-ethoxy)-phenyl]-piperidine-1-carboxylic acid 4-isopropyl-phenyl ester;
(R)-3-[3-(1-Carboxy-1-methyl-ethoxy)-phenyl]-piperidine-1-carboxylic acid 4-isopropyl-phenyl ester;
3-[3-(1-Carboxy-1-methyl-ethoxy)-phenyl]-piperidine-1-carboxylic acid 4-isopropyl-phenyl ester;
2-{3-[1-(4-Isopropyl-benzylcarbamoyl)-piperidin-3-yl]-phenoxy}-2-methyl-propionic acid;
(S)-2-{3-[1-(4-Isopropyl-benzylcarbamoyl)-piperidin-3-yl]-phenoxy}-2-methyl-propionic acid;
(R)-2-{3-[1-(4-Isopropyl-benzylcarbamoyl)-piperidin-3-yl]-phenoxy}-2-methyl-propionic acid;
3-[3-(1-Carboxy-1-methyl-ethoxy)-phenyl]-piperidine-1-carboxylic acid 4-trifluoromethyl-benzyl ester;
(S)-3-[3-(1-Carboxy-1-methyl-ethoxy)-phenyl]-piperidine-1-carboxylic acid 4-trifluoromethyl-benzyl ester;
(R)-3-[3-(1-Carboxy-1-methyl-ethoxy)-phenyl]-piperidine-1-carboxylic acid 4-trifluoromethyl-benzyl ester;
(S)-2-Methyl-2-{3-[1-(4-trifluoromethoxy-benzylcarbamoyl)-piperidin-3-yl]-phenoxy}-propionic acid;
(R)-2-Methyl-2-{3-[1-(4-trifluoromethoxy-benzylcarbamoyl)-piperidin-3-yl]-phenoxy}-propionic acid;
2-Methyl-2-{3-[1-(4-trifluoromethoxy-benzylcarbamoyl)-piperidin-3-yl]-phenoxy}-propionic acid;
(S)-2-Methyl-2-(3-{1-[4-methyl-2-(4-trifluoromethyl-phenyl)-thiazole-5-carbonyl]-piperidin-3-yl}-phenoxy)-propionic acid;
(R)-2-Methyl-2-(3-{1-[4-methyl-2-(4-trifluoromethyl-phenyl)-thiazole-5-carbonyl]-piperidin-3-yl}-phenoxy)-propionic acid;
2-Methyl-2-(3-{1-[4-methyl-2-(4-trifluoromethyl-phenyl)-thiazole-5-carbonyl]-piperidin-3-yl}-phenoxy)-propionic acid;
3-[3-(1-Carboxy-1-methyl-ethoxy)-phenyl]-piperidine-1-carboxylic acid 4-cyclopropyl-benzyl ester;
(S)-3-[3-(1-Carboxy-1-methyl-ethoxy)-phenyl]-piperidine-1-carboxylic acid 4-cyclopropyl-benzyl ester;
(R)-3-[3-(1-Carboxy-1-methyl-ethoxy)-phenyl]-piperidine-1-carboxylic acid 4-cyclopropyl-benzyl ester;
(S)-(2-methyl-5-{1-[4-methyl-2-(4-trifluoromethyl-phenyl)-thiazole-5-carbonyl]-piperidin-3-yl}-phenoxy)-acetic acid;
(R)-(2-methyl-5-{1-[4-methyl-2-(4-trifluoromethyl-phenyl)-thiazole-5-carbonyl]-piperidin-3-yl}-phenoxy)-acetic acid;
(2-methyl-5-{1-[4-methyl-2-(4-trifluoromethyl-phenyl)-thiazole-5-carbonyl]-piperidin-3-yl}-phenoxy)-acetic acid;
(S)-2-Methyl-2-(2-methyl-5-{1-[4-methyl-2-(4-trifluoromethyl-phenyl)-thiazole-5-carbonyl]-piperidin-3-yl}-phenoxy)-propionic acid;
(R)-2-Methyl-2-(2-methyl-5-{1-[4-methyl-2-(4-trifluoromethyl-phenyl)-thiazole-5-carbonyl]-piperidin-3-yl}-phenoxy)-propionic acid;
2-Methyl-2-(2-methyl-5-{1-[4-methyl-2-(4-trifluoromethyl-phenyl)-thiazole-5-carbonyl]-piperidin-3-yl}-phenoxy)-propionic acid;
(S)-3-(3-carboxymethoxy-4-methyl-phenyl)-piperidine-1-carboxylic acid 4-trifluoromethyl-benzyl ester;
(R)-3-(3-carboxymethoxy-4-methyl-phenyl)-piperidine-1-carboxylic acid 4-trifluoromethyl-benzyl ester;
3-(3-carboxymethoxy-4-methyl-phenyl)-piperidine-1-carboxylic acid 4-trifluoromethyl-benzyl ester;
(S)-3-[3-(1-Carboxy-1-methyl-ethoxy)-4-methyl-phenyl]-piperidine-1-carboxylic acid 4-trifluoromethyl-benzyl ester;
(R)-3-[3-(1-Carboxy-1-methyl-ethoxy)-4-methyl-phenyl]-piperidine-1-carboxylic acid 4-trifluoromethyl-benzyl ester;
3-[3-(1-Carboxy-1-methyl-ethoxy)-4-methyl-phenyl]-piperidine-1-carboxylic acid 4-trifluoromethyl-benzyl ester.
2-methyl-5-{1-[4-methyl-2-(4-trifluoromethyl-phenyl)-thiazole-5-carbonyl]-piperidin-3-yl}-benzoic acid;
(S)-2-methyl-5-{1-[4-methyl-2-(4-trifluoromethyl-phenyl)-thiazole-5-carbonyl]-piperidin-3-yl}-benzoic acid;
(R)-2-methyl-5-{1-[4-methyl-2-(4-trifluoromethyl-phenyl)-thiazole-5-carbonyl]-piperidin-3-yl}-benzoic acid;
3-(3-carboxy-4-methyl-phenyl)-piperidine-1-carboxylic acid 4-trifluoromethyl-benzyl ester;
(S)-3-(3-carboxy-4-methyl-phenyl)-piperidine-1-carboxylic acid 4-trifluoromethyl-benzyl ester;
(R)-3-(3-carboxy-4-methyl-phenyl)-piperidine-1-carboxylic acid 4-trifluoromethyl-benzyl ester;

(R)-2-methyl-5-{1-[4-methyl-2-(4-trifluoromethyl-phenyl)-thiazole-5-carbonyl]-piperidin-3-yl}-benzoic acid;
(S)-2-methyl-5-{1-[4-methyl-2-(4-trifluoromethyl-phenyl)-thiazole-5-carbonyl]-piperidin-3-yl}-benzoic acid;
2-methyl-5-{1-[4-methyl-2-(4-trifluoromethyl-phenyl)-thiazole-5-carbonyl]-piperidin-3-yl}-benzoic acid;
(S)-2-methyl-5-{1-[4-methyl-2-(4-trifluoromethyl-phenyl)-thiazole-5-carbonyl]-piperidin-3-yl}-benzoic acid;
(R)-2-methyl-5-{1-[4-methyl-2-(4-trifluoromethyl-phenyl)-thiazole-5-carbonyl]-piperidin-3-yl}-benzoic acid;
2-methyl-5-{1-[4-methyl-2-(4-trifluoromethyl-phenyl)-thiazole-5-carbonyl]-piperidin-3-yl}-benzoic acid;
(R)-3-(3-carboxy-4-methyl-phenyl)-piperidine-1-carboxylic acid 4-trifluoromethyl-benzyl ester;
(S)-3-(3-carboxy-4-methyl-phenyl)-piperidine-1-carboxylic acid 4-trifluoromethyl-benzyl ester;
3-(3-carboxy-4-methyl-phenyl)-piperidine-1-carboxylic acid 4-trifluoromethyl-benzyl ester;
2-Methoxy-5-{1-[4-methyl-2-(4-trifluoromethyl-phenyl)-thiazole-5-carbonyl]-piperidin-3-yl}-benzoic acid;
(S)-2-Methoxy-5-{1-[4-methyl-2-(4-trifluoromethyl-phenyl)-thiazole-5-carbonyl]-piperidin-3-yl}-benzoic acid;
(R)-2-Methoxy-5-{1-[4-methyl-2-(4-trifluoromethyl-phenyl)-thiazole-5-carbonyl]-piperidin-3-yl}-benzoic acid;
2-Fluoro-5-{1-[4-methyl-2-(4-trifluoromethyl-phenyl)-thiazole-5-carbonyl]-piperidin-3-yl}-benzoic acid;
(S)-2-Fluoro-5-{1-[4-methyl-2-(4-trifluoromethyl-phenyl)-thiazole-5-carbonyl]-piperidin-3-yl}-benzoic acid;
(R)-2-Fluoro-5-{1-[4-methyl-2-(4-trifluoromethyl-phenyl)-thiazole-5-carbonyl]-piperidin-3-yl}-benzoic acid;
2-Methyl-5-{1-[4-methyl-2-(4-trifluoromethyl-phenyl)-thiazole-5-carbonyl]-piperidin-3-yl}-benzamide;
(S)-2-Methyl-5-{1-[4-methyl-2-(4-trifluoromethyl-phenyl)-thiazole-5-carbonyl]-piperidin-3-yl}-benzamide;
(R)-2-Methyl-5-{1-[4-methyl-2-(4-trifluoromethyl-phenyl)-thiazole-5-carbonyl]-piperidin-3-yl}-benzamide;
(R)-3-(3-Carboxy-4-methyl-phenyl)-piperidine-1-carboxylic acid 2-(4-trifluoromethyl-phenyl)-ethyl ester;
(S)-3-(3-Carboxy-4-methyl-phenyl)-piperidine-1-carboxylic acid 2-(4-trifluoromethyl-phenyl)-ethyl ester;
3-(3-Carboxy-4-methyl-phenyl)-piperidine-1-carboxylic acid 2-(4-trifluoromethyl-phenyl)-ethyl ester.

The present invention also provides compounds of formula III

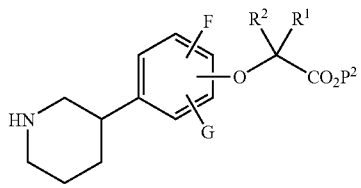

III which is racemic or which is an enantiomer thereof, or a pharmaceutically acceptable salt of said compound, wherein $P^2$ is methyl, ethyl or benzyl;

F and G are each independently a) hydrogen, b) halo, c) $(C_1-C_4)$alkyl optionally substituted with one to nine fluoro, d) $(C_3-C_6)$cycloalkyl, e) hydroxy, f) $(C_1-C_4)$alkoxy or g) $(C_1-C_4)$alkylthio;

$R^1$ is a) H, b) $(C_1-C_4)$alkyl, or c) $(C_3-C_6)$cycloalkyl;

$R^2$ is a) H, b) $(C_3-C_6)$cycloalkyl or c) a fully or partially saturated or fully unsaturated one to four membered straight or branched carbon chain; wherein the carbon(s) in the carbon chain may optionally be replaced with one or two heteroatoms selected independently from oxygen and sulfur; and wherein the sulfur is optionally mono- or di-substituted with oxo;

wherein the carbon(s) in the carbon chain in $R^2$ is optionally substituted as follows: a) the carbon(s) is optionally mono-, di- or tri-substituted independently with halo, b) the carbon(s) is optionally mono-substituted with hydroxy or $(C_1-C_4)$alkoxy, and c) the carbon(s) is optionally mono-substituted with oxo; and wherein the carbon(s) in the carbon chain in $R^2$ is optionally mono-substituted with Q;

wherein Q is a partially or fully saturated or fully unsaturated three to eight membered ring optionally having one to four heteroatoms selected independently from oxygen, sulfur and nitrogen, or is a bicyclic ring consisting of two fused partially or fully saturated or fully unsaturated three to six membered rings, taken independently; wherein the bicyclic ring optionally has one to four heteroatoms selected independently from oxygen, sulfur and nitrogen;

wherein the Q ring is optionally mono-, di- or tri-substituted independently with a) halo, b) $(C_2-C_6)$alkenyl, c) $(C_1-C_6)$ alkyl, d) hydroxy, e) $(C_1-C_6)$alkoxy, f) $(C_1-C_4)$alkylthio, g) amino, h) nitro, i) cyano, j) oxo, k) carboxy, l) $(C_1-C_6)$alkyloxycarbonyl, or m) mono-N- or di-N,N-$(C_1-C_6)$alkylamino; wherein the $(C_1-C_6)$alkyl and $(C_1-C_6)$alkoxy substituents on the Q ring is optionally mono-, di- or tri-substituted independently with a) halo, b) hydroxy, c) $(C_1-C_6)$alkoxy, d) $(C_1-C_4)$alkylthio, e) amino, f) nitro, g) cyano, h) oxo, i) carboxy, j) $(C_1-C_6)$alkyloxycarbonyl, or k) mono-N- or di-N,N-$(C_1-C_6)$alkylamino; wherein the $(C_1-C_6)$alkyl substituent is on the Q ring is also optionally substituted with one to nine fluoro;

or wherein $R^1$ and $R^2$ are linked together to form a three to six membered fully saturated carbocyclic ring, optionally having one heteroatom selected from oxygen, sulfur and nitrogen to form a heterocyclic ring.

More particularly, the present invention provides such compounds of the formula

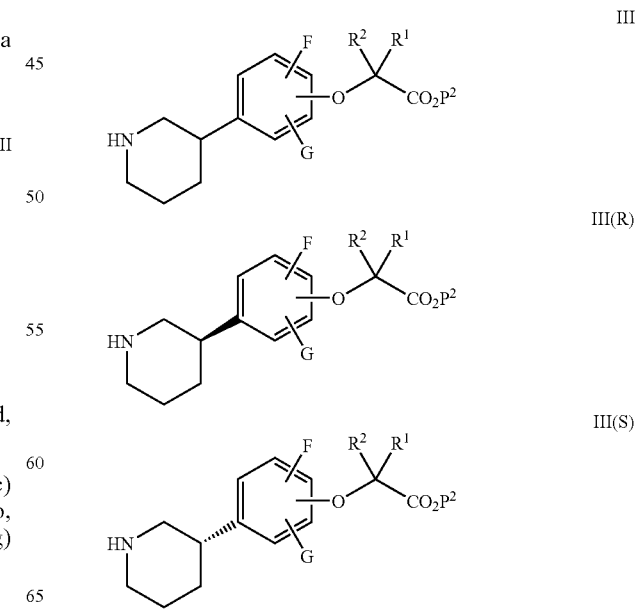

wherein $R^1$ and $R^2$ are each a) hydrogen or b) methyl;

F and G are each a) hydrogen, b) methyl or c) halo;

$P^2$ is methyl, ethyl or benzyl;

or a pharmaceutically acceptable salt thereof.

Even more particularly, the present invention provides compounds, such as the following:

2-methyl-2-(3-piperidin-3-yl-phenoxy)-propionic acid methyl ester;

(3S)-2-methyl-2-(3-piperidin-3-yl-phenoxy)-propionic acid methyl ester;

(3R)-2-methyl-2-(3-piperidin-3-yl-phenoxy)-propionic acid methyl ester;

2-methyl-2-(3-piperidin-3-yl-phenoxy)-propionic acid ethyl ester;

(3S)-2-methyl-2-(3-piperidin-3-yl-phenoxy)-propionic acid ethyl ester;

(3R)-2-methyl-2-(3-piperidin-3-yl-phenoxy)-propionic acid ethyl ester;

2-methyl-2-(3-piperidin-3-yl-phenoxy)-propionic acid benzyl ester;

(3S)-2-methyl-2-(3-piperidin-3-yl-phenoxy)-propionic acid benzyl ester;

(3R)-2-methyl-2-(3-piperidin-3-yl-phenoxy)-propionic acid benzyl ester; or the D- or L-tartrate salt thereof.

The present invention also provides processes for obtaining a compound of formula III (S) or formula III (R)

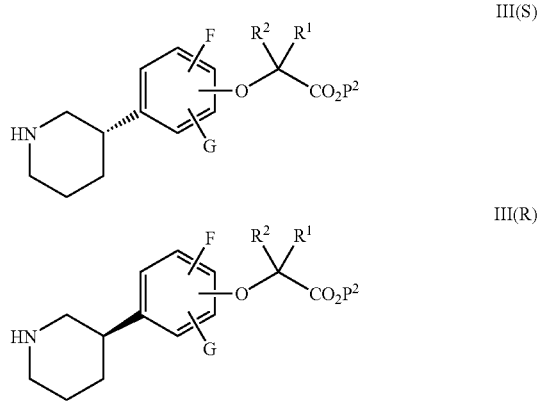

wherein $R^1$ and $R^2$ are each a) hydrogen or b) methyl;

F and G are each a) hydrogen, b) methyl or c) halo;

$P^2$ is methyl, ethyl or benzyl;

which comprises the chiral chromatography of the compound of formula III

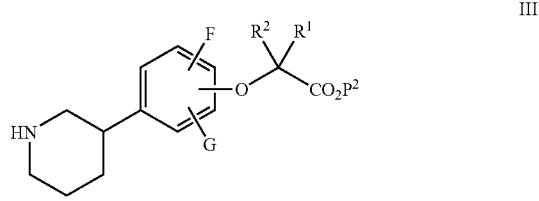

to give the compounds of formula III (S) and III (R).

The present invention also provides processes for obtaining a compound of formula III (S) or formula III (R)

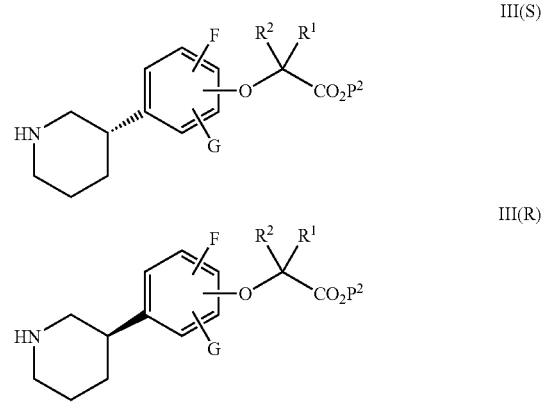

wherein $R^1$ and $R^2$ are each a) hydrogen or b) methyl;

F and G are each a) hydrogen, b) methyl or c) halo;

$P^2$ is methyl, ethyl or benzyl;

which comprises:

(a) reacting a compound of formula III

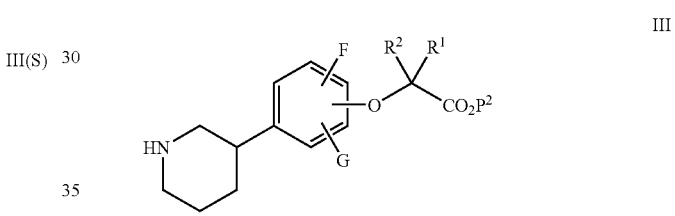

with L-(+)-tartaric acid or D-(−)-tartaric acid in the presence of a solvent;

(b) separating the resulting compounds by fractional crystallization; and (c) treating the separated compounds with a base to give the compounds of formula III (S) and III (R);

More particularly, the present invention provides such processes wherein the solvent in step (a) is ethanol or tetrahydrofuran.

More particularly, the present invention provides such processes wherein the base in step (c) is sodium carbonate, potassium carbonate, sodium hydroxide or postassium hydroxide.

More particularly, the present invention provides such processes, which further comprise:

(d) reacting an alcohol of formula A-W—OH wherein W is a) —($C_1$–$C_4$)alkyl- or b) —($C_1$–$C_4$)alkyl-O—, provided that the first atom in W, which is attached to the hydroxy group, is a carbon atom; and A is phenyl optionally substituted with a) —($C_1$–$C_4$)alkyl, b) —$CF_3$, c) —$OCF_3$ d) —($C_1$–$C_4$)alkoxy, e) cyclopropyl, f) halo, g) —($C_1$–$C_4$)alkylthio or hydroxy; or wherein W is a bond; and A is thiazolyl optionally substituted with a) one or two methyl or b)-phenyl optionally substituted with 1) —($C_1$–$C_4$)alkyl, 2) —$CF_3$, 3) —$OCF_3$ 4) —($C_1$–$C_4$)alkoxy, 0.5) cyclopropyl, 6) halo, 7) —($C_1$–$C_4$)alkylthio or 8) hydroxy;

with carbonyldiimidazole (CDI) to give a compound of formula

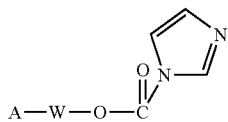

(e) reacting the resulting compound of step (d) with the compound of formula III (S) or formula III (R) from step (c) in a reaction-inert solvent at a temperature of about room temperature to about 100° C. to give a compound of formula

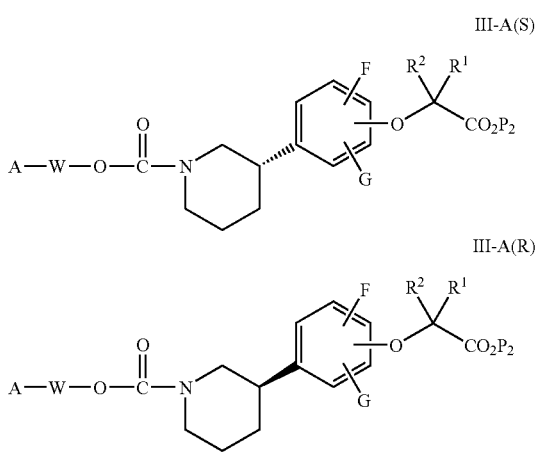

wherein $R^1$ and $R^2$ are each a) hydrogen or b) methyl;
F and G are each a) hydrogen, b) methyl or c) halo;
$P^2$ is methyl, ethyl or benzyl; and the other variables are as defined above.

More particularly, the present invention provides such processes wherein the reaction-inert solvent is tetrahydrofuran, ethyl acetate, toluene or methylene chloride.

More particularly, the present invention provides such processes, which further comprise:
(f) hydrolyzing the resulting compound of step (e) with a base in an aqueous solvent to give the compound of formula

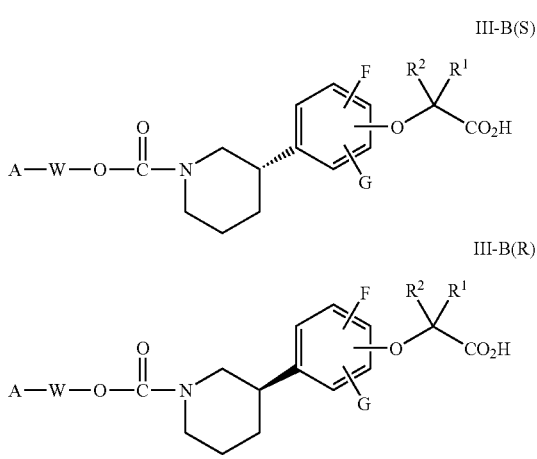

wherein the variables are as defined above.

More particularly, the present invention provides such processes wherein in step (f) the base is sodium carbonate, potassium carbonate, sodium hydroxide or postassium hydroxide; and the solvent is methanol, ethanol or tetrahydrofuran.

Another aspect of the present invention provides methods of treating obesity, overweight condition, hypertriglyceridemia, hyperlipidemia, hypoalphalipoproteinemia, metabolic syndrome, diabetes mellitus (especially Type II), hyperinsulinemia, impaired glucose tolerance, insulin resistance, diabetic complications, atherosclerosis, hypertension, coronary heart disease, hypercholesterolemia, inflammation, osteoporosis, thrombosis or congestive heart failure in a mammal (including a human being) which comprise administering to said mammal a therapeutically effective amount of a compound of Formula I, a prodrug of said compound, or a pharmaceutically acceptable salt of said compound or prodrug.

Yet another aspect of the present invention provides methods for treating obesity in a mammal (including a human being) by administering to a mammal in need of such treatment an obesity-treating amount of a Formula I compound, a prodrug thereof, or a pharmaceutically acceptable salt of said compound or of said prodrug.

Yet another aspect of the present invention provides methods for inducing weight loss in a mammal (including a human being) by administering to a mammal a therapeutically effective amount of a Formula I compound, a prodrug of thereof, or a pharmaceutically acceptable salt of thereof said compound or of said prodrug.

Yet another aspect of the present invention provides methods for treating an overweight condition in a mammal (including a human being) by administering to a mammal in need of such treatment an overweight condition-treating amount of a Formula I compound, a prodrug thereof, or a pharmaceutically acceptable salt of said compound or of said prodrug.

Yet another aspect of the present invention provides methods for treating hypertriglyceridemia in a mammal (including a human being) by administering to a mammal in need of such treatment a hypertriglyceridemia-treating amount of a Formula I compound, a prodrug thereof, or a pharmaceutically acceptable salt of said compound or of said prodrug.

Yet another aspect of the present invention provides methods for treating hyperlipidemia in a mammal (including a human being) by administering to a mammal in need of such treatment a hyperlipidemia-treating amount of a Formula I compound, a prodrug thereof, or a pharmaceutically acceptable salt of said compound or of said prodrug.

Yet another aspect of the present invention provides methods for treating hypoalphalipoproteinemia in a mammal (including a human being) by administering to a mammal in need of such treatment a hypoalphalipoproteinemia-treating amount of a Formula I compound, a prodrug thereof, or a pharmaceutically acceptable salt of said compound or of said prodrug.

Yet another aspect of the present invention provides methods for treating metabolic syndrome in a mammal (including a human being) by administering to a mammal in need of such treatment a metabolic syndrome-treating amount of a Formula I compound, a prodrug thereof, or a pharmaceutically acceptable salt of said compound or of said prodrug.

Yet another aspect of the present invention provides methods for treating diabetes mellitus (especially Type II) in a mammal (including a human being) by administering to a mammal in need of such treatment a diabetes mellitus-treating amount of a Formula I compound, a prodrug thereof, or a pharmaceutically acceptable salt of said compound or of said prodrug.

Yet another aspect of the present invention provides methods for treating hyperinsulinemia in a mammal (including a human being) by administering to a mammal in need of such treatment a hyperinsulinemia-treating amount of a Formula I compound, a prodrug thereof, or a pharmaceutically acceptable salt of said compound or of said prodrug.

Yet another aspect of the present invention provides methods for treating impaired glucose tolerance in a mammal (including a human being) by administering to a mammal in need of such treatment an impaired glucose tolerance disease-treating amount of a Formula I compound, a prodrug thereof, or a pharmaceutically acceptable salt of said compound or of said prodrug.

Yet another aspect of the present invention provides methods for treating insulin resistance in a mammal (including a human being) by administering to a mammal in need of such treatment an insulin resistance-treating amount of a Formula I compound, a prodrug thereof, or a pharmaceutically acceptable salt of said compound or of said prodrug.

Yet another aspect of the present invention provides methods for treating diabetic complications (e.g., neuropathy, nephropathy, retinopathy or cataracts) in a mammal (including a human being) by administering to a mammal in need of such treatment a diabetic complications-treating amount of a Formula I compound, a prodrug thereof, or a pharmaceutically acceptable salt of said compound or of said prodrug.

Yet another aspect of the present invention provides to methods for treating atherosclerosis in a mammal (including a human being) by administering to a mammal in need of such treatment an atherosclerotic-treating amount of a Formula I compound, a prodrug thereof, or a pharmaceutically acceptable salt of said compound or of said prodrug.

Yet another aspect of the present invention provides methods for treating hypertension in a mammal (including a human being) by administering to a mammal in need of such treatment a hypertension-treating amount of a Formula I compound, a prodrug thereof, or a pharmaceutically acceptable salt of said compound or of said prodrug.

Yet another aspect of the present invention provides methods for treating coronary heart disease in a mammal (including a human being) by administering to a mammal in need of such treatment a coronary heart disease-treating amount of a Formula I compound, a prodrug thereof, or a pharmaceutically acceptable salt of said compound or of said prodrug.

Yet another aspect of the present invention provides methods for treating hypercholesterolemia in a mammal (including a human being) by administering to a mammal in need of such treatment a hypercholesterolemia-treating amount of a Formula I compound, a prodrug thereof, or a pharmaceutically acceptable salt of said compound or of said prodrug.

Yet another aspect of the present invention provides methods for treating inflammation in a mammal (including a human being) by administering to a mammal in need of such treatment an inflammation-treating amount of a Formula I compound, a prodrug thereof, or a pharmaceutically acceptable salt of said compound or of said prodrug.

Yet another aspect of the present invention provides methods for treating osteoporosis in a mammal (including a human being) by administering to a mammal in need of such treatment an osteoporosis-treating amount of a Formula I compound, a prodrug thereof, or a pharmaceutically acceptable salt of said compound or of said prodrug.

Yet another aspect of the present invention provides methods for treating congestive heart failure in a mammal (including a human being) by administering to a mammal in need of such treatment a congestive heart failure-treating amount of a Formula I compound, a prodrug thereof, or a pharmaceutically acceptable salt of said compound or of said prodrug.

A dosage range for the compounds of the present invention is about 0.001 to about 100 mg/kg/day of a Formula I compound, a prodrug thereof, or a pharmaceutically acceptable salt of said compound or of said prodrug. More particularly, the dosage range for the compounds of the present invention is about 0.005 to about 5 mg/kg/day of a Formula I compound, a prodrug thereof, or a pharmaceutically acceptable salt of said compound or of said prodrug.

The present invention also provides pharmaceutical compositions which comprise a compound of Formula I, a prodrug thereof, or a pharmaceutically acceptable salt of said compound or of said prodrug and a pharmaceutically acceptable vehicle, carrier or diluent. Preferably the composition comprises a therapeutically effective amount of the Formula I compound.

The present invention also provides pharmaceutical compositions for the treatment of obesity, an overweight condition, hypertriglyceridemia, hyperlipidemia, hypoalphalipoproteinemia, metabolic syndrome, diabetes mellitus (especially Type II), hyperinsulinemia, impaired glucose tolerance, insulin resistance, diabetic complications, atherosclerosis, hypertension, coronary heart disease, hypercholesterolemia, inflammation, osteoporosis or congestive heart failure in a mammal (including a human being) which comprise a therapeutically effective amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of obesity in a mammal (including a human being) which comprise an obesity-treating amount of a compound of Formula I, a prodrug thereof, or a pharmaceutically acceptable salt of said compound or of said prodrug and a pharmaceutically acceptable vehicle, diluent or carrier.

Yet another aspect of the present invention provides pharmaceutical compositions for inducing weight loss in a mammal (including a human being) which comprise a therapeutically effective amount of a Formula I compound, a prodrug of thereof, or a pharmaceutically acceptable salt of thereof said compound or of said prodrug and a pharmaceutically acceptable vehicle, diluent or carrier.

The present invention also provides pharmaceutical compositions for the treatment of an overweight condition in a mammal (including a human being) which comprise an overweight condition-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of hypertriglyceridemia in a mammal (including a human being) which comprise a hypertriglyceridemia-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of hyperlipidemia in a mammal (including a human being) which comprise a hyperlipidemia-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of hypoalphalipoproteinemia in a mammal (including a human being) which comprise a hypoalphalipoproteinemia-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of metabolic syndrome in a mammal (including a human being) which comprise a metabolic syndrome-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of diabetes mellitus (especially Type II) in a mammal (including a human being) which comprise a diabetes mellitus-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of hyperinsulinemia in a mammal (including a human being) which comprise a hyperinsulinemia-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of impaired glucose tolerance in a mammal (including a human being) which comprise an impaired glucose tolerance-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of insulin resistance in a mammal (including a human being) which comprise an insulin resistance-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of a diabetic complication (e.g., neuropathy, nephropathy, retinopathy or cataracts) in a mammal (including a human being) which comprise a diabetic complication-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of atherosclerosis in a mammal (including a human being) which comprise an atherosclerosis-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of hypertension in a mammal (including a human being) which comprise a hypertension-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of coronary heart disease in a mammal (including a human being) which comprise a coronary heart disease-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of hypercholesterolemia in a mammal (including a human being) which comprise a hypercholesterolemia-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of inflammation in a mammal (including a human being) which comprise an inflammation-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of osteoporosis in a mammal (including a human being) which comprise an osteoporosis-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical compositions for the treatment of congestive heart failure in a mammal (including a human being) which comprise a congestive heart failure-treating amount of a compound of Formula I, a prodrug thereof, or a pharmaceutically acceptable salt of said compound or of said prodrug and a pharmaceutically acceptable vehicle, diluent or carrier.

The present invention also provides pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, a microsomal triglyceride transfer protein (MTP)/Apo B secretion inhibitor, a cholesterol ester transfer protein (CETP) inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhbitior, a fibrate, niacin, a combination of niacin and lovastatin, an ion-exchange resin, an antioxidant, an acyl-CoA:cholesterol acyl transferase (ACAT) inhibitor or a bile acid sequestrant; and/or optionally a pharmaceutically acceptable vehicle, diluent or carrier.

Specific embodiments of the second compounds are an HMG-CoA reductase inhibitor and a CETP inhibitor.

Specific embodiments of the HMG-CoA reductase inhibitors are lovastatin, rosuvastatin, pitavastatin, simvastatin, pravastatin, fluvastatin, atorvastatin and cerivastatin, or a pharmaceutically acceptable salt thereof.

Specific embodiments of the CETP inhibitor include, for example, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

In another aspect, the present invention provides methods for treating atherosclerosis in a mammal comprising administering to a mammal suffering from atherosclerosis:

a first compound, said first compound being a Formula I compound, a prodrug thereof, or a pharmaceutically acceptable salt of said compound or of said prodrug; and a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, a MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor or a bile acid sequestrant wherein the amounts of the first and second compounds result in a therapeutic effect.

One embodiment of the above methods is wherein the second compound is an HMG-CoA reductase inhibitor or a CETP inhibitor.

Another embodiment of the above methods is wherein the HMG-CoA reductase inhibitor is lovastatin, rosuvastatin, pitavastatin, simvastatin, pravastatin, fluvastatin, atorvastatin or cerivastatin or a pharmaceutically acceptable salt thereof.

Specific embodiments of the CETP inhibitor include, for example, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

In another aspect, the present invention provides kits comprising:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a combination of niacin and lovastatin, an ion-exchange resin, an antioxidant, an ACAT inhibitor or a bile acid sequestrant and a pharmaceutically acceptable carrier, vehicle or diluent in a second unit dosage form;

c. means for containing said first and second dosage forms wherein the amounts of the first and second compounds result in a therapeutic effect.

An embodiment of the second compound is an HMG-CoA reductase inhibitor or a CETP inhibitor.

An embodiment of the HMG-CoA reductase inhibitor is lovastatin, rosuvastatin, pitavastatin, simvastatin, pravastatin, fluvastatin, atorvastatin or cerivastatin or pharmaceutically acceptable salts thereof.

Specific embodiments of the CETP inhibitor include, for example, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

The present invention also provides pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being a diabetic-treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas, sulfonylureas analogs, biguanides, imidazolines, insulin secretagogues, linogliride, glitazones, non-glitazone PPARγ agonists, PPARβ agonists, glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide; and/or optionally a pharmaceutical vehicle, diluent or carrier.

Particular embodiments among the second compounds are chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, rosiglitazone, englitazone, darglitazone, clomoxir and etomoxir.

More particular embodiments of the second compounds are glibenclamide, Glypizide®, glimepiride, repaglinide, metformin, and pioglitazone.

In another aspect, the present invention provides methods for treating diabetes in a mammal comprising administering to a mammal suffering from diabetes a first compound, said first compound being a Formula I compound a prodrug thereof, or a pharmaceutically acceptable salt of said compound or of said prodrug; and a second compound, said second compound being a diabetic treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas and analogs, biguanides, imidazolines, insulin secretagogues, linogliride, glitazones, non-glitazone PPARγ agonists, PPARβ agonists, α-glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide wherein the amounts of the first and second compounds result in a therapeutic effect.

A particular embodiment of the above methods is wherein the second compound is chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, englitazone, darglitazone, clomoxir or etomoxir.

A particular embodiment of the above methods is wherein the second compound is glibenclamide, Glypizide®, glimepiride, repaglinide, metformin, pioglitazone or rosiglitazone.

In another aspect, the present invention provides kits comprising:

a. a first compound, said first compound being a Formula I compound, a prodrug thereof, or a pharmaceutically acceptable salt of said compound or of said prodrug and a pharmaceutically acceptable vehicle, diluent or carrier in a first unit dosage form;

b. a second compound, said second compound being a diabetic treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas and analogs, biguanides, imidazolines, insulin secretagogues, linogliride, glitazones, non-glitazone PPARγ agonists, PPARβ agonists, glucosidase inhibitors, acarbose, miglitol, emiglitate, voglibose, camiglibose, β-agonists, phosphodiesterase inhibitors, vanadate, vanadium complexes (e.g. Nagliван®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide and a pharmaceutically acceptable vehicle, diluent or carrier in a second unit dosage form; and c. means for containing said first and second dosage forms wherein the amounts of the first and second compounds result in a therapeutic effect.

An embodiment of the second compound is chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, rosiglitazone, englitazone, darglitazone, clomoxir or etomoxir.

A particular embodiment of the second compound is glibenclamide, Glypizide®, glimepiride, repaglinide, metformin, pioglitazone or rosiglitazone.

The present invention also provides pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being phenylpropanolamine, ephedrine, pseudoephedrine, phentermine, a neuropeptide Y antagonist, a β$_3$-adrenergic receptor agonist, an apolipoprotein-B secretion/microsomal triglyceride transfer protein (apo-B/MTP) inhibitor, an MCR-4 agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a 5HT2c agonist, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, an anorectic agent, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, a ciliary neurotrophic factor, a human agouti-related protein (AGRP), a ghrelin receptor antagonist, histamine 3 receptor antagonist or inverse agonist, or a neuromedin U receptor agonist; and/or optionally a pharmaceutical vehicle, diluent or carrier.

Specific embodiments of the second compounds are orlistat, sibutramine and bromocriptine.

In another aspect, the present invention provides methods for treating obesity in a mammal comprising administering to a mammal suffering from obesity a first compound, said first compound being a Formula I compound a prodrug thereof, or a pharmaceutically acceptable salt of said compound or of said prodrug; and a second compound, said second compound being phenylpropanolamine, ephedrine, pseudoephedrine, phentermine, a neuropeptide Y antagonist, a β$_3$-adrenergic receptor agonist, an apolipoprotein-B secretion/microsomal triglyceride transfer protein (apo-B/MTP) inhibitor, an MCR-4 agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a 5HT2c agonist, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, an anorectic agent, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, a ciliary neurotrophic factor, a human agouti-related protein (AGRP), a ghrelin receptor antagonist, histamine 3 receptor antagonist or inverse agonist, or a neuromedin U receptor agonist; wherein the amounts of the first and second compounds result in a therapeutic effect.

An embodiment of the above methods is wherein the second compound is orlistat, sibutramine or bromocriptine.

In another aspect, the present invention provides kits comprising:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being phenylpropanolamine, ephedrine, pseudoephedrine, phentermine, a neuropeptide Y antagonist, a β3-adrenergic receptor agonist, an apolipoprotein-B secretion/microsomal triglyceride transfer protein (apo-B/MTP) inhibitor, an MCR-4 agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a 5HT2c agonist, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, an anorectic agent, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, a ciliary neurotrophic factor, a human agouti-related protein (AGRP), a ghrelin receptor antagonist, histamine 3 receptor antagonist or inverse agonist, or a neuromedin U receptor agonist; or a pharmaceutically acceptable vehicle, diluent or carrier in a second unit dosage form; and c. means for containing said first and second dosage forms wherein the amounts of the first and second compounds result in a therapeutic effect.

An embodiment of the second compound is orlistat, sibutramine or bromocriptine.

The present invention also provides pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being an anti-hypertensive agent; and/or optionally a pharmaceutical vehicle, diluent or carrier.

Specific embodiments of anti-hypertensive agents are a calcium channel blocker, an angiotensin converting enzyme (ACE) inhibitor and a diuretic.

In another aspect, the present invention provides methods for treating hypertension in a mammal comprising administering to a mammal suffering from hypertension a first compound, said first compound being a Formula I compound a prodrug thereof, or a pharmaceutically acceptable salt of said compound or of said prodrug; and a second compound, said second compound being an antihypertensive agent wherein the amounts of the first and second compounds result in a therapeutic effect.

Embodiments of the anti-hypertensive agents are a calcium channel blocker, an angiotensin converting enzyme (ACE) inhibitor and a diuretic.

In another aspect, the present invention provides kits comprising:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being an anti-hypertensive agent and a pharmaceutically acceptable vehicle, diluent or carrier in a second unit dosage form; and c. means for containing said first and second dosage forms wherein the amounts of the first and second compounds result in a therapeutic effect.

Embodiments of anti-hypertensive agents are a calcium channel blocker, an angiotensin converting enzyme (ACE) inhibitor and a diuretic.

Embodiments of anti-osteporosis agents are selective estrogen agonists/antagonists, such as lasofoxifene, raloxifene, TSE-424 and arazoxifene, and bisphosphonates, such as alendronate and resindronate.

The term "treating", "treat" or "treatment" as used herein includes preventative (e.g., prophylactic) and palliative treatment.

By "pharmaceutically acceptable" is meant the carrier, diluent, vehicle, excipient, and/or salt must be compatible with the other ingredients of the formulation, and not deleterious to the recipient thereof.

As used herein, "therapeutically effective amount of a compound" means an amount that is effective to exhibit therapeutic or biological activity at the site(s) of activity in a mammalian subject, without undue adverse side effects (such as undue toxicity, irritation or allergic response), commensurate with a reasonable benefit/risk ratio when used in the manner of the present invention.

The phrase "compound(s) useful in the methods of the present invention," and the like, shall at all times be understood to include all active forms of such compounds, including, for example, the free form thereof, e.g., the free acid or base form, and also, all prodrugs, polymorphs, hydrates, solvates, tautomers, stereoisomers, e.g., diastereomers and enantiomers, and the like, and all pharmaceutically acceptable salts as described above, unless specifically stated otherwise. It will also be appreciated that suitable active metabolites of such compounds, in any suitable form, are also included herein.

Metabolic syndrome, also known as Syndrome X, refers to a common clinical disorder that is defined as the presence of increased insulin concentrations in association with other disorders including viceral obesity, hyperlipidemia, dyslipidemia, hyperglycemia, hypertension, and potentially hyperuricemis and renal dysfunction.

The expression "prodrug" refers to compounds that are drug precursors which following administration release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

The following paragraphs describe exemplary ring(s) for the generic ring descriptions contained herein:

The term het refers to an optionally substituted 5-, 6- or 7-membered saturated, partially saturated or unsaturated heterocyclic ring containing from 1 to 3 heteroatoms selected from the group consisting of nitrogen, oxygen and sulfur; and including any bicyclic group in which any of the above heterocyclic rings is fused to a benzene ring or another heterocyclic ring; and the nitrogen atom may be in the oxidized state giving the N-oxide form; and substituted by 0 to 3 independent substituents.

Exemplary five to six membered aromatic rings, optionally having one or two heteroatoms selected independently from oxygen, nitrogen and sulfur, include phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered rings, optionally having one to four heteroatoms selected independently from oxygen, sulfur and nitrogen, include cyclopentyl, cyclohexyl, cycloheptyl, cyclooctyl and phenyl. Further exemplary five membered rings include 2H-pyrrolyl, 3H-pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings include 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl.

Further exemplary seven membered rings include azepinyl, oxepinyl, and thiepinyl.

Further exemplary eight membered rings include cyclooctyl, cyclooctenyl and cyclooctadienyl.

Exemplary bicyclic rings consisting of two fused partially saturated, fully saturated or fully unsaturated five or six membered rings, taken independently, optionally having one to four heteroatoms selected independently from nitrogen, sulfur and oxygen, include indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, 7-bicyclo[4.2.0]octa-1,3,5-trienyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

By alkenyl is meant straight chain unsaturated hydrocarbon or branched chain unsaturated hydrocarbon. Exemplary of such groups (assuming the designated length encompasses the particular example) are ethenyl, propenyl, butenyl, pentenyl, hexenyl and heptenyl, and all isomeric forms and straight and branched forms thereof.

By halo is meant fluoro, chloro, bromo or iodo.

By alkyl is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl. This term also includes a saturated hydrocarbon (straight chain or branched) wherein a hydrogen atom is removed from each of the terminal carbons.

By alkoxy is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

The carbon atom content of various hydrocarbon-containing moieties is indicated by a prefix designating the minimum and maximum number of carbon atoms in the moiety, i.e., the prefix $C_i$–$C_j$ indicates a moiety of the integer "i" to the integer "j" carbon atoms, inclusive. Thus, for example, $C_1$–$C_3$ alkyl refers to alkyl of one to three carbon atoms, inclusive, or methyl, ethyl, propyl and isopropyl, and all isomeric forms and straight and branched forms thereof.

By aryl is meant an optionally substituted six-membered aromatic ring, including polyaromatic rings. Examples of aryl include phenyl, naphthyl and biphenyl.

As used herein the term mono-N- or di-N,N-($C_1$–$C_x$) alkyl . . . refers to the ($C_1$–$C_x$)alkyl moiety taken independently when it is di-N,N-($C_1$–$C_x$)alkyl . . . (x refers to integers).

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

References (e.g., claim 1) to "said carbon" in the phrase "said carbon is optionally mono-, di- or tri-substituted independently with halo, said carbon is optionally mono-substituted with hydroxy, said carbon is optionally mono-substituted with oxo" refers to each of the carbons in the carbon chain including the connecting carbon.

Certain variables in the formulas used herein may appear between other variables and thus link one variable to another, such as the variable "W" appears between and thus links variables "E" and "A" in formula I herein. Such variables like "W" are defined by certain moieties, which have a bond at each end of the moiety. It is intended that these moieties may be read and thus inserted into the formula at the appropriate place, by going either from left to right or from right to left. Thus, both orientations of these moieties are included within the scope of the present invention.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or a mixture thereof which does not interact with starting materials, reagents, intermediates or products in a manner which adversely affects the yield of the desired product.

The chemist of ordinary skill will recognize that certain compounds of the present invention will contain one or more atoms, which may be in a particular stereochemical or geometric configuration, giving rise to stereoisomers and configurational isomers. All such isomers and mixtures thereof are included in the present invention. Hydrates and solvates of the compounds of the present invention are also included.

The present invention also includes isotopically-labeled compounds, which are structurally identical to those disclosed herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out known or referenced procedures and by substituting a readily available isotopically labeled reagent for a non-isotopically labeled reagent.

All patents and patent applications referred to herein are hereby incorporated by reference.

DTT means dithiothreitol. DMSO means dimethyl sulfoxide. EDTA means ethylenediamine tetraacetic acid.

DETAILED DESCRIPTION OF THE INVENTION

In general the compounds of the present invention can be made by processes, which include processes analogous to those known in the chemical arts, particularly in light of the description contained herein. Certain processes for the manufacture of the compounds of the present invention are provided as further features of this invention and are illustrated by the following reaction schemes. Other processes are described in the experimental section.

As an initial note, in the preparation of the Formula I compounds, it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparative methods and can be readily determined by one of ordinary skill in the art. The use of such protection/deprotection methods is also within the ordinary skill in the art. For a general description of protecting groups and their use, see T. W. Greene, *Protective Groups in Organic Synthesis*, John Wiley & Sons, New York, 1991.

For example, in the reaction schemes below, certain Formula I compounds contain primary amines or carboxylic acid functionalities, which may interfere with reactions at other sites of the molecule if left unprotected. Accordingly, such functionalities may be protected by an appropriate protecting group, which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I compound.

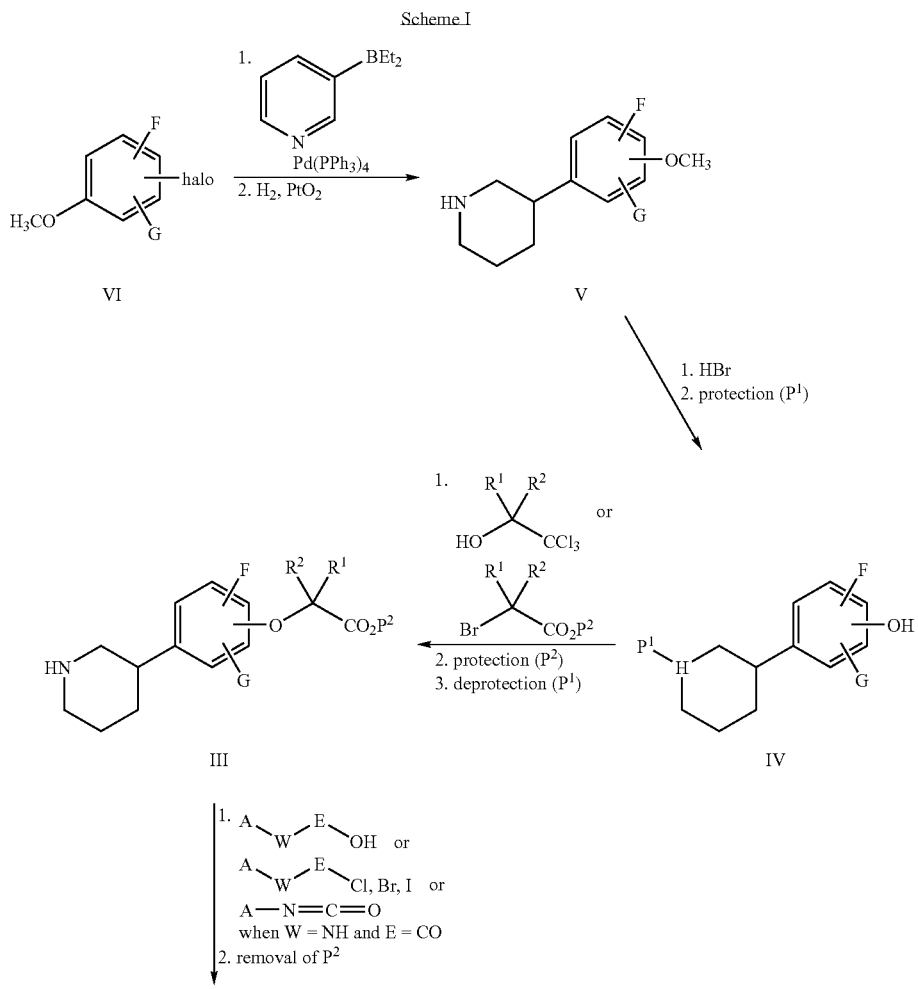

-continued

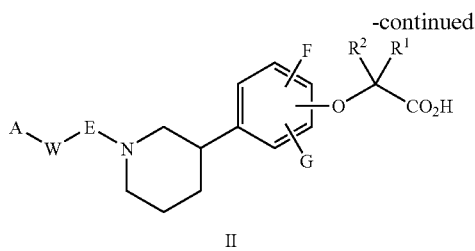

II

Scheme I

According to reaction Scheme I, the desired Formula I compounds, wherein X is —B—C(R¹R²)-Z, m=n=1, V is methylene, Y is methylene, F, G, R¹, R², A, W and E are as described above, B is O, Z is carboxyl and the piperidinyl ring is substituted at the 3-position by the phenyl ring (depicted as Formula II compounds), are prepared by acylating the corresponding Formula III compounds with an acyl chloride, sulfonyl chloride, isocyanate or carboxylic acid; or by treating the corresponding Formula III compounds with an alcohol and carbonyldiimidazole; or by alkylating the corresponding Formula III compounds with an alkyl halide; followed by hydrolyzing the resulting Formula II compound, wherein Z is CO₂P² and P² is a known carboxyl protecting group (see Greene as cited above), to produce the corresponding carboxylic acid. Alternatively, the hydrolysis can be omitted when the ester is a suitable prodrug for the carboxylic acid.

Generally, the desired Formula III compounds are acylated with the appropriate acyl chloride or the appropriate sulfonyl chloride in a reaction-inert solvent such as methylene chloride in the presence of an amine base such as triethylamine at a temperature of about 10° C. to about 50° C., typically ambient for about 6 to about 18 hours; with the appropriate isocyanate in a reaction-inert solvent such as toluene in the presence of a tertiary amine base such as Hunig's base at a temperature of about 10° C. to about 150° C., typically ambient for about 6 to about 18 hours; or with the appropriate carboxylic acid in a reaction-inert solvent such as methylene chloride in the presence of a carbodiimide (e.g., 1-(3-dimethylaminopropyl)-3-ethylcarbodiimide hydrochloride) at a temperature of about 10° C. to about 50° C., typically ambient for about 6 to about 24 hours. Alternatively, the desired Formula III compounds are acylated with the activated complex derived from reacting the the appropriate alcohol with carbonyldiimidazole (prepared in a reaction-inert solvent such as toluene at a temperature of about 10° C. to about 130° C., typically ambient, for about 12 to about 24 hours) in a reaction-inert solvent such as toluene in the presence of a catalyst such as 4-dimethylaminopyridine at a temperature of about 10° C. to about 130° C., typically ambient, for about 12 to about 24 hours. The desired Formula III compounds are alkylated with the appropriate alkyl halide in a polar solvent such a dimethylformamide in the presence of a base such as lithium diisopropylamine at a temperature of about −80° C. to 50° C. for about 6 to about 18 hours. The ester moiety can then be hydrolyzed in an aqueous alcoholic solvent such as methanol/water with a base such as potassium carbonate at a temperature of about 40° C. to about 80° C., preferably at reflux, for about 2 hours to about 18 hours to provide the Formula II compounds. Alternatively, the protecting group P in some instances can be removed by hydrogenation (or transfer hydrogenation) preferably at atmospheric pressure over a catalyst such as 10% palladium on carbon in a polar solvent such as methanol at ambient temperature for a period of 1 hour to 24 hours.

The desired Formula III compounds, wherein F, G, R¹ and R² are as described above and P² is a known carboxyl protecting group, are prepared by alkylation of the corresponding Formula IV compounds, followed by protection of the resulting carboxyl group, if necessary, and then removal of the amine protecting group P¹. Generally, the Formula IV compound is combined with the appropriate alkylhaloalkylcarboxylate in the presence of a base such as cesium carbonate in a polar solvent such as dimethylformamide at a temperature of about 10° C. to about 100° C., typically ambient, for about 2 to about 18 hours. Alternatively, the Formula IV compound can be combined with the appropriate trichloroalkylcarbinol (e.g., chloretone) in the corresponding ketone solvent (e.g., acetone) in the presence of a strong base such as sodium hydroxide at a temperature of about −20° C. to about 60° C., typically ambient, for about 6 to about 24 hours. The resulting compounds having a carboxyl group may be protected (for example, with a P² protecting group) by mixing with the appropriate alkyl halide in the presence of a base such as potassium carbonate in an inert solvent such as dimethylformamide at a temperature of about 15° C. to about 100° C. for about 1 hour to about 24 hours, or by mixing with the appropriate alcohol as the solvent in the presence of a catalytic amount of acid such as concentrated sulfuric acid at a temperature of about 20° C. to about 120° C., preferably at reflux, for about 1 hour to about 24 hours. The amine protecting group (P¹) can then be removed by treatment with acid, such as trifluoroacetic acid, in a reaction inert solvent such as methylene chloride at a temperature of about 0° C. to about 50° C., preferably ambient, for less than 1 hour, preferably 30 minutes, when the protecting group P¹ is tert-butyl carbonate, for example.

The desired Formula IV compounds, wherein F and G are as described above and P¹ is a known amine protecting group, are prepared by demethylation, followed by protection of the resulting amine, if necessary, of the corresponding Formula V compounds. Generally, the Formula V compound is combined with a strong protic acid such as 48% hydrobromic acid at a temperature of about 20° C. to about 150° C., preferably at reflux, for about 1 hour to about 6 hours, preferably 3. The resulting compounds having an amine group can be protected by mixing with di-tert-butyl carbonate in the presence of a base such as sodium bicarbonate in a polar solvent such as tetrahydrofuran/water at a temperature of about 15° C. to about 100° C., preferably reflux, for about 30 minutes to about 6 hours.

The desired Formula V compounds, wherein F and G are as described above, are prepared by Suzuki coupling of the corresponding Formula VI compounds, followed by reduction. Generally, the Formula VI compound is combined with the appropriate diethylpyridyl borane in a reaction-inert solvent such as toluene in the presence of an aqueous base such as sodium carbonate and a catalyst such as tetrakis(triphenylphosphine)palladium (0) in ethanol at a temperature of about 10° C. to about 120° C., typically reflux for about 3 to about 18 hours. The resulting methoxy-substituted-3-phenyl-pyridine is then reduced by hydrogenation, preferably at 55 psi pressure, over a catalyst such as platinum (IV) oxide in a polar protic solvent such as acetic acid at ambient temperature for a period of 1 hour to 18 hours, preferably 6 hours. The Formula VI compounds are commercially available and/or can be prepared by literature procedures, which would be readily known and available to one of ordinary skill in the art of organic synthesis.

pounds with an acyl chloride, sulfonyl chloride or isocyanate; or by treating the corresponding Formula VIII compounds with an alcohol and carbonyldiimidazole; or by alkylating the corresponding Formula VIII compounds with an alkyl halide; followed by optional hydrolysis of the resulting compound to remove the carboxyl protecting group $P^2$ (see Greene as cited above) to produce the corresponding carboxylic acid. Alternatively, the hydrolysis can be omitted when the ester is a suitable prodrug for the carboxylic acid. Generally, this reaction can be performed as described above in Scheme I for the preparation of the Formula II compounds, though a stronger base (lithium diisopropylamine for example) may be required in the acylation reactions.

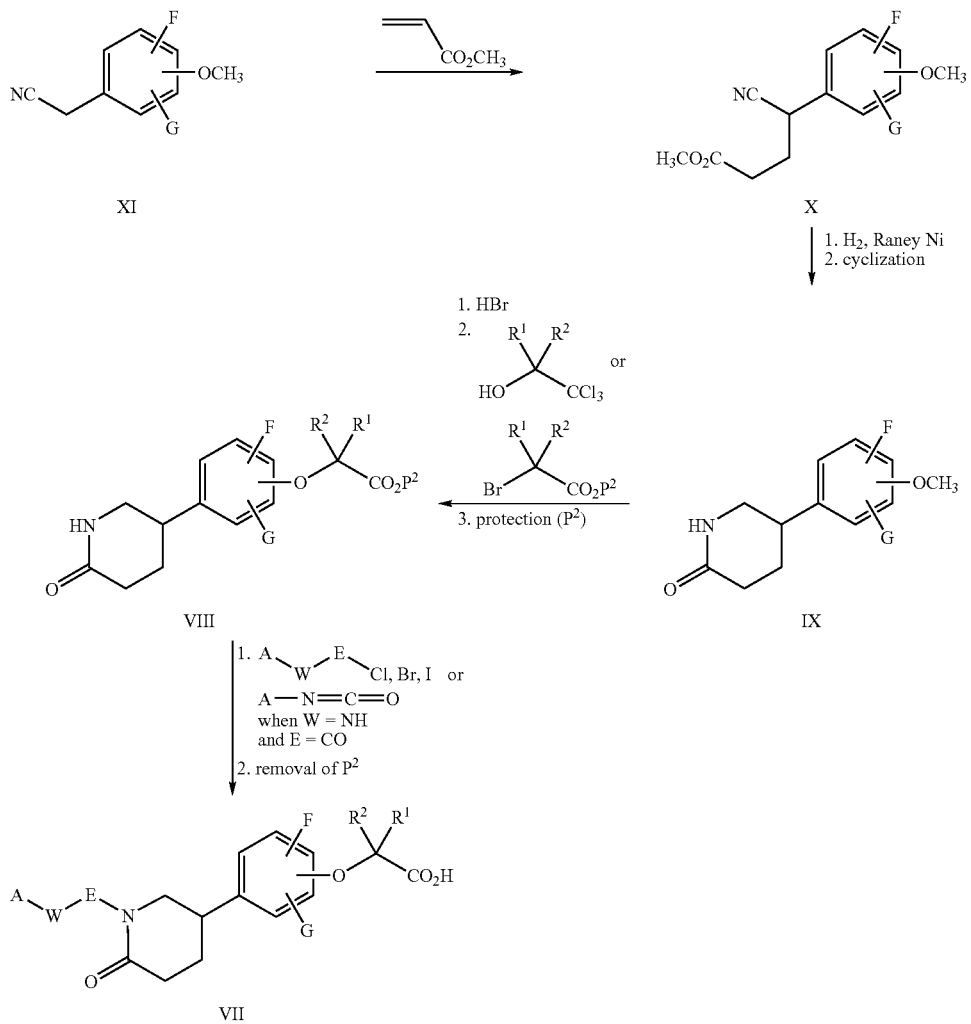

Scheme II

According to reaction Scheme II, the desired Formula I compounds, wherein X is —B—C($R^1R^2$)-Z, m=n=1, one of V and Y is methylene and the other is carbonyl, F, G, $R^1$, $R^2$, A, W and E are as described above, B is O, Z is carboxyl and the piperidinyl ring is substituted at the 3-position by the phenyl ring (depicted as Formula VII compounds), are prepared by acylating the corresponding Formula VIII compounds The desired Formula VIII compounds, wherein F, G, $R^1$ and $R^2$ are as described above and $P^2$ is a known carboxyl protecting group, can be prepared by demethylation of the corresponding Formula IX compounds followed by alkylation of the resulting phenol and protection of the carboxyl group, if necessary. Generally, this reaction can be performed as described above in Scheme I for the preparation of the Formula IV and III compounds, though no protection of the amide functionality is necessary.

The desired Formula IX compounds, wherein F and G are as described above, having the 5-phenyl-2-piperidone core, can be prepared by reduction of the corresponding Formula X compounds, with concomitant intramolecular cyclization external cooling. The Formula VI compounds are commercially available and/or can be prepared by literature procedures, which would be readily known and available to one of ordinary skill in the art of organic synthesis.

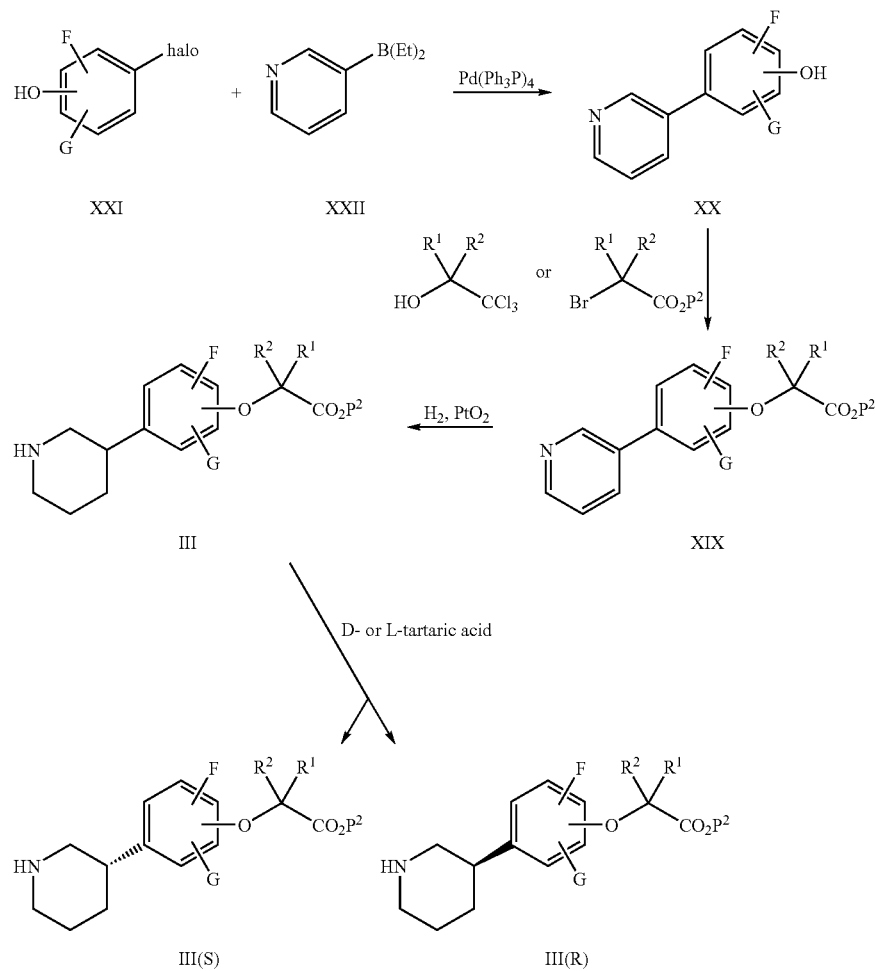

Scheme III of the resulting aminocarboxylate moiety. Generally, the Formula X compound is combined with a reducing agent such as hydrogen and a catalyst such as Raney Nickel preferably under 55 psi pressure in a polar solvent such as methanol/ammonia at a temperature of about 10° C. to about 150° C., typically ambient temperature, for a period of about 6 hours to about 18 hours. Compounds analogous to the compounds of Formula IX, but which have a 3-phenyl-2-piperidone core, can be prepared as described above, except that the nitrile and ester moieties in the compound of Formula X are transposed by methods known to one of ordinary skill in the art of organic synthesis.

The desired Formula X compounds, wherein F and G are as described above, are prepared by Michael reaction of the corresponding methoxybenzyl nitrile (depicted as Formula XI compounds, where F and G are as described above) with an acrylate derivative. Generally, the Formula XI compound is combined with methyl acrylate and treated with a basic catalytic solution, such as sodium methoxide, at a temperature of about −10° C. to about 50° C., as maintained by Scheme III The desired Formula I compounds, wherein X is —B—C(R$^1$R$^2$)-Z, m=n=1, V is methylene, Y is methylene, F, G, R$^1$, R$^2$, A, W and E are as described above, B is O, Z is carboxyl and the piperidinyl ring is substituted at the 3-position by the phenyl ring (depicted as Formula II compounds in Scheme I), can be prepared by a shorter route than that described in Scheme I and in optically pure form, as depicted in Scheme III.

If desired, in Scheme III, Formula III compounds, wherein F, G, R$^1$ and R$^2$ are as described above and P$^2$ is a known carboxyl protecting group, can be prepared in optically pure form by crystallization via salt formation with an optically pure acid. Generally, the Formula III compound is combined with L-tartaric acid in the presence of a solvent, such as ethanol or tetrahydrofuran/water, separating the diastereomers by fractional crystallization, followed by neutralization to break the salt, to provide one of the corresponding pure enantiomers of the Formula III compounds in Scheme III. Alternatively, the D-tartaric acid isomer can be used to provide the other enantiomer of the Formula III compounds in Scheme III. The preferred $P^2$ group is methyl. Alternatively, compounds of Formula III (S) and III (R) can be prepared from the Formula III compounds by separation using chiral chromatography methods known in the art. For example, compounds of Formula III (S) and III (R) can be prepared from the Formula III compounds by separation using simulated moving bed chromatography.

The desired Formula III compounds, wherein F, G, $R^1$ and $R^2$ are as described above and $P^2$ is a known carboxyl protecting group, can be prepared by reduction of the corresponding Formula XIX compounds. Generally, the Formula XIX compound is reduced by hydrogenation preferably at 55 psi pressure over a catalyst such as platinum (IV) oxide or Pt/C in an acidic medium such as acetic acid or an acid (such as HCl or $H_2SO_4$) in an alcoholic solvent at temperatures of about 20° C. to about 60° C. for a period of about 1 hour to about 18 hours; preferably, this reduction is conducted using Pt/C in aq. HCl in methanol at 50° C. for two hours.

The desired Formula XIX compounds, wherein F, G, $R^1$ and $R^2$ are as described above and $P^2$ is a known carboxyl protecting group, can be prepared by alkylation of the corresponding Formula XX compounds, followed by protection of the resulting carboxyl group, if necessary. Generally, the Formula XX compound is combined with the appropriate alkyl haloalkylcarboxylate in the presence of a base such as potassium carbonate in a polar solvent such as dimethylformamide at a temperature of about 10° C. to about 120° C., typically 95° C., for about 2 to about 18 hours. The preferred $P^2$ protecting group is methyl. Alternatively, the Formula XX compound can be combined with the appropriate trichloroalkylcarbinol (e.g., chloretone) in the corresponding ketone solvent (e.g., acetone) in the presence of a strong base such as sodium hydroxide at a temperature of about −20° C. to about 60° C., typically ambient, for about 6 to about 24 hours. The resulting compounds having a carboxyl group may be protected by mixing with the appropriate alkyl halide in the presence of a base such as potassium carbonate in an inert solvent such as dimethylformamide at a temperature of about 15° C. to about 100° C. for about 1 hour to about 24 hours, or by mixing with the appropriate alcohol as solvent in the presence of a catalytic amount of acid such as concentrated sulfuric acid at a temperature of about 20° C. to about 120° C., preferably at reflux, for about 1 hour to about 24 hours.

The desired Formula XX compounds, wherein F and G are as described above, can be prepared by Suzuki coupling of the corresponding Formula XXI and Formula XXII compounds, which are commercially available or which may be prepared by literature procedures. Generally, the Formula XXI compound is combined with the appropriate diethylpyridyl borane (depicted as Formula XXII) in a reaction-inert solvent such as toluene in the presence of an aqueous base such as sodium carbonate and a catalyst such as tetrakis(triphenylphosphine)palladium (0) in ethanol at a temperature of about 10° C. to about 120° C., typically reflux for about 3 to about 18 hours.

It should be noted that optically pure Formula I compounds can be prepared by alternative methods other than those described above and are known to one skilled in the art. Some of the Formula I compounds of this invention or intermediates in their synthesis have asymmetric carbon atoms and therefore are enantiomers or diastereomers. Diastereomeric mixtures can be separated into their individual diastereomers on the basis of their physical chemical differences by methods known in the art, for example, by chromatography and/or fractional crystallization. Enantiomers can be separated by, for example, chiral HPLC methods or converting the enantiomeric mixture into a diastereomeric mixture by reaction with an appropriate optically active compound (e.g. alcohol), separating the diastereomers and converting (e.g. hydrolyzing) the individual diastereomers to the corresponding pure enatiomoers. Also, an enantiomeric mixture of the Formula I compounds or an intermediate in their synthesis, which contain an acidic or basic moiety, can be separated into their corresponding pure enantiomers by forming a disteromeric salt with an optically pure chiral base or acid (e.g. 1-phenyl-ethyl amine or tartic acid) and separating the diastereomers by fractional crystallization followed by neutralization to break the salt, thus providing the corresponding pure enantiomers. All such isomers, including diastereomers, enantiomers and mixtures thereof are considered as part of this invention. Also, some of the compounds of this invention are atropisomers (e.g. substituted biaryls) and are considered as part of this invention.

Preparation of Formula I compounds, wherein X is —B—C($R^1R^2$)-Z, F, G, $R^1$, $R^2$, A, W and E are as described above, B is 0 and Z is carboxyl, with other permutations of m, n, V and Y, can be prepared using procedures similar to those described in schemes above.

Scheme IV

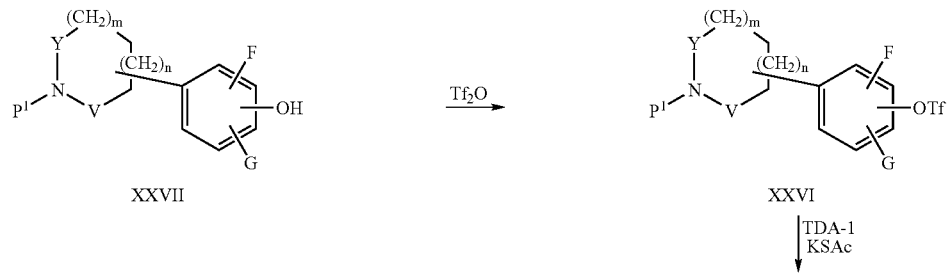

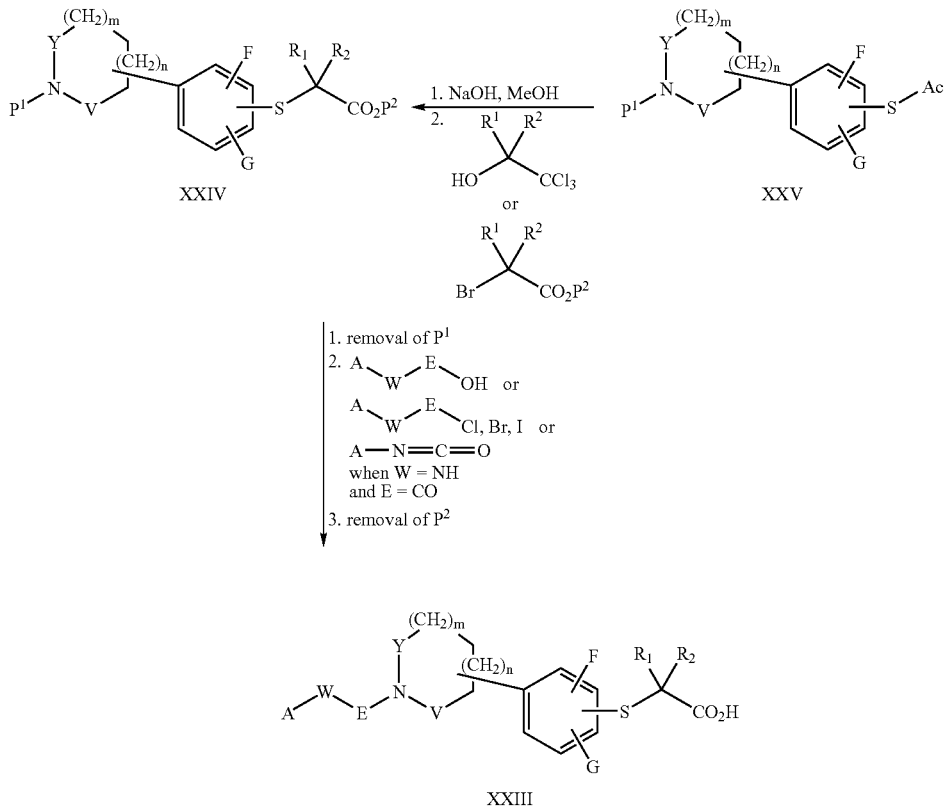

Scheme IV

According to reaction Scheme IV, the desired Formula I compounds, wherein X is —B—C(R$^1$R$^2$)-Z, m, n, V, Y, F, G, R$^1$, R$^2$, A, W and E are as described above, B is S, and Z is carboxyl (depicted as Formula XXIII compounds), can be prepared from the corresponding Formula XXIV compounds by removal of the amine protecting group P$^1$, followed by acylation with an acyl chloride, sulfonyl chloride or isocyanate; or by treatment with an alcohol and carbonyldiimidazole; or by alkylation with an alkyl halide; followed by optional hydrolysis of the resulting compound to remove the carboxyl protecting group P$^2$ (see Greene as cited above) to produce the corresponding carboxylic acid. Alternatively, the hydrolysis may be omitted when the ester is a suitable prodrug for the carboxylic acid. Generally, these reactions can be performed as described above for the preparation of the Formula II compounds in Scheme I.

The desired Formula XXIV compounds, wherein m, n, Y, V, F, G, R$^1$ and R$^2$ are as described above and P$^1$ and P$^2$ are known protecting groups, can be prepared from the corresponding Formula XXV compounds by deprotection of the thiophenol, followed by alkylation. Generally, the Formula XXV compound is combined with a base such as sodium hydroxide in a polar protic solvent such as methanol at a temperature of about 20° C. to about 150° C., preferably at reflux, typically for a period of about 12 hours to about 24 hours. The resulting thiophenol is then alkylated as described above in Scheme I for the preparation of the Formula III compounds.

The desired Formula XXV compounds, wherein m, n, Y, V, F and G are as described above, P$^1$ is a known amine protecting group and Ac is acetyl, can be prepared from the corresponding Formula XXVI compounds by phase transfer catalyzed aromatic nucleophilic substitution. Generally, the Formula XXVI compound is combined with a phase transfer catalyst such as tris[2-(2-methoxethoxy)ethyl]amine (TDA-1) and a nucleophile such as potassium thioacetate in a non-polar solvent such as toluene at a temperature of about 20° C. to about 150° C., preferably at reflux, typically for a period of about 12 hours to about 24 hours.

The desired Formula XXVI compounds, wherein m, n, Y, V, F and G are as described above, P$^1$ is a known amine protecting group and TfO is triflate, can be prepared from the corresponding Formula XXVII compounds by triflation. Generally, the Formula XXVII compound (which is prepared, for example, as the Formula IV compound in Scheme I) is combined with triflic anhydride and a base such as pyridine in a non-polar solvent such as methylene chloride at a temperature of about −80° C. to about ambient temperature, preferably 0° C., typically for a period of about 1 hours to about 5 hours.

If desired, the phenylsulfanyl compounds of Formula XXIII can be oxidized to the corresponding phenylsulfinyl or phenylsulfonyl compounds by treatment with an oxidizing agent such as meta-chloroperoxybenzoic acid in a reaction-inert solvent such as dichloromethane at a temperature of about −78° C. for the preparation of the sulfoxide and at a temperature between about 0° C. and about 25° C. for the preparation of the sulfone, for a period of about 1 to about 6 hours.

Scheme V

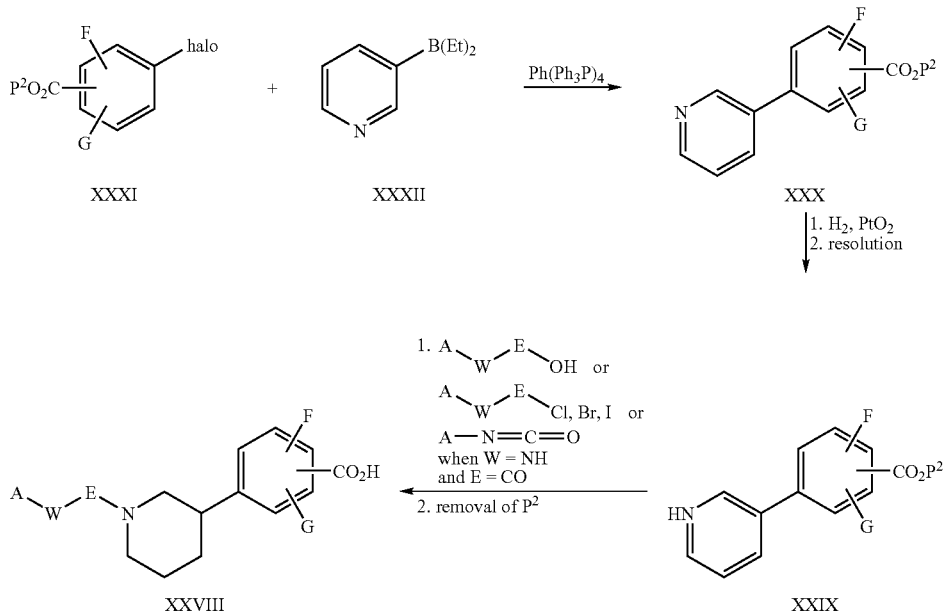

Scheme V

According to reaction Scheme V, the desired Formula I compounds, wherein X is Z, m=n=1, V is methylene, Y is methylene, F, G, A, W and E are as described above, Z is carboxyl and the piperidinyl ring is substituted at the 3-position by the phenyl ring (depicted as Formula XXVIII compounds), can be prepared by acylating the corresponding Formula XXIX compounds with an acyl chloride, sulfonyl chloride, isocyanate or carboxylic acid; or by treating the corresponding Formula XXIX compounds with an alcohol and carbonyldiimidazole; or by alkylating the corresponding Formula XXIX compounds with an alkyl halide; followed by hydrolyzing the resulting Formula XXVIII compound wherein the carboxyl group is protected with a known carboxyl protecting group (see Greene as cited above) to produce the corresponding carboxylic acid. Alternatively, the hydrolysis may be omitted when the ester is a suitable prodrug for the carboxylic acid. Generally, these reactions can be performed as described above for preparation of the Formula II compounds in Scheme I.

The desired Formula XXIX compounds, wherein F and G are as described above and $P^2$ is a known carboxyl protecting group, can be prepared by reduction of the corresponding Formula XXX compounds, followed by resolution to obtain enantiomerically pure material. Generally, the reduction and resolution can be performed as described above for the preparation of the Formula III compounds, as described in Scheme III.

The desired Formula XXX compounds, wherein F and G are as described above and $P^2$ is a known carboxyl protecting group, can be prepared by Suzuki coupling of the corresponding Formula XXXI wherein F and G are as described above and $P^2$ is a known carboxyl protecting group and Formula XXXII compounds, which are commercially available or which can be prepared by literature methods. Generally, this reaction can be performed as described above for the preparation of the Formula XX compounds in Scheme III.

Scheme VI

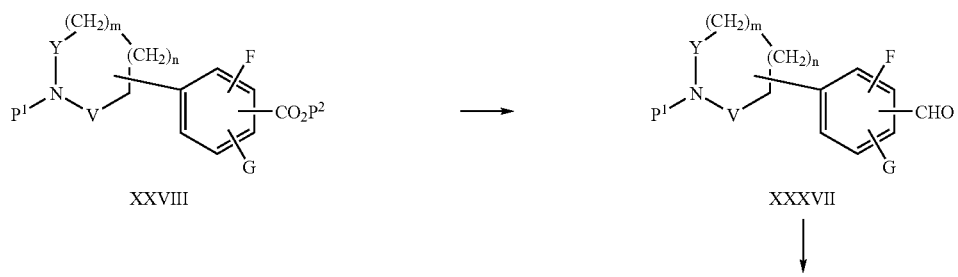

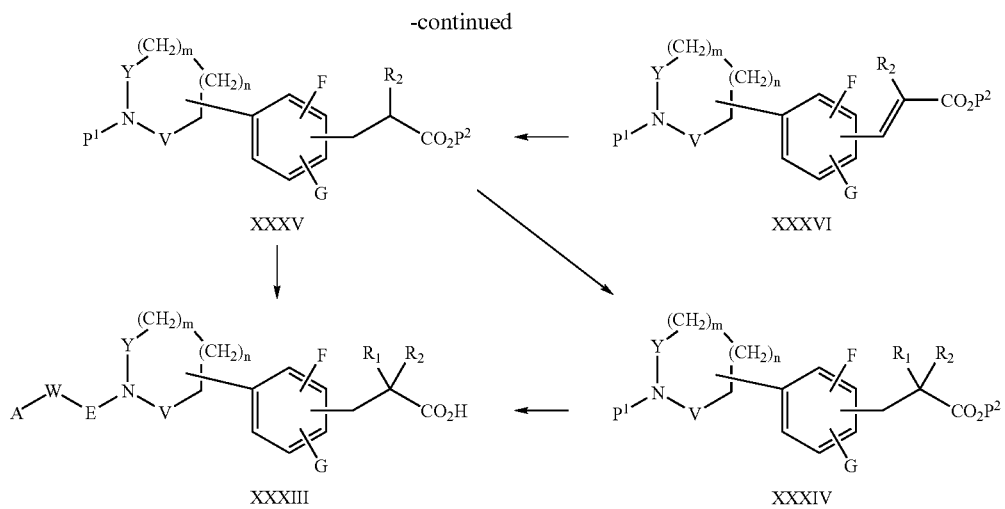

Scheme VI

According to reaction Scheme VI, the desired Formula I compounds, wherein X is —B—C(R$^1$R$^2$)-Z, m, n, V, Y, F, G, R$^1$, R$^2$, A, W and E are as described above, B is methylene, and Z is carboxyl (depicted as Formula XXXIII compounds), can be prepared from the corresponding Formula XXXIV compounds by removal of the amine protecting group P$^1$, followed by acylation with an acyl chloride, sulfonyl chloride or isocyanate; or by treatment with an alcohol and carbonyldiimidazole; or by alkylation with an alkyl halide; followed by optional hydrolysis of the resulting compound to remove the carboxyl protecting group P$^2$ (see Greene as cited above) to produce the corresponding carboxylic acid. Alternatively, the hydrolysis may be omitted when the ester is a suitable prodrug for the carboxylic acid. Generally, these reactions can be performed as described above for the preparation of the Formula II compounds in Scheme I.

The desired Formula XXXIV compounds, wherein m, n, Y, V, F, G and R$^2$ are as described above, R$^1$ is —(C$_1$–C$_4$) alkyl or (C$_3$–C$_6$)cycloalkyl, and P$^1$ and P$^2$ are known protecting groups, can be prepared from the corresponding Formula XXXV compounds by alkylation. Generally, the Formula XXXV compound is treated with a strong base such as lithium hexamethyldisilazide in an inert solvent such as tetrahydrofuran preferably at about −78° C. for a period of about 30 minutes to about 3 hours. The appropriate alkylating agent such as an alkyl or cycloalkyl bromide or iodide is then added and the reaction allowed to proceed for about 1 to 24 hours at a temperature of about −78° C. to about 25° C.

Alternatively, the desired Formula I compounds, wherein X is —B—C(R$^1$R$^2$)Z, m, n, V, Y, F, G, R$^2$, A, W and E are as described above, R$^1$ is hydrogen, B is methylene, and Z is carboxyl (depicted as Formula XXXIII compounds), can be prepared from the corresponding Formula XXXV compounds by removal of the amine protecting group P$^1$, followed by acylation with an acyl chloride, sulfonyl chloride or isocyanate; or by treatment with an alcohol and carbonyldiimidazole; or by alkylation with an alkyl halide; followed by optional hydrolysis of the resulting compound to remove the carboxyl protecting group P$^2$ (see Greene as cited above) to produce the corresponding carboxylic acid. Alternatively, the hydrolysis may be omitted when the ester is a suitable prodrug for the carboxylic acid. Generally, these reactions can be performed as described above for preparation of the Formula II compounds in Scheme I.

The desired Formula XXXV compounds, wherein m, n, Y, V, F, G and R$^2$ are as described above, P$^1$ is a known amine protecting group and P$^2$ is a known carboxyl protecting group, can be prepared from the corresponding Formula XXXVI compounds by reduction. Generally, the Formula XXXVI compound is hydrogenated in the presence of a suitable catalyst such as palladium supported on carbon 5–10% w/w under a hydrogen pressure of 15–55 p.s.i., preferably 55, for a period of about 2 to about 24 hours. Alternatively, the reduction may be carried out in a suitable alcohol solvent, preferably methanol in the presence of magnesium metal, which dissolves in the course of the reaction. Under these conditions, the reduction may be accompanied by a transesterification with the alcohol solvent. The outcome of the subsequent reaction is typically unaffected by this change.

The desired Formula XXXVI compounds, wherein m, n, Y, V, F, G and R$^2$ is as described above, P$^1$ is a known amine protecting group and P$^2$ is a known carboxyl protecting group, can be prepared from the corresponding Formula XXXVII compounds by a Wittig-Horner reaction. Generally, the Formula XXXVII compound is added to the Wittig-Horner reagent, generated by heating a 2-diphenylphosphinoyl-2-alkoxyacetic acid ester and chlorodiphenylphosphine in a reaction inert solvent such as tetrahydrofuran with a base such as sodium hydride at a temperature between about −78° C. and room temperature, and the resulting mixture brought to reflux if necessary for a period of about 10–60 minutes.

The desired Formula XXXVII compounds, wherein m, n, Y, V, F and G are as described above and P$^1$ is a known amine protecting group, can be prepared from the corresponding Formula XXXVIII compounds (preparation of which described in preceeding schemes, see, e.g., Scheme V wherein the compound of Formula XXIX is prepared and which may be protected by methods described herein) by reduction. Generally, the Formula XXXVIII compound is reacted with a reducing agent, such as diisobutylaluminium hydride, in a non-protic solvent such as toluene at a temperature of −78° C. to ambient temperature, preferable −78°

C. In some instances, the Formula XXXVIII compounds may overreduce to the corresponding alcohol which can be oxidized to the corresponding Formula XXXVII compounds by treatment with an appropriate oxidizing agent such as manganese dioxide in a suitable inert solvent such as ether for a period of about 1 to about 12 hours at room temperature or with a combination of oxalyl chloride and dimethylsulfoxide under typical Swern oxidation conditions.

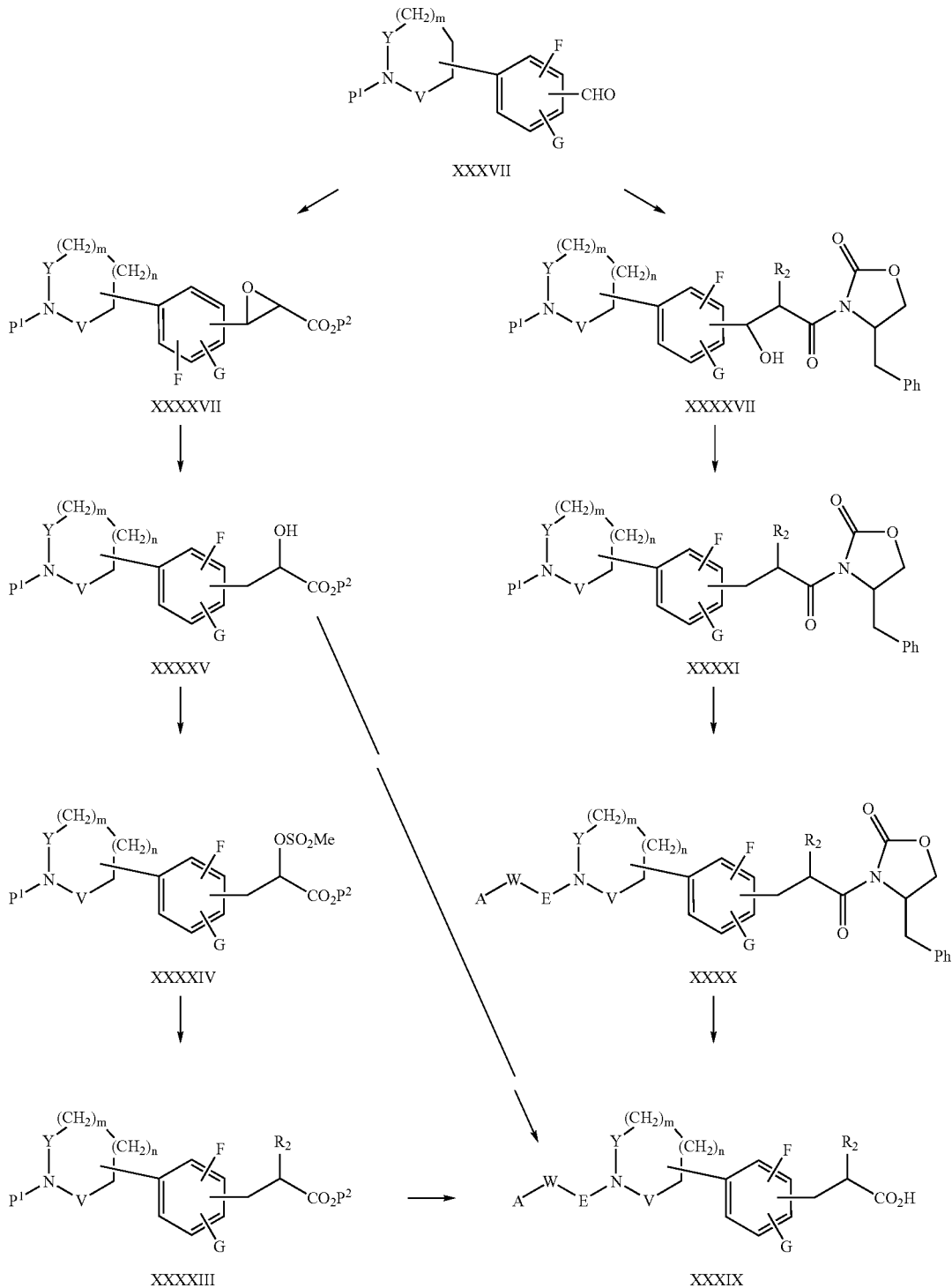

Scheme VII

Reaction Scheme VII provides an alternative method to prepare the desired Formula I compounds, wherein X is —B—C($R^1R^2$)-Z, m, n, V, Y, F, G, A, W and E are as described above, $R^1$ is H, $R^2$ is as described above wherein the first carbon atom of the chain is replaced with an oxygen atom, B is methylene, and Z is carboxyl (depicted as Formula XXXIX compounds), from the corresponding Formula XXXX compounds by hydrolysis of the amide to produce the corresponding carboxylic acid. Optionally, the hydrolysis may be omitted when the amide is a suitable prodrug for the carboxylic acid.

The desired Formula XXXX compounds, wherein m, n, V, Y, F, G, A, W and E are as described above, $R^1$ is H, $R^2$ is as described above wherein the first carbon atom of the chain is replaced with an oxygen atom, and Ph is phenyl, can be prepared from the corresponding Formula XXXXI compounds by removal of the amine protecting group $P^1$, followed by acylation with an acyl chloride, sulfonyl chloride or isocyanate; or by treatment with an alcohol and carbonyldiimidazole; or by alkylation with an alkyl halide. Generally, these reactions may be performed as described above for preparation of the Forumla II compounds in Scheme I.

The desired Formula XXXXI compounds, wherein m, n, V, Y, F and G are as described above, $R^1$ is H, $R^2$ is as described above wherein the first carbon atom of the chain is replaced with an oxygen atom, $P^1$ is an amine protecting group, and Ph is phenyl, can be prepared from the corresponding compound of Formula XXXXII by reduction. Generally, the Formula XXXXII compound is acylated, for example with acetic anhydride in the presence of a base such as pyridine, followed by hydrogenation in a reaction inert solvent with a catalyst such as palladium on carbon, or by transfer hydrogenation using ammonium formate in refluxing methanol in the presence of a catalyst such as palladium on carbon in a reaction inert solvent such as methanol or ethanol at a temperature between about 0° C. to about 80° C., typically about 25° C. to about 50° C.

Alternatively, the corresponding thionocarbonate can be prepared using an aryl chlorothionoformate in the presence of a base such as pyridine followed by reduction with tri-n-butyltin hydride in a reaction inert solvent such as toluene in the presence of a radical initiator such as azobisisobutyronitrile at an elevated temperature typically about 80° C. to about 110° C.

The desired Formula XXXXII compounds, wherein m, n, V, Y, F and G are as described above, $R^1$ is H, $R^2$ is as described above wherein the first carbon atom of the chain is replaced with an oxygen atom, $P^1$ is an amine protecting group and Ph is phenyl, can be prepared from the corresponding Formula XXXVII compounds (prepared as described in Scheme VI) by an aldol condensation. Generally, the Formula XXXVII compound is treated with the desired 4-benzyl-3-alkoxyacetyl-oxazolidin-2-one in the presence of di-n-butylboron triflate under conditions described by Hulin et. al (*J. Med. Chem.*, 1996, 39, 3897). With the appropriate choice of enantiomerically pure chiral auxiliary, the absolute configuration of the two new chiral centers can be controlled.

In another aspect of Scheme VII, the desired Formula I compounds, wherein X is —B—C($R^1R^2$)-Z, m, n, V, Y, F, G, A, W and E are as described above, $R^1$ is H, $R^2$ is as described above wherein the first carbon atom of the chain is replaced with a sulfur atom, B is methylene and Z is carboxyl (depicted as Formula XXXIX compounds), can be prepared by deprotection of the compound of Formula XXXXIII compounds by removal of the amine protecting group $P^1$; followed by acylation with an acyl chloride, sulfonyl chloride or isocyanate; or by treatment with an alcohol and carbonyldiimidazole; or by alkylation with an alkyl halide; followed by optional hydrolysis of the resulting compound to remove the carboxyl protecting group $P^2$ (see Greene as cited above) to produce the corresponding carboxylic acid. Alternatively, the hydrolysis may be omitted when the ester is a suitable prodrug for the carboxylic acid. Generally, these reactions can be performed as described above for preparation of the Forumla II compounds in Scheme I.

The desired Formula XXXXIII compounds, wherein m, n, V, Y, F and G are as described above, $R^1$ is H, $R^2$ is described above wherein the first carbon atom of the chain is replaced with a sulfur atom, $P^1$ is a known amine protecting group and $P^2$ is a known carboxyl protecting group, can be prepared from the corresponding Formula XXXXIV compounds by $S_N2$ displacement on the mesyloxy group with a thiolate anion. Generally, the Formula XXXXIV compound is treated with an alkyl or aryl mercaptan in the presence of a suitable base such as potassium hydroxide or t-butoxide in a reaction inert solvent such as tetrahydrofuran or dimethylformamide at a temperature of about 0° C. to about 50° C., typically about 25° C.

The desired Formula XXXXIV compounds, wherein m, n, V, Y, F and G are as described above, $P^1$ is a known amine protecting group and $P^2$ is a known carboxyl protecting group, can be prepared from the corresponding compound of Formula XXXXV compounds by mesylation. Generally, the Formula XXXXV compound is treated with a suitable mesylating agent such as methanesulfonic anhydride or methanesulfonyl chloride in the presence of a suitable base such as pyridine in a reaction inert solvent such as pyridine, tetrahydrofuran or dimethylformamide at a temperature between about 0° C. to about 50° C., typically about 25° C.

The desired Formula XXXXV compounds, wherein m, n, V, Y, F and G are as described above, $P^1$ is a known amine protecting group and $P^2$ is a known carboxyl protecting group, can be prepared from the corresponding Formula XXXXVI compounds by reduction. Generally, the Formula XXXXVI compound is hydrogenated in a reaction inert solvent with a catalyst such as palladium on carbon, or by transfer hydrogenation using ammonium formate in refluxing methanol in the presence of a catalyst such as palladium on carbon in a reaction inert solvent such as methanol or ethanol at a temperature between about 0° C. to about 80° C., typically about 25° C. to about 50° C.

The desired Formula XXXXVI compounds, wherein m, n, V, Y, F and G are as described above, $P^1$ is a known amine protecting group and $P^2$ is a known carboxyl protecting group, can be prepared from the corresponding Formula XXXVII compounds (prepared as described in Scheme VI) by a Darzens condensation. Generally, the Formula XXXVII compound is reacted with a suitable α-haloester such as ethyl-2-chloroacetate in the presence of a suitable base such as sodium hydride in a reaction inert solvent such as tetrahydrofuran at a temperature between about 25° C. to about 80° C., typically at reflux.

In another aspect of Scheme VII, the desired Formula I compounds, wherein X is —B—C($R^1R^2$)-Z, m, n, V, Y, F, G, A, W and E are as described above, $R^1$ is H, $R^2$ is as described above wherein the first carbon atom of the chain is replaced with an oxygen atom, B is methylene and Z is carboxyl (depicted as Formula XXXIX compounds), can be prepared from the corresponding Formula XXXXV compounds by alkylation. Generally, the Formula XXXXV compound is treated with an alkyl, cycloalkyl or benzyl bromide or iodide in the presence of cesium hydroxide or cesium carbonate, tetrabutylammonium iodide and molecular sieves as described by Dueno et. al (Tetrahedron Letters 1999, 40, 1843).

Scheme VIII

According to reaction Scheme VIII, the desired Formula I compounds, wherein X is —B—C($R^1R^2$)-Z, m=n=1, V is methylene, Y is methylene, F, G, $R^1$, $R^2$, A, W and E are as described above, B is NH, Z is carboxyl and the piperidinyl

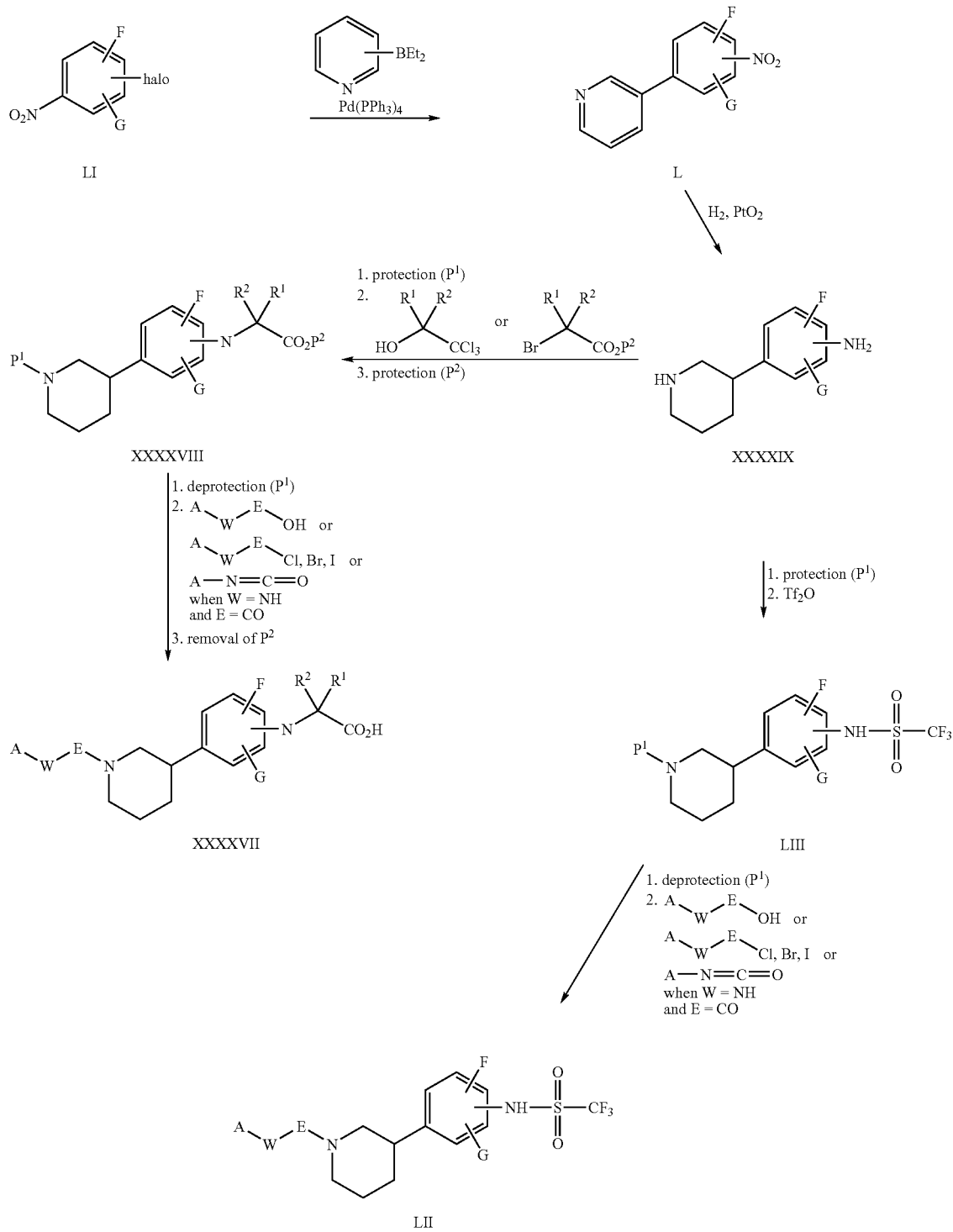

ring is substituted at the 3-position by the phenyl ring (depicted as Formula XXXXVII compounds), can be prepared from the corresponding Formula XXXXVIII compounds by removal of the amine protecting group $P^1$; followed by acylation with an acyl chloride, sulfonyl chloride or isocyanate; or by treatment with an alcohol and carbonyldiimidazole; or by alkylation with an alkyl halide; followed by optional hydrolysis of the resulting compound to remove the carboxyl protecting group $P^2$ (see Greene as cited above) to produce the corresponding carboxylic acid. Alternatively, the hydrolysis may be omitted when the ester is a suitable prodrug for the carboxylic acid. Generally, these reactions may be performed as described above for preparation of the Forumla II compounds in Scheme I.

The desired Formula XXXXVIII compounds, wherein F, G, $R^1$ and $R^2$ are as described above, $P^1$ is an amine protecting group and $P^2$ is a known carboxyl protecting group, can be prepared from the corresponding Formula XXXXIX compounds by selective protection of the piperidine nitrogen ($P^1$), followed by alkylation and protection ($P^2$) of the resulting carboxyl group, if necessary. Generally, the Formula XXXXIX compound is combined with a suitable protecting group anhydride in a biphasic mixture of aqueous base such as aqueous sodium hydroxide and a polar solvent such as tetrahydrofuran at a temperature of about 0° C. to about 50° C., preferably ambient, for a period of 1 to 6 hours, preferably 2 hours. The resulting aniline is then alkylated and subsequently optionally protected as described above for Formula III compounds in Scheme I.

The desired Formula XXXXIX compounds, wherein F and G are as described above, can be prepared from the corresponding Formula L compounds by simultaneous reduction of the nitro functionality and pyridine ring. Generally, this reduction can be performed as described above for preparation of Formula V compounds in Scheme I.

The desired Formula L compounds, wherein F and G are as described above, can be prepared from the corresponding Formula LI compounds by Suzuki coupling as described above for preparation of Formula V compounds above in Scheme I.

In another aspect of Scheme VIII, the desired Formula I compounds wherein X=Z=—NHSO$_2$R$^4$, m=n=1, V is methylene, Y is methylene, F, G, A, W and E are as described above, and the piperidinyl ring is substituted at the 3-position by the phenyl ring (depicted as Formula LII compounds) can be prepared from the corresponding Formula LIII compounds by removal of the amine protecting group $P^1$; followed by acylation with an acyl chloride, sulfonyl chloride or isocyanate; or by treatment with an alcohol and carbonyldiimidazole; or by alkylation with an alkyl halide. Generally, these reactions may be performed as described above for preparation of the Formula XXXXVII compounds.

The desired Formula LIII compounds, wherein $P^1$ is an amine protecting group and F and G, are as described above may be prepared from the corresponding Formula XXXXIX compounds by selective protection of the piperidine nitrogen ($P^1$), followed by acylation of the resulting aniline group. Selective protection of the Formula XXXXIX compound is performed as described above for the preparation of Formula XXXXVIII compounds. The resulting aniline is then acylated with trifluoromethane sulfonic anhydride in a reaction-inert solvent such as methylene chloride in the presence of an amine base such as triethylamine at a temperature of about −20° C. to about 50° C., typically 0° C. for about 0.5 to about 2 hours.

Preparation of Formula I compounds, wherein X is —B—C(R$^1$R$^2$)-Z, F, G, R$^1$, R$^2$, A, W and E are as described above, B is NH and Z is carboxyl, with other permutations of m, n, V and Y, can be prepared using procedures similar to those described in schemes above. Preparation of Formula I compounds, wherein X=Z=—NHSO$_2$R$^4$, F, G, A, W and E are as described above, with other permutations of m, n, V and Y, can be prepared using procedures similar to those described in schemes above.

The starting materials and reagents for the above described reaction schemes (e.g., 3-bromo anisole, diethyl-(3-pyridyl)borane, 3-bromopyridine, 3-methoxybenzene boronic acid, 3-bromophenol, 5-chloro-2-methylbenzoic acid, 2-nitro-4-bromotoluene, prodrug residues, protected forms and others) are readily available or can be easily synthesized by those skilled in the art using conventional methods of organic synthesis. Some of the preparation methods described herein will require protection of remote functionality (i.e., carboxyl). The need for these protecting groups will vary depending on the nature of the remote functionality and the conditions of the preparation methods and can be readily determined by one skilled in the art. For a general description of protecting groups (e.g., halo(C$_1$–C$_4$) alkyl, (C$_1$–C$_4$)alkoxymethyl, arylmethyl and tri(C$_1$–C$_4$) alkylsilyl) and their use, see T. W. Greene, *Protective Groups in Organic Synthesis*, John Wiley & Sons, New York, 1991.

Additional methods to prepare Formula I compounds would be readily known to one of ordinary skill in the art of organic chemistry and may be further exemplified in the literature and in the Preparations and Examples below.

The desired Formula I compound wherein Z is tetrazol-5-yl can be prepared from the corresponding Formula I compound wherein Z is carboxyl by converting the carboxyl group to a carboxamide group (Z=CONH$_2$), dehydrating the carboxamide to the nitrile (Z=CN) and reacting the nitrile with an appropriate azide to form the tetrazole group. Generally, the acid is converted to the imidazolide by reaction with carbonyldiimidazole in an aprotic solvent such as methylene chloride at a temperature of about 15° C. to about 40° C. for about 30 minutes to about 4 hours, conveniently at room temperature for 1 hour. The resulting imidazolide is converted to the corresponding amide by bubbling ammonia gas into the reaction mixture at a temperature of about 10° C. to about 40° C. for about 3 minutes to about 30 minutes, preferably at room temperature for about 5 minutes or until the reaction is complete by TLC analysis. The amide is converted to the nitrile by treatment with trifluoroacetic anhydride and triethylamine in an inert solvent such as methylene chloride at about 0° C. for about 25 minutes to about 2 hours, preferably 30 minutes. Treatment of the nitrile with sodium azide and ammonium chloride in dimethylformamide at a temperature of about 90° C. to about 130° C. for about 7 hours to about 60 hours, preferably at a temperature of 120° C. for 24 hours, yields the desired tetrazole group.

The desired Formula I compound wherein Z is 4,5-dihydro-5-oxo-1,2,4-oxadiazol-3-yl can be prepared from the corresponding Formula I compound wherein Z is CN by converting the nitrile to the amide oxime and reacting the amide oxime with a carbonylating agent to form the corresponding 4,5-dihydro-5-oxo-1,2,4-oxadiazole derivative. Generally, the nitrile is converted to the amide oxime by reaction with hydroxylamine hydrochloride in the presence of a base such as potassium carbonate in an alcoholic solvent at a temperature of about 60° C. to about 110° C. for about 5 hours to about 24 hours, preferably in refluxing ethanol for about 18 hours. The amide oxime is converted to the corresponding 4,5-dihydro-5-oxo-1,2,4-oxadiazole derivative by reaction with carbonyldiimidazole and triethylamine in refluxing ethyl acetate for about 24 hours.

Prodrugs of the compounds of Formula I can be prepared according to methods analogous to those known to those skilled in the art. Exemplary processes are described below.

Prodrugs of this invention where a carboxyl group in a carboxylic acid of Formula I is replaced by an ester can be prepared by combining the carboxylic acid with the appropriate alkyl halide in the presence of a base such as potassium carbonate in an inert solvent such as dimethylformamide at a temperature of about 0° C. to about 100° C. for about 1 to about 24 hours. Alternatively, the acid is combined with appropriate alcohol as solvent in the presence of a catalytic amount of acid such as concentrated sulfuric acid at a temperature of about 20° C. to about 100° C., preferably at a reflux, for about 1 hour to about 24 hours. Another method is the reaction of the acid with a stoichiometric amount of the alcohol in the presence of a catalytic amount of acid in an inert solvent such as toluene or tetrahydrofuran, with concomitant removal of the water being produced by physical (e.g., Dean-Stark trap) or chemical (e.g., molecular sieves) means.

Prodrugs of this invention where an alcohol function has been derivatized as an ether can be prepared by combining the alcohol with the appropriate alkyl bromide or iodide in the presence of a base such as potassium carbonate in an inert solvent such as dimethylformamide at a temperature of about 0° C. to about 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl) amides and N-(1-hydroxy-1-(alkoxycarbonyl)methyl) amides can be prepared by the reaction of the parent amide with the appropriate aldehyde under neutral or basic conditions (e.g., sodium ethoxide in ethanol) at temperatures between 25° C. and 70° C. N-alkoxymethyl or N-1-(alkoxy)alkyl derivatives can be obtained by reaction of the N-unsubstituted compound with the necessary alkyl halide in the presence of a base in an inert solvent.

The compounds of the present invention can also be used in conjunction with other pharmaceutical agents for the treatment of the diseases/conditions as described herein.

In combination therapy treatment, both the compounds of the present invention and the other drug therapies are administered to mammals (e.g., humans, male or female) by conventional methods. The compounds of the present invention can also be administered in combination with naturally occurring compounds that act to lower plasma cholesterol levels. These naturally occurring compounds are commonly called nutraceuticals and include, for example, garlic extract and niacin. A slow-release form of niacin is available and is known as Niaspan. Niacin may also be combined with other therapeutic agents such as lovastatin, which is an HMG-CoA reductase inhibitor and described further below. This combination therapy is known as ADVICOR™ (Kos Pharmaceuticals Inc.).

Any cholesterol absorption inhibitor can be used as the second compound in the combination aspect of the present invention. The term cholesterol absorption inhibition refers to the ability of a compound to prevent cholesterol contained within the lumen of the intestine from entering into the intestinal cells and/or passing from within the intestinal cells into the blood stream. Such cholesterol absorption inhibition activity is readily determined by those skilled in the art according to standard assays (e.g., J. Lipid Res. (1993) 34: 377–395). Cholesterol absorption inhibitors are known to those skilled in the art and are described, for example, in PCT WO 94/00480. An example of a recently approved cholesterol absorption inhibitor is ZETIA™ (ezetimibe) (Merck/Schering-Plough).

Any HMG-CoA reductase inhibitor can be used as the second compound in the combination aspect of the present invention. The term HMG-CoA reductase inhibitor refers to compounds, which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455–509, and references cited therein). A variety of these compounds are described and referenced below; however, other HMG-CoA reductase inhibitors will be known to those skilled in the art. U.S. Pat. No. 4,231,938 discloses certain compounds isolated after cultivation of a microorganism belonging to the genus *Aspergillus*, such as lovastatin. Also, U.S. Pat. No. 4,444,784 discloses synthetic derivatives of the aforementioned compounds, such as simvastatin. Also, U.S. Pat. No. 4,739,073 discloses certain substituted indoles, such as fluvastatin. Also, U.S. Pat. No. 4,346,227 discloses ML-236B derivatives, such as pravastatin. Also, EP-491226A discloses certain pyridyldihydroxyheptenoic acids, such as cerivastatin. In addition, U.S. Pat. No. 5,273,995 discloses certain 6-[2-(substituted-pyrrol-1-yl)alkyl]pyran-2-ones such as atorvastatin and the hemicalcium salt thereof (Lipitor®). Additional HMG-CoA reductase inhibitors include rosuvastatin and pitavostatin.

Any MTP/Apo B secretion (microsomal triglyceride transfer protein and/or apolipoprotein B secretion) inhibitor can be used as the second compound in the combination aspect of the present invention. The term MTP/Apo B secretion inhibitor refers to compounds which inhibit the secretion of triglycerides, cholesteryl ester and phospholipids. Such inhibition is readily determined by those skilled in the art according to standard assays (e.g., Wetterau, J. R. 1992; Science 258:999). A variety of these compounds are known to those skilled in the art, including imputapride (Bayer) and additional compounds such as those disclosed in WO 96/40640 and WO 98/23593.

Any HMG-CoA synthase inhibitor can be used as the second compound in the combination aspect of the present invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (e.g., Meth Enzymol. 1975; 35:155–160: Meth. Enzymol. 1985; 110:19–26 and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression can be used as the second compound in the combination aspect of the present invention. These agents can be HMG-CoA reductase transcription inhibitors that block or decrease the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (e.g., Meth. Enzymol. 1985;110:9–19). Inhibitors of HMG-CoA reductase gene expression will be known to those skilled in the art, for example, U.S. Pat. No. 5,041,432 discloses certain 15-substituted lanosterol derivatives. Other oxygenated sterols that suppress synthesis of HMG-CoA reductase are discussed by E. I. Mercer (Prog. Lip. Res. 1993;32: 357–416).

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in commonly assigned U.S. Pat. No. 6,140,343 and commonly assigned U.S. Pat. No. 6,197,786. CETP inhibitors disclosed in these patents include compounds, such as [2R,4S]4-[(3, 5-bis-trifluoromethyl-benzyl)-methoxycarbonyl-amino]-2-ethyl-6-trifluoromethyl-3,4-dihydro-2H-quinoline-1-carboxylic acid ethyl ester, which is also known as torcetrapib. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.;* 6:1951–1954 (1996), respectively.

Any squalene synthetase inhibitor can be used as the second compound of the present invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (e.g., Meth. Enzymol. 1969; 15: 393–454 and Meth. Enzymol. 1985; 110:359–373 and references contained therein). A variety of these compounds are known to those skilled in the art, for example, U.S. Pat. No. 5,026,554 discloses fermentation products of the microorganism MF5465 (ATCC 74011) including zaragozic acid. A summary of other squalene synthetase inhibitors has been compiled (see, e.g., Curr. Op. Ther. Patents (1993) 861–4).

Any squalene epoxidase inhibitor can be used as the second compound in the combination aspect of the present invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (e.g., Biochim. Biophys. Acta 1984; 794:466–471). A variety of these compounds are known to those skilled in the art, for example, U.S. Pat. Nos. 5,011,859 and 5,064,864 disclose certain fluoro analogs of squalene. EP publication 395,768 A discloses certain substituted allylamine derivatives. PCT publication WO 9312069 A discloses certain amino alcohol derivatives. U.S. Pat. No. 5,051,534 discloses certain cyclopropyloxy-squalene derivatives.

Any squalene cyclase inhibitor can be used as the second component in the combination aspect of the present invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (e.g., FEBS Lett. 1989;244:347–350). Squalene cyclase inhibitors are known to those skilled in the art. For example, PCT publication WO9410150 and French patent publication 2697250 disclose squalene cyclase inhibitors.

Any combined squalene epoxidase/squalene cyclase inhibitor can be used as the second component in the combination aspect of the present invention. The term combined squalene epoxidase/squalene cyclase inhibitor refers to compounds that inhibit the bioconversion of squalene to lanosterol via a squalene-2,3-epoxide intermediate. In some assays, it is not possible to distinguish between squalene epoxidase inhibitors and squalene cyclase inhibitors. However, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of squalene epoxidase/squalene cyclase inhibitors are known to those skilled in the art. U.S. Pat. Nos. 5,084,461 and 5,278,171 disclose certain azadecalin derivatives. EP publication 468,434 discloses certain piperidyl ether and thio-ether derivatives such as 2-(1-piperidyl)pentyl isopentyl sulfoxide and 2-(1-piperidyl)ethyl ethyl sulfide. PCT publication WO 9401404 discloses certain acyl-piperidines such as 1-(1-oxopentyl-5-phenylthio)-4-(2-hydroxy-1-methyl)-ethyl)piperidine. U.S. Pat. No. 5,102,915 discloses certain cyclopropyloxy-squalene derivatives.

Any ACAT inhibitor can serve as the second compound in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Eli Lilly and Pierre Fabre).

A lipase inhibitor can serve as the second compound in the combination therapy aspect of the present invention. A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Methods Enzymol. 286: 190–231).

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Methods Enzymol. 286: 190–231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology,* 92,125 (1987). Such gastric lipase inhibition activity is readily determined by those skilled in the art according to standard assays (e.g., Methods Enzymol. 286: 190–231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen,* 562, 205–229 (1949).

A variety of pancreatic lipase inhibitors are described herein below. The pancreatic lipase inhibitors lipstatin, (2S,3S,5S,7Z,10Z)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of *Actinomycetes* strain MG147-CF2, are disclosed in Kitahara, et al., *J. Antibiotics,* 40 (11), 1647–1650 (1987). The pancreatic lipase inhibitors, ebelactone A and ebelactone B, and a process for the preparation thereof by the microbial cultivation of *Actinomycetes* strain MG7-G1, are disclosed in Umezawa, et al., *J. Antibiotics,* 33, 1594–1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricor®.

Diabetes can be treated by administering to a patient having diabetes (especially Type II), insulin resistance, impaired glucose tolerance, or the like, or any of the diabetic complications such as neuropathy, nephropathy, retinopathy or cataracts, a therapeutically effective amount of a Formula I compound in combination with other agents (e.g., insulin) that can be used to treat diabetes. This includes the classes of anti-diabetic agents (and specific agents) described herein.

Any glycogen phosphorylase inhibitor can be used as the second agent in combination with a Formula I compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41 (1998) 2934–2938). A variety of glycogen phosphorylase inhibitors are known to those skilled in the art including those described in WO 96/39384 and WO 96/39385.

Any aldose reductase inhibitor can be used in combination with a Formula I compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, *Diabetes,* 29:861–864 (1980). "Red Cell Sorbitol, an Indicator of Diabetic Control"). A variety of aldose reductase inhibitors are known to those skilled in the art.

Any sorbitol dehydrogenase inhibitor can be used in combination with a Formula I compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem (2000) 280: 329–331). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a Formula I compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214).

A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Methods Enzymol. (1955) 1: 149). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R, 3R,4R,5S)-3,4,5-trihydroxy-2-(hydroxymethyl)piperidino]-α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed in U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Additional anti-diabetic compounds, which can be used as the second agent in combination with a Formula I compound of the present invention, includes, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase (Metabasis/Sankyo), GLP-1/analogs (AC 2993, also known as exendin-4), insulin and insulin mimetics (Merck natural products). Other examples would include PKC-β inhibitors and AGE breakers.

The Formula I compounds of the present invention can be used in combination with other anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, $\beta_3$ adrenergic receptor agonists, apolipoprotein-B secretion/microsomal triglyceride transfer protein (apo-B/MTP) inhibitors, MCR-4 agonists, cholecystokinin-A (CCK-A) agonists, monoamine reuptake inhibitors (e.g., sibutramine), sympathomimetic agents, serotoninergic agents, cannabinoid receptor antagonists (e.g., rimonabant (SR-141,716A)), dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like.

Any thyromimetic can be used as the second agent in combination with a Formula I compound of the present invention. Such thyromimetic activity is readily determined by those skilled in the art according to standard assays (e.g., Atherosclerosis (1996) 126: 53–63). A variety of thyromimetic agents are known to those skilled in the art, for example those disclosed in U.S. Pat. Nos. 4,766,121; 4,826, 876; 4,910,305; 5,061,798; 5,284,971; 5,401,772; 5,654, 468; and 5,569,674. Other antiobesity agents include sibutramine which can be prepared as described in U.S. Pat. No. 4,929,629. and bromocriptine which can be prepared as described in U.S. Pat. Nos. 3,752,814 and 3,752,888.

The Formula I compounds of the present invention can also be used in combination with other antihypertensive agents. Any anti-hypertensive agent can be used as the second agent in such combinations and examples are provided herein. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase three-fold over the next 60 years, and one study has estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of Formula I of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, the disclosure of which is incorporated herein by reference. Preferred polyphosphonates are geminal diphosphonates (also referred to as bis-phosphonates). Tiludronate disodium is an especially preferred polyphosphonate. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods, and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below.

Another preferred estrogen agonist/antagonist is 3-(4-(1,2-diphenyl-but-1-enyl)-phenyl)-acrylic acid, which is disclosed in Willson et al., Endocrinology, 1997, 138, 3901–3911.

Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate (1:1)) and related compounds which are disclosed in U.S. Pat. No. 4,536,516, the disclosure of which is incorporated herein by reference.

Another related compound is 4-hydroxy tamoxifen, which is disclosed in U.S. Pat. No. 4,623,660, the disclosure of which is incorporated herein by reference.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)-hydrochloride) which is disclosed in U.S. Pat. No. 4,418,068, the disclosure of which is incorporated herein by reference.

Another preferred estrogen agonist/antagonist is toremifene: (ethanamine, 2-(4-(4-chloro-1,2-diphenyl-1- butenyl)phenoxy)-N,N-dimethyl-, (Z)-, 2-hydroxy-1,2,3-propanetricarboxylate (1:1) which is disclosed in U.S. Pat. No. 4,996,225, the disclosure of which is incorporated herein by reference.

Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287, the disclosure of which is incorporated herein by reference. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155, the disclosure of which is incorporated herein by reference.

Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058, the disclosure of which is incorporated herein by reference.

Another preferred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795, the disclosure of which is incorporated herein by reference.

Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc.

Other preferred estrogen agonist/antagonists include the compounds, TSE-424 (Wyeth-Ayerst Laboratories) and arazoxifene.

Other preferred estrogen agonist/antagonists include compounds as described in commonly assigned U.S. Pat. No. 5,552,412, the disclosure of which is incorporated herein by reference. Especially preferred compounds described therein are:
cis-6-(4-fluoro-phenyl)-5-(4-(2-piperidin-1-yl-ethoxy)-phenyl)-5,6,7,8-tetrahydro-naphthalene-2-ol;
(−)-cis-6-phenyl-5-(4-(2-pyrrolidin-1-yl-ethoxy)-phenyl)-5,6,7,8-tetrahydro-naphthalene-2-ol (also known as lasofoxifene);
cis-6-phenyl-5-(4-(2-pyrrolidin-1-yl-ethoxy)-phenyl)-5,6,7,8-tetrahydro-naphthalene-2-ol;
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalene-2-ol; and
1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is incorporated herein by reference). U.S. Pat. No. 4,133,814 discloses derivatives of 2-phenyl-3-aroyl-benzothiophene and 2-phenyl-3-aroylbenzothiophene-1-oxide.

Other anti-osteoporosis agents, which can be used as the second agent in combination with a Formula I compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; and vitamin D and vitamin D analogs.

The starting materials and reagents for the above described Formula I compounds of the present invention and combination agents, are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Some of the Formula I compounds of the present invention or intermediates in their synthesis have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by, for example, chiral HPLC methods or converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the Formula I compounds or an intermediate in their synthesis which contain an acidic or basic moiety may be separated into their compounding pure enantiomers by forming a diastereomeric salt with an optically pure chiral base or acid (e.g., 1-phenyl-ethyl amine or tartaric acid) and separating the diastereomers by fractional crystallization followed by neutralization to break the salt, thus providing the corresponding pure enantiomers. All such isomers, including diastereomers, enantiomers and mixtures thereof are considered as part of the present invention. Also, some of the compounds of the present invention are atropisomers (e.g., substituted biaryls) and are considered as part of the present invention.

More specifically, the Formula I compounds of the present invention can be obtained by fractional crystallization of the basic intermediate with an optically pure chiral acid to form a diasteromeric salt. Neutralization techniques are used to remove the salt and provide the enantiomerically pure compounds. Alternatively, the Formula I compounds of the present invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcel™ AD or OD (obtained from Chiral Technologies, Exton, Pa.)) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine). Concentration of the product containing fractions affords the desired materials.

Some of the Formula I compounds of the present invention are acidic and they form a salt with a pharmaceutically acceptable cation. Some of the Formula I compounds of the present invention are basic and they form a salt with a pharmaceutically acceptable anion. All such salts are within the scope of the present invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

Those skilled in the art will recognize that some of the compounds herein can exist in several tautomeric forms. All such tautomeric forms are considered as part of the present invention. For example all enol-keto forms of the compounds of Formula I of the present invention are included in this invention.

In addition, when the Formula I compounds of the present invention form hydrates or solvates they are also within the scope of the present invention.

The Formula I compounds of the present invention, their prodrugs and the salts of such compounds and prodrugs are all adapted to therapeutic use as agents that activate peroxisome proliferator activator receptor (PPAR) activity in mammals, particularly humans. Thus, it is believed the compounds of the present invention, by activating the PPAR receptor, stimulate transcription of key genes involved in fatty acid oxidation and also those involved in high density lipoprotein (HDL) assembly (for example apolipoprotein AI gene transcription), accordingly reducing whole body fat and increasing HDL cholesterol. By virtue of their activity, these agents also reduce plasma levels of triglycerides, VLDL cholesterol, LDL cholesterol and their associated components in mammals, particularly humans, as well as increasing HDL cholesterol and apolipoprotein AI. Hence, these compounds are useful for the treatment and correction of the various dyslipidemias observed to be associated with the development and incidence of atherosclerosis and cardiovascular disease, including hypoalphalipoproteinemia and hypertriglyceridemia.

Given the positive correlation between triglycerides, LDL cholesterol, and their associated apolipoproteins in blood with the development of cardiovascular, cerebral vascular and peripheral vascular diseases, the Formula I compounds of the present invention, their prodrugs and the salts of such compounds and prodrugs, by virtue of their pharmacologic action, are useful for the prevention, arrestment and/or regression of atherosclerosis and its associated disease states. These include cardiovascular disorders (e.g., angina, cardiac ischemia and myocardial infarction) and complications due to cardiovascular disease.

Thus, given the ability of the Formula I compounds of the present invention, their prodrugs and the salts of such compounds and prodrugs to reduce plasma triglycerides and total plasma cholesterol, and increase plasma HDL cholesterol, they are of use in the treatment of diabetes, including impaired glucose tolerance, diabetic complications, insulin resistance and metabolic syndrome, as described previously. In addition, the Formula I compounds are useful for the treatment of polycystic ovary syndrome. Also, the Formula I compounds are useful in the treatment of obesity given the ability of the Formula I compounds of this invention, their prodrugs and the salts of such compounds and prodrugs to increase hepatic fatty acid oxidation.

The utility of the Formula I compounds of the present invention, their prodrugs and the salts of such compounds and prodrugs as medical agents in the treatment of the above described disease/conditions in mammals (e.g. humans, male or female) is demonstrated by the activity of the compounds of the present invention in one or more of the conventional assays and in vivo assays described below. The in vivo assays (with appropriate modifications within the skill in the art) can be used to determine the activity of other lipid or triglyceride controlling agents as well as the compounds of the present invention. Thus, the protocols described below can also be used to demonstrate the utility of the combinations of the agents (i.e., the compounds of the present invention) described herein. In addition, such assays provide a means whereby the activities of the Formula I compounds of the present invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases. The following protocols can of course be varied by those skilled in the art.

PPAR FRET Assay

Measurement of coactivator recruitment by a nuclear receptor after receptor-ligand association is a method for evaluating the ability of a ligand to produce a functional response through a nuclear receptor. The PPAR FRET (Fluorescence Resonance Energy Transfer) assay measures the ligand-dependent interaction between nuclear receptor and coactivator. GST/PPAR ($\alpha$, $\beta$, and $\gamma$) ligand binding domain (LBD) is labeled with a europium-tagged anti-GST antibody, while an SRC-1 (Sterol Receptor Coactivator-1) synthetic peptide containing an amino terminus long chain biotin molecule is labeled with streptavidin-linked allophycocyanin (APC). Binding of ligand to the PPAR LBD causes a conformational change that allows SRC-1 to bind. Upon SRC-1 binding, the donor FRET molecule (europium) comes in close proximity to the acceptor molecule (APC), resulting in fluorescence energy transfer between donor (337 nm excitation and 620 nm emission) and acceptor (620 nm excitation and 665 nm emission). Increases in the ratio of 665 nm emission to 620 nm emission is a measure of the ability of the ligand-PPAR LBD to recruit SRC-1 synthetic peptide and therefore a measure of the ability of a ligand to produce a functional response through the PPAR receptor.

[1] GST/PPAR LBD Expression. The human PPAR$\alpha$ LBD (amino acids 235–507) is fused to the carboxy terminus of glutathione S-transferase (GST) in pGEX-6P-1 (Pharmacia, Piscataway, N.J.). The GST/PPAR$\alpha$ LBD fusion protein is expressed in BL21[DE3]pLysS cells using a 50 uM IPTG induction at room temperature for 16 hr (cells induced at an $A_{600}$ of ~0.6). Fusion protein is purified on glutathione sepharose 4B beads, eluted in 10 mM reduced glutathione, and dialyzed against 1×PBS at 4° C. Fusion protein is quantitated by Bradford assay (M. M. Bradford, Analst. Biochem. 72:248–254; 1976), and stored at −20° C. in 1×PBS containing 40% glycerol and 5 mM DTT.

[2] FRET Assay. The FRET assay reaction mix consists of 1×FRET buffer (50 mM Tris-Cl pH 8.0, 50 mM KCl, 0.1 mg/ml BSA, 1 mM EDTA, and 2 mM DTT) containing 20 nM GST/PPAR$\alpha$ LBD, 40 nM of SRC-1 peptide (amino acids 676–700, 5'-long chain biotin-CPSSHSSLTERH-KILHRLLQEGSPS-NH$_2$, purchased from American Peptide Co., Sunnyvale, Calif.), 2 nM of europium-conjugated anti-GST antibody (Wallac, Gaithersburg, Md.), 40 nM of streptavidin-conjugated APC (Wallac), and control and test compounds. The final volume is brought to 100 ul with water and transferred to a black 96-well plate (Microfuor B, Dynex (Chantilly, Va.)). The reaction mixes are incubated for 1 hr at 4° C. and fluorescence is read in Victor 2 plate reader (Wallac). Data is presented as a ratio of the emission at 665 nm to the emission at 615 nm.

Assessment of Lipid-modulating Activity in Mice

[1] Triglyceride lowering. The hypolipidemic treating activity of the compounds of the present invention can be demonstrated by methods based on standard procedures. For example, the in vivo activity of these compounds in decreasing plasma triglyceride levels may be determined in hybrid B6CBAF1/J mice.

Male B6CVAF1/J mice (8–11 week old) are obtained from The Jackson Laboratory and housed 4–5/cage and maintained in a 12 hr light/12 hr dark cycle. Animals have ad lib. access to Purina rodent chow and water. The animals are dosed daily (9 AM) by oral gavage with vehicle (water or 0.5% methyl cellulose 0.05% Tween 80) or with vehicle containing test compound at the desired concentration. Plasma triglycerides levels are determined 24 hours after the administration of the last dose (day 3) from blood collected retro-orbitally with heparinized hematocrit tubes. Triglyceride determinations are performed using a commercially available Triglyceride E kit from Wako (Osaka, Japan).

[2] HDL cholesterol elevation. The activity of the compounds of the present invention for raising the plasma level of high density lipoprotein (HDL) in a mammal can be demonstrated in transgenic mice expressing the human apoAI and CETP transgenes (HuAICETPTg). The transgenic mice for use in this study are described previously in Walsh et al., J. Lipid Res. 1993, 34: 617–623, Agellon et al., J. Biol. Chem. 1991, 266: 10796–10801. Mice expressing the human apoAI and CETP transgenes are obtained by mating transgenic mice expressing the human apoAI transgene (HuAITg) with CETP mice (HuCETPTg).

Male HuAICETPTg mice (8–11 week old) are grouped according to their human apo AI levels and have free access to Purina rodent chow and water. Animals are dosed daily by oral gavage with vehicle (water or 0.5% methylcellulose 0.05% Tween 80) or with vehicle containing test compound at the desired dosed for 5 days. HDL-cholesterol and human apoAI are determined initially (day 0) and 90 minutes post dose (day 5) using methods based on standard procedures. Mouse HDL is separated from apoB-containing lipoproteins by dextran sulfate precipitation as described elsewhere (Francone et al., J. Lipid. Res. 1996, 37:1268–1277). Cholesterol is measured enzymatically using a commercially available cholesterol/HP Reagent kit (Boehringer MannHeim, Indianapolis, Ind.) and spectrophotometrically quantitated on a microplate reader. Human apoAI is measured by a sandwich enzyme-linked immunosorbent assay as previously described (Francone et al., J. Lipid. Res. 1996, 37:1268–1277).

Measurement of Glucose Lowering in the ob/ob Mouse

The hypoglycemic activity of the compounds of the present invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Five to eight week old male C57BL/6J-ob/ob mice (obtained from Jackson Laboratory, Bar Harbor, Me.) are housed five per cage under standard animal care practices. After a one-week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: (1) 0.25% w/v methyl cellulose in water without pH adjustment; or (2) 0.1% Pluronic® P105 Block Copolymer Surfactant (BASF Corporation, Parsippany, N.J.) in 0.1% saline without pH adjustment. On day 5, the animals are weighed again and then dosed orally with a test compound or the vehicle alone. All compounds are administered in vehicle consisting of either: (1) 0.25% w/v methyl cellulose in water; (2) 10% DMSO/0.1% Pluronic® in 0.1% saline without pH adjustment; or 3) neat PEG 400 without pH adjustment. The animals are then bled from the retro-orbital sinus three hours later for determination of blood metabolite levels. The freshly collected samples are centrifuged for two minutes at 10,000×g at room temperature. The supernatant is analyzed for glucose, for example, by the Abbott VP™ (Abbott Laboratories, Diagnostics Division, Irving, Tex.) and VP Super System® Autoanalyzer (Abbott Laboratories, Irving, Tex.), or by the Abbott Spectrum CCX™ (Abbott Laboratories, Irving, Tex.) using the A-Gent™Glucose-UV Test reagent system (Abbott Laboratories, Irving, Tex.) (a modification of the method of Richterich and Dauwalder, Schweizerische Medizinische Wochenschrift, 101: 860 (1971)) (hexokinase method) using a 100 mg/dl standard. Plasma glucose is then calculated by the equation: Plasma glucose (mg/dl)=Sample value×8.14 where 8.14 is the dilution factor, adjusted for plasma hematocrit (assuming the hematocrit is 44%).

The animals dosed with vehicle maintain substantially unchanged hyperglycemic glucose levels (e.g., greater than or equal to 250 mg/dl), animals treated with compounds having hypoglycemic activity at suitable doses have significantly depressed glucose levels. Hypoglycemic activity of the test compounds is determined by statistical analysis (unpaired t-test) of the mean plasma glucose concentration between the test compound group and vehicle-treated group on day 5. The above assay carried out with a range of doses of a test compound allows the determination of an approximate minimal effective dose (MED) value for the in vivo reduction of plasma glucose concentration.

Measurement of Insulin, Triglyceride, and Cholesterol Levels in the ob/ob Mouse

The compounds of the present invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of the present invention, by virtue of their hypocholesterolemic action, prevent, arrest and/or regress atherosclerosis.

Since the concentration of insulin in blood is related to the promotion of vascular cell growth and increased renal sodium retention, (in addition to the other actions, e.g., promotion of glucose utilization) and these functions are known causes of hypertension, the compounds of the present invention, by virtue of their hypoinsulinemic action, prevent, arrest and/or regress hypertension.

Since the concentration of triglycerides in blood contributes to the overall levels of blood lipids, the compounds of the present invention, by virtue of their triglyceride lowering and/or free fatty acid lowering activity prevent, arrest and/or regress hyperlipidemia.

Free fatty acids contribute to the overall level of blood lipids and independently have been negatively correlated with insulin sensitivity in a variety of physiologic and pathologic states.

Five to eight week old male C57BL/6J-ob/ob mice (obtained from Jackson Laboratory, Bar Harbor, Me.) are housed five per cage under standard animal care practices and fed standard rodent diet ad libitum. After a one-week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weight/volume (w/v)) in either (1) 10% DMSO/ 0.1% Pluronic® P105 Block Copolymer Surfactant (BASF Corporation, Parsippany, N.J.) in 0.1% saline without pH adjustment or (2) 0.25% w/v methylcellulose in water without pH adjustment. Alternatively, the compound to be tested can be administered by oral gavage dissolved in or in suspension in neat PEG 400. Single daily dosing (s.i.d.) or twice daily dosing (b.i.d.) is maintained for 1 to, for example, 15 days. Control mice receive the 10% DMSO/ 0.1% Pluronic® P105 in 0.1% saline without pH adjustment or the 0.25% w/v methylcellulose in water without pH adjustment, or the neat PEG 400 without pH adjustment.

Three hours after the last dose is administered, the animals are sacrificed and blood is collected into 0.5 ml serum separator tubes containing 3.6 mg of a 1:1 weight/weight sodium fluoride: potassium oxalate mixture. The freshly collected samples are centrifuged for two minutes at 10,000×g at room temperature, and the serum supernatant is transferred and diluted 1:1 volume/volume with a 1 TIU/ml aprotinin solution in 0.1% saline without pH adjustment.

The diluted serum samples are then stored at −80° C. until analysis. The thawed, diluted serum samples are analyzed for insulin, triglycerides, free fatty acids and cholesterol levels. Serum insulin concentration is determined using Equate® RIA INSULIN kits (double antibody method; as specified by the manufacturer) available from Binax, South Portland, Me. The interassay coefficient of variation is ≦10%. Serum triglycerides are determined using the Abbott VP™ and VP Super System® Autoanalyzer (Abbott Laboratories, Irving, Tex.), or the Abbott Spectrum CCX™ (Abbott Laboratories, Irving, Tex.) using the A-Gent™ Triglycerides Test reagent system (Abbott Laboratories, Diagnostics Division, Irving, Tex.) (lipase-coupled enzyme method; a modification of the method of Sampson, et al., *Clinical Chemistry* 21: 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. *Clinical Chemistry* 20: 470 (1974)) using 100 and 300 mg/dl standards. Serum free fatty acid concentration is determined utilizing a kit from WAKO (Osaka, Japan), as adapted for use with the Abbott VP™ and VP Super System® Autoanalyzer (Abbott Laboratories, Irving, Tex.), or the Abbott Spectrum CCX™ (Abbott Laboratories, Irving, Tex.). Serum insulin, triglycerides, free fatty acids and total cholesterol levels are then calculated by the equations: Serum insulin ($\mu$U/ml)=Sample value×2; Serum triglycerides (mg/dl)=Sample value×2; Serum total cholesterol (mg/dl)=Sample value×2; Serum free fatty acid ($\mu$Eq/l)=Sample value×2; where 2 is the dilution factor.

The animals dosed with vehicle maintain substantially unchanged, elevated serum insulin (e.g., 275 $\mu$U/ml), serum triglycerides (e.g., 235 mg/dl), serum free fatty acid (1500 mEq/ml) and serum total cholesterol (e.g., 190 mg/dl) levels. The serum insulin, triglycerides, free fatty acid and total cholesterol lowering activity of the test compounds are determined by statistical analysis (unpaired t-test) of the mean serum insulin, triglycerides, or total cholesterol concentration between the test compound group and the vehicle-treated control group.

Measurement of Energy Expenditure in Rats

As would be appreciated by those skilled in the relevant art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity.

The ability of the Formula I compounds of the present invention to generate a thermogenic response can be demonstrated according to the following protocol: This in vivo screen is designed to evaluate the efficacy of compounds that are PPAR agonists, using as an efficacy endpoint measurement of whole body oxygen consumption. The protocol involves: (a) dosing fatty Zucker rats for about 6 days, and (b) measuring oxygen consumption. Male fatty Zucker rats having a body weight range of from about 400 g to about 500 g are housed for from about 3 to about 7 days in individual cages under standard laboratory conditions prior to the initiation of the study. A compound of the present invention and a vehicle is administered by oral gavage as a single daily dose given between about 3 p.m. to about 6 p.m. for about 6 days. A compound of the present invention is dissolved in vehicle containing about 0.25% of methyl cellulose. The dosing volume is about 1 ml.

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment. The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 L/min to about 1.7 L/min. The Oxymax software then calculates the oxygen consumption (mL/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 min for from about 5 h to about 6.5 h. Resting oxygen consumption is calculated on individual rats by averaging the values excluding the first 5 values and the values obtained during time periods where ambulatory activity exceeds about 100 counts.

In Vivo Atherosclerosis Assay

Anti-atherosclerotic effects of the compounds of the present invention can be determined by the amount of compound required to reduce the lipid deposition in rabbit aorta. Male New Zealand White rabbits are fed a diet containing 0.2% cholesterol and 10% coconut oil for 4 days (meal-fed once per day). Rabbits are bled from the marginal ear vein and total plasma cholesterol values are determined from these samples. The rabbits are then assigned to treatment groups so that each group has a similar mean ±SD for total plasma cholesterol concentration, HDL cholesterol concentration and triglyceride concentration. After group assignment, rabbits are dosed daily with compound given as a dietary admix or on a small piece of gelatin based confection. Control rabbits receive only the dosing vehicle, be it the food or the gelatin confection. The cholesterol/coconut oil diet is continued along with the compound administration throughout the study. Plasma cholesterol, HDL-cholesterol, LDL cholesterol and triglyceride values can be determined at any point during the study by obtaining blood from the marginal ear vein. After 3–5 months, the rabbits are sacrificed and the aortae are removed from the thoracic arch to the branch of the iliac arteries. The aortae are cleaned of adventitia, opened longitudinally and then stained with Sudan IV as described by Holman et. al. (Lab. Invest. 1958, 7, 42–47). The percent of the surface area stained is quantitated by densitometry using an Optimas Image Analyzing System (Image Processing Solutions; North Reading Mass.). Reduced lipid deposition is indicated by a reduction in the percent surface area stained in the compound-receiving group in comparison with the control rabbits.

Administration of the compounds of the present invention can be via any method which delivers a compound of this invention systemically and/or locally. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate or where the patient is unable to ingest the drug.

In general an amount of a compound of the present invention is used that is sufficient to achieve the therapeutic effect desired (e.g., lipid lowering).

In general an effective dosage for the Formula I compounds of the present invention, their prodrugs and the salts of such compounds and prodrugs is in the range of about 0.001 to about 100 mg/kg/day, preferably about 0.005 to about 5 mg/kg/day.

A dosage of the combination pharmaceutical agents to be used in conjunction with the PPAR agonists is used that is effective for the indication being treated. Such dosages can be determined by standard assays such as those referenced above and provided herein. The combination agents may be administered simultaneously or sequentially in any order.

For example, typically an effective dosage for HMG-CoA reductase inhibitors is in the range of about 0.01 to about 100 mg/kg/day.

The compounds of the present invention are generally administered in the form of a pharmaceutical composition comprising at least one of the compounds of this invention together with a pharmaceutically acceptable vehicle, diluent or carrier. Thus, the compounds of the present invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol™ or Capmul™, in a soft gelatin capsule. Antioxidants may be added to prevent long term degradation as appropriate. When aqueous suspensions and/or elixirs are desired for oral administration, the compounds of the present invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 19th Edition (1995).

Pharmaceutical compositions according to the present invention may contain 0.1%–95% of the compound(s) of the present invention, preferably 1%–70%. In any event, the composition or formulation to be administered will contain a quantity of a compound(s) according to the present invention in an amount effective to treat the disease/condition of the subject being treated, e.g., atherosclerosis.

Since the present invention has an aspect that relates to the treatment of the disease/conditions described herein with a combination of active ingredients, which may be administered separately, the invention also relates to combining separate pharmaceutical compositions in kit form. The kit comprises two separate pharmaceutical compositions: a compound of Formula I of the present invention, a prodrug thereof or a salt of such compound or prodrugs and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . ." etc. Other variations of memory aids will be readily apparent. A "daily dose" can be a single tablet or capsule or several pills or capsules to be taken on a given day. Also, a daily dose of a compound of the present invention can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention either alone or in combination with each other or other compounds generally will be administered in a convenient formulation. The following formulation examples only are illustrative and are not intended to limit the scope of the present invention.

In the formulations which follow, "active ingredient" means a compound of the present invention.

| Formulation 1: Gelatin Capsules Hard gelatin capsules are prepared using the following: | |
|---|---|
| Ingredient | Quantity (mg/capsule) |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

| Formulation 2: Tablets | |
|---|---|
| Ingredient | Quantity (mg/tablet) |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

| Formulation 3: Tablets | |
|---|---|
| Ingredient | Quantity (mg/tablet) |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

| Formulation 4: Suspensions | |
|---|---|
| Ingredient | Quantity (mg/5 ml) |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

| Formulation 5: Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6: Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
|---|---|
| Ingredient | Quantity |
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

| Formulation 8: Soft Gelatin Capsule with Oil Formulation | |
|---|---|
| Ingredient | Quantity (mg/capsule) |
| Active ingredient | 10–500 |
| Olive Oil or Miglyol ™ Oil | 500–1000 |

The active ingredient above may also be a combination of therapeutic agents.

General Experimental Procedures

NMR spectra were recorded on a Varian XL-300 (Varian Co., Palo Alto, Calif.), a Bruker AM-300 spectrometer (Bruker Co., Billerica, Mass.) or a Varian Unity 400 at ambient temperature. Chemical shifts are expressed in parts per million (δ) relative to residual solvent as an internal reference. The peak shapes are denoted as follows: s, singlet; d, doublet; dd, doublet of doublets, t, triplet, q, quartet; m, multiplet; brs=broad singlet; 2s, two singlets. Atmospheric pressure chemical ionization (APCI) mass spectra in alternating positive and negative ion mode were obtained on a Fisons Platform II Spectrometer, Fisons Instruments Manchester U.K.). Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. Optical rotations were determined on a Perkin-Elmer 241 polarimeter (Perkin-Elmer Instruments, Norwalk, Conn.) using the sodium D line (λ=589 nm) at the indicated temperature and are reported as follows $[\alpha]_D^{temp}$, concentration (c=g/100 mL), and solvent.

Column chromatography was performed with either Baker Silica Gel (40 μm) (J. T. Baker, Phillipsburg, N.J.) or Silica Gel 50 (EM Sciences, Gibbstown, N.J.) in glass columns or in Flash 40 (Biotage, Dyar Corp. Charlottesville, Va.) columns under low nitrogen pressure. Radial Chromatography was performed using a Chromatron (model 7924T, Harrison Research, Palo Alto, Calif.). Unless otherwise specified, reagents were used as obtained from commercial sources. Dimethylformamide, 2-propanol, tetrahydrofuran, toluene and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "evaporated" refer to removal of solvent at 5–200 mm of mercury pressure on a rotary evaporator with a bath temperature of less than 45° C. Reactions conducted at "0–20° C." or "0–25° C." were conducted with initial cooling of the vessel in an insulated ice bath which was then allowed to warm to room temperature. The abbreviation "min" and "h" stand for "minutes" and "hours" respectively. The abbreviation "rt" stands for "room temperature." Other abbreviations, which would be readily understandable to one of ordinary skill in the art, are used, such as the following: "$N_2$" stands for nitrogen; "$CH_2Cl_2$" stands for dichloromethane; "THF" stands for tetrahydrofuran; "$NaHCO_3$" stands for sodium bicarbonate.

Preparation 1

3-(3-Methoxyphenyl)-1H-piperidine

Method A:

3-(3-Methoxyphenyl)pyridine 3-bromo anisole (17.4 g, 93.03 mmol) was dissolved in 650 mL tetrahydrofuran and 210 mL water in a 2 L round bottom flask equipped with a magnetic stirrer. Diethyl-(3-pyridyl)borane (15.73 g, 106.99 mmol), sodium carbonate (44.4 g, 418.64 mmol) and dichlorobis(triphenylphosphine) palladium (II) (9.8 g, 13.95 mmol) were added and the mixture heated at reflux for 4 h then cooled to ambient temperature. The mixture was diluted with 300 mL water and extracted with diethyl ether (2×300 mL). The extracts were combined and dried over anhydrous sodium sulfate, filtered and concentrated under reduced pressure. The resultant oil was purified by flash chromatography (1:1 ethyl acetate/hexanes). Product fractions were concentrated under reduced pressure to yield 17.75 g (99%) of the desired compound as a pale yellow oil.

MS (APCI) 186.1 (M+H)+.

¹H NMR (400 MHz, CDCl₃) δ 8.85 (d, 1H), 8.60 (d, 1H), 7.92 (dd, 1H), 7.39 (m, 2H), 7.13 (dd, 1H), 7.08 (t, 1H), 6.94 (dd, 1H), 3.85 (s, 3H).

3-(3-Methoxyphenyl)-1H-piperidine 3-(3-methoxyphenyl)pyridine (17.75 g, 95.4 mmol) was dissolved in 200 mL methanol. 30 mL of 12N HCl and 1.8 g platinum(II)oxide were added and the suspension was hydrogenated at 55 psi for 6 h. The reaction mixture was filtered through celite and the filter plug was washed with 200 mL methanol. The filtrate was concentrated under reduced pressure. The resultant slurry was taken up in 200 mL water and made basic with 5N aqueous sodium hydroxide and extracted with ethyl acetate (3×300 mL). The extracts were combined and dried over anhydrous sodium sulfate, filtered and concentrated under reduced pressure. The resultant solid was taken up in 200 mL diethyl ether. Anhydrous hydrogen chloride gas was bubbled into the ether solution forming a white precipitate that was collected by filtration. The white solid was recrystallized from hot ethanol/diethyl ether to yield 10.22 g (47%) of the desired compound as a white solid.

LC-MS 192.4 (M+H)+.

¹H NMR (400 MHz, CDCl₃) δ 9.86 (br s, 1H), 9.61 (brs, 1H), 7.21 (m, 1H), 6.79 (t, 2H), 6.73 (s, 1H), 3.79 (s, 3H), 3.55 (d, 3H), 3.21 (t, 1H), 2.88 (m, 2H), 2.08 (m, 3H), 1.63 (m, 1H).

Method B:

3-(3-Methoxyphenyl)pyridine 3-bromopyridine (37.49 g, 237.2 mmol) and 3-methoxybenzene boronic acid (36.06 g, 237.3 mmol) were dissolved in 300 mL dimethoxyethane in a 1 L round bottom flask equipped with a magnetic stirrer. Sodium carbonate (50.3 g, 474.6 mmol) was added as a solution in 200 mL water.

Tetrakis(triphenylphosphine)palladium(0) (6.85 g, 5.93 mmol) was added and the mixture was heated at reflux for 4 h then cooled to ambient temperature and diluted with 400 mL water. The mixture was extracted with diethyl ether (2×300 mL). The organic phases were combined and extracted with 1N HCl (2×300 mL). The acidic extractions were combined and made basic with 5N aqueous sodium hydroxide. This basic layer was extracted with diethyl ether (2×500 mL) and the extracts were combined and dried over anhydrous sodium sulfate, filtered and concentrated under reduced pressure to yield 43.89 g (99%) of the desired compound as a pale yellow oil.

MS (APCI) 186.1 (M+H)+.

¹H NMR (400 MHz, CDCl₃) δ 8.85 (d, 1H), 8.60 (d, 1H), 7.92 (dd, 1H), 7.39 (m, 2H), 7.13 (dd, 1H), 7.08 (t, 1H), 6.94 (dd, 1H), 3.85 (s, 3H).

3-(3-Methoxyphenyl)-1H-piperidine

A 2 L hydrogenation vessel was charged with 4.4 g platinum(II)oxide and purged with nitrogen. 3-(3-methoxyphenyl)pyridine (43.89 g, 235.47 mmol) was added as a solution in 500 mL acetic acid. The suspension was hydrogenated at 45 psi for 6 h. The catalyst was filtered through celite and the filter plug was washed with 200 mL acetic acid. The filtrate was concentrated under reduced pressure. The resultant oil was taken up in 500 mL water and made basic with 5N aqueous sodium hydroxide. This basic layer was extracted with diethyl ether (2×500 mL) and the extracts were combined and dried over anhydrous sodium sulfate, filtered and concentrated under reduced pressure. The resultant solid was taken up in 200 mL diethyl ether. Anhydrous hydrogen chloride gas was bubbled into the ether solution forming a white precipitate that was collected by filtration. The white solid was recrystallized from hot ethanol/diethyl ether to yield 22.50 g (58%) of the desired compound as a white solid.

LC-MS 192.4 (M+H)+.

¹H NMR (400 MHz, CDCl₃) δ 9.86 (br s, 1H), 9.61 (br s, 1H), 7.21 (m, 1H), 6.79 (t, 2H), 6.73 (s, 1H), 3.79 (s, 3H), 3.55 (d, 3H), 3.21 (t, 1H), 2.88 (m, 2H), 2.08 (m, 3H), 1.63 (m, 1H).

Preparation 2

Preparation of
2-methyl-2-(3-piperidin-3-yl-phenoxy)-propionic acid alkyl esters Method C: Preparation of 2-methyl-2-(3-piperidin-3-yl-phenoxy)-propionic acid benzyl ester 3-Hydroxyphenyl-1H-piperidine 3-methoxyphenyl-1H-piperidine (Methods A and B; 22.50 g, 98.8 mmol) was slowly dissolved in hydrobromic acid (100 mL) and the resulting mixture heated at 140° C. for 4 h. After cooling to ambient temperature, the hydrobromic acid and water were distilled off and the resulting brown oil was azeotroped with toluene (3×100 mL) and dried under high vacuum for 18 h. The resultant tan solid was taken on to the next step without further purification.

MS (APCI) 178.1 (M+H)+.

¹H NMR (400 MHz, DMSO$_{d6}$) δ 8.80 (br s, 1H), 8.51 (br s, 1H), 7.10 (t, 1H), 6.65 (t, 2H), 6.63 (s, 1H), 3.26 (d, 2H), 3.00–2.80 (m, 3H), 2.48 (br s, 2H), 1.77–1.59 (m, 2H).

3-(3-Hydroxy-phenyl)-piperidine-1-carboxylic acid tert-butyl ester 3-hydroxyphenyl-1H-piperidine (15.85 g, 61.39 mmol) was dissolved in 140 mL of 2:1 tetrahydrofuran/water. Sodium bicarbonate (5.16 g, 61.39 mmol) and di-t-butyl dicarbonate (13.40 g, 61.39 mmol) were added and the reaction was heated at reflux for 4 h then cooled to ambient temperature. The mixture was diluted with 300 mL water and extracted with ethyl acetate (3×250 mL). The extracts were combined, dried over anhydrous sodium sulfate, filtered and concentrated under reduced pressure. The resultant yellow oil was taken on to the next step without further purification.

LC-MS 276.3 (M+H)+.

¹H NMR (400 MHz, CDCl₃) δ 7.16 (t, 1H), 6.77 (d, 1H), 6.71 (d, 1H), 6.69 (dd, 1H), 4.15 (t, 2H), 2.72 (t, 2H), 2.62 (t, 1H), 1.98 (m, 1H), 1.76 (m, 1H), 1.58 (m, 1H), 1.47 (s, 9H).

3-[3-(1-Carboxy-1-methyl-ethoxy)-phenyl]-piperidine-1-carboxylic acid tert-butyl ester 3-(3-Hydroxy-phenyl)-piperidine-1-carboxylic acid tert-butyl ester (17.03 g, 61.39 mmol) was dissolved in 420 mL acetone in a 3-neck 1 L round bottom flask equipped with a mechanical stirrer. 1,1,1-trichloro-2-methyl-2-propanol hydrate (21.80 g, 122.78 mmol) was added and the solution was cooled to 0° C. Sodium hydroxide pellets (19.65 g, 491.12 mmol) were added to the solution at 0° C. over 4 h in four portions. The reaction mixture warmed to ambient temperature between additions and then recooled. Once the additions were complete, the reaction mixture was allowed to stir at ambient temperature for 24 h and then concentrated under reduced pressure. The resulting residue was taken up in water (500 mL), acidified with 6N aqueous hydrochloric acid, stirred 10 min and then extracted with ethyl acetate (3×300 mL). The combined organics were washed with saturated aqueous sodium chloride, dried over anhydrous sodium sulfate, filtered and concentrated under reduced pressure to provide 3-[3-(1-Carboxy-1-methyl-ethoxy)-phenyl]-piperidine-1-carboxylic acid tert-butyl ester as a brown oil which was taken on to the next step without further purification.

LC-MS 362.4 (M+H)+.

3-[3-(1-Benzyloxycarbonyl-1-methyl-ethoxy)-phenyl]-piperidine-1-carboxylic acid tert-butyl ester Cesium carbonate (24.00 g, 73.67 mmol) and benzyl bromide (8.03 mL, 67.53 mmol) were added sequentially to a solution of of 3-[3-(1-Carboxy-1-methyl-ethoxy)-phenyl]-piperidine-1-carboxylic acid tert-butyl ester (22.31 g, 61.39 mmol) and dimethylformamide (100 mL) at ambient temperature. The resulting mixture was warmed to 60° C., stirred 1.5 h, cooled to ambient temperature and diluted with water (600 mL). The aqueous solution was extracted with diethyl ether (2×300 mL). The organic extracts were combined and washed with saturated aqueous sodium chloride, dried over anhydrous sodium sulfate, filtered, and concentrated under reduced pressure. The resultant oil was purified by flash column chromatography (7:1 hexanes/ethyl acetate) to provide 3-[3-(1-Benzyloxycarbonyl-1-methyl-ethoxy)-phenyl]-piperidine-1-carboxylic acid tert-butyl ester as a pale-yellow oil.

$^1$H NMR (400 MHz, CDCl$_3$) δ 7.30 (m, 3H), 7.23 (m, 2H), 7.09 (t, 1H), 6.83 (d, 1H), 6.70 (d, 1H), 6.59 (dd, 1H), 5.19 (s, 2H), 4.14 (d, 2H), 2.65 (m, 2H), 2.54 (m, 1H), 1.93 (m, 1H), 1.71 (m, 1H), 1.60 (s, 6H), 1.46 (s, 9H).

2-Methyl-2-(3-piperidin-3-yl-phenoxy)-propionic acid benzyl ester

3-[3-(1-Benzyloxycarbonyl-1-methyl-ethoxy)-phenyl]-piperidine-1-carboxylic acid tert-butyl ester was dissolved in 125 mL of 20% trifluoroacetic acid/methylene chloride and stirred for 20 minutes. The reaction mixture was evaporated under reduced pressure. The resultant oil was taken up in 400 mL water, made basic with 5N aqueous sodium hydroxide and extracted with ethyl acetate (3×300 mL). The extracts were combined, dried over anhydrous sodium sulfate, filtered and concentrated under reduced pressure to yield 11.72 g (54% 3 steps) of 2-methyl-2-(3-piperidin-3-yl-phenoxy)-propionic acid benzyl ester as a pale yellow oil.

LC-MS 354.4 (M+H)+.

$^1$H NMR (400 MHz, CDCl$_3$) δ 7.29 (m, 3H), 7.23 (m, 2H), 7.08 (t, 1H), 6.81 (d, 1H), 6.69 (d, 1H), 6.58 (dd, 1H), 5.19 (s, 2H), 3.11 (m, 2H), 2.61 (m, 3H), 1.93 (m, 1H), 1.75 (m, 1H), 1.61 (s, 6H), 1.57 (m, 1H).

Method D: Preparation of 2-methyl-2-(3-piperidin-3-yl-phenoxy)-propionic acid ethyl ester L-tartrate salt 3-(3-Hydroxyphenyl)pyridine 3-bromophenol (49.42 g, 285.66 mmol) and diethyl-(3-pyridyl)borane (40.00 g, 272.05 mmol) were dissolved in 945 mL of a 4:2:1 mixture of THF/H$_2$O/ethanol in a 2 L round bottom flask equipped with a magnetic stirrer. Sodium carbonate (57.7 g, 544.11 mmol) and tetrakis(triphenylphosphine)palladium(0) (3.14 g, 2.72 mmol) was added and the mixture was heated at reflux for 2 h then cooled to ambient temperature and stirred an additional 18 h. The mixture was diluted with 400 mL water and extracted with ethyl acetate (3×500 mL). The organic phases were combined and dried over anhydrous sodium sulfate, filtered and concentrated to a volume of 1 L. The organic solution was diluted with 500 mL water and made acidic with 12N HCl. The layers were separated and the organic phase extracted with water (2×300 mL). The acidic extractions were combined and made basic with 5N aqueous sodium hydroxide. This basic layer was extracted with diethyl ether (3×500 mL) and the extracts were combined, washed with 500 mL brine, dried over anhydrous sodium sulfate, filtered and concentrated under reduced pressure to yield 40.91 g (88%) of 3-(3-hydroxyphenyl)pyridine as a pale yellow oil which crystallized on standing.

LC-MS 172.1 (M+H)+.

$^1$H NMR (400 MHz, CD$_3$OD) δ 8.74 (d, 1H), 8.49 (dd, 1H), 8.04 (dd, 1H), 7.49 (dt, 1H), 7.30 (t, 1H), 7.09 (dd, 1H), 7.04 (t, 1H), 6.84 (dd, 1H).

2-Methyl-2-(3-pyridin-3-yl-phenoxy)-propionic acid ethyl ester

To a solution of 3-(3-hydroxyphenyl)pyridine (40.91 g, 0.239 mol) in 500 mL dimethylformamide was added potassium carbonate (148.62 g, 1.075 mol) and ethyl-2-bromoisobutyrate (157.8 mL, 1.075 mol). The mixture was heated to reflux under N$_2$ with stirring for 18 h and cooled to ambient temperature. The resultant brown suspension was diluted with 1 L water and extracted with diethyl ether (3×500 mL). The organic phases were combined and dried over anhydrous sodium sulfate, filtered and concentrated to a volume of 1 L. The organic solution was diluted with 1 L water and made acidic with 6N HCl. The layers were separated and the organic phase extracted with 500 mL water. The acidic extractions were combined and made basic with 5N aqueous sodium hydroxide. This basic layer was extracted with diethyl ether (4×500 mL) and the extracts were combined, washed with 500 mL brine, dried over anhydrous sodium sulfate, filtered and concentrated under reduced pressure to yield crude 2-methyl-2-(3-pyridin-3-yl-phenoxy)-propionic acid ethyl ester as a pale yellow oil which was taken on to the next step without further purification.

LC-MS 286.4 (M+H)+.

$^1$H NMR (400 MHz, CDCl$_3$) δ 8.82 (brs, 1H), 8.59 (d, 1H), 7.89 (d, 1H), 7.40 (m, 1H), 7.35 (t, 1H), 7.21 (d, 1H), 7.10 (t, 1H), 6.86 (dd, 1H), 4.24 (q, 2H), 1.64 (s, 6H), 1.25 (t, 3H).

2-Methyl-2-(3-piperidin-3-yl-phenoxy)-propionic acid ethyl ester L-tartrate salt A 2 L hydrogenation vessel was charged with 5.0 g platinum(II)oxide and purged with nitrogen. Crude 2-methyl-2-(3-pyridin-3-yl-phenoxy)-propionic acid ethyl ester (approximately 68.20 g, 238.96 mmol) was added as a solution in 800 mL acetic acid. The suspension was hydrogenated at 45 psi for 18 h. The catalyst was filtered through celite and the filter plug was washed with 200 mL acetic acid. The filtrate was concentrated under reduced pressure. The resultant oil was taken up in 500 mL water and made basic with 5N aqueous sodium hydroxide. This basic layer was extracted with diethyl ether (3×500 mL) and the extracts were combined and dried over anhydrous sodium sulfate, filtered and concentrated under reduced pressure. The resultant solid was taken up in 500 mL diethyl ether. L-(+)-tartaric acid was added into the ether solution and was allowed to stir at ambient temperature for 48 h, forming a white precipitate that was collected by filtration. The white solid was recrystallized from hot ethanol (1.5 L) to yield 78.0 g (74%, 2 steps) of the desired compound as a white solid.

LC-MS 292.4 (M+H)+.

$^1$H NMR (400 MHz, DMSO$_{d6}$) δ 7.21 (t, 1H), 6.89 (d, 1H), 6.71 (s, 1H), 6.63 (dd, 1H), 4.15 (q, 2H), 3.90 (s, 2H), 3.25 (d, 2H), 2.90 (m, 3H), 1.84 (d, 2H), 1.73 (d, 1H), 1.64 (t, 1H), 1.51 (s, 6H), 1.15 (t, 3H).

Method E: Preparation of (3S)-2-methyl-2-(3-piperidin-3-yl-phenoxy)-propionic acid methyl ester 3-Pyridin-3-yl-phenol A mixture of diethyl(3-pyridyl)borane (11.80 g, 80.0 mmol), 3-bromophenol (16.60 g, 96.0 mmol), Pd(PPh$_3$)$_4$ (0.92 g, 0.80 mmol), and Na$_2$CO$_3$ (17.0 g, 160.0 mmol) in toluene/water/ethanol (160/80/40 mL) was purged with nitrogen for 5 min and then heated at reflux under nitrogen for 2 h. After solvent removal, the aqueous residue was partitioned between ethyl acetate/brine (400/250 mL). The separated organic layer was washed with brine, filtered, and concentrated. The solid residue was taken up in 130 mL of 3 M HCl, stirred for 15 min, diluted with brine (150 mL), and extracted with ethyl acetate (2×250 mL). The separated aqueous layer was cooled in ice/water bath, adjusted to pH 10 with solid NaOH and Na$_2$CO$_3$, and extracted with ethyl acetate (2×300 mL). The organic extract was dried over sodium sulfate and concentrated to give 12.60 g (92%) of 3-pyridin-3-yl-phenol as a light yellow solid: $^1$H NMR (CDCl$_3$) δ 6.99 (m, 1H), 7.08 (m, 1H), 7.22 (m, 1H), 7.36 (m, 1H), 7.43 (m, 1H), 8.00 (dd, 1H), 8.60 (d, 1H), 9.00 (s, 1H); MS m/z (relative intensity) 171 (M$^+$, 100), 142 (17), 115 (21).

2-Methyl-2-(3-pyridin-3-yl-phenoxy)-propionic acid ethyl ester

A mixture of 3-pyridin-3-yl-phenol (5.14 g, 30.0 mmol), ethyl 2-bromoisobutyrate (26.3 g, 135.0 mmol), and K$_2$CO$_3$ (18.7 g, 135.0 mmol) in anhydrous DMF (60 mL) was heated at 95° C. under nitrogen for 5 h. After cooling, brine (200 mL) was added and the mixture was extracted with ethyl acetate (250 mL). The separated organic layer was washed with brine, filtered, and concentrated. The oil residue was taken up in 80 mL of 3 M HCl, stirred for 15 min, diluted with brine (100 mL), and extracted with ethyl acetate (2×150 mL). The separated aqueous layer was cooled in ice/water bath, adjusted to pH 10 with solid Na$_2$CO$_3$, and extracted with ethyl acetate (2×200 mL). The organic extract was dried over sodium sulfate and concentrated to afford 6.70 g (78%) of 2-methyl-2-(3-pyridin-3-yl-phenoxy)-propionic acid ethyl ester as a light brown oil: $^1$H NMR (CDCl$_3$) δ 1.22 (t, 3H), 1.61 (s, 6H), 4.22 (q, 2H), 6.82 (dd, 1H), 7.08 (s, 1H), 7.20 (dd, 1H), 7.38 (m, 2H), 7.81 (dd, 1H), 8.59 (br s, 1H), 8.80 (br s, 1H); MS m/z (relative intensity) 285 (M$^+$, 11), 212 (22), 171 (100).

2-Methyl-2-(3-piperidin-3-yl-phenoxy)-propionic acid methyl ester 2-methyl-2-(3-pyridin-3-yl-phenoxy)-propionic acid ethyl ester (6.0 g, 21.03 mmol) was dissolved in methanol (70 mL) and followed by the addition of 37% HCl (5.3 mL) and 10% Pt/C (0.60 g). The mixture was shaken with hydrogen under 50 psi at 50° C. in a Parr bottle for 5 h, filtered through a pad of Celite, and rinsed with methanol. GC/MS showed complete hydrogenation and only 50% of methyl ester conversion. Concentrated H$_2$SO$_4$ (2.0 mL) was added to the filtrate and the resulting solution was allowed to reflux under nitrogen overnight. After removal of excess methanol, the residue was treated with saturated Na$_2$CO$_3$ (150 mL) and extracted with ethyl acetate (2×200 mL). The organic extract was washed with water, dried over sodium sulfate, and concentrated to give 4.80 g (82%) of 2-methyl-2-(3-piperidin-3-yl-phenoxy)-propionic acid methyl ester as a yellow oil: $^1$H NMR (CDCl$_3$) δ 1.59 (s, 6H), 1.78 (br, 1H), 1.97 (br d, 1H), 2.02 (br, 2H), 2.61 (m, 3H), 3.06 –3.13 (m, 2H), 3.76 (s, 3H), 6.61 (dd, 1H), 6.70 (s, 1H), 6.83 (d, 1H), 7.14 (t, 1H); MS m/z (relative intensity) 277 (M$^+$, 2), 218 (6), 176 (100).

2-Methyl-2-(3-piperidin-3-yl-phenoxy)-propionic acid methyl ester tartrate salt

2-Methyl-2-(3-piperidin-3-yl-phenoxy)-propionic acid methyl ester (4.80 g, 17.31 mmol) was dissolved in THF (80 mL) and followed by the addition of L-(+)-tartaric acid (2.86 g, 19.04 mmol). The resulting mixture was refluxed under nitrogen for 3 h. While the mixture was still hot, the solid was collected by vacuum-filtration, rinsed with THF, and further dried to afford 7.13 g (96%) of 2-methyl-2-(3-piperidin-3-yl-phenoxy)-propionic acid methyl ester tartrate salt as a white solid: $^1$H NMR (DMSO-d$_6$) δ 1.50 (s, 6H), 1.60–1.73 (m, 2H), 1.83 (d, 2H), 2.80–2.94 (m, 3H), 3.24 (d, 2H), 3.67 (s, 3H), 3.87 (s, 2H), 6.60 (d, 1H), 6.69 (s, 1H), 6.89 (d, 1H), 7.21 (t, 1H); MS m/z (relative intensity) 277 (M$^+$, 2), 218 (6), 176 (100).

(3S)-2-Methyl-2-(3-piperidin-3-yl-phenoxy)-propionic acid methyl ester

2-Methyl-2-(3-piperidin-3-yl-phenoxy)-propionic acid methyl ester tartrate salt (19.00 g) was dissolved in refluxing anhydrous THF/H$_2$O (475/22.3 mL). The solution was allowed to cool down slowly and stand at rt for 3 days. The solid was collected by vacuum-filtration and further dried to give 8.91 g (47%) of white solid.

8.84 g of the above solid was dissolved in refluxing anhydrous THF/H$_2$O (221/13.3 mL). The solution was allowed to cool down slowly and stand at rt for 3 days. The solid was collected by vacuum-filtration and further dried to afford 5.50 g (62%) of white, crystalline solid with 93.1% ee and an overall yield of 29%.

The resolved tartrate salt (5.50 g) was partitioned between saturated aqueous sodium carbonate (60 mL) and ethyl acetate (80 mL). The separated aqueous layer was extracted with ethyl acetate (50 mL) and the combined organic extract was dried over sodium sulfate. Solvent removal afforded 3.54 g (99%) of (3S)-2-methyl-2-(3-piperidin-3-yl-phenoxy)-propionic acid methyl ester as a colorless oil: $^1$H NMR (CDCl$_3$) δ 1.54 (m, 1H), 1.58 (s, 6H), 1.70 (br, 1H), 1.75 (br, 1H), 1.95 (br d, 1H), 2.59 (m, 3H), 3.05–3.12 (m, 2H), 3.76 (s, 3H), 6.60 (dd, 1H), 6.70 (s, 1H), 6.83 (d, 1H), 7.14 (t, 1H); MS m/z (relative intensity) 277 (M$^+$, 2), 218 (6), 176 (100).

HPLC analysis conditions: Daicel Chiralpak AD, 4.6×250 mm; hexanes/2-propanol/diethylamine (95/5/0.2); 1.5 mL/min; 270 nm.

Method F: Preparation of 2-Methyl-2-(3-piperidin-3-yl-phenoxy)-propionic acid methyl ester 2-Methyl-2-(3-pyridin-3-yl-phenoxy)-propionic acid methyl ester A mixture of 3-pyridin-3-yl-phenol (0.86 g, 5.0 mmol), methyl 2-bromoisobutyrate (3.60 g, 20.0 mmol), and K$_2$CO$_3$ (2.76 g, 20.0 mmol) in anhydrous DMF (10 mL) was heated at 93° C. under nitrogen for 3 h. After cooling, brine (40 mL) was added and the mixture was extracted with ethyl acetate (50 mL). The separated organic layer was washed with brine, filtered, and concentrated. The oil residue was taken up in 10 mL of 3 M HCl, stirred for 10 min, diluted with brine (10 mL), and extracted with ethyl acetate (2×30 mL). The separated aqueous layer was cooled in ice/water bath, adjusted to pH 10 with solid Na$_2$CO$_3$, and extracted with ethyl acetate (2×40 mL). The organic extract was dried over sodium sulfate and concentrated to afford 1.09 g (80%) of 2-methyl-2-(3-pyridin-3-yl-phenoxy)-propionic acid methyl ester as a yellow oil: $^1$H NMR (CDCl$_3$) δ 1.62 (s, 6H), 3.79 (s, 3H), 6.82 (dd, 1H), 7.08 (s, 1H), 7.20 (d, 1H), 7.38 (m, 2H), 7.81 (d, 1H), 8.59 (d, 1H), 8.80 (s, 1H); MS m/z (relative intensity) 271 (M$^+$, 20), 212 (30), 171 (100).

2-Methyl-2-(3-piperidin-3-yl-phenoxy)-propionic acid methyl ester

2-Methyl-2-(3-pyridin-3-yl-phenoxy)-propionic acid methyl ester (4.07 g, 15.0 mmol) was dissolved in methanol (40 mL) and followed by the addition of 37% HCl (3.8 mL) and 10% Pt/C (0.41 g). The mixture was shaken with hydrogen under 50 psi at 50° C. in a Parr bottle for 2 h, filtered through a pad of Celite, and rinsed with methanol. After solvent removal, the residue was treated with saturated aqueous $Na_2CO_3$ (100 mL) and extracted with ethyl acetate (2×100 mL). The organic extract was washed with water, dried over sodium sulfate, and concentrated to give 3.70 g (89%) of 2-methyl-2-(3-piperidin-3-yl-phenoxy)-propionic acid methyl ester as a yellow oil: $^1$H NMR (CDCl$_3$) δ 1.57 (br m, 1H), 1.60 (s, 6H), 1.78 (br, 1H), 1.86 (br, 1H), 1.97 (brd, 1H), 2.61 (m, 3H), 3.06–3.13 (m, 2H), 3.76 (s, 3H), 6.61 (dd, 1H), 6.70 (s, 1H), 6.83 (d, 1H), 7.14 (t, 1H); MS m/z (relative intensity) 277 (M$^+$, 2), 218 (6), 176 (100).

Preparation 3

Resolution of 2-methyl-2-(3-piperidin-3-yl-phenoxy)-propionic acid alkyl esters

Method E: Resolution of 2-methyl-2-(3-pyridin-3-yl-phenoxy)-propionic acid methyl ester Concentrated sulfuric acid (25 mL) was added to a solution of 2-methyl-2-(3-piperidin-3-yl-phenoxy)-propionic acid ethyl ester L-tartrate salt (Preparation 2, Method D; 110.0 g, 249.17 mmol) in 500 mL methanol. The solution was heated at reflux for 18 h and allowed to cool to ambient temperature. The methanol was removed under reduced pressure and the resultant oil taken up in 1 L water, made basic with 5N aqueous NaOH and extracted with ethyl acetate (2×500 mL). The extracts were combined and dried over anhydrous sodium sulfate, filtered and concentrated under reduced pressure. The resultant oil was taken up in 500 mL ethanol and L-(+)-tartaric acid (37.4 g, 249.17 mmol) was added and the suspension heated until all the solids were dissolved. The hot solution was allowed to cool to ambient temperature and stirred 18 h. The white precipitate (2-methyl-2-(3-pyridin-3-yl-phenoxy)-propionic acid methyl ester-(L)-tartrate salt) was collected by filtration. The white solid was recrystallized in hot THF to yield 56.23 g of partially resolved product (1:3 R/S) which was subjected to a second recrystallization in 5.8% water/THF (1.52 L) to yield 27.95 g of (S)-2-methyl-2-(3-pyridin-3-yl-phenoxy)-propionic acid methyl ester-(L)-tartrate salt (26.2%, 92.2% ee; $[α]_D^{25}$=12.3° (c 0.61, CH$_3$OH); HPLC analysis: chiralpak AD 1.5 mL/min, 5% isopropanol/hexanes w/0.5% diethylamine, retention time=6.15 min (R) and 7.46 min (S)) as a white solid. An analogous crystallization procedure with D-tartaric acid will yield the (R)-2-methyl-2-(3-pyridin-3-yl-phenoxy)-propionic acid methyl ester-(D)-tartrate salt.

LC-MS 278.4 (M+H)$^+$.

$^1$H NMR (400 MHz, DMSO$_{d6}$) δ 7.22 (t, 1H), 6.89 (d, 1H), 6.70 (s, 1H), 6.61 (dd, 1H), 3.84 (s, 2H), 3.68 (s, 3H), 3.25 (d, 2H), 2.83 (m, 2H), 1.84 (d, 2H), 1.69 (m, 2H), 1.51 (s, 6H).

Method F: Resolution of 2-methyl-2-(3-piperidin-3-yl-phenoxy)-propionic acid benzyl ester To a solution of L-(+)-tartaric acid in refluxing 2.5% water/2-butanone (105 mL) was added 2-methyl-2-(3-piperidin-3-yl-phenoxy)-propionic acid benzyl ester (Preparation 2, Method C; 9.11 g, 25.8 mmol) in 2.5% water/2-butanone (20 mL). The resulting solution was allowed to cool to ambient temperature with stirring. As the mixture cooled, a white solid precipitated out. The suspension was allowed to stir at ambient temperature for 64 h. The precipitate was collected on a Buchner funnel and rinsed with 2-butanone and dried under vacuum to yield 5.66 g (44%) of 2-methyl-2-(3-piperidin-3-yl-phenoxy)-propionic acid benzyl ester-L-(+)-tartrate salt (87.5% ee). The white solid was slurried in 2.5% water/2-butanone (59.5 mL) and heated to reflux. Water was added slowly until the milky suspension became clear. The resulting solution was allowed to cool to ambient temperature with stirring. As the mixture cooled, a white solid precipitated out. The suspension was allowed to stir at ambient temperature for 64 h. The precipitate was collected on a Buchner funnel and rinsed with 2-butanone and dried under vacuum to yield 4.86 g (37% overall) of (S)-2-methyl-2-(3-piperidin-3-yl-phenoxy)-propionic acid benzyl ester-L-(+)-tartrate salt (98% ee; $[α]_D^{25}$=11.2° (c 0.86, CH$_3$OH); HPLC analysis: chiralpak AD 1.5 mL/min, 5% isopropanol/hexanes w/0.5% diethylamine, retention time=6.65 min (R) and 8.08 min (S)).

An analogous crystallization procedure with D-tartaric acid will yield the (R)-2-methyl-2-(3-piperidin-3-yl-phenoxy)-propionic acid benzyl ester-(D)-tartrate salt: (R)-enriched 2-methyl-2-(3-piperidin-3-yl-phenoxy)-propionic acid benzyl ester free base was recovered from the mother liquor of the L-(+)-tartaric acid resolution that gave the resolved (S) enantiomer by partitioning between 0.5M aqueous NaOH and Et$_2$O. Concentration of the Et$_2$O phase gave an orange oil that showed an enantiomer ratio of 83:17, R:S by chiral HPLC.

D-(−)-tartaric acid (3.80 g, 25.3 mmol) was suspended in 105 mL of 2-butanone containing 2.5% water, then the suspension was warmed to reflux to give a clear solution. (R)-enriched 2-methyl-2-(3-piperidin-3-yl-phenoxy)-propionic acid benzyl ester (9.10 g, 25.7 mmol) was dissolved in 15 mL of of 2-butanone containing 2.5% water and was then added to the refluxing solution of D-(−)-tartaric acid. The reaction solution stirred at reflux for 15 minutes, then cooled slowly to room temperature and stirred for 16 hr. The resulting white precipitate was collected by filtration and rinsed with 2-butanone followed by drying in vacuo to give (R)-2-methyl-2-(3-piperidin-3-yl-phenoxy)-propionic acid benzyl ester-(D)-tartrate salt (9.64 g, 89%, 93% e.e.) as a white solid.

LC-MS 354.4 (M+H)$^+$.

$^1$H NMR (400 MHz, DMSO$_{d6}$) δ 7.31 (m, 3H), 7.15 (m, 2H), 6.88 (d, 1H), 6.69 (s, 1H), 6.57 (dd, 1H), 5.16 (s, 1H), 3.85 (s, 1H), 3.22 (d, 1H), 2.87 (q, 1H), 2.81 (m, 2H), 1.80 (t, 2H), 1.71 (m, 1H), 1.58 (m, 1H), 1.52 (s, 6H).

EXAMPLE 1

2-(3-{1-[(4-Isopropyl-phenyl)-acetyl]-piperidin-3-yl}-phenoxy)-2-methyl-propionic acid benzyl ester To a solution of 2-methyl-2-(3-piperidin-3-yl-phenoxy)-propionic acid benzyl ester (Preparation 2, Method C; 0.54 g, 1.52 mmol) in 5 mL methylene chloride was added 4-isopropylphenyl acetic acid (0.33 g, 1.83 mmol) and 1-(3-dimethylaminopropyl)-3-ethylcarbodiimide hydrochloride (0.58 g, 3.04 mmol) and allowed to stir 18 h at ambient temperature. The reaction was concentrated under reduced pressure and the resultant oil flash chromatographed with 30% ethyl acetate/hexanes to yield 0.696 g (89%) of 2-(3-{1-[(4-Isopropyl-phenyl)-acetyl]-piperidin-3-yl}-phenoxy)-2-methyl-propionic acid benzyl ester as a clear oil.

LC-MS 514.6 (M+H)⁺.

¹H NMR (400 MHz, CDCl₃) δ Rotomeric mixture: 1.25 (d, 6H), 1.52(m, 2H), 1.59(s, 6H), 1.75(m, 1H), 1.86(m, 1H), 2.13(m, 1H), 2.47(m, 1H), 2.82(t, 1H), 2.91(m, 1H), 3.71(m, 3H), 4.72(d, 1H), 5.18(s, 2H), 6.42(d, 0.5H), 6.51 (s, 0.5H), 6.58(t, 1H), 6.71 (s, 0.5H), 6.83(m, 0.5H), 7.06(m, 1H), 7.18(m, 3H), 7.21(m, 2H), 7.29(m, 3H).

2-(3-{1-[(4-Isopropyl-phenyl)-acetyl]-piperidin-3-yl}-phenoxy)-2-methyl-propionic acid 10% Palladium on carbon (50 mg, 10 wt %) was added to a solution of 2-(3-{1-[(4-isopropyl-phenyl)-acetyl]-piperidin-3-yl}-phenoxy)-2-methyl-propionic acid benzyl ester (494 mg, 0.96 mmol) in methanol (15 mL) and the resulting mixture hydrogenated at atmospheric pressure for 3 h. The reaction mixture was filtered through a plug of celite and the celite plug washed thoroughly with ethyl acetate. The combined filtrates were concentrated under reduced pressure to provide 319 mg (78%) of 2-(3-{1-[(4-Isopropyl-phenyl)-acetyl]-piperidin-3-yl}-phenoxy)-2-methyl-propionic acid as a clear oil.

LC-MS 424.5 (M+H)⁺.

¹H NMR (400 MHz, DMSO$_{d6}$) δ 1.18(m, 6H), 1.33(s, 6H), 1.70(m, 3H), 2.08(t, 1H), 2.37(t, 1H), 2.55(m, 1H), 2.84 (m, 1H) 2.90(q, 1H), 3.65(m, 2H), 3.78(d, 1H), 3.95(d, 1H), 4.42(dd, 1H), 6.32(d, 1H), 6.49(s, 1H), 6.63(m, 2H), 6.98(dt, 1H), 7.14(m, 3H).

Examples 1-1 to 1-64 were prepared from analogous starting materials using methods analogous to those described in Example 1.

EXAMPLE 1-1

2-(3-{1-[(3-Methoxy-phenyl)-acetyl]-piperidin-3-yl}-phenoxy)-2-methyl-propionic acid ¹H NMR (400 MHz, CDCl₃) δ Rotomeric mixture: 1.31 (m, 0.5H), 1.42(m, 0.5H), 1.55(s, 6H), 1.62(m, 0.5H), 1.76 (d, 0.5H), 1.92(dd, 0.5H), 2.18(t, 0.5H), 2.51(t, 0.5H), 2.60(d, 0.5H), 2.89(t, 0.5H), 2.95(t, 0.5H), 3.76(m, 5H), 4.62(m, 1H), 6.52(s, 0.5H), 6.62(d, 0.5H), 6.78(m, 4H), 7.21(t, 1H), 7.19(m, 1H).

APCI-MS (M+1=412.3).

EXAMPLE 1-2

2-(3-{1-[(4-Methoxy-phenyl)-acetyl]-piperidin-3-yl}-phenoxy)-2-methyl-propionic acid ¹H NMR (400 MHz, CDCl₃) δ Rotomeric mixture: 1.24 (m, 1H), 1.45(m, 1H), 1.55(s, 6H), 1.63(m, 0.5H), 1.71(m, 0.5H), 1.83(d, 0.5H), 1.95(d, 0.5H), 2.04(t, 0.5H), 2.56(m, 1H), 2.89(m, 1H), 3.63(m, 2H), 3.68(s, 1H), 3.76(s, 2H), 4.61 (dd, 1H), 6.45(s, 0.5H), 6.63(d, 0.5H), 6.75(t, 1H), 6.86(m, 3H), 7.13(m, 3H).

APCI-MS (M+1=412.3).

EXAMPLE 1-3

2-(3-{1-[(4-Fluoro-phenyl)-acetyl]-piperidin-3-yl}-phenoxy)-2-methyl-propionic acid ¹H NMR (400 MHz, CDCl₃) δ Rotomeric mixture: 1.21 (m, 1H), 1.47(m, 1H), 1.55(s, 6H), 1.72(m, 1H), 1.93(t, 1H), 2.12(t, 0.5H), 1.52(t, 0.5H), 1.59(m, 1H), 2.96(m, 1H), 3.65(d, 1H), 3.71 (s, 1H), 3.82(d, 1H), 4.61 (dd, 1H), 6.60(s, 0.5H), 6.63(d, 0.5H), 6.74(t, 1H), 6.77(s, 0.5H), 6.85(d, 0.5H), 6.98(m, 2H), 7.18(m, 3H).

APCI-MS (M+1=400.2).

EXAMPLE 1-4

2-(3-{1-[(4-Hydroxy-phenyl)-acetyl]-piperidin-3-yl}-phenoxy)-2-methyl-propionic acid ¹H NMR (400 MHz, CDCl₃) δ 1.56(s, 6H), 1.69(t, 1H), 1.90(m, 1H), 2.51(t, 1H), 2.61 (m, 1H), 2.93(m, 1H), 3.6²(q, 1H), 3.67(s, 1H), 3.81 (dd, 1H), 4.62(dd, 1H), 6.32(s, 1H), 6.76(m, 4H), 7.02(m, 2H), 7.13(m, 1H).

APCI-MS (M+1=398.2).

EXAMPLE 1-5

2-{3-[1-(4-Isopropyl-benzoyl)-piperidin-3-yl]-phenoxy}-2-methyl-propionic acid

¹H NMR (400 MHz, CDCl₃) δ 1.23(d, 6H, 5.4 Hz), 1.57(s, 6H), 1.70(d, 2H), 2.06(d, 2H), 2.89(brm, 4H), 3.51 (brm, 3H), 3.85(brs, 1H), 4.74(brs, 1H), 6.83(brm, 4H), 7.25(brm, 2H), 7.32(brm, 2H).

APCI-MS (M+1=410.3).

EXAMPLE 1-6

2-(3-{1-[(2,4-Dimethoxy-phenyl)-acetyl]-piperidin-3-yl}-phenoxy)-2-methyl-propionic acid ¹H NMR (400 MHz, CDCl₃) δ 1.55(t, 6H), 1.70(m, 1H), 1.86(m, 1H), 2.61(m, 2H), 2.92(m, 2H), 3.43(d, 1H), 3.64 (dd, 1H), 3.79 (s, 3H), 3.83(s, 3H), 4.66(m, 2H), 6.46(d, 1H), 6.49 (dd, 1H), 6.68(m, 1H), 6.78(d, 1H), 6.91(d, 1H), 7.17(m, 3H).

APCI-MS (M+1=442.3).

EXAMPLE 1-7

2-Methyl-2-(3-{1-[(4-trifluoromethyl-phenyl)-acetyl]-piperidin-3-yl}-phenoxy)-propionic acid ¹H NMR (400 MHz, CDCl₃) δ 1.55(s, 6H), 1.72(m, 1H), 1.94(t, 1H), 2.25(t, 1H), 2.61(m, 2H), 2.98(m, 2H), 3.78(m, 4H), 4.64(m, 2H), 6.61(m, 1H), 6.76(d, 1H), 6.87(d, 1H), 7.15(q, 1H), 7.36(d, 2H), 7.57(d, 2H).

APCI-MS (M+1=450.2).

EXAMPLE 1-8

2-(3-{1-[3-(3-Methoxy-phenyl)-propionyl]-piperidin-3-yl}-phenoxy)-2-methyl-propionic acid ¹H NMR (400 MHz, CDCl₃) δ 1.47 (m, 1H), 1.59 (m, 6H), 1.79 (m, 1H), 2.00(t, 1H), 2.40(t, 1H), 2.60(m, 2H), 2.95(m, 2H), 3.77(d, 3H, 9.1 Hz), 4.64(d, 2H), 6.78(m, 4H), 6.90(d, 1H), 7.19(m, 3H).

APCI-MS (M+1=426.3).

EXAMPLE 1-9

2-Methyl-2-{3-[1-(pyridin-2-yl-acetyl)-piperidin-3-yl]-phenoxy}-propionic acid

¹H NMR (400 MHz, CDCl₃) δ 1.67(dd, 6H), 1.78(m, 2H), 2.09(d, 1H), 2.80(m, 1H), 2.87(t, 1H), 3.79(t, 1H), 2.91(d,

1H), 4.16(d, 1H), 4.22(d, 1H), 6.77(dd, 2H), 6.96(s, 1H), 7.18(m, 1H), 7.26(m, 1H), 7.49(d, 1H), 7.72(dd, 1H), 8.54 (d, 1H).

APCI-MS (M+1=383.2).

EXAMPLE 1-10

2-Methyl-2-{3-[1-(pyridin-3-yl-acetyl)-piperidin-3-yl]-phenoxy}-propionic acid $^1$H NMR (400 MHz, CDCl$_3$) δ 1.57(d, 6H), 1.69(m, 2H), 1.84(d, 2H), 2.50(dt, 1H), 3.00(t, 1H), 3.56(d, 1H), 3.80(d, 1H), 3.93(d, 1H), 4.63(d, 1H), 6.49(s, 1H), 6.82(m, 2H), 7.21 (m, 1H), 7.43(dd, 1H), 8.04(d, 1H), 8.51 (d, 1H), 8.57(d, 1H).

APCI-MS (M+1=383.2).

EXAMPLE 1-11

2-Methyl-2-{3-[1-(pyridin-4-yl-acetyl)-piperidin-3-yl]-phenoxy}-propionic acid $^1$H NMR (400 MHz, CD$_3$OD) δ 1.55(d, 6H), 1.80(m, 2H), 2.03(d, 1H), 2.66(t, 1H), 2.78(t, 1H), 3.24(t, 1H), 4.03(t, 1H), 4.19(q, 1H), 4.52(t, 1H), 6.76(m, 1H), 6.83(d, 1H), 6.93(dd, 1H), 7.20(q, 1H), 7.99(dd, 2H), 8.79(d, 2H).

LC-MS (M+1=383.5).

EXAMPLE 1-12

2-[3-(1-Cyclohexylacetyl-piperidin-3-yl)-phenoxy]-2-methyl-propionic acid $^1$H NMR (400 MHz, CD$_3$OD) δ 1.00(m, 3H), 1.26(m, 4H), 1.54(s, 6H), 1.77(m, 7H), 1.99(d, 1H), 2.28(m, 2H), 2.61(m, 2H), 3.14(q, 1H), 3.96(dd, 1H), 4.58(m, 1H), 6.78 (d, 2H), 6.82(s, 1H), 7.12(q, 1H).

LC-MS (M+1=388.5).

EXAMPLE 1-13

(S)-2-(3-{1-[(4-Isopropyl-phenyl)-acetyl]-piperidin-3-yl}-phenoxy)-2-methyl-propionic acid $^1$H NMR (400 MHz, DMSO$_{d6}$) δ 1.18(m, 6H), 1.33(s, 6H), 1.70(m, 3H), 2.08(t, 1H), 2.37(t, 1H), 2.55(m, 1H), 2.84 (m, 1H) 2.90(q, 1H), 3.65(m, 2H), 3.78(d, 1H), 3.95(d, 1H), 4.42(dd, 1H), 6.32(d, 1H), 6.49(s, 1H), 6.63(m, 2H), 6.98(dt, 1H), 7.14(m, 3H).

LC-MS (M+1=424.4).

[α]$_D^{25}$=−79.6° (c 2.03, CH$_3$OH).

EXAMPLE 1-14

(R)-2-(3-{1-[(4-Isopropyl-phenyl)-acetyl]-piperidin-3-yl}-phenoxy)-2-methyl-propionic acid $^1$H NMR (400 MHz, DMSO$_{d6}$) δ 1.18(m, 6H), 1.33(s, 6H), 1.70(m, 3H), 2.08(t, 1H), 2.37(t, 1H), 2.55(m, 1H), 2.84 (m, 1H) 2.90(q, 1H), 3.65(m,2H), 3.78(d, 1H), 3.95(d, 1H), 4.42(dd, 1H), 6.32(d, 1H), 6.49(s, 1H), 6.63(m, 2H), 6.98(dt, 1H), 7.14(m, 3H).

LC-MS (M+1=424.4).

[α]$_D^{25}$=82.2° (c 2.17, CH$_3$OH).

EXAMPLE 1-15

2-[3-(1-Isobutyryl-piperidin-3-yl)-phenoxy]-2-methyl-propionic acid $^1$H NMR (400 MHz, CDCl$_3$) δ 1.10(m, 6H), 1.24(s, 1H), 1.60(m, 6H), 1.81 (m, 1H), 2.02(m, 1H), 2.58(m, 2H), 2.81 (m, 1H), 3.02(m, 1H), 3.95(m, 1H), 4.68(m, 1H), 6.79(d, 1H), 6.81(s, 1H), 6.90(d, 1H), 7.19(m, 1H).

APCI-MS (M+1=334.2).

EXAMPLE 1-16

2-Methyl-2-[3-(1-phenylacetyl-piperidin-3-yl)-phenoxy]-propionic acid $^1$H NMR (400 MHz, CDCl$_3$) δ 1.56(m, 6H), 1.84 (m, 1H), 1.91(m, 1H), 2.16(t, 1H), 2.56(m, 2H), 2.91 (m, 2H), 3.77 (m, 4H), 4.68(m, 2H), 6.57(s, 1H), 6.77(m, 2H), 6.87(d, 1H), 7.13(m, 1H), 7.24(m, 3H), 7.31(m, 2H).

APCI-MS (M+1=382.2).

EXAMPLE 1-17

2-Methyl-2-{3-[1-(3-phenyl-propionyl)-piperidin-3-yl]-phenoxy}-propionic acid $^1$H NMR (400 MHz, CDCl$_3$) δ 1.41 (m, 1H), 1.61 (s, 6H) 1.75(m, 1H), 1.97(m, 1H), 2.38(m, 1H), 2.61(m, 4H), 2.93 (m, 3H), 3.78(d, 2H, 13.7 Hz), 4.67(m, 2H), 6.78(m, 3H), 6.89(d, 1H), 7.22(m, 6H).

APCI-MS (M+1=396.3).

EXAMPLE 1-18

2-Methyl-2-[3-(1-m-tolylacetyl-piperidin-3-yl)-phenoxy]-propionic acid $^1$H NMR (400 MHz, CDCl$_3$) δ 1.47 (m, 1H), 1.59 (s, 6H), 1.63 (m, 1H), 1.78 (m, 1H), 1.93 (dd, 1H), 2.12 (t, 1H), 2.33 (s, 3H), 2.56 (t, 1H), 2.61 (d, 1H), 2.91 (t, 1H), 2.96 (t, 1H), 3.67 (q, 1H), 3.71 (d, 1H), 3.83 (d, 1H), 4.64 (m, 1H), 6.57 (s, 1H), 6.71 (t, 1H), 6.81 (m, 1H), 6.89 (m, 1H), 7.02–7.21 (m, 4H).

APCI-MS (M+1=396.3).

EXAMPLE 1-19

2-Methyl-2-{3-[1-(pyridine-2-carbonyl)-piperidin-3-yl]-phenoxy}-propionic acid $^1$H NMR (400 MHz, CDCl$_3$) δ 1.54(m, 6H), 1.73(m, 1H), 1.97(m, 1H), 2.85(m, 2H), 3.12(t, 1H), 3.19 (t, 1H), 3.67(d, 1H), 3.78 (d, 1H), 4.46(d, 1H), 4.73(d, 1H), 6.74(d, 1H), 6.80(d, 1H), 6.95(s, 1H), 7.14(t,1H), 7.21(t, 1H), 7.42(brm, 1H), 7.62(brm, 1H), 7.86(m, 1H), 8.66(brs, 1H).

APCI-MS (M+1=369.2).

EXAMPLE 1-20

2-Methyl-2-{3-[1-(pyridine-3-carbonyl)-piperidin-3-yl]-phenoxy}-propionic acid $^1$H NMR (400 MHz, CD$_3$OD) δ 1.53(s, 6H), 1.78(m, 2H), 2.04(m, 1H), 2.78(m, 1H), 2.90(m, 1H), 3.20(q, 1H), 3.62

(m, 2H), 4.66(d, 1H), 6.69(s, 1H), 6.78(m, 1H), 6.87(s, 1H), 6.97(m, 1H), 7.12(m, 1H), 7.22(m, 1H), 7.55(brs, 1H), 7.74(d, 1H), 7.93(brs, 1H).
APCI-MS (M+1=369.2).

EXAMPLE 1-21

2-[3-(1-Benzoyl-piperidin-3-yl)-phenoxy]-2-methyl-propionic acid $^1$H NMR (400 MHz, CD$_3$OD) δ 1.29(m, 1H), 1.47(s, 3H), 1.53(s, 3H), 1.76(m, 2H), 1.92(m, 1H), 2.02(d, 1H), 2.70(m, 1H), 2.87(q, 1H), 3.11(q, 1H), 3.69(m, 1H), 4.67(m, 1H), 6.60(d, 1H), 6.68(m, 1H), 6.80(dd, 1H), 7.01 (dt, 1H,7.1 Hz), 7.42(m, 5H).
APCI-MS (M+1=368.5).

EXAMPLE 1-22

2-(3-{1-[(3-Fluoro-phenyl)-acetyl]-piperidin-3-yl}-phenoxy)-2-methyl-propionic acid $^1$H NMR (400 MHz, CDCl$_3$) δ 1.35 (m, 1H), 1.59(s, 6 h), 1.70(t, 1H), 1.93(t, 1H), 2.24(t, 1H), 2.58(m, 2H), 2.97(m, 1H), 3.73(m, 3H), 4.65(m, 1H), 6.63(m, 1H), 6.78(m, 1H), 6.89(m, 4H), 7.16(brs, 1H), 7.28(m, 2H).
APCI-MS (M+1=400.2).

EXAMPLE 1-23

2-(3-{1-[(3-Chloro-phenyl)-acetyl]-piperidin-3-yl}-phenoxy)-2-methyl-propionic acid $^1$H NMR (400 MHz, CDCl$_3$) δ 1.58(s, 6H), 1.65(m, 1H), 1.76(m, 1H), 2.00(m, 1H), 2.24(m, 1H), 2.61 (m, 2H), 2.99(m, 1H), 3.72(m, 2H), 3.83(m, 1H), 4.65(m, 1H), 6.64 (m, 1H), 6.78(m, 2H), 6.91(d, 1H), 7.16(m, 5H).
APCI-MS (M+1=416.2).

EXAMPLE 1-24

2-(3-{1-[(4-Chloro-phenyl)-acetyl]-piperidin-3-yl}-phenoxy)-2-methyl-propionic acid $^1$H NMR (400 MHz, CDCl$_3$) δ 1.37(m, 1H), 1.58(s, 6H), 1.70(m, 1H), 1.99(m, 1H), 2.25(m, 1H), 2.61 (m, 2H), 2.97(m, 1H), 3.70(m, 2H), 3.82(d, 1H), 4.64(m, 1H), 6.60 (brs, 1H), 6.67(d, 1H), 6.77(m, 1H), 6.89(d, 1H), 7.17(m, 2H), 7.27(m, 1H).
APCI-MS (M+1=416.2).

EXAMPLE 1-25

2-Methyl-2-(3-{1-[(4-trifluoromethoxy-phenyl)-acetyl]-piperidin-3-yl}-phenoxy)-propionic acid $^1$H NMR (400 MHz, CDCl$_3$) δ 1.42(m, 1H), 1.58(s, 6H), 1.74(dt, 1H), 1.95(t, 1H), 2.25(t, 1H), 2.57(m, 2H), 2.98(t, 1H), 3.01 (t, 1H), 3.69(d, 1H), 3.76(s, 1H), 3.82(m, 1H), 4.66(m, 1H), 6.61(m, 1H), 6.76(m, 2H), 6.86(d, 1H), 7.14 (m, 2H), 7.26(m, 1H).

EXAMPLE 1-26

2-Methyl-2-{3-[1-(3-piperidin-1-yl-propionyl)-piperidin-3-yl]-phenoxy}-propionic acid $^1$H NMR (400 MHz, CDCl$_3$) δ 1.42(m, 1H), 1.55(s, 3H), 1.62(s, 3H), 1.86(m, 4H), 2.17(d, 1H), 2.21(m, 2H), 2.68(m, 4H), 2.88(t, 1H), 3.08(m, 1H), 3.25(brs, 2H), 3.42(m, 1H), 3.59(m, 1H), 3.79(m, 2H), 4.42(d, 1H), 6.82(m, 3H), 7.21 (t, 1H).
APCI-MS (M+1=403.3).

EXAMPLE 1-27

2-Methyl-2-{3-[1-(3-methyl-butyryl)-piperidin-3-yl]-phenoxy}-propionic acid $^1$H NMR (400 MHz, CDCl$_3$) δ 0.96(d, 6H), 1.58(s, 6H), 1.69(m, 1H), 1.82(m, 1H), 2.08(m, 2H), 2.24(m, 2H), 2.54 (m, 4H), 3.03(m, 1H), 3.90(d, 1H), 4.65(d, 1H), 6.80(m, 2H), 6.93(d, 1H), 7.20(m, 1H).
APCI-MS (M+1=348.2).

EXAMPLE 1-28

2-(3-{1-[(4-Ethoxy-phenyl)-acetyl]-piperidin-3-yl}-phenoxy)-2-methyl-propionic acid $^1$H NMR (400 MHz, CDCl$_3$) δ Rotomeric mixture: 1.42 (dt, 3H), 1.58(d, 6H), 1.70(m, 1H), 1.92(dd, 1H), 1.97(m, 1H), 2.55(t, 1H), 2.63(m, 1H), 2.95(q, 1H), 3.65(q, 1H), 3.69(s, 1H), 3.84(t,1H), 4.04(q, 2H), 4.11(m, 1H), 4.66(dd, 1H), 6.42(s, 1H), 6.67(d, 1H), 6.83(m, 3H), 7.16(m, 3H.)
APCI-MS (M+1=426.3).

EXAMPLE 1-29

2-(3-{1-[(2-Methoxy-phenyl)-acetyl]-piperidin-3-yl}-phenoxy)-2-methyl-propionic acid $^1$H NMR (400 MHz, CDCl$_3$) δ rotomeric mixture: 1.55(s, 6H), 1.71(m, 1H), 1.91(dd, 1H), 2.14(t, 0.5H), 2.51(t, 0.5H), 2.59(d, 1H), 2.84(t, 0.5H), 2.95(t, 0.5H), 3.55–3.85(m, 8H), 4.63(m, 1H), 6.57(m, 1H), 6.73(t, 1H), 6.85(m, 3H), 7.19(m, 3H).
APCI-MS (M+1=412.3).

EXAMPLE 1-30

2-Methyl-2-[3-(1-o-tolylacetyl-piperidin-3-yl)-phenoxy]-propionic acid $^1$H NMR (400 MHz, CDCl$_3$) δ rotomeric mixture: 1.54(d, 6H), 1.68(m, 1H), 1.96(m, 1H), 2.23(d, 3H), 2.62(m, 1H), 2.91(dt, 1H), 3.69(m, 3H), 4.66(m, 2H), 6.54(s, 0.5H), 6.59(d, 0.5H), 6.74(dd, 1H), 6.81(s, 0.5H), 6.89(d, 0.5H), 7.14(m, 5H).
APCI-MS (M+1=396.3).

EXAMPLE 1-31

2-Methyl-2-[3-(1-p-tolylacetyl-piperidin-3-yl)-phenoxy]-propionic acid $^1$H NMR (400 MHz, CDCl$_3$) δ 1.57(s, 6H), 1.93(m, 1H), 2.19(m, 1H), 2.33(s, 3H), 2.60(brm, 2H), 3.72(m, 4H), 3.86(brm, 1H), 4.66(brm, 1H), 6.56(m, 1H), 6.64(m, 1H), 6.78(m, 3H), 6.95(m, 1H), 7.16(m, 3H).
APCI-MS (M+1=396.3).

EXAMPLE 1-32

2-(3-{1-[(3,5-Dimethoxy-phenyl)-acetyl]-piperidin-3-yl}-phenoxy)-2-methyl-propionic acid $^1$H NMR (400 MHz, CDCl$_3$) δ Rotomeric mixture: 1.51 (s, 6H), 1.71(m, 1H), 1.89(m, 1H), 2.13(t, 1H), 2.50(m, 1H), 2.89(m, 2H), 3.23(m, 3H), 3.61(m, 2H), 3.71(d, 6H), 3.82(d, 1H), 4.59(d, 1H), 6.31 (m, 2H), 6.52(m, 1H), 6.68(m, 2H), 6.79(d, 1H), 6.98(d, 0.5H), 7.08(dt, 2H).
APCI-MS (M+1=442.3).

EXAMPLE 1-33

2-Methyl-2-(3-{1-[(3-trifluoromethyl-phenyl)-acetyl]-piperidin-3-yl}-phenoxy)-propionic acid $^1$H NMR (400 MHz, CDCl$_3$) δ 1.55(s, 6H), 1.65(d,1H), 1.79(m, 1H), 1.97(m, 1H), 2.27(brm, 1H), 2.62(brs, 2H), 3.02(brm, 1H), 3.81 (brm, 4H), 4.65(brs, 2H), 6.63(s, 1H), 6.77(m, 2H), 6.91(brs, 1H), 7.17(m, 2H), 7.48(m, 4H).
APCI-MS (M+1=450.3).

EXAMPLE 1-34

2-(3-{1-[(3,5-Bis-trifluoromethyl-phenyl)-acetyl]-piperidin-3-yl}-phenoxy)-2-methyl-propionic acid $^1$H NMR (400 MHz, CDCl$_3$) δ 1.58(s, 6H), 1.69(q, 1H), 1.85(d, 1H), 2.03(m, 1H), 2.42(m, 1H), 2.67(m, 1H), 3.11 (m, 1H), 3.83(m, 4H), 4.64(m, 2H), 6.76(m, 3H), 6.93(brm, 1H), 7.20(q, 1H), 7.71(s, 2H), 7.79(s, 1H).
APCI-MS (M+1=518.3).

EXAMPLE 1-35

2-Methyl-2-(3-{1-[(3-trifluoromethoxy-phenyl)-acetyl]-piperidin-3-yl}-phenoxy)-propionic acid $^1$H NMR (400 MHz, CDCl$_3$) δ 1.33(m, 1H), 1.51(m, 1H), 1.61(s, 6H), 1.75(m, 1H), 1.96(t, 1H), 2.26(t, 1H), 2.57(m, 1H), 2.97(dt, 1H), 3.73(m, 4H), 4.68(m, 1H), 6.61(m, 1H), 6.77(m, 1H), 6.87(m, 1H), 6.97(d, 0.5H), 7.16(m, 4H), 7.37(m, 1H).
LC-MS (M+1=466.4).

EXAMPLE 1-36

2-Methyl-2-(3-{1-[3-(3-trifluoromethoxy-phenyl)-propionyl]-piperidin-3-yl}-phenoxy)-propionic acid $^1$H NMR (400 MHz, CDCl$_3$) δ 1.62(s, 6H), 1.78(d, 1H), 2.01(d, 1H), 2.62(m, 4H), 2.97(m, 3H), 3.79(d, 1H), 4.65(m, 1H), 6.79(m, 2H), 6.89(d, 1H), 7.06(m, 2H), 7.16(m, 2H), 7.29(m, 2H).
LC-MS (M+1=480.4).

EXAMPLE 1-37

2-Methyl-2-{3-[1-(piperidin-1-yl-acetyl)-piperidin-3-yl]-phenoxy}-propionic acid $^1$H NMR (400 MHz, DMSO$_{d6}$) δ rotomeric mixture: 1.25(m, 1H), 1.42(m, 1H), 1.50(s, 6H), 1.72(m, 3H), 1.90(d, 1H), 2.63 (m, 1H), 2.71(m, 1H), 2.93(brs, 1H), 3.09(m, 1H), 3.40(m, 1H), 3.63(t, 1H), 4.34(m, 3H), 6.63(m, 1H), 6.73(s, 0.5H), 6.81 (s, 0.5H), 6.89(dd, 1H, 7.9 Hz), 7.21 (m, 1H), 9.37(brs, 1H), 13.02(brs, 1H).
LC-MS (M+1=389.5).

EXAMPLE 1-38

2-Methyl-2-{3-[1-(morpholin-4-yl-acetyl)-piperidin-3-yl]-phenoxy}-propionic acid $^1$H NMR (400 MHz, DMSO$_{d6}$) δ rotomeric mixture: 1.50(s, 6H), 1.68(m, 1H), 1.77(m, 1H), 1.90(m, 1H), 2.71(dt, 1H), 3.11(m, 3H), 3.42(m, 1H), 3.62(t, 1H), 3.78(m, 1H), 3.92(m, 1H), 4.39(dd, 2H), 6.64(m, 1H), 6.73(s, 0.5H), 6.82(s, 0.5H), 6.86(dd, 1H), 7.21 (m, 1H), 10.20(s, 1H).
LC-MS (M+1=391.5).

EXAMPLE 1-39

2-Methyl-2-{3-[1-(piperazin-1-yl-acetyl)-piperidin-3-yl]-phenoxy}-propionic acid $^1$H NMR (400 MHz, DMSO$_{d6}$) δ rotomeric mixture: 1.50(s, 6H), 1.71(m, 2H), 1.89(m, 1H), 2.69(m, 2H), 3.10(t, 1H), 4.68(m, 2H), 6.64(s, 1H), 6.72(s, 0.5H), 6.81(s, 0.5H), 6.89(dd, 1H), 7.20(m, 1H), 9.97(brs, 1H).
LC-MS (M+1=390.0).

EXAMPLE 1-40

2-(3-{1-[(1H-Benzoimidazol-2-yl)-acetyl]-piperidin-3-yl}-phenoxy)-2-methyl-propionic acid $^1$H NMR (400 MHz, DMSO$_{d6}$) δ rotomeric mixture: 1.50(d, 6H), 1.74(m, 2H), 1.91 (m, 1H), 2.71 (m, 1H), 3.21 (m, 2H), 3.97(dd, 1H), 4.45(m, 3H), 6.65(d, 1H), 6.72(s, 0.5H), 6.84(s, 0.5H), 6.89(dd, 1H), 7.21(q, 1H), 7.50(m, 2H), 7.78(m, 2H).
LC-MS (M+1=422.5).

EXAMPLE 1-41

2-{3-[1-(Benzo[1,3]dioxol-5-yl-acetyl)-piperidin-3-yl]-phenoxy}-2-methyl-propionic acid $^1$H NMR (400 MHz, CDCl$_3$) δ 1.59(s, 6H), 1.75(m, 1H), 1.94(m, 1H), 2.27(m, 1H), 2.58(m, 2H), 2.98(m, 2H), 3.63 (d, 1H), 3.68(s, 1H), 3.87(d, 1H), 4.66(t, 1H), 5.96(d, 2H), 6.60(s, 1H), 6.69(m, 3H), 6.77(m, 1H), 6.92(d, 1H), 7.19(t, 1H).
LC-MS (M+1=426.4).

EXAMPLE 1-42

2-(3-{1-[(2-Hydroxy-phenyl)-acetyl]-piperidin-3-yl}-phenoxy)-2-methyl-propionic acid $^1$H NMR (400 MHz, CDCl$_3$) δ 1.55(m, 1H), 1.59(s, 3H), 1.64(s, 3H), 1.69(m, 1H), 1.80(dd, 1H), 2.00(t, 1H), 2.57(t, 1H), 2.61(m, 1H), 3.15(q, 1H), 3.76(d, 2H), 4.18(m, 1H), 4.65(m, 1H), 6.90(m, 5H), 6.98(m, 2H), 7.04(d, 1H), 7.19(t, 1H).
LC-MS (M+1=398.4).

EXAMPLE 1-43

2-(3-{1-[(4-tert-Butyl-phenyl)-acetyl]-piperidin-3-yl}-phenoxy)-2-methyl-propionic acid $^1$H NMR (400 MHz, CDCl$_3$) δ Rotomeric mixture: 1.32 (d, 9H), 1.54 (d, 6H), 1.69(t, 1H), 1.81(t, 1H), 1.92(d, 0.5H), 2.06(t, 0.5H), 2.61(m, 1H), 2.97(t, 0.5H), 3.07(t, 0.5H), 3.71 (abq, 1H), 3.79(s, 1H), 3.89(d, 0.5H), 4.02(d, 0.5H), 4.60 (dd, 1H), 6.48(d, 0.5H), 6.52(s, 0.5H), 6.69(dd, 0.5H), 6.75(dd, 0.5H), 6.71(s, 0.5H), 7.12(t, 0.5H) 7.19(m, 2H), 7.38(m, 1.5H).
LC-MS (M+1=438.5).

EXAMPLE 1-44

2-(3-{1-[(4-Ethyl-phenyl)-acetyl]-piperidin-3-yl}-phenoxy)-2-methyl-propionic acid $^1$H NMR (400 MHz, CDCl$_3$) δ 1.23(t, 3H), 1.62(s, 6H), 1.74(m, 1H), 1.92(m, 1H), 2.63(q, 2H), 3.87(m, 2H), 6.59 (brm, 1H), 6.77(d, 1H), 7.15(s, 4H).
LC-MS (M+1=410.5).

EXAMPLE 1-45

2-{3-[1-(4-Isobutyl-benzoyl)-piperidin-3-yl]-phenoxy}-2-methyl-propionic acid $^1$H NMR (400 MHz, CDCl$_3$) δ 0.89(d, 6H), 1.57(s, 6H), 1.71(m, 1H), 1.85(m, 2H), 2.07(m, 1H), 2.48(d, 2H), 2.78 (brm, 1H), 2.89(brm, 2H), 6.77(m, 2H), 6.88(m, 1H), 7.17 (m, 3H), 7.32(d, 2H).
LC-MS (M+1=424.4).

EXAMPLE 1-46

2-(3-{1-[(4-Isobutyl-phenyl)-acetyl]-piperidin-3-yl}-phenoxy)-2-methyl-propionic acid $^1$H NMR (400 MHz, CDCl$_3$) δ 0.89(d, 6H), 1.58(s, 6H), 1.85(m, 1H), 1.91(m, 1H), 2.45(d, 2H), 2.61 (m, 1H), 3.75(m, 2H), 3.88(m, 1H), 4.66(m, 2H), 6.60 (m, 1H), 6.76(d, 1H), 7.14(m, 6H).
LC-MS (M+1=438.4).

EXAMPLE 1-47

2-Methyl-2-(3-{1-[4-(2,2,2-trifluoro-1-hydroxy-1-trifluoromethyl-ethyl)-benzoyl]-piperidin-3-yl}-phenoxy)-propionic acid $^1$H NMR (400 MHz, CDCl$_3$) δ 1.48(brs, 1H), 1.57(m, 6H), 1.75(m, 2H), 2.09(m, 1H), 2.80(m, 1H), 3.72(m, 1H), 4.75(brs, 1H), 6.61 (m, 1H), 6.84(m, 3H), 7.39(m, 2H), 7.73(m, 2H).
LC-MS (M+1=534.4).

EXAMPLE 1-48

(S)-2-(3-{1-[(4-tert-Butyl-phenyl)-acetyl]-piperidin-3-yl}-phenoxy)-2-methyl-propionic acid $^1$H NMR (400 MHz, CDCl$_3$) δ Rotomeric mixture: 1.32 (d, 9H), 1.54 (d, 6H), 1.69(t, 1H), 1.81(t, 1H), 1.92(d, 0.5H), 2.06(t, 0.5H), 2.61(m, 1H), 2.97(t, 0.5H), 3.07(t, 0.5H), 3.71(abq, 1H), 3.79(s, 1H), 3.89(d, 0.5H), 4.02(d, 0.5H), 4.60(dd, 1H), 6.48(d, 0.5H), 6.52(s, 0.5H), 6.69(dd, 0.5H), 6.75(dd, 0.5H), 6.71 (s, 0.5H), 7.12(t, 0.5H) 7.19(m, 2H), 7.38(m, 1.5H).
LC-MS (M+1=438.5).
[α]$_D^{25}$=−66.9° (c 1.12, CH$_3$OH).

EXAMPLE 1-49

(S)-2-Methyl-2-(3-{1-[(4-trifluoromethoxy-phenyl)-acetyl]-piperidin-3-yl}-phenoxy)-propionic acid $^1$H NMR (400 MHz, CDCl$_3$) δ 1.42(m, 1H), 1.58(s, 6H), 1.74(dt, 1H), 1.95(t, 1H), 2.25(t, 1H), 2.57(m, 2H), 2.98(t, 1H), 3.01 (t, 1H), 3.69(d, 1H), 3.76(s, 1H), 3.82(m, 1H), 4.66(m, 1H), 6.61(m, 1H), 6.76(m, 2H), 6.86(d, 1H), 7.14 (m, 2H), 7.26(m, 1H).
APCI-MS (M+1=466.2).
[α]$_D^{25}$=−65.7° (c 0.60, CH$_3$OH).

EXAMPLE 1-50

(R)-2-Methyl-2-(3-{1-[(4-trifluoromethoxy-phenyl)-acetyl]-piperidin-3-yl}-phenoxy)-propionic acid $^1$H NMR (400 MHz, CDCl$_3$) δ 1.42(m, 1H), 1.58(s, 6H), 1.74(dt, 1H), 1.95(t, 1H), 2.25(t, 1H), 2.57(m, 2H), 2.98(t, 1H), 3.01 (t, 1H), 3.69(d, 1H), 3.76(s, 1H), 3.82(m, 1H), 4.66(m, 1H), 6.61(m, 1H), 6.76(m, 2H), 6.86(d, 1H), 7.14 (m, 2H), 7.26(m, 1H).
APCI-MS (M+1=466.2).
[α]$_D^{25}$=64.2° (c 1.16, CH$_3$OH).

EXAMPLE 1-51

(R)-2-(3-{1-[(4-tert-Butyl-phenyl)-acetyl]-piperidin-3-yl}-phenoxy)-2-methyl-propionic acid $^1$H NMR (400 MHz, CDCl$_3$) δ Rotomeric mixture: 1.32 (d, 9H), 1.54 (d, 6H), 1.69(t, 1H), 1.81(t, 1H), 1.92(d, 0.5H), 2.06(t, 0.5H), 2.61(m, 1H), 2.97(t, 0.5H), 3.07(t, 0.5H), 3.71(abq, 1H), 3.79(s, 1H), 3.89(d, 0.5H), 4.02(d, 0.5H), 4.60(dd, 1H), 6.48(d, 0.5H), 6.52(s, 0.5H), 6.69(dd, 0.5H), 6.75(dd, 0.5H), 6.71(s, 0.5H), 7.12(t, 0.5H) 7.19(m, 2H), 7.38(m, 1.5H).
LC-MS (M+1=438.5).
[α]$_D^{25}$=72.6° (c 1.31, CH$_3$OH).

EXAMPLE 1-52

(S)-2-(3-{1-[(4-Cyclohexyl-phenyl)-acetyl]-piperidin-3-yl}-phenoxy)-2-methyl-propionic acid $^1$H NMR (400 MHz, CD$_3$OD) δ 1.44(m, 4H), 1.53(s, 6H), 1.67(m, 1H), 1.75(m, 1H), 1.89(m, 6H), 2.04(t, 1H), 2.55 (brm, 2H), 2.61 (q, 1H), 3.00(m, 1H), 3.76(abq, 1H), 3.95 (dd, 1H), 4.59(dd, 1H), 6.49(d, 0.5H), 6.51(d, 0.5H), 6.69 (dd, 0.5H), 6.74(dd, 0.5H), 6.80(s, 0.5H), 6.89(d, 0.5H), 7.09(t, 0.5H), 7.16(m, 3H), 7.21(m, 1H).
LC-MS (M+1=464.5).

EXAMPLE 1-53

(S)-2-(3-{1-[(4-Methanesulfonyl-phenyl)-acetyl]-piperidin-3-yl}-phenoxy)-2-methyl-propionic acid $^1$H NMR (400 MHz, CD$_3$OD) δ 1.28(m, 1H), 1.49(m, 1H), 1.54(d, 6H), 1.79(m, 2H), 1.98(t, 1H), 2.36(t, 0.5H), 2.51(t, 0.5H), 2.71(q, 1H), 3.12(d, 3H), 3.95(m, 3H), 4.59 (dd, 1H), 6.61 (s, 0.5H), 6.72(m, 1.5H), 6.81(s, 0.5H), 6.90(d, 0.5H), 7.16(m, 1H), 7.53(t, 2H), 7.93(t, 2H).
LC-MS (M+1=460.5).

EXAMPLE 1-54

(S)-2-{3-[1-(Biphenyl-4-yl-acetyl)-piperidin-3-yl]-phenoxy}-2-methyl-propionic acid $^1$H NMR (400 MHz, CD$_3$OD) δ 1.49(s, 3H), 1.55(s, 3H), 1.65–1.98(m, 3H), 2.14(t, 1H), 2.65(m, 1H), 3.06(m, 1H), 3.86(abq, 2H), 3.97(d, 1H), 4.08(d, 1H), 4.61(dd, 1H), 6.52(s, 0.5H), 6.61(d, 0.5H), 6.69(dd, 0.5H), 6.74(dd, 0.5H), 6.81 (s, 0.5H), 6.91(d, 0.5H), 7.10(t, 0.5H), 7.18(t, 0.5H), 7.34(m, 3H), 7.43(m, 2H), 7.62(m, 4H).
LC-MS (M+1=458.5).

EXAMPLE 1-55

(S)-2-Methyl-2-{3-[1-(naphthalen-2-yl-acetyl)-piperidin-3-yl]-phenoxy}-propionic acid $^1$H NMR (400 MHz, CD$_3$OD) δ rotomeric mixture: 1.54(m, 6H), 1.68(m, 1H), 1.80(m, 1H), 1.91 (m, 1H), 2.02(m, 1H), 2.58(t, 1H), 2.66(m, 1H), 3.07(m, 1H), 3.99(m, 3H), 4.62(dd, 1H), 6.33(d, 0.5H), 6.44(s, 0.5H), 6.66(d, 0.5H), 6.74(d, 0.5H), 6.80(s, 0.5H), 6.90(d, 0.5H), 6.99(t, 0.5H), 7.18(t, 0.5H, 7.9 Hz), 7.46(m, 3H), 7.73(d, 1H), 7.84(m, 3H).
LC-MS (M+1=432.4).

EXAMPLE 1-56

(S)-2-Methyl-2-(3-{1-[4-methyl-2-(4-trifluoromethyl-phenyl)-thiazole-5-carbonyl]-piperidin-3-yl}-phenoxy)-propionic acid $^1$H NMR (400 MHz, CD$_3$OD) δ 1.53(s, 6H), 1.68(m, 1H), 1.83(m, 2H), 2.04(m, 1H), 2.48(s, 1H), 2.76(t, 1H), 6.73(m, 1H), 6.80(brm, 1H), 6.91(brm, 1H), 7.19(t, 1H), 7.78(d, 2H), 7.90(s, 1H), 8.13(d, 2H).
LC-MS (M+1=533.1).

EXAMPLE 1-57

(S)-2-Methyl-2-{3-[1-(naphthalen-1-yl-acetyl)-piperidin-3-yl]-phenoxy}-propionic acid $^1$H NMR (400 MHz, CD$_3$OD) δ Rotomeric mixture: 1.47(s, 3H), 1.53(s, 3H), 1.84(m, 2H), 1.98(d, 1H), 2.23(t, 1H), 2.70(m, 2H), 3.04(t, 1H), 3.14(t, 1H), 3.90(d, 1H), 4.04(d, 1H), 4.23(abq, 1H), 4.33(d, 1H), 4.63(t, 1H), 6.44(d, 0.5H), 6.49(s, 0.5H), 6.65(dd, 0.5H), 6.75(d, 0.5H), 6.82(s, 0.5H), 6.91(d, 0.5H), 7.02(t, 0.5H), 7.18(t, 0.5H), 7.37(t, 1H), 7.49(m, 3H), 7.86(m, 2H), 8.02(d, 1H).
LC-MS (M+1=432.2).

EXAMPLE 1-58

20 (S)-2-Methyl-2-(3-{1-[(4-trifluoromethyl-phenyl)-acetyl]-piperidin-3-yl}-phenoxy)-propionic acid $^1$H NMR (400 MHz, CD$_3$OD) δ 1.53(s, 6H), 1.76(m, 2H), 1.93(t, 1H), 2.27(t, 0.5H), 2.59(t, 0.5H), 2.66(q, 1H), 3.10(q, 1H), 3.87(abq, 1H), 3.94(s, 1H), 4.01(dd, 1H), 4.58(dd, 1H), 6.64(m, 1H), 6.73(dt, 1H), 6.80(d, 0.5H), 6.90(d, 0.5H, 7.9 Hz), 7.16(dt, 1H), 7.46(t, 2H), 7.64(t, 2H).
LC-MS (M+1=450.2).

EXAMPLE 1-59

2-(4-{1-[(4-Isopropyl-phenyl)-acetyl]-piperidin-3-yl}-phenoxy)-2-methyl-propionic acid MS (APCI) 424.3 (M+H)$^+$.
$^1$H NMR (400 MHz, CDCl$_3$) δ Rotomeric mixture: 7.18 (m, 4H), 7.11 (d, 1H), 6.87 (m, 1H), 6.79 (dd, 2H), 4.73 (t, 1H), 3.91 (d, 0.5H), 2.82 (d, 0.5H), 3.75 (d, 0.5H), 3.73 (s, 1H), 3.66 (d, 0.5H), 2.89 (m, 2H), 2.62 (t, 0.5H), 2.52 (t, 1H), 2.13 (t, 0.5H), 1.93 (dd, 1H), 1.73 (dd, 1H), 1.56 (d, 6H), 1.24 (m, 6H).

EXAMPLE 1-60

2-Methyl-2-(4-{1-[(4-trifluoromethyl-phenyl)-acetyl]-piperidin-3-yl}-phenoxy)-propionic acid MS (APCI) 450.2 (M+H)$^+$.
$^1$H NMR (400 MHz, CDCl$_3$) δ Rotomeric mixture: 7.59 (d, 2H), 7.38 (t, 2H), 7.12 (d, 1H), 6.86 (m, 3H), 4.71 (d, 1H), 3.82 (m, 3H), 3.02 (t, 0.5H), 2.97 (t, 0.5H), 2.59 (m, 1.5H), 2.24 (t, 0.5H), 1.97 (dd, 1H), 1.78 (dd, 1H), 1.64 (m, 1H), 1.57 (d, 6H), 1.18 (m, 1H).

EXAMPLE 1-61

2-{4-[1-(4-Isopropyl-benzoyl)-piperidin-3-yl]-phenoxy}-2-methyl-propionic acid

MS (APCI) 410.3 (M+H)$^+$.
$^1$H NMR (400 MHz, CDCl$_3$) δ Rotomeric mixture: 7.34 (m, 4H), 7.19 (d, 1H), 7.03 (d, 1H), 6.87 (m, 1H), 6.76 (d, 1H), 4.63 (t, 1H), 3.78 (dd, 1H), 3.22 (q, 1H), 2.92 (m, 1H), 2.84 (t, 1H), 2.74 (m, 1H), 2.03 (d, 1H), 1.91 (m, 0.5H), 1.78 (m, 1.5H), 1.53 (d, 6H), 1.27 (d, 6H).

EXAMPLE 1-62

2-Methyl-2-{4-[1-(pyridin-2-yl-acetyl)-piperidin-3-yl]-phenoxy}-propionic acid

MS (APCI) 383.3 (M+H)$^+$.
$^1$H NMR (400 MHz, CDCl$_3$) δ Rotomeric mixture: 8.48 (d, 1H), 7.80 (t, 1H), 7.38 (d, 1H), 7.32 (q, 1H), 7.14 (d, 1H), 7.01 (d, 1H), 6.83 (dd, 1H), 4.58 (dd, 1H), 4.03 (dd, 1H), 3.98 (m, 1H), 3.12 (t, 0.5H), 3.09 (t, 0.5H), 2.67 (q, 1H), 2.59 (t, 0.5H), 2.41 (t, 0.5H), 1.96 (t, 1H), 1.78 (m, 3H), 1.52 (d, 6H).

EXAMPLE 1-63

2-(4-{1-[3-(4-isopropyl-phenyl)-propionyl]-piperidin-3-yl}-phenoxy)-2-methyl-propionic acid MS (LC-MS) 438.5 (M+H)$^+$.
$^1$H NMR (400 MHz, CDCl$_3$) δ 7.15 (m, 5H), 7.06 (d, 1H), 6.89 (d, 1H), 4.73 (d, 1H), 3.82 (t, 1H), 2.93 (m, 4H), 2.62 (m, 2H), 2.51 (q, 1H), 2.43 (t, 1H), 1.98 (t, 1H), 1.77 (t, 1H), 1.63 (t, 1H), 1.58 (s, 6H), 1.40 (m, 1H), 1.22 (t, 6H).

Example 1-64 was prepared using methods analogous to those described in Example 1 using the appropriate alkyl haloalkylcarboxylate in Preparation 2, Method D.

EXAMPLE 1-64

(3-{1-[(4-Isopropyl-phenyl)-acetyl]-piperidin-3-yl}-phenoxy)-acetic acid $^1$H NMR (400 MHz, CDCl$_3$) δ 7.75 (brm, 1H), 7.16 (m, 4H), 6.74 (m, 2H), 6.51 (d, 1H), 4.72 (brm, 1H), 4.63 (s, 2H), 3.86 (m, 1H), 3.80 (s, 1H), 3.73 (m, 1H), 3.00 (m, 1H), 2.90 (brm, 1H), 2.64 (m, 2H), 2.17 (brm, 1H), 1.94 (m, 1H), 1.82 (m, 1H), 1.65 (q, 1H), 1.24 (d, 6H).
LC-MS (M+1=396.4).

EXAMPLE 2

2-(3-{1-[(4-Isopropyl-phenoxy)-acetyl]-piperidin-3-yl}-phenoxy)-2-methyl-propionic acid To a solution of 4-isopropylphenol (1.007 g, 7.39 mmol) in 15 mL dimethylformamide was added potassium carbonate (2.04 g, 14.79 mmol) and ethyl bromoacetate (1.23 mL, 11.09 mmol). The reaction was stirred for 48 h at ambient temperature. The mixture was diluted with 500 mL water and extracted with diethyl ether (2×200 mL). The organic extracts were combined, dried over anhydrous sodium sulfate, filtered and concentrated under reduced pressure. The resultant oil was flash chromatographed with 10% ethyl acetate/hexanes to yield 1.61 g (98%) of ethyl-(4-isopropylphenoxy)acetate as a clear oil.

MS (APCI) 223.3 (M+H)$^+$.

$^1$H NMR (400 MHz, CDCl$_3$) δ 7.14 (d, 2H), 6.84 (d, 2H), 4.59 (s, 2H), 4.27 (q, 2H), 2.86 (m, 1H), 1.30 (t, 3H), 1.21 (d, 6H).

A mixture of ethyl-(4-isopropylphenoxy)acetate (1.61 g, 7.24 mmol) and 2N NaOH(aq) (10.9 mL) in 20 mL of methanol was stirred at ambient temperature for 3 h and concentrated under reduced pressure. The resulting residue was taken up in water (100 mL), acidified with 1N aqueous hydrochloric acid and extracted with ethyl acetate (2×100 mL). The organic extracts were combined, dried over anhydrous sodium sulfate, filtered and concentrated under reduced pressure to yield 1.32 g (94%) of 4-isopropylphenoxyacetic acid as a white solid.

MS (APCI) 195.3 (M+H)$^+$.

$^1$H NMR (400 MHz, CDCl$_3$) δ 7.17 (d, 2H), 6.86 (d, 2H), 4.66 (s, 2H), 2.87 (m), 1H), 1.22 (d, 6H).

To a solution of 2-methyl-2-(3-piperidin-3-yl-phenoxy)-propionic acid benzyl ester (Preparation 2, Method C; 30 mg, 0.085 mmol) in 1 mL methylene chloride was added 4-isopropylphenoxyacetic acid (33 mg, 0.17 mmol) and 1-(3-dimethylaminopropyl)-3-ethylcarbodiimide hydrochloride (33 mg, 0.17 mmol) and allowed to stir 18 h at ambient temperature. The reaction was concentrated under reduced pressure and the resultant oil flash chromatographed with 30% ethyl acetate/hexanes to yield 35 mg (78%) of 2-(3-{1-[(4-Isopropyl-phenoxy)-acetyl]-piperidin-3-yl}-phenoxy)-2-methyl-propionic acid benzyl ester as a clear oil.

LC-MS 530.6 (M+H)$^+$.

$^1$H NMR (400 MHz, CDCl$_3$) δ 7.24 (m, 5H), 7.14 (m, 3H), 6.89 (m, 2H), 6.83 (m, 1H), 6.71 (s, 1H), 6.61 (d, 1H), 5.19 (s, 2H), 4.64 (m, 3H), 4.07 (d, 1H), 3.04 (t, 1H), 2.97 (m, 1H), 2.89 (m, 1H), 2.47 (m, 2H), 1.95 (m, 1H), 1.82 (m, 1H), 1.61, (s, 6H), 1.21 (d, 6H).

10% Palladium on carbon (4 mg, 10 wt %) was added to a solution of 2-(3-{1-[(4-Isopropyl-phenoxy)-acetyl]-piperidin-3-yl}-phenoxy)-2-methyl-propionic acid benzyl ester (35 mg, 0.066 mmol) in methanol (2 mL) and the resulting mixture hydrogenated at atmospheric pressure for 3 h. The reaction mixture was filtered through a plug of celite and the celite plug washed thoroughly with ethyl acetate. The combined filtrates were concentrated under reduced pressure to provide 29 mg (99%) of 2-(3-{1-[(4-Isopropyl-phenoxy)-acetyl]-piperidin-3-yl}-phenoxy)-2-methyl-propionic acid as a clear oil.

LC-MS 440.5 (M+H)$^+$.

$^1$H NMR (400 MHz, CDCl$_3$) δ 7.19 (t, 1H), 7.14 (t, 2H), 6.87 (m, 3H), 6.81 (m, 2H), 4.66 (m, 3H), 4.04 (dd, 1H), 3.05 (m, 1H), 2.85 (m, 1H), 2.65 (m, 2H), 2.02 (t, 1H), 1.82 (t, 1H), 1.65 (m, 1H), 1.59, (s, 6H), 1.21. (d, 6H).

Examples 2-1 to 2-11 were prepared from analogous starting materials using methods analogous to those described in Example 2.

EXAMPLE 2-1

2-(3-{1-[2-(4-Isopropyl-phenoxy)-2-methyl-propionyl]-piperidin-3-yl}-phenoxy)-2-methyl-propionic acid $^1$H NMR (400 MHz, CDCl$_3$) δ 1.22(m, 6H), 1.58(m, 6H), 1.65(m, 6H), 1.85(m, 2H), 2.12(t, 1H), 2.53(m, 2H), 2.87(m, 2H), 2.93(t, 1H), 4.79(m, 3H), 6.60(s, 1H), 6.76(m, 4H), 6.92(d, 1H), 7.08(t, 2H), 7.18(m, 1H).

LC-MS (M+1=468.5).

EXAMPLE 2-2

2-Methyl-2-(3-{1-[(4-trifluoromethoxy-phenoxy)-acetyl]-piperidin-3-yl}-phenoxy)-propionic acid $^1$H NMR (400 MHz, CDCl$_3$) δ 1.55(m, 1H), 1.59(d, 6H), 1.67(m, 1H), 1.83(t, 1H, 13.3 Hz), 2.03(t, 1H), 2.67(m, 2H), 3.05(m, 1H), 3.96(dd, 1H), 4.59(d, 1H), 4.61(t, 1H), 4.70(s, 1H), 6.81(m, 2H), 6.92(m, 3H), 7.14(m, 2H), 7.20(m, 1H).

LC-MS (M+1=482.4).

EXAMPLE 2-3

(S)-2-(3-{1-[(4-Isopropyl-phenoxy)-acetyl]-piperidin-3-yl}-phenoxy)-2-methyl-propionic acid $^1$H NMR (400 MHz, CDCl$_3$) δ 1.22(m, 6H), 1.59(s, 6H), 1.67(m, 1H), 1.80(t, 1H), 2.02(t, 1H), 2.65(m, 2H), 2.85(6, 1H), 3.03(dt, 1H), 4.04(dd, 1H), 4.64(m, 4H), 6.79(m, 1H), 6.89(m, 3H), 7.17(m, 3H).

LC-MS (M+1=440.5).

$[α]_D^{25}$=−73.8° (c 1.97, CH$_3$OH.)

EXAMPLE 2-4

(R)-2-(3-{1-[(4-Isopropyl-phenoxy)-acetyl]-piperidin-3-yl}-phenoxy)-2-methyl-propionic acid $^1$H NMR (400 MHz, CDCl$_3$) δ 1.22(m, 6H), 1.59(s, 6H), 1.67(m, 1H), 1.80(t, 1H), 2.02(t, 1H), 2.65(m, 2H), 2.85(6, 1H), 3.03(dt, 1H), 4.04(dd, 1H), 4.64(m, 4H), 6.79(m, 1H), 6.89(m, 3H), 7.17(m, 3H).

LC-MS (M+1=440.5).

$[α]_D^{25}$=74.1° (c 1.95, CH$_3$OH).

EXAMPLE 2-5

(S)-2-Methyl-2-(3-{1-[(4-trifluoromethoxy-phenoxy)-acetyl]-piperidin-3-yl}-phenoxy)-propionic acid $^1$H NMR (400 MHz, CDCl$_3$) δ 1.55(m, 1H), 1.59(d, 6H), 1.67(m, 1H), 1.83(t, 1H), 2.03(t, 1H), 2.67(m, 2H), 3.05(m, 1H), 3.96(dd, 1H), 4.59(d, 1H), 4.61 (t, 1H), 4.70(s, 1H), 6.81(m, 2H), 6.92(m, 3H), 7.14(m, 2H), 7.20(m, 1H)

LC-MS (M+1=482.4).

$[α]_D^{25}$=−55.0° (c 1.14, CH$_3$OH).

EXAMPLE 2-6

(R)-2-Methyl-2-(3-{1-[(4-trifluoromethoxy-phenoxy)-acetyl]-piperidin-3-yl}-phenoxy)-propionic acid $^1$H NMR (400 MHz, CDCl$_3$) δ 1.55(m, 1H), 1.59(d, 6H), 1.67(m, 1H), 1.83(t, 1H), 2.03(t, 1H), 2.67(m, 2H), 3.05(m, 1H), 3.96(dd, 1H), 4.59(d, 1H), 4.61 (t, 1H), 4.70(s, 1H), 6.81(m, 2H), 6.92(m, 3H), 7.14(m, 2H), 7.20(m, 1H).
LC-MS (M+1=482.4).
$[\alpha]_D^{25}$=63.9° (c 1.13, CH$_3$OH).

EXAMPLE 2-7

2-(3-{1-[(3-Isopropyl-phenoxy)-acetyl]-piperidin-3-yl}-phenoxy)-2-methyl-propionic acid $^1$H NMR (400 MHz, CD$_3$OD) δ 1.23(dd, 6H), 1.53(s, 6H), 1.78(m, 1H), 1.86(t, 1H), 2.00(m, 1H), 2.59(m, 1H), 2.71(m, 2H), 2.87(m, 1H), 3.12(q, 1H), 4.06(m, 1H), 4.54(t, 1H), 4.74(m, 2H), 6.75(t, 2H), 6.81(d, 1H), 6.86(s, 2H), 6.90(d, 1H), 7.19(t, 2H).
LC-MS (M+1=440.5).

EXAMPLE 2-8

2-(3-{1-[(4-tert-Butyl-phenoxy)-acetyl]-piperidin-3-yl}-phenoxy)-2-methyl-propionic acid $^1$H NMR (400 MHz, CD$_3$OD) δ 1.28(s, 9H), 1.54(s, 6H), 1.79(m, 1H), 1.84(t, 1H), 1.99(m, 1H), 2.61(t, 1H), 2.72(m, 1H), 3.13(q, 1H), 4.02(d, 1H), 4.53(t, 1H), 4.74(m, 2H), 6.75(d, 1H), 6.82(d, 1H), 6.89(m, 3H), 7.19(t, 1H), 7.32(dd, 2H).
LC-MS (M+1=454.5).

EXAMPLE 2-9

2-Methyl-2-[3-(1-m-tolyloxyacetyl-piperidin-3-yl)-phenoxy]-propionic acid $^1$H NMR (400 MHz, CD$_3$OD) δ 1.52(s, 6H), 1.74(m, 1H), 1.86(t, 1H), 2.00(brm, 1H), 2.31 (d, 3H), 2.61 (t, 1H), 2.71 (m, 1H), 3.13(q, 1H), 4.02(d, 1H), 4.53(t, 1H), 4.75(m, 2H), 6.78(m, 4H), 6.91(d, 1H), 7.17(m, 2H).
LC-MS (M+1=412.5).

EXAMPLE 2-10

2-Methyl-2-(3-{1-[(3-trifluoromethyl-phenoxy)-acetyl]-piperidin-3-yl}-phenoxy)-propionic acid $^1$H NMR (400 MHz, CD$_3$OD) δ 1.54(s, 6H), 1.74(m, 1H), 1.87(t, 1H), 2.02(m, 1H), 2.62(t, 1H), 2.74(m, 1H), 3.17(t, 1H), 3.97(d,1H), 4.53(t, 1H), 4.82(m, 2H), 6.75(d, 1H), 6.83(d, 1H), 6.92(t, 1H), 7.22(m, 4H), 7.48(t, 1H).
LC-MS (M+1=466.5).

EXAMPLE 2-11

(S)-2-(3-{1-[(3-Isopropyl-phenoxy)-acetyl]-piperidin-3-yl}-phenoxy)-2-methyl-propionic acid $^1$H NMR (400 MHz, CD$_3$OD) δ 1.23(dd, 6H), 1.53(t, 6H), 1.78(m, 1H), 1.89(t, 1H), 1.99(m, 1H), 2.59(t, 1H), 2.67(m, 1H), 2.87(m, 1H), 3.13(q, 1H), 4.05(m, 1H), 4.54(t, 1H), 4.76(abq, 1H), 4.85(m, 1H), 6.75(t, 2H), 6.82(d, 1H), 6.85(t, 2H), 6.90(d, 1H), 7.19(dt, 2H).
LC-MS (M+1=440.5).

EXAMPLE 3

2-(3-{1-[3-(4-Isopropyl-phenyl)-propionyl]-piperidin-3-yl}-phenoxy)-2-methyl-propionic acid To a solution of 2-methyl-2-(3-piperidin-3-yl-phenoxy)-propionic acid benzyl ester (Preparation 2, Method C; 99 mg, 0.28 mmol) in 2 mL methylene chloride was added 4-isopropyl-trans-cinnamic acid (59 mg, 0.31 mmol) and 1-(3-dimethylaminopropyl)-3-ethylcarbodiimide hydrochloride (81 mg, 0.42 mmol) and allowed to stir 18 h at ambient temperature. The reaction was concentrated under reduced pressure and the resultant oil flash chromatographed with 30% ethyl acetate/hexanes to yield 89 mg (60%) of 2-(3-{1-[3-(4-Isopropyl-phenyl)-acryloyl]-piperidin-3-yl}-phenoxy)-2-methyl-propionic acid benzyl ester as a clear oil.
LC-MS 530.6 (M+H)$^+$.
$^1$H NMR (400 MHz, CDCl$_3$) δ 7.67 (d, 2H), 7.45 (d, 2H), 7.31 (m, 3H), 7.19 (m, 4H), 7.11 (t, 1H), 6.84 (m, 2H), 6.71 (s, 1H), 6.61 (dd, 1H), 5.18 (s, 2H), 2.90 (m, 1H), 2.60 (m, 1H), 1.98 (m, 1H), 1.83 (m, 1H), 1.61, (s, 6H), 1.24 (d, 6H).

10% Palladium on carbon (10 mg, 10 wt %) was added to a solution of 2-(3-{1-[3-(4-Isopropyl-phenyl)-acryloyl]-piperidin-3-yl}-phenoxy)-2-methyl-propionic acid benzyl ester (89 mg, 0.17 mmol) in methanol (2 mL) and the resulting mixture hydrogenated at atmospheric pressure for 3 h. The reaction mixture was filtered through a plug of celite and the celite plug washed thoroughly with ethyl acetate. The combined filtrates were concentrated under reduced pressure to provide 73 mg (99%) of 2-(3-{1-[3-(4-Isopropyl-phenyl)-propionyl]-piperidin-3-yl}-phenoxy)-2-methyl-propionic acid as a clear oil.
MS (APCI) 438.3 (M+H)$^+$.
$^1$H NMR (400 MHz, CDCl$_3$) δ 7.13 (m, 5H), 6.90 (d, 1H), 6.79 (m, 2H), 4.66 (m, 1H), 3.78 (m, 1H), 3.05 (m, 1H), 2.91 (m, 3H), 2.62 (m, 3H), 2.37 (m, 1H), 1.96 (t, 1H), 1.75 (m, 1H), 1.59, (s, 6H), 1.21 (d, 6H).

Examples 3-1 and 3-2 were prepared from analogous starting materials using methods analogous to those described in Example 3.

EXAMPLE 3-1

2-Methyl-2-(3-{1-[3-(4-trifluoromethyl-phenyl)-propionyl]-piperidin-3-yl}-phenoxy)-propionic acid $^1$H NMR (400 MHz, CDCl$_3$) δ 1.47(m, 1H), 1.58(s, 6H), 1.79(d, 1H), 2.00(brs, 1H), 2.47 (m, 1H), 2.64(m, 3H), 3.02(brs, 3H), 3.79(d, 1H), 4.64(brs, 1H), 6.79(m, 2H), 6.89(m, 1H), 7.19(t, 1H), 7.32(brs, 2H), 7.53(brs, 2H).
LC-MS (M+1=464.5).

EXAMPLE 3-2

2-Methyl-2-(3-{1-[3-(4-trifluoromethoxy-phenyl)-propionyl]-piperidin-3-yl}-phenoxy)-propionic acid $^1$H NMR (400 MHz, CDCl$_3$) δ 1.53(m, 1H), 1.60(m, 6H), 1.64(m, 1H), 1.77(m, 1H), 2.00(m, 1H), 2.45(t, 1H), 2.61(m, 4H), 2.97(m, 4H), 3.79(d, 1H), 4.64(m, 1H), 6.81(m, 3H), 6.93(dd, 1H), 7.13(t, 2H), 7.21(m, 2H).
LC-MS (M+1=480.4).

EXAMPLE 4

3-[3-(1-Carboxy-1-methyl-ethoxy)-phenyl]-piperidine-1-carboxylic acid 4-isopropyl-phenyl ester To a solution of 4-isopropylphenol (1.54 g, 11.32 mmol) in 10 mL toluene was added 1,1'-carbonyldiimidazole (1.84 g, 11.32 mmol). This solution was stirred 18 h at ambient temperature. 2-methyl-2-(3-piperidin-3-yl-phenoxy)-propionic acid benzyl ester (Preparation 2, Method C; 2.0 g, 5.66 mmol) was added in 5 mL toluene and the resultant solution was stirred 18 h at ambient temperature. The reaction was diluted with water (200 mL), acidified with 1N aqueous hydrochloric acid and extracted with diethyl ether (2×150 mL). The organic extracts were combined, dried over anhydrous sodium sulfate, filtered and concentrated under reduced pressure. The resultant oil was flash chromatographed with 10% ethyl acetate/hexanes to yield 1.76 g (60%) of the desired 3-[3-(1-benzyloxycarbonyl-1-methyl-ethoxy)-phenyl]-piperidine-1-carboxylic acid 4-isopropyl-phenyl ester as a clear oil.

LC-MS 516.5 (M+H)$^+$.

$^1$H NMR (400 MHz, CDCl$_3$) δ 7.29 (m, 3H), 7.21 (m, 4H), 7.11 (t, 1H), 7.03 (d, 2H), 6.86 (d, 2H), 6.74 (s, 1H), 6.62 (dd, 1H), 5.19 (s, 2H), 4.32 (br d, 2H), 2.90 (m, 1H), 2.68 (m, 1H), 2.01 (m, 1H), 1.81 (m, 1H), 1.62, (s, 6H), 1.23 (d, 6H).

10% Palladium on carbon (180 mg, 10 wt %) was added to a solution of 3-[3-(1-Benzyloxycarbonyl-1-methyl-ethoxy)-phenyl]-piperidine-1-carboxylic acid 4-isopropyl-phenyl ester (1.76 g, 3.41 mmol) in methanol (15 mL) and the resulting mixture hydrogenated at atmospheric pressure for 3 h. The reaction mixture was filtered through a plug of celite and the celite plug washed thoroughly with ethyl acetate. The combined filtrates were concentrated under reduced pressure to provide 1.26 g (87%) of: 3-[3-(1-Carboxy-1-methyl-ethoxy)-phenyl]-piperidine-1-carboxylic acid 4-isopropyl-phenyl ester as a clear oil.

$^1$H NMR (400 MHz, DMSO$_{d6}$) δ 1.17(d, 6H), 1.33(s, 6H), 1.59(brm, 1H), 1.63(t, 1H), 1.74(d, 1H), 1.89(m, 1H), 2.64 (m, 1H), 2.87(m, 2H), 3.01(m, 1H), 4.02(m, 1H), 4.11(dd, 1H), 6.68(m, 3H), 7.02(m, 3H), 7.21(d, 2H).

LC-MS (M+1=426.5).

Examples 4-1 to 4-4 were prepared from analogous starting materials using methods analogous to those described in Example 4.

EXAMPLE 4-1

3-[3-(1-Carboxy-1-methyl-ethoxy)-phenyl]-piperidine-1-carboxylic acid 3-isopropyl-phenyl ester $^1$H NMR (400 MHz, CDCl$_3$) δ 1.24 (d, 6H), 1.52 (s, 6H), 1.73 (m, 2H), 1.84 (d, 1H), 2.03 (d, 1H), 2.73 (brm, 2H), 2.91 (m, 2H), 3.09 (q, 1H), 4.18 (d, 1H), 4.31 (t, 1H), 6.77 (dd, 1H), 6.85 (brs, 2H), 6.90 (d, 1H), 6.96 (s, 1H), 7.09 (d, 1H), 7.14 (t, 1H), 7.27 (t, 1H).

LC-MS (M+1=426.2).

EXAMPLE 4-2

3-[3-(1-Carboxy-1-methyl-ethoxy)-phenyl]-piperidine-1-carboxylic acid 4-tert-butyl-phenyl ester $^1$H NMR (400 MHz, CDCl$_3$) δ 1.34(s, 9H), 1.59(s, 6H), 1.67(m, 2H), 1.84(m, 1H), 2.06(m, 1H), 2.78(m, 1H), 2.91 (brm, 1H), 2.98 (br m, 1H), 4.32(brm, 1H), 6.81 (dd, 1H), 6.86(s, 1H), 7.01 (m, 3H), 7.23(m, 1H), 7.36(d, 1H).

LC-MS (M+1=440.5).

EXAMPLE 4-3

(R)-3-[3-(1-Carboxy-1-methyl-ethoxy)-phenyl]-piperidine-1-carboxylic acid 4-isopropyl-phenyl ester $^1$H NMR (400 MHz, DMSO$_{d6}$) δ 1.17(d, 6H), 1.33(s, 6H), 1.59(brm, 1H), 1.63(t, 1H), 1.74(d, 1H), 1.89(m, 1H), 2.64 (m, 1H), 2.87(m, 2H), 3.01 (m, 1H), 4.02(m, 1H), 4.11 (dd, 1H), 6.68(m, 3H), 7.02(m, 3H), 7.21 (d, 2H).

LC-MS (M+1=426.5).

$[α]_D^{25}$=68.1° (c 0.83, CH$_3$OH).

EXAMPLE 4-4

(S)-3-[3-(1-Carboxy-1-methyl-ethoxy)-phenyl]-piperidine-1-carboxylic acid 4-isopropyl-phenyl ester $^1$H NMR (400 MHz, DMSO$_{d6}$) δ 1.17(d, 6H), 1.33(s, 6H), 1.59(brm, 1H), 1.63(t, 1H), 1.74(d, 1H), 1.89(m, 1H), 2.64 (m, 1H), 2.87(m, 2H), 3.01(m, 1H), 4.02(m, 1H), 4.11(dd, 1H), 6.68(m, 3H), 7.02(m, 3H), 7.21(d, 2H).

LC-MS (M+1=426.5).

$[α]_D^{25}$=−77.4° (c 0.92, CH$_3$OH).

EXAMPLE 5

3-[3-(1-carboxy-1-methyl-ethoxy)-phenyl]-piperidine-1-carboxylic acid 4-isopropyl-benzyl ester To a solution of 4-isopropylbenzyl alcohol (0.86 g, 5.75 mmol) in 10 mL toluene was added 1,1'-carbonyldiimidazole (0.87 g, 5.40 mmol). This solution was stirred 18 h at ambient temperature. 2-methyl-2-(3-piperidin-3-yl-phenoxy)-propionic acid benzyl ester (Preparation 2, Method C; 1.27 g, 3.59 mmol) was added in 5 mL toluene and the resultant solution was stirred 18 h at ambient temperature. The reaction was diluted with water (200 mL), acidified with 1N aqueous hydrochloric acid and extracted with diethyl ether (2×150 mL). The organic extracts were combined, dried over anhydrous sodium sulfate, filtered and concentrated under reduced pressure. The resultant oil was flash chromatographed with 10% ethyl acetate/hexanes to yield 1.07 g (56%) of the desired 3-[3-(1-Benzyloxycarbonyl-1-methyl-ethoxy)-phenyl]-piperidine-1-carboxylic acid 4-isopropyl-benzyl ester as a clear oil.

LC-MS 547.4 (M+H$_2$O)$^+$.

$^1$H NMR (400 MHz, CDCl$_3$) δ 7.32–7.20 (m, 9H), 7.09 (t, 1H), 6.82 (d, 2H), 6.69 (s, 1H), 6.60 (dd, 1H), 5.18 (s, 2H), 5.11 (abq, 2H), 4.22 (br s, 2H), 2.90 (m, 1H), 2.74 (m, 2H), 2.57 (m, 1H), 1.94 (m, 1H), 1.75 (m, 1H), 1.61, (s, 6H), 1.53 (m, 1H), 1.24 (d, 6H).

A mixture of 3-[3-(1-Benzyloxycarbonyl-1-methyl-ethoxy)-phenyl]-piperidine-1-carboxylic acid 4-isopropyl-benzyl ester (1.07 g, 2.02 mmol), potassium carbonate (0.56 g, 4.04 mmol), methanol (15 mL) and water (3 mL) was heated at reflux for 3 h, cooled to room temperature and concentrated under reduced pressure. The resulting residue was taken up in water (150 mL), acidified with 1N aqueous hydrochloric acid and extracted with ethyl acetate (2×100 mL). The combined organic extracts were washed with saturated aqueous sodium chloride, dried over anhydrous sodium sulfate, filtered and concentrated under reduced pressure. The resultant oil was eluted through a 20 g plug of silica with 300 mL methylene chloride then 300 mL ethyl acetate. Fractions containing product were combined and concentrated under reduced pressure to yield 835 mg (94%) of 3-[3-(1-carboxy-1-methyl-ethoxy)-phenyl]-piperidine-1-carboxylic acid 4-isopropyl-benzyl ester as a clear glassy solid.

$^1$H NMR (400 MHz, DMSO$_{d6}$) δ 1.16(d, 6H), 1.46(s, 6H), 1.58(q, 1H), 1.68(d, 1H), 1.84(d, 1H), 2.55(t, 1H), 2.84(brm, 3H), 4.00(m, 2H), 5.01 (s, 2H), 6.62(d, 1H), 6.70(s, 1H), 6.84(m, 1H), 7.20(m, 5H).

LC-MS (M+1=440.5).

Examples 5-1 to 5-12 were prepared from analogous starting materials using methods analogous to those described in Example 5.

EXAMPLE 5-1

(S)-3-[3-(11-Carboxy-1-methyl-ethoxy)-phenyl]-piperidine-1-carboxylic acid 4-trifluoromethyl-benzyl ester $^1$H NMR (400 MHz, DMSO$_{d6}$) δ 1.48(s, 6H), 1.61(q, 1H), 1.71(d, 1H), 1.86(d, 1H), 2.58(brm, 1H), 2.82(brm, 1H), 2.91(brm, 1H), 3.99(m, 2H), 5.17(s, 2H), 6.63(d, 1H), 6.71(s, 1H), 6.85(d, 1H), 7.18(t, 1H), 7.56(brm, 1H), 7.72(d, 1H, 7.5 Hz).
LC-MS (M+1=466.5).
Rotation data for the S-isomer [α]$_D^{25}$–56.7° (c 0.84, CH$_3$OH)

EXAMPLE 5-2

(R)-3-[3-(1-Carboxy-1-methyl-ethoxy)-phenyl]-piperidine-1-carboxylic acid 4-isopropyl-benzyl ester $^1$H NMR (400 MHz, DMSO$_{d6}$) δ 1.16(d, 6H), 1.46(s, 6H), 1.58(q, 1H), 1.68(d, 1H), 1.84(d, 1H), 2.55(t, 1H), 2.84(brm, 3H), 4.00(m, 2H), 5.01(s, 2H), 6.62(d, 1H), 6.70(s, 1H), 6.84(m, 1H), 7.20(m, 5H).
LC-MS (M+1=440.5).
[α]$_D^{25}$=57.3° (c 0.65, CH$_3$OH).

EXAMPLE 5-3

(S)-3-[3-(1-Carboxy-1-methyl-ethoxy)-phenyl]-piperidine-1-carboxylic acid 4-isopropyl-benzyl ester $^1$H NMR (400 MHz, DMSO$_{d6}$) δ 1.16(d, 6H), 1.46(s, 6H), 1.58(q, 1H), 1.68(d, 1H), 1.84(d, 1H), 2.55(t, 1H), 2.84(brm, 3H), 4.00(m, 2H), 5.01 (s, 2H), 6.62(d, 1H), 6.70(s, 1H), 6.84(m, 1H), 7.20(m, 5H).
LC-MS (M+1=440.5).
[α]$_D^{25}$=–63.8° (c 0.81, CH$_3$OH).

EXAMPLE 5-4

(S)-3-[3-(1-Carboxy-1-methyl-ethoxy)-phenyl]-piperidine-1-carboxylic acid 4-cyclohexyl-benzyl ester $^1$H NMR (400 MHz, CD$_3$OD) δ 1.43(t, 3H), 1.54(s, 6H), 1.76(m, 2H), 1.84(d, 3H), 1.98(d, 1H), 2.51(m, 1H), 2.62(m, 1H), 2.86(brm, 2H), 4.11(m, 3H), 5.08(s, 2H), 5.49(s, 2H), 6.74(dd, 1H), 6.79(s, 1H), 6.87(brs, 1H), 7.18(m, 3H), 7.26(m, 2H).
LC-MS (M+1=480.5).

EXAMPLE 5-5

(S)-3-[3-(1-Carboxy-1-methyl-ethoxy)-phenyl]-piperidine-1-carboxylic acid 4-ethyl-benzyl ester $^1$H NMR (400 MHz, CDCl$_3$) δ 1.23(t, 3H), 1.60(s, 6H), 1.76(d, 1H), 1.99(m, 3H), 2.64(q, 2H), 2.80(m, 2H), 4.20(m, 2H), 5.10(s, 2H), 6.80(m, 1H), 6.94(d, 1H), 7.20(t, 2H), 7.26(m, 3H).
LC-MS (M+1=426.3).

EXAMPLE 5-6

(S)-3-[3-(1-Carboxy-1-methyl-ethoxy)-phenyl]-piperidine-1-carboxylic acid 3-trifluoromethyl-benzyl ester $^1$H NMR (400 MHz, CDCl$_3$) δ 1.60(s, 6H), 1.64(m, 1H), 1.78(d, 1H), 2.02(d, 1H), 2.66(brm, 1H), 2.82(brm, 2H), 4.21(brm, 2H), 6.79(m, 2H), 6.92(d, 1H), 7.21(t, 1H), 7.54 (m, 3H).
LC-MS (M+1=466.2).
rotation data for the S-isomer [α]$_D^{25}$–52.6° (c 0.57, CH$_3$OH)

EXAMPLE 5-7

(S)-3-[3-(1-Carboxy-1-methyl-ethoxy)-phenyl]-piperidine-1-carboxylic acid 4-trifluoromethoxy-benzyl ester $^1$H NMR (400 MHz, CDCl$_3$) δ 1.59(s, 6H), 1.62(m, 1H), 1.77(d, 1H), 2.01(d, 1H), 2.66(brm, 1H), 2.80(brm, 2H), 4.20(brm, 2H), 5.14 (s, 2H), 6.79(m, 2H), 6.92(d, 1H), 7.20(m, 3H), 7.38(d, 2H).
LC-MS (M+1=482.2).

EXAMPLE 5-8

(S)-3-[3-(1-Carboxy-1-methyl-ethoxy)-phenyl]-piperidine-1-carboxylic acid benzyl ester $^1$H NMR (400 MHz, CD$_3$OD) δ 1.55(s, 6H), 1.68(q, 1H), 1.77(d, 1H), 1.96(d, 1H), 2.60(t, 1H), 2.88(brm, 2H), 4.15(d, 2H), 5.12(s, 2H), 6.74(d, 1H), 6.79(brs, 1H), 6.88(brs, 1H), 7.17(t, 1H), 7.33(m, 5H).
LC-MS (M+1=420.2).

EXAMPLE 5-9

(S)-3-[3-(1-Carboxy-1-methyl-ethoxy)-phenyl]-piperidine-1-carboxylic acid 4-fluoro-benzyl ester $^1$H NMR (400 MHz, CD$_3$OD) δ 1.54(s, 6H), 1.66(q, 1H), 1.79(d, 1H), 1.96(d, 1H), 2.60(t, 1H), 2.87(brm, 1H), 4.14(d, 2H), 5.10(s, 2H), 6.74(d, 1H), 6.78(brs, 1H), 6.88(brs, 1H), 7.08(t, 2H), 7.17(t, 1H), 7.39(t, 2H).
LC-MS (M+1=438.1).

EXAMPLE 5-10

(S)-3-[3-(1-Carboxy-1-methyl-ethoxy)-phenyl]-piperidine-1-carboxylic acid 4-fluoro-3-trifluoromethyl-benzyl ester $^1$H NMR (400 MHz, CD$_3$OD) δ 1.56(d, 6H), 1.67(q, 1H), 1.78(d, 1H), 1.97(d, 1H), 2.62(t, 1H), 2.87(brm, 2H), 4.14(d, 2H), 5.16(s, 1H), 6.74(dd, 1H), 6.79(brs, 1 h), 6.88(brs, 1H), 7.17(t, 1H), 7.33(t, 1H), 7.71(m, 2H).
LC-MS (M+1=484.1).

EXAMPLE 5-11

(S)-3-[3-(1-Carboxy-1-methyl-ethoxy)-phenyl]-piperidine-1-carboxylic acid 3-fluoro-4-trifluoromethyl-benzyl ester $^1$H NMR (400 MHz, CD$_3$OD) δ 1.54(s, 6H), 1.69(q, 1H), 1.81(d, 1H), 1.99(d, 1H), 2.66(t, 1H), 2.90(m, 2H), 4.16

(brm, 2H), 5.20(s, 1H), 6.74(dd, 1H), 6.80(s, 1H), 6.89(d, 1H), 7.18(t, 1H), 7.33(brs, 2H), 7.68(t, 1H, 7.6 Hz).
LC-MS (M+1=484.1).

EXAMPLE 5-12

(S)-3-[3-(1-Carboxy-1-methyl-ethoxy)-phenyl]-piperidine-1-carboxylic acid 3-trifluoromethoxy-benzyl ester $^1$H NMR (400 MHz, CD$_3$OD) δ 1.54(s, 1H), 1.68(q, 1H), 1.79(d, 1H), 1.97(d, 1H), 2.62(t, 1H), 2.87(brm, 1H), 4.15(d, 2H), 5.17(s, 2H), 6.74(dd, 1H), 6.79(s, 1H), 6.88(brs, 1H), 7.15(t, 1H), 7.22(d, 1H), 7.28(s, 1H), 7.36(m, 1H), 7.46(t, 1H).
LC-MS (M+1=482.1).

EXAMPLE 6

3-[3-(1-carboxy-1-methyl-ethoxy)-phenyl]-piperidine-1-carboxylic acid 4-isopropyl-benzyl ester To a solution of 4-isopropylbenzyl alcohol (4.51 g, 30.02 mmol) in 50 mL toluene was added 1,1'-carbonyldiimidazole (4.87 g, 30.02 mmol). This solution was stirred 18 h at ambient temperature. White precipitate was filtered off and the filtrate was concentrated under reduced pressure. The resultant oil was flash chromatographed with 15% ethyl acetate/hexanes to yield 6.41 g (87%) of imidazole-1-carboxylic acid-(4-isopropyl)benzyl ester, a clear oil.
$^1$H NMR (400 MHz, CDCl$_3$) δ 8.16 (s, 1H), 7.43 (t, 1H), 7.37 (d, 2H), 7.27 (d, 2H), 7.05 (d, 1H), 5.39 (s, 2H), 2.93 (m, 1H), 1.25 (d, 6H).
To a solution of 2-methyl-2-(3-piperidin-3-yl-phenoxy)-propionic acid ethyl ester (Preparation 2; Method D; 7.60 g, 17.21 mmol) in 20 mL toluene was added imidazole-1-carboxylic acid-(4-isopropyl)benzyl ester (4.20 g, 17.21 mmol) and stirred for 18 h at ambient temperature. The reaction was diluted with water (300 mL), acidified with 1 N HCl and extracted with diethyl ether (2×200 mL). The organic extracts were combined, dried over anhydrous sodium sulfate, filtered and concentrated under reduced pressure. The resultant oil was flash chromatographed with 10% ethyl acetate/hexanes to yield 6.23 g (77%) of 3-[3-(1-ethoxycarbonyl-1-methyl-ethoxy)-phenyl]-piperidine-1-carboxylic acid 4-isopropyl-benzyl ester as a clear oil.
LC-MS 468.5 (M+H)$^+$.
$^1$H NMR (400 MHz, CDCl$_3$) δ 7.30–7.20 (m, 4H), 7.15 (t, 1H), 6.84 (d, 2H), 6.73 (s, 1H), 6.66 (dd, 1H), 5.10 (abq, 2H), 4.22 (q, 4H), 2.90 (m, 1H), 2.76 (brm, 2H), 2.61 (m, 1H), 1.98 (m, 1H), 1.75 (m, 1H), 1.67 (s, 1H), 1.59, (s, 6H), 1.25 (d, 6H).
A mixture of 3-[3-(1-ethoxycarbonyl-1-methyl-ethoxy)-phenyl]-piperidine-1-carboxylic acid 4-isopropyl-benzyl ester (6.23 g, 13.32 mmol), potassium carbonate (3.68 g, 26.64 mmol), methanol (100 mL) and water (20 mL) was heated at reflux for 3 h, cooled to room temperature and concentrated under reduced pressure. The resulting residue was taken up in water (250 mL), acidified with 1N aqueous hydrochloric acid and extracted with ethyl acetate (2×200 mL). The combined organic extracts were washed with saturated aqueous sodium chloride, dried over anhydrous sodium sulfate, filtered, concentrated under reduced pressure to provide 5.86 g (99%) of 3-[3-(1-carboxy-1-methyl-ethoxy)-phenyl]-piperidine-1-carboxylic acid 4-isopropyl-benzyl ester as a clear glassy solid.
LC-MS 440.5 (M+H)$^+$.

$^1$H NMR (400 MHz, CD$_3$OD) δ 7.33–7.150 (m, 5H), 6.87 (brs, 1H), 6.79 (s, 1H), 6.74 (dd, 1H), 5.09 (s, 2H), 4.15 (br d, 2H), 2.89 (m, 3H), 2.61 (m, 1H), 1.96 (m, 1H), 1.89 (m, 1H), 1.64 (q, 1H), 1.54 (s, 6H), 1.23 (d, 6H).

Examples 6-1 and 6-2 were prepared from analogous starting materials using methods analogous to those described in Example 6.

EXAMPLE 6-1

(3S)-3-[3-(1-Carboxy-1-methyl-ethoxy)-phenyl]-piperidine-1-carboxylic acid 4-trifluoromethyl-benzyl ester 4-(Trifluoromethyl)benzyl alcohol (0.88 g, 5.0 mmol) was dissolved in toluene (5 mL) and followed by the addition of 1,1'-carbonyldiimidazole (0.89 g, 5.5 mmol). The resulting mixture was stirred under nitrogen at rt for 1 h. A solution of (3S)-2-methyl-2-(3-piperidin-3-yl-phenoxy)-propionic acid methyl ester (Preparation 2; Method E) (1.39 g, 5.0 mmol) in toluene (8 mL) was then introduced and the reaction mixture was heated at 60° C. for 2 h. After cooling, the reaction solution was diluted with ethyl acetate (30 mL) and washed with 1 M HCl (30 mL) and brine (30 mL). The separated organic layer was dried over sodium sulfate and concentrated to yield 2.43 g (100%) of (3S)-3-[3-(1-methoxycarbonyl-1-methyl-ethoxy)-phenyl]-piperidine-1-carboxylic acid 4-trifluoromethyl-benzyl ester as a light yellow oil: $^1$H NMR (CDCl$_3$) δ 1.58 (s, 8H), 1.77 (br m, 1H), 2.00 (br m, 1H), 2.61 (br, 1H), 2.80 (br, 2H), 3.74 (s, 3H), 4.21 (br s, 2H), 5.19 (s, 2H), 6.63 (dd, 1H), 6.72 (s, 1H), 6.83 (br d, 1H), 7.16 (t, 1H), 7.46 (br s, 2H), 7.60 (d, 2H); MS m/z (relative intensity) 479 (M$^+$, 25), 420 (20), 395 (20), 276 (20), 220 (60), 202 (42), 176 (45), 159 (100).

A mixture of (3S)-3-[3-(1-methoxycarbonyl-1-methyl-ethoxy)-phenyl]-piperidine-1-carboxylic acid 4-trifluoromethyl-benzyl ester (2.43 g, 5.0 mmol) and potassium carbonate (1.38 g, 10.0 mmol) in MeOH/H$_2$O (10/3 mL) was refluxed under nitrogen for 1.5 h. After solvent removal, the residue was taken up in water (40 mL) and adjusted to pH 2 with 3 M HCl cautiously. The resulting mixture was extracted with ethyl acetate (2×40 mL). The organic extract was washed with brine (50 mL), dried over sodium sulfate, and concentrated to give 2.40 g of sticky, light yellow oil. Hexane (24 mL) was added to the oil residue and the mixture was heated at reflux with stirring. White solid formed and ethanol (1.6 mL) was added dropwise to the refluxing mixture to redissolve the solid. The resulting solution was cooled to rt with vigorous stirring to prevent the product from precipitating as oil. White solid formed gradually and stirring was continued overnight. The first crop gave 1.78 g of solid with 99.5% ee; the second crop yielded 0.15 g with 96.3% ee. A total of 1.93 g (83%) of (3S)-3-[3-(1-carboxy-1-methyl-ethoxy)-phenyl]-piperidine-1-carboxylic acid 4-trifluoromethyl-benzyl ester as a white crystalline solid was obtained: $^1$H NMR (CDCl$_3$) δ 1.58 (s, 8H), 1.77 (br m, 1H), 2.00 (br m, 1H), 2.61 (br, 1H), 2.80 (br m, 2H), 4.19 (br s, 2H), 5.18 (s, 2H), 6.76 (d, 1H), 6.80 (s, 1H), 6.89 (br d, 1H), 7.18 (t, 1H), 7.45 (br s, 2H), 7.59 (d, 2H); MS m/z 466 (MH$^+$).

HPLC analysis conditions: Daicel Chiralpak OJ, 4.6×250 mm; hexanes/2-propanol/TFA (90/10/0.1); 1.5 mL/min; 210 nm.

EXAMPLE 6-2

3-[3-(1-Carboxy-1-methyl-ethoxy)-phenyl]-piperidine-1-carboxylic acid 4-cyclopropyl-benzyl ester $^1$H NMR (400 MHz, CD$_3$OD) δ 7.24–7.15 (m, 3H), 7.06 (d, 2H), 6.78–6.73 (m, 3H), 5.07 (s, 2H), 4.14 (d, 2H), 2.95–2.50 (m, 3H), 1.90–1.45 (m, 5H), 1.54 (s, 6H), 0.95 (m, 2H) 0.66 (m, 2H).
MS (LC-MS) 436.1 (M–H)$^-$.

EXAMPLE 7

(S)-3-[3-(1-carboxy-1-methyl-ethoxy)-phenyl]-piperidine-1-carboxylic acid methyl ester (S)-2-methyl-2-(3-piperidin-3-yl-phenoxy)-propionic acid benzyl ester-L-(+)-tartrate salt (Preparation 3, Method F; 119 mg, 0.24 mmol) was dissolved in 2 mL methlyene chloride and 1 mL water. Sodium bicarbonate (79 mg, 0.95 mmol) and methyl chloroformate (37 mL, 0.47 mmol) were added, and the biphasic mixture and resulting mixture stirred at ambient temperature for 2 h. The mixture was diluted with water (50 mL), acidified with 1N aqueous hydrochloric acid and extracted with diethyl ether (2×50 mL). The combined organic extracts were dried over anhydrous sodium sulfate, filtered and concentrated under reduced pressure to provide 90 mg (93%) of (S)-3-[3-(1-Benzyloxycarbonyl-1-methyl-ethoxy)-phenyl]-piperidine-1-carboxylic acid methyl ester as a clear oil.
LC-MS 412.3 (M+H)$^+$.
$^1$H NMR (400 MHz, CDCl$_3$) δ 7.30 (m, 2H), 7.25 (m, 3H), 7.09 (t, 1H), 6.83 (d, 1H), 6.70 (s, 1H), 6.60 (dd, 1H), 5.19 (s, 2H), 4.18 (brd, 2H), 3.70 (s, 3H), 2.68 (m, 2H), 2.56 (m, 1H), 1.95 (m, 1H), 1.73 (m, 1H), 1.61, (s, 6H), 1.53 (m, 1H).

10% Palladium on carbon (18 mg, 10 wt %) was added to a solution of (S)-3-[3-(1-Benzyloxycarbonyl-1-methyl-ethoxy)-phenyl]-piperidine-1-carboxylic acid methyl ester (90 mg, 0.22 mmol) in methanol (3 mL) and the resulting mixture hydrogenated at atmospheric pressure for 3 h. The reaction mixture was filtered through a plug of celite and the celite plug washed thoroughly with ethyl acetate. The combined filtrates were concentrated under reduced pressure to provide 65 mg (92%) of (S)-3-[3-(1-carboxy-1-methyl-ethoxy)-phenyl]-piperidine-1-carboxylic acid methyl ester as a clear oil.
LC-MS 322.3 (M+H)$^+$.
$^1$H NMR (400 MHz, CD$_3$OD) δ 7.18 (t, 1H), 6.89 (d, 2H), 6.79 (s, 1H), 6.74 (dd, 1H), 4.11 (brd, 2H), 3.69 (s, 3H), 2.82 (br, 2H), 2.61 (m, 1H), 1.95 (m, 1H), 1.78 (m, 1H), 1.65 (m, 1H) 1.55, (s, 6H).

Examples 7-1 to 7-5 were prepared from analogous starting materials using methods analogous to those described in Example 7.

EXAMPLE 7-1

(S)-3-[3-(1-Carboxy-1-methyl-ethoxy)-phenyl]-piperidine-1-carboxylic acid 2-methoxy-ethyl ester $^1$H NMR (400 MHz, CD$_3$OD) δ 1.55(s, 6H), 1.68(m, 1H), 1.79(d, 1H), 1.97(d, 1H), 2.61(t, 1H), 2.84(brm, 2H), 3.37(s, 3H), 3.60(t, 2H), 4.14(d, 2H), 4.21(brs, 1H), 6.74(dd, 1H), 6.80(s, 1H), 6.89(d, 1H), 7.17(t, 1H).
LC-MS (M+1=366.4).

EXAMPLE 7-2

(S)-3-[3-(1-Carboxy-1-methyl-ethoxy)-phenyl]-piperidine-1-carboxylic acid isopropyl ester $^1$H NMR (400 MHz, CD$_3$OD) δ 1.25(s, 6H), 1.57(s, 6H), 1.67(q, 1H), 1.77(d, 1H), 1.97(d, 1H), 2.59(t, 1H), 2.83(brs, 2H), 4.12(d, 2H), 4.82(m, 1H), 6.74(dd, 1H), 6.79(s, 1H), 6.89(d, 1H), 7.18(t, 1H, 7.9 Hz).
LC-MS (M+1=350.4).

EXAMPLE 7-3

(S)-3-[3-(1-Carboxy-1-methyl-ethoxy)-phenyl]-piperidine-1-carboxylic acid ethyl ester $^1$H NMR (400 MHz, CD$_3$OD) δ 1.25(t, 3H), 1.57(s, 6H), 1.67(q, 1H), 1.77(d, 1H), 1.97(d, 1H), 2.60(t, 1H), 2.83(brs, 2H), 4.12(m, 4H), 6.74(dd, 1H), 6.80(s, 1H), 6.89(d, 1H), 7.19(t, 1H).
LC-MS (M+1=336.3).

EXAMPLE 7-4

(S)-3-[3-(1-Carboxy-1-methyl-ethoxy)-phenyl]-piperidine-1-carboxylic acid isobutyl ester $^1$H NMR (400 MHz, CD$_3$OD) δ 0.95(d, 6H), 1.56(s, 6H), 1.67(q, 1H), 1.79(dd, 1H), 1.95(m, 2H), 2.61(t, 1H), 2.86 (brm, 2H), 3.86(d, 2H), 4.13(d, 2H), 6.75(dd, 1H), 6.80(s, 1H), 6.89(d, 1H), 7.19(t, 1H, 7.9 Hz).
LC-MS (M+1=364.3).

EXAMPLE 7-5

(S)-3-[3-(1-Carboxy-1-methyl-ethoxy)-phenyl]-piperidine-1-carboxylic acid cyclohexylmethyl ester $^1$H NMR (400 MHz, CD$_3$OD) δ 1.02(q, 2H), 1.26(m, 3H), 1.56(s, 6H), 1.72(m, 7H), 1.99(d, 1H), 2.60(t, 1H), 2.88 (brm, 2H), 3.89(d, 2H), 4.13(d, 2H), 6.75(dd, 1H), 6.80(s, 1H), 6.89(d, 1H), 7.19(t, 1H).
LC-MS (M+1=404.2).

EXAMPLE 8

2-methyl-2-{3-[1-(4-trifluoromethyl-benzylcarbamoyl)-piperidin-3-yl]-phenoxy}-propionic acid To a solution of 4-trifluoromethylbenzyl amine (170 mL, 1.19 mmol) in 5 mL toluene was added 1,1'-carbonyldiimidazole (193 mg, 1.19 mmol). This solution was stirred 18 h at ambient temperature. 2-methyl-2-(3-piperidin-3-yl-phenoxy)-propionic acid benzyl ester (Preparation 2, Method C; 421 mg, 1.19 mmol) was added in 5 mL toluene and the resultant solution was stirred 18 h at ambient temperature. The reaction was diluted with water (100 mL), acidified with 1N aqueous hydrochloric acid and extracted with ethyl acetate (2×50 mL). The organic extracts were combined, dried over anhydrous sodium sulfate, filtered and concentrated under reduced pressure. The resultant oil was flash chromatographed with 35% ethyl acetate/hexanes to yield 473 mg (72%) of the desired 2-methyl-2-{3-[1-(4-trifluoromethyl-benzylcarbamoyl)-piperidin-3-yl]-phenoxy}-propionic acid benzyl ester as a clear oil.
LC-MS 599.4 (M+H)$^+$.

¹H NMR (400 MHz, CDCl₃) δ 7.58 (d, 2H), 7.43 (d, 2H), 7.26 (m, 6H), 7.10 (t, 1H), 6.83 (d, 1H), 6.70 (s, 1H), 6.60 (dd, 1H), 5.19 (s, 2H), 4.80 (m, 1H), 4.49 (d, 2H), 4.07 (d, 1H), 3.91 (d, 1H), 2.76 (m, 2H), 2.59 (m, 1H), 1.97 (m, 1H), 1.78 (m, 1H), 1.60, (s, 6H).

10% Palladium on carbon (53 mg, 50 wt %) was added to a solution of 2-methyl-2-{3-[1-(4-trifluoromethyl-benzylcarbamoyl)-piperidin-3-yl]-phenoxy}-propionic acid benzyl ester (111 mg, 0.226 mmol) in methanol (5 mL) and the resulting mixture hydrogenated at 50 psi for 4 h. The reaction mixture was filtered through a plug of celite and the celite plug washed thoroughly with ethyl acetate. The combined filtrates were concentrated under reduced pressure. The resultant oil was flash chromatographed with 2% methanol/chloroform to provide 46.6 mg (51%) of 2-methyl-2-{3-[1-(4-trifluoromethyl-benzylcarbamoyl)-piperidin-3-yl]-phenoxy}-propionic acid as a clear oil.

LC-MS 465.5 (M+H)⁺.

¹H NMR (400 MHz, CDCl₃) δ 7.60 (d, 2H), 7.46 (d, 2H), 7.18 (t, 1H), 6.91 (d, 1H), 6.83 (s, 1H), 6.74 (dd, 1H), 4.42 (s, 2H), 4.09 (t, 1H), 2.85 (m, 2H), 2.64 (m, 1H), 1.99 (m, 1H), 1.81 (m, 1H), 1.70 (m, 2H), 1.54, (s, 6H).

Examples 8-1 to 8-6 were prepared from analogous starting materials using methods analogous to those described in Example 8.

EXAMPLE 8-1

2-{3-[1-(4-Isopropyl-benzylcarbamoyl)-piperidin-3-yl]-phenoxy}-2-methyl-propionic acid ¹H NMR (400 MHz, CD₃OD) δ 1.22(m, 6H), 1.55(s, 6H), 1.64(m, 1H), 1.78(d, 1H, 12.9 Hz), 1.97(d, 1H), 2.62(t, 1H), 2.83(m, 2H), 4.08(m, 2H), 4.31(s, 2H), 6.73(dd, 1H), 6.82(t, 1H), 6.91(d, 1H), 7.18(m, 5H).

LC-MS (M+1=439.5).

EXAMPLE 8-2

2-Methyl-2-{3-[1-(4-trifluoromethoxy-benzylcarbamoyl)-piperidin-3-yl]-phenoxy}-propionic acid ¹H NMR (400 MHz, CD₃OD) δ 1.54(s, 6H), 1.59(m, 1H), 1.68(m, 1H), 1.79(d, 1H), 1.99(d, 1H), 2.64(t, 1H), 2.84(q, 2H), 4.08(t, 2H), 4.36(s, 1H), 6.74(dd, 1H), 6.82(t, 1H), 6.92(d, 1H), 7.18(m, 3H), 7.37(d, 1H).

LC-MS (M+1=481.3).

EXAMPLE 8-3

(S)-2-Methyl-2-{3-[1-(4-trifluoromethoxy-benzylcarbamoyl)-piperidin-3-yl]-phenoxy}-propionic acid ¹H NMR (400 MHz, CD₃OD) δ 1.54(s, 6H), 1.59(m, 1H), 1.68(m, 1H), 1.79(d, 1H), 1.99(d, 1H), 2.64(t, 1H), 2.84(q, 2H), 4.08(t, 2H), 4.36(s, 1H), 6.74(dd, 1H), 6.82(t, 1H), 6.92(d, 1H), 7.18(m, 3H), 7.37(d, 1H).

LC-MS (M+1=481.5).

EXAMPLE 8-4

(S)-2-{3-[1-(4-Isopropyl-benzylcarbamoyl)-piperidin-3-yl]-phenoxy}-2-methyl-propionic acid ¹H NMR (400 MHz, CD₃OD) δ 1.22(m, 6H), 1.55(s, 6H), 1.64(m, 1H), 1.78(d, 1H), 1.97(d, 1H), 2.62(t, 1H), 2.83(m, 2H), 4.08(m, 2H), 4.31(s, 2H), 6.73(dd, 1H), 6.82(t, 1H), 6.91(d, 1H), 7.18(m, 5H).

LC-MS (M+1=439.5).

EXAMPLE 8-5

(S)-2-{3-[1-(Cyclohexylmethyl-carbamoyl)-piperidin-3-yl]-phenoxy}-2-methyl-propionic acid ¹H NMR (400 MHz, CD₃OD) δ 0.91(q, 2H), 1.23(m, 3H), 1.56(s, 6H), 1.70(m, 6H), 1.98(d, 1H), 2.61(t, 1H), 2.80(q, 2H), 2.98(d, 2H), 4.04(t, 2H), 6.74(dd, 1H), 6.81(s, 1H), 6.91(d, 1H), 7.18(t, 1H).

LC-MS (M+1=403.3).

EXAMPLE 8-6

2-{3-[1-(4-Isopropyl-phenylcarbamoyl)-piperidin-3-yl]-phenoxy}-2-methyl-propionic acid ¹H NMR (400 MHz, CDCl₃) δ 7.25–7.19 (m, 3H), 7.13 (d, 2H), 6.93 (d, 1H), 6.84 (s, 1H), 6.81 (d, 1H), 6.38 (s, 1H), 4.06–3.98 (m, 2H), 2.91–2.73 (m, 4H), 2.02 (m, 1H), 1.82 (m, 1H), 1.70–1.50 (m, 2H), 1.21 (d, 6H).

LC-MS (M+1=425.3)

Example 9

(R)-3-(3-carboxy-4-methyl-phenyl)-piperidine-1-carboxylic acid 4-trifluoromethyl-benzyl ester 5-chloro-2-methylbenzoic acid (5.04 g, 29.5 mmol) was dissolved in 100 mL ethanol in a 250 mL round bottom flask fitted with a water condenser. 0.5 mL concentrated sulfuric acid was added and the solution heated to reflux. The solution was heated for 48 h and cooled to ambient temperature. The ethanol was removed under reduced pressure. The resultant oil was taken up in 300 mL diethyl ether and washed with saturated aqueous sodium bicarbonate (2×300 mL). The organic layer was dried over Na₂SO₄, filtered and concentrated under reduced pressure to yield 5.12 (87%) of ethyl 5-chloro-2-methylbenzoate as a clear oil.

¹H NMR (400 MHz, CDCl₃) δ 7.88 (d, 1H), 7.35 (dd, 1H), 7.18 (d, 1H), 4.36 (q, 2H), 2.56 (s, 3H), 1.40 (t, 3H).

Ethyl 5-chloro-2-methylbenzoate (16.60 g, 83.56 mmol) and diethyl-(3-pyridyl)borane (13.52 g, 91.92 mmol) were dissolved in 100 mL tetrahydrofuran in a 500 mL round bottom flask equipped with a magnetic stirrer. Sodium carbonate (26.57 g, 250.69 mmol) and 50 mL water were added followed by palladium acetate (0.38 g, 1.67 mmol) and (2'-dicyclohexylphosphanyl-biphenyl-2-yl)-dimethylamine (AmPhos, 0.92 g, 2.51 mmol) and 25 mL ethanol. The mixture was heated at reflux for 6 h then cooled to ambient temperature. The mixture was diluted with 600 mL water and extracted with diethyl ether (2×300 mL). The organic phases were combined and extracted with 1N HCl (3×200 mL). The acidic extractions were combined and made basic with 5N aqueous sodium hydroxide. This basic layer was extracted with diethyl ether (3×500 mL) and the extracts were combined and dried over anhydrous sodium sulfate, filtered and concentrated under reduced pressure to yield 19.57 g (97%) of ethyl 5-(3-pyridyl)-2-methylbenzoate as a brown oil.

MS (LC-MS) 242.2 (M+H)⁺.

¹H NMR (400 MHz, CDCl₃) δ 8.87 (d, 1H), 8.61 (dd, 1H), 8.13 (d, 1H), 7.95 (dd, 1H), 7.62 (dd, 1H), 7.44 (dd, 1H), 7.37 (d, 1H), 4.40 (t, 2H), 2.65 (s, 3H), 1.42 (q, 3H).

A 500 mL hydrogenation vessel was charged with 2.0 g platinum(II)oxide and purged with nitrogen. Ethyl 5-(3-pyridyl)-2-methylbenzoate (19.57 g, 81.10 mmol) was added as a solution in 200 mL acetic acid. The suspension was hydrogenated at 45 psi for 18 h. The catalyst was filtered through celite and the filter plug was washed with 200 mL acetic acid. The filtrate was concentrated under reduced pressure. The resultant oil was taken up in 500 mL water and made basic with 5N aqueous sodium hydroxide. This basic layer was extracted with ethyl acetate (2×500 mL) and the extracts were combined and dried over anhydrous sodium sulfate, filtered and concentrated under reduced pressure. The resultant oil was taken up in 200 mL hot ethanol. L-(+)-tartaric acid (12.17 g, 81.1 mmol) was added into the ethanol solution and was allowed to stir at ambient temperature for 48 h, forming a white precipitate that was collected by filtration. The white solid was recrystallized from hot 5% $H_2O$/ethanol (300 mL) and then from 350 mL hot 20% $H_2O$/ethanol to yield 11.25 g (35%, 95.8% ee) of (S)-ethyl 5-(3-piperidinyl)-2-methylbenzoate-L-tartaric acid salt as a white solid. The mother liquors were combined and concentrated under reduced pressure. The resultant oil was taken up in 300 mL water and made basic with 5N aqueous sodium hydroxide. This basic layer was extracted with ethyl acetate (2×300 mL) and the extracts were combined and dried over anhydrous sodium sulfate, filtered and concentrated under reduced pressure. The resultant oil was taken up in 200 mL hot ethanol. D-(−)-tartaric acid (6.82 g, 45.4 mmol) was added into the ethanol solution and was allowed to stir at ambient temperature for 48 h, forming a white precipitate that was collected by filtration. The white solid was recrystallized from hot 5% $H_2O$/ethanol (300 mL) and then from 350 mL hot 20% $H_2O$/ethanol to yield 13.51 g (42%, 100% ee) of (R)-ethyl 5-(3-piperidinyl)-2-methylbenzoate-D-tartaric acid salt as a white solid.

MS (LC-MS) 248.2 $(M+H)^+$.

$^1$H NMR (400 MHz, $CDCl_3$) δ 7.73 (d, 1H), 7.24 (dd, 1H), 7.18 (d, 1H), 4.35 (q, 2H), 3.18 (t, 2H), 2.78 (t, 1H), 2.68 (m, 2H), 2.54 (s, 3H), 2.38 (br, 1H), 2.01 (d, 1H), 1.82 (m, 1H), 1.64 (6, 2H), 1.40 (t, 3H).

HPLC analysis: Chiralcel AD, 1 mL/min, 10% ethanol/heptane 0.025% diethylamine, rt=8.36 min, 9.00 min (R)-Ethyl 5-(3-piperidinyl)-2-methylbenzoate-D-tartaric acid (2.02 g, 5.08 mmol) was dissolved in 100 mL ethyl acetate and washed with 100 mL saturated aqueous $NaHCO_3$. The organic phase was dried over $Na_2SO_4$ and concentrated under reduced pressure. The resultant oil was taken up in 10 mL toluene and imidazole-1-carboxylic acid 4-trifluoromethyl-benzyl ester (1.37 g, 5.08 mmol) was added. The reaction was stirred for 72 h at room temperature under nitrogen. The reaction was diluted with water (200 mL), acidified with 1N aqueous hydrochloric acid and extracted with diethyl ether (2×150 mL). The organic extracts were combined, dried over anhydrous sodium sulfate, filtered and concentrated under reduced pressure. The resultant oil was flash chromatographed with 10% ethyl acetate/hexanes to yield 2.12 g (93%) of the desired (R)-3-(3-ethoxycarbonyl-4-methyl-phenyl)-piperidine-1-carboxylic acid 4-trifluoromethyl-benzyl ester as a clear oil.

MS (LC-MS) 450.1 $(M+H)^+$.

$^1$H NMR (400 MHz, $CDCl_3$) δ 7.75 (brs, 1H), 7.60 (brs, 2H), 7.46 (brs, 2H) 7.23 (s, 1H), 7.18 (d, 1H), 5.20 (s, 2H), 4.36 (q, 2H), 4.23 (brm, 2H), 2.92 (br, 2H), 2.77 (m, 1H), 2.55 (s, 3H), 2.02 (d, 1H), 1.82 (d, 1H), 1.61 (m, 4H), 1.39 (t, 3H).

A mixture of (R)-3-(3-ethoxycarbonyl-4-methyl-phenyl)-piperidine-1-carboxylic acid 4-trifluoromethyl-benzyl ester (2.12 g, 4.72 mmol), potassium carbonate (1.30 g, 9.43 mmol), methanol (25 mL) and water (6 mL) was heated at reflux for 3 h, cooled to room temperature and concentrated under reduced pressure. The resulting residue was taken up in water (150 mL), acidified with 1N aqueous hydrochloric acid and extracted with ethyl acetate (2×100 mL). The combined organic extracts were washed with saturated aqueous sodium chloride, dried over anhydrous sodium sulfate, filtered, concentrated under reduced pressure to yield 1.98 g (99%) (R)-3-(3-carboxy-4-methyl-phenyl)-piperidine-1-carboxylic acid 4-trifluoromethyl-benzyl ester as a white solid.

MS (LC-MS) 420.0 $(M+H)^+$.

$^1$H NMR (400 MHz, $CD_3OD$) δ 7.80 (d, 1H), 7.67 (d, 2H), 7.55 (brs, 2H), 7.32 (d, 1H), 7.22 (d, 1H), 5.22 (s, 2H), 4.17 (d, 2H), 2.90 (brm, 2H), 2.72 (t, 1H), 2.53 (s, 3H), 2.02 (d, 1H), 1.82 (m, 2H), 1.61 (m, 1H).

EXAMPLE 9-1

(R)-2-methyl-5-{1-[4-methyl-2-(4-trifluoromethyl-phenyl)-thiazole-5-carbonyl]-piperidin-3-yl}-benzoic acid (R)-ethyl 5-(3-piperidinyl)-2-methylbenzoate-D-tartaric acid (Example 9; 2.13 g, 5.36 mmol) was dissolved in 100 mL ethyl acetate and washed with 100 mL saturated aqueous $NaHCO_3$. The organic phase was dried over $Na_2SO_4$ and concentrated under reduced pressure. The resultant oil was taken up in 20 mL $CH_2Cl_2$ and 1-(3-dimethylaminopropyl)-3-ethyl carbodiimide (2.05 g, 10.72 mmol) and 4-methyl-2-[4-(trifluoromethyl)phenyl]-1,3-thiazole-5-carboxylic acid (1.69 g, 5.90 mmol) were added. The reaction was stirred at ambient temperature under nitrogen for 72 h. The reaction was diluted with 200 mL diethyl ether and washed with water (100 mL), saturated aqueous $NaHCO_3$ (2×100 mL), 0.5 N HCl (2×100 mL), water (100 mL), and brine (100 mL), dried over $Na_2SO_4$ and concentrated under reduced pressure to yield (R)-2-methyl-5-{1-[4-methyl-2-(4-trifluoromethyl-phenyl)-thiazole-5-carbonyl]-piperidin-3-yl}-benzoic acid ethyl ester (2.62 g, 95%) as a clear oil.

MS (LC-MS) 517.1 $(M+H)^+$.

$^1$H NMR (400 MHz, $CDCl_3$) δ 8.02 (d, 2H), 7.75 (brs, 1H), 7.69 (d, 2H), 7.19 (m, 1H), 4.35 (q, 2H), 3.01 (brm, 1H), 2.79 (brm, 1H), 2.55 (s, 3H), 2.52 (s, 3H), 2.12 (d, 1H), 1.92 (d, 1H), 1.78 (q, 1H), 1.63 (m, 2H), 1.38 (t, 3H).

A mixture of (R)-2-methyl-5-{1-[4-methyl-2-(4-trifluoromethyl-phenyl)-thiazole-5-carbonyl]-piperidin-3-yl}-benzoic acid ethyl ester (3.31 g, 6.41 mmol), potassium carbonate (1.77 g, 12.82 mmol), methanol (25 mL) and water (6 mL) was heated at reflux for 3 h, cooled to room temperature and concentrated under reduced pressure. The resulting residue was taken up in water (150 mL), acidified with 1N aqueous hydrochloric acid and extracted with ethyl acetate (2×100 mL). The combined organic extracts were washed with saturated aqueous sodium chloride, dried over anhydrous sodium sulfate, filtered, concentrated under reduced pressure to yield 2.95 g (94%) (R)-2-methyl-5-{1-[4-methyl-2-(4-trifluoromethyl-phenyl)-thiazole-5-carbonyl]-piperidin-3-yl}-benzoic acid as a white solid.

MS (LC-MS) 489.0 $(M+H)^+$.

$^1$H NMR (400 MHz, $CD_3OD$) δ 8.13 (d, 2H), 7.82 (brs, 1H), 7.79 (d, 2H), 7.35 (m, 1H), 7.24 (m, 1H), 2.84 (t, 1H), 2.53 (s, 3H), 2.49 (s, 3H), 2.07 (d, 1H), 1.90 (m, 2H), 1.71 (m, 2H).

Examples 9-2 to 9-31 were prepared from analogous starting materials using methods analogous to those described in Example 9 and 9-1.

EXAMPLE 9-2

(S)-2-methyl-5-{1-[4-methyl-2-(4-trifluoromethyl-phenyl)-thiazole-5-carbonyl]-piperidin-3-yl}-benzoic acid MS (LC-MS) 489.0 (M+H)$^+$.
$^1$H NMR (400 MHz, CD$_3$OD) δ 8.13 (d, 2H), 7.82 (brs, 1H), 7.79 (d, 2H), 7.35 (m, 1H), 7.24 (m, 1H), 2.84 (t, 1H), 2.53 (s, 3H), 2.49 (s, 3H), 2.07 (d, 1H), 1.90 (m, 2H), 1.71 (m, 2H).

EXAMPLE 9-3

2-methyl-5-{1-[4-methyl-2-(4-trifluoromethyl-phenyl)-thiazole-5-carbonyl]-piperidin-3-yl}-benzoic acid MS (LC-MS) 489.0 (M+H)$^+$.
$^1$H NMR (400 MHz, CD$_3$OD) δ 8.13 (d, 2H), 7.82 (brs, 1H), 7.79 (d, 2H), 7.35 (m, 1H), 7.24 (m, 1H), 2.84 (t, 1H), 2.53 (s, 3H), 2.49 (s, 3H), 2.07 (d, 1H), 1.90 (m, 2H), 1.71 (m, 2H).

EXAMPLE 9-4

(S)-3-(3-carboxy-4-methyl-phenyl)-piperidine-1-carboxylic acid 4-trifluoromethyl-benzyl ester MS (LC-MS) 420.0 (M+H)$^+$.
$^1$H NMR (400 MHz, CD$_3$OD) δ 7.80 (d, 1H), 7.67 (d, 2H), 7.55 (brs, 2H), 7.32 (d, 1H), 7.22 (d, 1H), 5.22 (s, 2H), 4.17 (d, 2H), 2.90 (brm, 2H), 2.72 (t, 1H), 2.53 (s, 3H), 2.02 (d, 1H), 1.82 (m, 2H), 1.61 (m, 1H).

EXAMPLE 9-5

3-(3-carboxy-4-methyl-phenyl)-piperidine-1-carboxylic acid 4-trifluoromethyl-benzyl ester MS (LC-MS) 420.0 (M+H)$^+$.
$^1$H NMR (400 MHz, CD$_3$OD) δ 7.80 (d, 1H), 7.67 (d, 2H), 7.55 (brs, 2H), 7.32 (d, 1H), 7.22 (d, 1H), 5.22 (s, 2H), 4.17 (d, 2H), 2.90 (brm, 2H), 2.72 (t, 1H), 2.53 (s, 3H), 2.02 (d, 1H), 1.82 (m, 2H), 1.61 (m, 1H).

EXAMPLE 9-6

2-Methyl-5-{1-[(4-trifluoromethoxy-phenyl)-acetyl]-piperidin-3-yl}-benzoic acid

MS (LC-MS) 422.2 (M+H)$^+$.
$^1$H NMR (400 MHz, CD$_3$OD) δ Rotomeric mixture: 7.80 (s, 0.5H), 7.60 (s, 0.5H), 7.34–7.09 (m, 6H) 4.58 (t, 1H), 3.98 (dd, 1H), 3.88 (d, 0.5H), 3.86 (s, 0.5H), 3.74 (d, 1H), 3.12 (d, 1H), 2.67 (m, 1.5H), 2.52 (s, 3H), 2.26 (t, 0.5H), 1.93 (dd, 1H), 1.76 (m, 2H), 1.47 (m, 1H).

EXAMPLE 9-7

5-{1-[(4-Isopropyl-phenyl)-acetyl]-piperidin-3-yl}-2-methyl-benzoic acid

MS (LC-MS) 380.3 (M+H)$^+$.
$^1$H NMR (400 MHz, CD$_3$OD) δ Rotomeric mixture: 7.47 (s, 0.5H), 7.33–7.12 (m, 6H) 6.97 (d, 0.5H), 4.60 (dd, 1H), 4.02 (d, 0.5H), 3.90 (d, 0.5H), 3.81 (d, 0.5H), 3.76 (s, 1H), 3.66 (d, 0.5H), 3.02 (m, 1H), 2.90 (m, 1H), 2.67 (m, 1.5H), 2.51 (d, 3H), 2.03 (t, 0.5H), 1.76 (m, 3H), 1.45 (m, 1H), 1.24 (dd, 6H).

EXAMPLE 9-8

2-Methyl-5-{1-[(4-trifluoromethyl-phenyl)-acetyl]-piperidin-3-yl}-benzoic acid

MS (LC-MS) 406.2 (M+H)$^+$.
$^1$H NMR (400 MHz, CD$_3$OD) δ Rotomeric mixture: 7.80 (s, 0.5H), 7.66 (d, 1H), 7.60 (dd, 1H), 7.46 (m, 1.5H), 7.33 (dd, 0.5H), 7.20 (dd, 1H), 7.11 (dd, 0.5H), 4.59 (t, 1H), 4.01 (dd, 1H), 3.95 (d, 0.5H), 3.91 (s, 1H), 3.81 (d, 0.5H), 2.11 (m, 1H), 2.73 (m, 1.5H), 2.52 (d, 3H), 2.26 (t, 0.5H), 1.92 (dd, 1H), 1.78 (m, 2H), 1.51 (m, 1H).

EXAMPLE 9-9

2-Methyl-5-{1-[3-(4-trifluoromethyl-phenyl)-acryloyl]-piperidin-3-yl}-benzoic acid MS (LC-MS) 418.2 (M+H)$^+$.
$^1$HNMR (400 MHz, DMSO$_{d6}$) δ 7.94 (m, 2H), 7.73 (m, 3H), 7.58–7.36 (m, 3H), 7.25 (d, 1H), 4.52 (t, 1H), 4.32 (t, 1H), 3.30 (s, 3H), 3.19 (m, 1H), 2.68 (m, 2H), 1.90 (m, 1H), 1.74 (m, 2H), 1.47 (m, 1H).

EXAMPLE 9-10

5-{1-[3-(4-Isopropyl-phenyl)-acryloyl]-piperidin-3-yl}-2-methyl-benzoic acid

MS (LC-MS) 392.3 (M+H)$^+$.
$^1$H NMR (400 MHz, DMSO$_{d6}$) δ 7.72 (d, 1H), 7.61 (t, 2H), 7.45 (d, 1H), 7.37 (m, 1H), 7.24 (m, 4H), 4.52 (t, 1H), 4.29 (t, 1H), 3.30 (s, 3H), 3.16 (dt, 1H), 2.88 (m, 1H), 2.68 (m, 2H), 1.89 (brm, 1H), 1.73 (m, 2H), 1.48 (brm, 1H), 1.18 (t, 6H).

EXAMPLE 9-11

2-Methyl-5-{1-[3-(4-trifluoromethyl-phenyl)-propionyl]-piperidin-3-yl}-benzoic acid MS (LC-MS) 418.2 (M+H)$^+$.
$^1$H NMR (400 MHz, CD$_3$OD) δ 7.77 (dd, 1H), 7.57 (dd, 2H), 7.43 (dd, 2H), 7.31 (dd, 1H), 7.22 (dd, 1H), 4.56 (d, 1H), 3.92 (dd, 1H), 3.05 (m, 3H), 2.79 (m, 1H), 2.67 (m, 2H), 2.53 (s, 3H), 2.42 (t, 1H), 1.95 (t, 1H), 1.78 (m, 2H), 1.45 (t, 1H).

EXAMPLE 9-12

5-{1-[3-(4-Isopropyl-phenyl)-propionyl]-piperidin-3-yl}-2-methyl-benzoic acid

MS (LC-MS) 394.3 (M+H)$^+$.
$^1$H NMR (400 MHz, CD$_3$OD) δ rotomeric mixture: 7.78 (d, 0.5H), 7.70 (d, 0.5H), 7.31 (dd, 0.5H), 7.21 (m, 1.5H), 7.15 (m, 5H), 4.58 (t, 1H), 3.83 (dd, 1H), 3.01 (t, 0.5H), 2.90 (m, 3H), 2.79 (m, 1H), 2.62 (m, 1H), 2.54 (m, 1H), 2.52 (s, 3H), 2.02 (t, 0.5H), 1.89 (dd, 1H), 1.70 (m, 2H). 1.40 (m, 1H), 1.21 (m, 6H).

EXAMPLE 9-13

3-(3-Carboxy-4-methyl-phenyl)-piperidine-1-carboxylic acid 4-isopropyl-benzyl ester MS (LC-MS) 394.1 (M−H)⁻.
¹H NMR (400 MHz, CD₃OD) δ 7.78 (brs, 1H), 7.24 (m, 6H), 5.09 (s, 2H), 4.14 (brm, 2H), 2.89 (m, 3H), 2.67 (br, 1H), 2.53 (s, 3H), 1.97 (m, 1H), 1.77 (t, 1H), 1.72 (t, 1H), 1.59 (m, 1H), 1.23 (d, 6H).

EXAMPLE 9-14

(R)-2-Methyl-5-[1-(4-trifluoromethyl-benzylcarbamoyl)-piperidin-3-yl]-benzoic acid MS (LC-MS) 421.2 (M+H)⁺.
¹H NMR (400 MHz, CD₃OD) δ 7.90 (d, 1H), 7.58 (d, 2H), 7.43 (d, 2H), 7.39 (dd, 1H), 7.31 (dd, 1H), 7.22 (d, 1H), 4.50 (s, 2H), 4.01 (dd, 2H), 2.88 (m, 3H), 2.60 (s, 3H), 2.04 (m, 1H), 1.84 (m, 1H), 1.69 (m, 2H), 1.25 (t, 1H).

EXAMPLE 9-15

(S)-2-Methyl-5-[1-(4-trifluoromethyl-benzylcarbamoyl)-piperidin-3-yl]-benzoic acid MS (LC-MS) 421.2 (M+H)⁺.
¹H NMR (400 MHz, CD₃OD) δ 7.90 (d, 1H), 7.58 (d, 2H), 7.43 (d, 2H), 7.39 (dd, 1H), 7.31 (dd, 1H), 7.22 (d, 1H), 4.50 (s, 2H), 4.01 (dd, 2H), 2.88 (m, 3H), 2.60 (s, 3H), 2.04 (m, 1H), 1.84 (m, 1H), 1.69 (m, 2H), 1.25 (t, 1H).

EXAMPLE 9-16

(R)-3-(3-Carboxy-4-methyl-phenyl)-piperidine-1-carboxylic acid 2-(4-trifluoromethyl-phenyl)-ethyl ester MS (LC-MS) 436.0 (M+H)⁺.
¹H NMR (400 MHz, CD₃OD) δ 1.49 (br, 1H), 1.69 (m, 2H), 1.94 (d, 1H), 2.41 (s, 3H), 2.53 (brm, 1H), 2.79 (m, 2H), 3.04 (t, 2H), 4.07 (m, 2H), 4.32 (brs, 2H), 6.95 (brs, 1H), 7.07 (d, 1H), 7.31 (s, 1H), 7.44 (brs, 2H), 7.58(brs, 2H).

EXAMPLE 9-17

2-Methyl-4-[1-(4-trifluoromethyl-benzoyl)-piperidin-3-yl]-benzoic acid

MS (LC-MS) 392.2 (M+H)⁺.
¹H NMR (400 MHz, CD₃OD) δ 8.19 (d, 1H), 7.78 (d, 2H), 7.62 (d, 1H), 7.22 (m, 1H), 7.04 (s, 1H), 4.67 (d, 1H), 3.62 (dd, 1H), 3.20 (m, 1H), 2.96 (q, 1H), 2.86 (m, 1H), 2.55 (d, 3H), 2.06 (d, 1H), 1.86 (m, 1H), 1.75 (m, 1H), 1.63 (m, 1H).

EXAMPLE 9-18

2-Methyl-4-{1-[(4-trifluoromethyl-phenyl)-acetyl]-piperidin-3-yl}-benzoic acid

MS (LC-MS) 406.1 (M+H)⁺.
¹H NMR (400 MHz, CD₃OD) δ Rotomeric mixture: 7.84 (dd, 1H), 7.65 (dd, 2H), 7.46 (t, 2H), 7.18 (s, 1H), 6.94 (d, 0.5H), 6.84 (s, 0.5H), 4.59 (dd, 1H), 4.04 (d, 0.5H), 3.92 (s, 1H), 3.89 (d, 0.5H), 3.88 (dd, 1H), 3.15 (t, 1H), 2.78 (t, 0.5H), 2.66 (q, 1H), 2.54 (d, 3H), 2.25 (t, 0.5H), 1.94 (dd, 1H), 1.78 (m, 2H), 1.53 (m, 0.5H), 1.41 (m, 0.5H).

EXAMPLE 9-19

2-Methyl-4-{1-[3-(4-trifluoromethyl-phenyl)-acryloyl]-piperidin-3-yl}-benzoic acid MS (LC-MS) 418.2 (M+H)⁺.
¹H NMR (400 MHz, CD₃OD) δ 1.67 (m, 1H), 1.89 (m, 2H), 2.05 (d, 1H), 2.57 (d, 3H), 2.82 (m, 2H), 3.24 (dd, 1H), 3.35 (t, 1H), 4.34 (dd, 1H), 4.67 (d, 1H), 7.21 (m, 2H), 7.32 (dd, 1H), 7.58 (q, 1H), 7.65 (m, 2H), 7.78 (d, 1H), 7.83 (d, 1H).

EXAMPLE 9-20

2-Methyl-4-{1-[4-methyl-2-(4-trifluoromethyl-phenyl)-thiazole-5-carbonyl]-piperidin-3-yl}-benzoic acid MS (LC-MS) 489.1 (M+H)⁺.
¹H NMR (400 MHz, CD₃OD) δ 8.15(dd, 2H), 7.90 (brs, 1H), 7.79 (d, 2H), 7.20 (m, 2H), 2.84 (t, 1H), 2.57 (s, 3H), 2.49 (s, 3H), 2.07 (d, 1H), 1.89 (q, 2H), 1.70 (m, 2H).

EXAMPLE 9-21

3-(4-Carboxy-3-methyl-phenyl)-piperidine-1-carboxylic acid 4-trifluoromethyl-benzyl ester MS (LC-MS) 420.0 (M−H)⁻.
¹H NMR (400 MHz, CD₃OD) δ 7.86 (d, 1H), 7.66 (d, 2H), 7.54 (brs, 2H), 7.16 (m, 2H), 5.22 (s, 2H), 4.17 (m, 2H), 2.98 (brm, 1H), 2.90 (m, 1H), 2.71 (t, 1H), 2.56 (s, 3H), 1.99 (d, 1H), 1.78 (m, 2H), 1.61 (m, 1H).

EXAMPLE 9-22

4-[1-(4-Isopropyl-benzoyl)-piperidin-3-yl]-2-methyl-benzoic acid

MS (LC-MS) 366.2 (M+H)⁺.
¹H NMR (400 MHz, CD₃OD) δ 7.89 (m, 1H), 7.35 (s, 4H), 7.24 (s, 1H), 7.04 (s, 1H), 4.65 (m, 1H), 3.78 (t, 1H), 3.18 (q, 1H), 2.94 (m, 2H), 2.82 (m, 1H), 2.55 (d, 3H), 2.04 (d, 1H), 2.00–1.60 (m, 3H), 1.26 (m, 6H).

EXAMPLE 9-23

4-{1-[(4-Isopropyl-phenyl)-acetyl]-piperidin-3-yl}-2-methyl-benzoic acid

MS (LC-MS) 380.2 (M+H)⁺.
¹H NMR (400 MHz, CD₃OD) δ Rotomeric mixture: 1.25 (m, 6H), 1.49 (q, 1H), 1.72 (t, 1H), 1.82 (t, 1H), 1.94 (d, 0.5H), 2.08 (t, 0.5H), 2.53 (d, 3H), 2.64 (t, 0.5H), 2.75 (t, 0.5H), 2.91 (m, 1H), 3.03 (t. 0.5H), 3.09 (t, 0.5H), 3.68 (d, 0.5H), 3.70 (s, 3H), 3.78 (d, 0.5H), 3.88 (d, 0.5H), 4.02 (d, 0.5H), 4.55 (d, 0.5H), 4.64 (d, 0.5H), 6.77 (d, 1H), 7.18 (m, 4H), 7.25 (d, 1H), 7.77 (d, 0.5H), 7.86 (d, 0.5H).

EXAMPLE 9-24

4-{1-[3-(4-Isopropyl-phenyl)-acryloyl]-piperidin-3-yl}-2-methyl-benzoic acid

MS (LC-MS) 426.3 (M+H)⁺.
¹H NMR (400 MHz, CD₃OD) δ Rotomeric mixture: 7.89 (d, 1H), 7.54 (m, 3H), 7.22 (m, 4H), 7.11 (dd, 1H), 4.66 (d, 1H), 4.29 (dd, 1H), 3.32 (m, 0.5H), 3.19 (m, 0.5H), 2.83 (m, 3H), 2.58 (s, 3H), 2.03 (d, 1H), 1.86 (m, 3H), 1.63 (m, 1H), 1.23 (m, 6H).

EXAMPLE 9-25

3-(4-Carboxy-3-methyl-phenyl)-piperidine-1-carboxylic acid 4-isopropyl-benzyl ester MS (LC-MS) 394.1 (M–H)⁻.
$^1$H NMR (400 MHz, CD$_3$OD) δ 7.85 (d, 1H), 7.27 (d, 2H), 7.22 (d, 2H), 7.13 (m, 2H), 5.08 (s, 2H), 4.15 (d, 2H), 2.89 (m, 3H), 2.67 (m, 1H), 2.55 (s, 3H), 1.97 (d, 1H), 1.75 (m, 2H), 1.58 (m, 1H), 1.23 (d, 6H).

EXAMPLE 9-26

2-Methyl-4-{1-[3-(4-trifluoromethyl-phenyl)-propionyl]-piperidin-3-yl}-benzoic acid MS (LC-MS) 420.2 (M+H)⁺.
$^1$H NMR (400 MHz, CD$_3$OD) δ 7.86 (dd, 1H), 7.57 (m, 2H), 7.44 (dd, 2H), 7.17 (m, 1H), 7.12 (m, 1H), 4.57 (t, 1H), 3.93 (dd, 1H), 3.24 (dd, 1H), 3.09 (q, 1H), 3.01 (m, 2H), 2.80 (m, 1H), 2.69 (m, 1H), 2.56 (d, 3H), 1.95 (t, 1H), 1.78 (m, 2H), 1.46 (m, 1H).

EXAMPLE 9-27

4-{1-[3-(4-Isopropyl-phenyl)-propionyl]-piperidin-3-yl}-2-methyl-benzoic acid

MS (LC-MS) 394.3 (M+H)⁺.
$^1$H NMR (400 MHz, CD$_3$OD) δ 7.86 (t, 1H), 7.16 (m, 5H), 7.07 (m, 1H), 4.58 (dd, 1H), 3.84 (dd, 1H), 3.05–2.61 (m, 7H), 2.56 (d, 3H), 2.19 (t, 1H), 1.89 (t, 1H), 1.71 (m, 2H), 1.40 (m, 1H), 1.28 (m, 1H), 1.22 (d, 6H).

EXAMPLE 9-28

Isomer of 2-methoxy-5-{1-[4-methyl-2-(4-trifluoromethyl-phenyl)-thiazole-5-carbonyl]-piperidin-3-yl}-benzoic acid from L tartaric acid Optically pure starting material used:
L-(+)-tartaric acid: 97.5% ee of methyl 5-(3-piperidinyl)-2-methoxylbenzoate-L-tartaric acid salt.
HPLC analysis: Chirobiotic V, 1 mL/min, 100% methanol, 0.1% triethylamine, 0.1% acetic acid; rt=6.29 min, 8.53 min.
MS (APCI) 504.8 (M+H)⁺.
$^1$H NMR (400 MHz, CD$_3$OD) δ 8.16 (d, 2H), 7.79 (d, 2H), 7.75 (br, 1H), 7.47 (br, 1H), 7.09 (d, 1H), 3.88 (s, 3H), 2.82 (t, 2H), 2.49 (s, 3H), 2.07 (d, 1H), 1.88 (m, 2H), 1.70 (m, 1H), 1.28 (s, 1H).

EXAMPLE 9-29

Isomer of 2-methoxy-5-{1-[4-methyl-2-(4-trifluoromethyl-phenyl)-thiazole-5-carbonyl]-piperidin-3-yl}-benzoic acid from D tartaric acid Optically pure starting material used:
D-(–)-tartaric acid: 91.8% ee of methyl 5-(3-piperidinyl)-2-methoxylbenzoate-D-tartaric acid salt
HPLC analysis: Chirobiotic V, 1 mL/min, 100% methanol, 0.1% triethylamine, 0.1% acetic acid; rt=6.29 min, 8.53 min
MS (APCI) 504.8 (M+H)⁺.
$^1$H NMR (400 MHz, CD$_3$OD) δ 8.16 (d, 2H), 7.79 (d, 2H), 7.75 (br, 1H), 7.47 (br, 1H), 7.09 (d, 1H), 3.88 (s, 3H), 2.82 (t, 2H), 2.49 (s, 3H), 2.07 (d, 1H), 1.88 (m, 2H), 1.70 (m, 1H), 1.28 (s, 1H).

EXAMPLE 9-30

2-Fluoro-5-{1-[4-methyl-2-(4-trifluoromethyl-phenyl)-thiazole-5-carbonyl]-piperidin-3-yl}-benzoic acid MS (LC-MS) 493.0 (M+H)⁺.
$^1$H NMR (400 MHz, CD$_3$OD) δ 8.13 (d, 2H), 7.85 (br s, 1H), 7.79 (d, 2H), 7.53 (br s, 1H), 7.15 (t, 1H), 2.89(t, 1H), 2.49 (s, 3H), 2.08 (d, 1H), 1.89 (m, 2H), 1.71 (m, 1H).

EXAMPLE 9-31

3-(3-Carboxy-4-fluoro-phenyl)-piperidine-1-carboxylic acid 4-trifluoromethyl-benzyl ester MS (LC-MS) 493.0 (M+H)⁺.
$^1$H NMR (400 MHz, CD$_3$OD) δ 8.13 (d, 2H), 7.85 (br s, 1H), 7.79 (d, 2H), 7.53 (br s, 1H), 7.15 (t, 1H), 2.89(t, 1H), 2.49 (s, 3H), 2.08 (d, 1H), 1.89 (m, 2H), 1.71 (m, 1H).

EXAMPLE 10

{3-[4-methyl-3-(1H-tetrazol-5-yl)-phenyl]-piperidin-1-yl}-[4-methyl-2-(4-trifluoromethyl-phenyl)-thiazol-5-yl]-methanone (R)-2-methyl-5-{1-[4-methyl-2-(4-trifluoromethyl-phenyl)-thiazole-5-carbonyl]-piperidin-3-yl}-benzoic acid (Example 9-1; 1.026 g, 2.10 mmol) was dissolved in 20 mL CH$_2$Cl$_2$ and treated with oxalyl chloride (0.22 mL, 2.52 mmol) and 10 mL of dimethyl formamide. The mixture was allowed to stir for 1 h until all solids had dissolved. 10 mL of THF saturated with ammonia was added slowly. A thick white precipitate formed. The slurry was stirred for 20 min then diluted with diethyl ether (100 mL), washed with 100 mL of each of H$_2$O, 0.2 N aqueous HCl, saturated aqueous NaHCO$_3$, and brine. The organic phase was dried over anhydrous sodium sulfate, filtered and concentrated under reduced pressure. The resultant oil was flash chromatographed with 50% ethyl acetate/hexanes to yield 740 mg (72%) of the desired 2-methyl-5-{1-[4-methyl-2-(4-trifluoromethyl-phenyl)-thiazole-5-carbonyl]-piperidin-3-yl}-benzamide as a clear oil.
MS (LC-MS) 488.6 (M+H)⁺.
$^1$H NMR (400 MHz, CDCl$_3$) δ 8.02 (d, 2H), 7.69 (d, 2H), 7.33 (brs, 1H), 7.19 (brs, 2H), 5.85 (brs, 2H), 3.01 (br, 2H), 2.79 (m, 1H), 2.51 (s, 3H), 2.45 (s, 3H), 2.08 (d, 1H), 1.89 (m, H), 1.77 (q, 1H), 1.67 (m, 1H).

(R)-2-methyl-5-{1-[4-methyl-2-(4-trifluoromethyl-phenyl)-thiazole-5-carbonyl]-piperidin-3-yl}-benzamide (230 mg, 0.47 mmol) was dissolved in pyridine (5 mL) and cooled to 0° C. Trifluoroacetic anhydride (0.67 mL, 4.72 mmol) was added dropwise. Stirred for 1 h at 0° C. after addition. The reaction was diluted with diethyl ether (100 mL) and washed with 1 N HCl (2×100 mL) and saturated NaHCO$_3$ (100 mL). The organic phase was dried over anhydrous sodium sulfate, filtered and concentrated under reduced pressure. The resultant oil was flash chromatographed with 33% ethyl acetate/hexanes to yield 262 mg (97%) of the desired 2-methyl-5-{1-[4-methyl-2-(4-trifluoromethyl-phenyl)-thiazole-5-carbonyl]-piperidin-3-yl}-benzonitrile as a clear oil.

MS (LC-MS) 470.0 (M+H)$^+$.

$^1$H NMR (400 MHz, CDCl$_3$) δ 7.99 (d, 2H), 7.74 (d, 2H), 7.46 (brs, 1H), 7.35 (brs, 1H), 7.19 (m, 1H), 2.82 (m, 1H), 2.53 (s, 3H), 2.52 (s, 3H), 2.14 (d, 1H), 1.97 (m, H), 1.78 (m, 2H).

(R)-2-methyl-5-{1-[4-methyl-2-(4-trifluoromethyl-phenyl)-thiazole-5-carbonyl]-piperidin-3-yl}-benzonitrile (262 mg, 0.56 mmol) was dissolved in toluene (5 mL). Trimethyltin azide (230 mg, 1.12 mmol) was added and the mixture heated at reflux for 24 h. The mixture was diluted with diethyl ether (100 mL) and washed with 0.1 N HCl (100 mL). The organic phase was dried over anhydrous sodium sulfate, filtered and concentrated under reduced pressure. The resultant oil was flash chromatographed with 7.5% methanol/chloroform (0.5% ammonium hydroxide modifier). The product fractions were combined and concentrated under reduced pressure. The resultant oil was taken up in 100 mL ethyl acetate and extracted with 0.1 N HCl (100 mL). The organic phase was dried over anhydrous sodium sulfate, filtered and concentrated under reduced pressure to yield 132 mg (46%) of the desired {3-[4-methyl-3-(1H-tetrazol-5-yl)-phenyl]-piperidin-1-yl}-[4-methyl-2-(4-trifluoromethyl-phenyl)-thiazol-5-yl]-methanone as a clear oil.

MS (LC-MS) 513.0 (M+H)$^+$.

$^1$H NMR (400 MHz, CD$_3$OD) δ 8.13 (d, 2H), 7.79 (d, 2H), 7.56 (brs, 1H), 7.39 (m, 2H), 2.89 (t, 1H), 2.49 (s, 3H), 2.44 (s, 3H), 2.10 (d, 1H), 1.90 (m, 2H), 1.72 (m, 1H).

EXAMPLE 11

(S)-2-Methyl-2-(2-methyl-5-{1-[4-methyl-2-(4-trifluoromethyl-phenyl)-thiazole-5-carbonyl]-piperidin-3-yl}-phenoxy)-propionic acid A 500 mL Parr bottle was charged with 2.0 g of 10% palladium on carbon (50% water) and covered with 50 mL ethanol. 2-methyl-5-nitroanisole (10.0 g, 59.8 mmol) was dissolved in 100 mL ethanol and added to the catalyst suspension. The reaction was hydrogenated at 50 psi for 3 h. The catalyst was filtered through a celite plug. The filter cake was washed with 150 mL ethanol and the filtrated concentrated under reduced pressure to yield 8.05 g (98%) of 5-amino-2-methylanisole as a clear oil.

$^1$H NMR (400 MHz, CDCl$_3$) δ 6.90 (d, 1H), 6.23 (m, 2H), 3.78 (s, 3H), 2.11 (s, 3H).

5-amino-2-methylanisole (8.05 g, 58.7 mmol) was dissolved in 244 mL water and 8.1 mL concentrated H$_2$SO$_4$ and cooled to 0° C. NaNO$_2$ (4.86 g, 70.4 mmol) in 61 mL water was added dropwise with stirring. Reaction was stirred 30 minutes at 0° C. Urea (0.70 g, 11.7 mmol) was added and stirring continued for an additional 30 minutes. The pale yellow solution was transferred to a dropping funnel and added slowly to a stirred solution of potassium iodide (19.48 g, 117.4 mmol) in 122 mL water. The solution was stirred at ambient temperature for 1 h after completion of the addition. The reaction was extracted with diethyl ether (3×300 mL). The organic extracts were combined and washed with 1M Na$_2$S$_2$O$_3$ (2×200 mL), dried over Na$_2$SO$_4$, filtered and concentrated under reduced pressure to yield 9.60 g (66%) of 5-iodo-2-methyl anisole as a brown oil.

$^1$H NMR (400 MHz, CDCl$_3$) δ 7.19 (dd, 1H), 7.10 (d, 1H), 6.86 (t, 1H), 3.81 (s, 3H), 2.15 (s, 3H).

5-iodo-2-methyl anisole (9.60 g, 38.70 mmol) and diethyl-(3-pyridyl)borane (5.70 g, 38.70 mmol) were dissolved in 60 mL tetrahydrofuran in a 250 mL round bottom flask equipped with a magnetic stirrer. Sodium carbonate (8.20 g, 77.40 mmol) and 30 mL water were added followed by tetrakis(triphenylphosphine)palladium(0) (0.90 g, 0.77 mmol) and 15 mL ethanol. The mixture was heated at reflux for 24 h under nitrogen then cooled to ambient temperature. The mixture was diluted with 200 mL water and extracted with diethyl ether (2×200 mL). The organic phases were combined and extracted with $^1$N HCl (3×150 mL). The acidic extractions were combined and made basic with 5N aqueous sodium hydroxide. This basic layer was extracted with diethyl ether (3×150 mL) and the extracts were combined and dried over anhydrous sodium sulfate, filtered and concentrated under reduced pressure to yield 7.71 g (99%) of 2-methyl-5-(3-pyridyl)-anisole as a brown oil.

MS (LC-MS) 200.1 (M+H)$^+$.

$^1$H NMR (400 MHz, CDCl$_3$) δ 8.87 (s, 1H), 8.60 (d, 1H), 8.03 (dd, 1H), 7.50 (m, 1H), 7.25 (d, 1H), 7.08 (d, 1H), 7.00 (s, 1H), 3.92 (s, 3H), 2.27 (s, 3H).

A 500 mL L hydrogenation vessel was charged with 0.77 g platinum(II)oxide and purged with nitrogen. 2-methyl-5-(3-pyridyl)-anisole (7.71 g, 38.7 mmol) was added as a solution in 150 mL acetic acid. The suspension was hydrogenated at 45 psi for 18 h. The catalyst was filtered through celite and the filter plug was washed with 200 mL acetic acid. The filtrate was concentrated under reduced pressure. The resultant oil was taken up in 300 mL water and made basic with 5N aqueous sodium hydroxide. This basic layer was extracted with ethyl acetate (2×300 mL) and the extracts were combined and dried over anhydrous sodium sulfate, filtered and concentrated under reduced pressure. The resultant oil was taken up in 300 mL hot ethanol. L-(+)-tartaric acid (5.81 g, 38.7 mmol) in 50 mL hot ethanol was added into the ethanol solution and was allowed to stir at ambient temperature for 24 h, forming a white precipitate that was collected by filtration. The white solid was recrystallized from hot 5% H$_2$O/ethanol (200 mL) to yield 4.88 g (35%) of 5-(3-piperidinyl)-2-methylanisole-L-tartaric acid salt as a white solid. The mother liquors were combined and concentrated under reduced pressure. The resultant oil was taken up in 500 mL diethyl ether and washed with 300 mL saturated aqueous NaHCO$_3$. The organic layer was dried over anhydrous sodium sulfate, filtered and concentrated under reduced pressure. The resultant oil was taken up in 200 mL hot ethanol. D-(−)-tartaric acid (3.75 g, 25.0 mmol) in 50 mL hot ethanol was added and was allowed to stir at ambient temperature for 48 h, forming a white precipitate that was collected by filtration. The white solid was recrystallized from hot 5% H$_2$O/ethanol (300 mL) to yield 5.36 g (39%) of 5-(3-piperidinyl)-2-methylanisole-D-tartaric acid salt as a white solid.

$^1$H NMR (400 MHz, DMSO$_{d6}$) δ 7.06 (d, 1H), 6.82 (d, 1H), 6.71 (dd, 1H), 3.87 (s, 2H), 3.77 (s, 3H), 3.27 (m, 2H), 2.97 (t, 1H), 2.86 (q, 2H), 2.09 (s, 3H), 1.85 (d, 2H), 1.69 (m, 2H).

3-(3-methoxy-4-methylphenyl)-1H-piperidine-L-tartaric acid salt (4.88 g, 13.73 mmol) was slowly dissolved in hydrobromic acid (50 mL) and the resulting mixture heated at 140° C. for 2 h. After cooling to ambient temperature, the hydrobromic acid and water were distilled off and the resulting brown oil was azeotroped with toluene (3×100 mL) and dried under hi vacuum for 18 h. The resultant tan solid (3-(3-hydroxy-4-methylphenyl)-1H-piperidine hydrobromide salt (3.74 g, 13.73 mmol)) was dissolved in 25 mL water and 50 mL tetrahydrofuran. Sodium bicarbonate (2.31 g, 27.46 mmol) was added followed by dibenzyl-dicarbonate (3.93 g, 13.73 mmol). The reaction was stirred for 1 h at ambient temperature then diluted with 300 mL diethyl ether and washed with 200 mL 0.5 N HCl. The organic phase was dried over anhydrous sodium sulfate, filtered and concentrated under reduced pressure. The resultant oil was flash chromatographed with 33% ethyl acetate/hexanes to yield 3.41 g (76%) of the desired 3-(3-hydroxy-4-methyl-phenyl)-piperidine-1-carboxylic acid benzyl ester as a clear oil.

MS (LC-MS) 324.2 (M−H)−.

$^1$H NMR (400 MHz, CDCl$_3$) δ 7.36 (m, 5H), 7.05 (d, 1H), 6.70 (dd, 1H), 6.63 (s, 1H), 5.14 (m, 2H), 4.22 (t, 2H), 2.79 (t, 2H), 2.61 (m, 1H), 2.21 (s, 3H), 1.97 (d, 1H), 1.76 (m, 1H), 1.57 (m, 2H).

HPLC analysis: Chiralcel OJ, 1 mL/min, 40% ethanol/heptane 0.2% diethylamine, rt=10.22 min.

ee=90.4%.

To a solution of 3-(3-hydroxy-4-methyl-phenyl)-piperidine-1-carboxylic acid benzyl ester (2.02 g, 6.21 mmol) in 15 mL dimethylformamide was added cesium carbonate (4.05 g, 12.42 mmol) and ethyl-2-bromoisobutyrate (3.64 mL, 24.83 mmol). The mixture was heated to 60° C. under N$_2$ with stirring for 18 h and cooled to ambient temperature. The resultant brown suspension was diluted with 300 mL water and extracted with diethyl ether (2×200 mL). The organic phases were combined and dried over anhydrous sodium sulfate, filtered and concentrated under reduced pressure. The resultant oil was flash chromatographed with 20% ethyl acetate/hexanes to yield 1.36 g (50%) of the desired 3-[3-(1-ethoxycarbonyl-1-methyl-ethoxy)-4-methyl-phenyl]-piperidine-1-carboxylic acid benzyl ester as a clear oil.

MS (LC-MS) 462.1 (M+Na)+.

$^1$H NMR (400 MHz, CDCl$_3$) δ 7.34 (m, 5H), 7.06 (d, 1H), 6.73 (d, 1H), 6.52 (s, 1H), 5.13 (m, 2H), 4.22 (m, 4H), 2.74 (q, 1H), 2.70 (t, 1H), 2.57 (m, 1H), 2.19 (s, 3H), 1.96 (d, 1H), 1.76 (m, 1H), 1.57 (d, 6H), 1.53 (s, 2H), 1.22 (t, 3H).

A 250 mL Parr bottle was charged with 0.27 g of 10% palladium on carbon (50% water) and covered with 20 mL ethanol. 3-[3-(1-ethoxycarbonyl-1-methyl-ethoxy)-4-methyl-phenyl]-piperidine-1-carboxylic acid benzyl ester (1.36 g, 3.09 mmol) was dissolved in 50 mL ethanol and added to the catalyst suspension. The reaction was hydrogenated at 50 psi for 2 h. The catalyst was filtered through a celite plug. The filter cake was washed with 150 mL ethanol and the filtrated concentrated under reduced pressure. The resultant oil was taken up in 20 mL hot ethanol to which was added L-tartaric acid (464 mg, 3.09 mmol) in 10 mL hot ethanol. The solution was allowed to stir 24 h at ambient temperature. The white crystalline precipitate was collected by filtration to yield 805 mg (57%) of 2-methyl-2-(2-methyl-5-piperidin-3-yl-phenoxy)-propionic acid ethyl ester L-tartaric acid salt as a white crystalline solid.

MS (LC-MS) 306.3 (M+H)+.

$^1$H NMR (400 MHz, DMSO$_{d6}$) δ 7.11 (d, 1H), 6.78 (d, 1H), 6.44 (s, 1H), 4.16 (q, 2H), 3.81 (s, 2H), 3.21 (t, 2H), 2.78 (m, 2H), 2.10 (s, 3H), 1.81 (m, 2H), 1.69 (m, 1H), 1.56 (m, 1H), 1.51 (s, 6H), 1.14 (t, 3H).

HPLC analysis: Chiralpak AD, 1 mL/min, 5% isopropanol/heptane 0.2% diethylamine, rt=9.75 min.

ee=100%.

2-methyl-2-(2-methyl-5-piperidin-3-yl-phenoxy)-propionic acid ethyl ester L-tartaric acid salt (155 mg, 0.34 mmol) was dissolved in 50 mL ethyl acetate and washed with 50 mL saturated aqueous NaHCO$_3$. The organic phase was dried over Na$_2$SO$_4$ and concentrated under reduced pressure. The resultant oil was taken up in 2 mL CH$_2$Cl$_2$ and 1-(3-dimethylaminopropyl)-3-ethyl carbodiimide (130 mg, 0.68 mmol) and 4-methyl-2-[4-(trifluoromethyl)phenyl]-1,3-thiazole-5-carboxylic acid (98 mg, 0.34 mmol) were added. The reaction was stirred at ambient temperature under nitrogen for 72 h. The reaction was diluted with 100 mL diethyl ether and washed with water (100 mL), 0.5 N HCl (2×100 mL), saturated aqueous NaHCO$_3$ (2×100 mL), dried over Na$_2$SO$_4$ and concentrated under reduced pressure to yield 2-methyl-2-(2-methyl-5-{1-[4-methyl-2-(4-trifluoromethyl-phenyl)-thiazole-5-carbonyl]-piperidin-3-yl}-phenoxy)-propionic acid ethyl ester (179 mg, 91%) as a clear oil.

MS (LC-MS) 575.0 (M−H)−.

$^1$H NMR (400 MHz, CDCl$_3$) δ 8.04 (d, 2H), 7.70 (d, 2H), 7.07 (d, 1H), 6.73 (m, 1H), 6.52 (m, 1H), 4.21 (m, 2H), 2.64 (m, 1H), 2.53 (s, 3H), 2.18 (s, 3H), 2.05 (m, 1H), 1.81 (m, 2H), 1.62 (m, 2H), 1.57 (m, 6H), 1.21 (m, 3H).

A mixture of 2-methyl-2-(2-methyl-5-{1-[4-methyl-2-(4-trifluoromethyl-phenyl)-thiazole-5-carbonyl]-piperidin-3-yl}-phenoxy)-propionic acid ethyl ester (179 mg, 0.31 mmol), potassium carbonate (86 mg, 0.62 mmol), methanol (10 mL) and water (2 mL) was heated at reflux for 3 h, cooled to room temperature and concentrated under reduced pressure. The resulting residue was taken up in water (50 mL), acidified with 1N aqueous hydrochloric acid and extracted with ethyl acetate (2×50 mL). The combined organic extracts were washed with saturated aqueous sodium chloride, dried over anhydrous sodium sulfate, filtered, concentrated under reduced pressure to yield 151 mg (89%) of 2-methyl-2-(2-methyl-5-{1-[4-methyl-2-(4-trifluoromethyl-phenyl)-thiazole-5-carbonyl]-piperidin-3-yl}-phenoxy)-propionic acid as a white solid.

MS (LC-MS) 547.0 (M+H)+.

$^1$H NMR (400 MHz, CD$_3$OD) δ 8.13 (d, 2H), 7.78 (d, 2H), 7.08 (d, 1H), 6.79 (m, 1H), 6.68 (m, 1H), 2.74 (m, 1H), 2.47 (s, 3H), 2.15 (s, 3H), 2.03 (d, 1H), 1.91 (brm, 2H), 1.79 (m, 2H), 1.54 (brs, 6H).

EXAMPLE 11-1

(S)-3-[3-(1-Carboxy-1-methyl-ethoxy)-4-methyl-phenyl]-piperidine-1-carboxylic acid 4-trifluoromethyl-benzyl ester 2-methyl-2-(2-methyl-5-piperidin-3-yl-phenoxy)-propionic acid ethyl ester L-tartaric acid salt (Example 11; 155 mg, 0.34 mmol) was dissolved in 50 mL ethyl acetate and washed with 50 mL saturated aqueous NaHCO$_3$. The organic phase was dried over Na$_2$SO$_4$ and concentrated under reduced pressure. The resultant oil was taken up in 3 mL toluene and imidazole-1-carboxylic acid 4-trifluoromethyl-benzyl ester (92 mg, 0.34 mmol) was added. The reaction was stirred for 18 h at room temperature under nitrogen. The reaction was flash chromatographed with 15% ethyl acetate/hexanes to yield 157 mg (91%) of the desired 3-[3-(1-ethoxycarbonyl-1-methyl-ethoxy)-4-methyl-phenyl]-piperidine-1-carboxylic acid 4-trifluoromethyl-benzyl ester as a clear oil.

MS (LC-MS) 525.2 (M+H)+.

$^1$H NMR (400 MHz, CDCl$_3$) δ 7.61(d, 2H), 7.46 (d, 2H), 7.07 (d, 1H), 6.74 (m, 1H), 6.52 (s, 1H), 5.19 (s, 2H), 4.21 (m, 2H), 2.73 (brm, 2H), 2.58 (m, 1H), 2.19 (s, 3H), 1.97 (d, 1H), 1.76 (m, 2H), 1.58 (m, 6H), 1.22 (m, 3H).

A mixture of 3-[3-(1-ethoxycarbonyl-1-methyl-ethoxy)-4-methyl-phenyl]-piperidine-1-carboxylic acid 4-trifluoromethyl-benzyl ester (156 mg, 0.31 mmol), potassium carbonate (85 mg, 0.62 mmol), methanol (10 mL) and water (2 mL) was heated at reflux for 3 h, cooled to room temperature and concentrated under reduced pressure. The resulting residue was taken up in water (50 mL), acidified with 1N aqueous hydrochloric acid and extracted with ethyl acetate (2×50 mL). The combined organic extracts were washed with saturated aqueous sodium chloride, dried over anhydrous sodium sulfate, filtered, concentrated under reduced pressure to yield 139 mg (94%) of 3-[3-(1-carboxy-1-methyl-ethoxy)-4-methyl-phenyl]-piperidine-1-carboxylic acid 4-trifluoromethyl-benzyl ester as a white solid.

MS (LC-MS) 478.1 (M−H)⁻.

$^1$H NMR (400 MHz, CDCl$_3$) δ 7.66 (d, 2H), 7.54 (m, 2H), 7.07 (d, 1H), 6.77 (d, 1H), 6.67 (s, 1H), 5.21 (s, 2H), 4.14 (m, 2H), 2.88 (brm, 2H), 2.58 (t, 1H), 2.17 (s, 3H), 1.96 (d, 1H), 1.77 (m, 2H), 1.62 (m, 1H), 1.57 (s, 6H).

Examples 11-2 and 11-3 were prepared from analogous starting materials using methods analogous to those described in Examples 11 and 11-1.

EXAMPLE 11-2

(R)-2-Methyl-2-(2-methyl-5-{1-[4-methyl-2-(4-trifluoromethyl-phenyl)-thiazole-5-carbonyl]-piperidin-3-yl}-phenoxy)-propionic acid 3-(3-methoxy-4-methylphenyl)-1H-piperidine-D-tartaric acid salt (Example 11; 5.36 g, 15.08 mmol) was slowly dissolved in hydrobromic acid (50 mL) and the resulting mixture heated at 140° C. for 2 h. After cooling to ambient temperature, the hydrobromic acid and water were distilled off and the resulting brown oil was azeotroped with toluene (3×100 mL) and dried under hi vacuum for 18 h. The resultant tan solid (3-(3-hydroxy-4-methylphenyl)-1H-piperidine hydrobromide salt (4.11 g, 15.08 mmol)) was dissolved in 25 mL water and 50 mL tetrahydrofuran. Sodium bicarbonate (2.54 g, 30.16 mmol) was added followed by dibenzyl-dicarbonate (4.32 g, 15.08 mmol). The reaction was stirred for 1 h at ambient temperature then diluted with 300 mL diethyl ether and washed with 200 mL 0.5 N HCl. The organic phase was dried over anhydrous sodium sulfate, filtered and concentrated under reduced pressure. The resultant oil was flash chromatographed with 33% ethyl acetate/hexanes to yield 3.82 g (78%) of the desired 3-(3-hydroxy-4-methyl-phenyl)-piperidine-1-carboxylic acid benzyl ester as a clear oil.

MS (LC-MS) 324.2 (M−H)⁻.

$^1$H NMR (400 MHz, CDCl$_3$) δ 7.36 (m, 5H), 7.05 (d, 1H), 6.70 (dd, 1H), 6.63 (s, 1H), 5.14 (m, 2H), 4.22 (t, 2H), 2.79 (t, 2H), 2.61 (m, 1H), 2.21 (s, 3H), 1.97 (d, 1H), 1.76 (m, 1H), 1.57 (m, 2H).

HPLC analysis: Chiralcel OJ, 1 mL/min, 40% ethanol/heptane 0.2% diethylamine, rt=8.55 min.

ee=85.8%.

To a solution of 3-(3-hydroxy-4-methyl-phenyl)-piperidine-1-carboxylic acid benzyl ester (2.24 g, 6.88 mmol) in 15 mL dimethylformamide was added cesium carbonate (4.49 g, 13.77 mmol) and ethyl-2-bromoisobutyrate (4.04 mL, 27.53 mmol). The mixture was heated to 60° C. under N$_2$ with stirring for 18 h and cooled to ambient temperature. The resultant brown suspension was diluted with 300 mL water and extracted with diethyl ether (2×200 mL). The organic phases were combined and dried over anhydrous sodium sulfate, filtered and concentrated under reduced pressure. The resultant oil was flash chromatographed with 20% ethyl acetate/hexanes to yield 1.36 g (45%) of the desired 3-[3-(1-ethoxycarbonyl-1-methyl-ethoxy)-4-methyl-phenyl]-piperidine-1-carboxylic acid benzyl ester as a clear oil.

MS (LC-MS) 462.1(M+Na)⁺.

$^1$H NMR (400 MHz, CDCl$_3$) δ 7.34 (m, 5H), 7.06 (d, 1H), 6.73 (d, 1H), 6.52 (s, 1H), 5.13 (m, 2H), 4.22 (m, 4H), 2.74 (q, 1H), 2.70 (t, 1H), 2.57 (m, 1H), 2.19 (s, 3H), 1.96 (d, 1H), 1.76 (m, 1H), 1.57 (d, 6H), 1.53 (s, 2H), 1.22 (t, 3H).

A 250 mL Parr bottle was charged with 0.27 g of 10% palladium on carbon (50% water) and covered with 20 mL ethanol. 3-[3-(1-ethoxycarbonyl-1-methyl-ethoxy)-4-methyl-phenyl]-piperidine-1-carboxylic acid benzyl ester (1.36 g, 3.09 mmol) was dissolved in 50 mL ethanol and added to the catalyst suspension. The reaction was hydrogenated at 50 psi for 2 h. The catalyst was filtered through a celite plug. The filter cake was washed with 150 mL ethanol and the filtrated concentrated under reduced pressure. The resultant oil was taken up in 20 mL hot ethanol to which was added D-tartaric acid (464 mg, 3.09 mmol) in 10 mL hot ethanol. The solution was allowed to stir 24 h at ambient temperature. The white crystalline precipitate was collected by filtration to yield 978 mg (69%) of 2-methyl-2-(2-methyl-5-piperidin-3-yl-phenoxy)-propionic acid ethyl ester D-tartaric acid salt as a white crystalline solid.

MS (LC-MS) 306.3 (M+H)⁺.

$^1$H NMR (400 MHz, DMSO$_{d6}$) δ 7.11 (d, 1H), 6.78 (d, 1H), 6.44 (s, 1H), 4.16 (q, 2H), 3.81 (s, 2H), 3.21 (t, 2H), 2.78 (m, 2H), 2.10 (s, 3H), 1.81 (m, 2H), 1.69 (m, 1H), 1.56 (m, 1H), 1.51 (s, 6H), 1.14 (t, 3H).

HPLC analysis: Chiralpak AD, 1 mL/min, 5% isopropanol/heptane 0.2% diethylamine, rt=8.90 min.

ee=98%.

2-Methyl-2-(2-methyl-5-piperidin-3-yl-phenoxy)-propionic acid ethyl ester D-tartaric acid salt was carried on using procedures analogous to those described in Example 11 to give the title compound, (R)-2-methyl-2-(2-methyl-5-{1-[4-methyl-2-(4-trifluoromethyl-phenyl)-thiazole-5-carbonyl]-piperidin-3-yl}-phenoxy)-propionic acid

MS (LC-MS) 547.0 (M+H)⁺.

$^1$H NMR (400 MHz, CD$_3$OD) δ 8.13 (d, 2H), 7.78 (d, 2H), 7.08 (d, 1H), 6.79 (m, 1H), 6.68 (m, 1H), 2.74 (m, 1H), 2.47 (s, 3H), 2.15 (s, 3H), 2.03 (d, 1H), 1.91 (brm, 2H), 1.79 (m, 2H), 1.54 (brs, 6H).

EXAMPLE 11-3

(R)-3-[3-(1-Carboxy-1-methyl-ethoxy)-4-methyl-phenyl]-piperidine-1-carboxylic acid 4-trifluoromethyl-benzyl ester The title compound was prepared using the starting material prepared in Example 11-2 and using procedures analogous to those described in Example 11-1.

MS (LC-MS) 478.1 (M−H)⁻.

$^1$H NMR (400 MHz, CDCl$_3$) δ 7.66 (d, 2H), 7.54 (m, 2H), 7.07 (d, 1H), 6.77 (d, 1H), 6.67 (s, 1H), 5.21 (s, 2H), 4.14 (m, 2H), 2.88 (brm, 2H), 2.58 (t, 1H), 2.17 (s, 3H), 1.96 (d, 1H), 1.77 (m, 2H), 1.62 (m, 1H), 1.57 (s, 6H).

Examples 11-4, 11-5 and 11-6 were prepared using methods analogous to those described in Example 11 and 11-1.

EXAMPLE 11-4

2-Methyl-2-(2-methyl-4-{1-[4-methyl-2-(4-trifluoromethyl-phenyl)-thiazole-5-carbonyl]-piperidin-3-yl}-phenoxy)-propionic acid

MS (LC-MS) 547.0 (M−H)⁻.

$^1$H NMR (400 MHz, CD$_3$OD) δ 8.17 (d, 2H), 7.78 (d, 2H), 7.06 (m, 2H), 6.96 (br, 1H), 6.73 (brm, 1H), 2.71 (t, 1H), 2.48 (s, 3H), 2.18 (brs, 3H), 2.02 (d, 1H), 1.84 (m, 2H), 1.67 (m, 1H), 1.54 (s, 6H).

EXAMPLE 11-5

3-[4-(1-Carboxy-1-methyl-ethoxy)-3-methyl-phenyl]-piperidine-1-carboxylic acid 4-trifluoromethyl-benzyl ester MS (LC-MS) 478.0 (M–H)$^-$.
$^1$H NMR (400 MHz, CD$_3$OD) δ 7.66 (d, 2H), 7.54 (m, 2H), 7.03 (s, 1H), 6.94 (d, 1H), 6.72 (d, 1H), 5.21 (s, 2H), 4.14 (m, 2H), 2.89 (brm, 2H), 2.57 (t, 1H), 2.19 (s, 3H), 1.93 (d, 1H), 1.79 (d, 1H), 1.70 (q, 1H), 1.58 (m, 1H), 1.55 (s, 6H).

EXAMPLE 11-6

(S)-3-[3-(1-Carboxy-1-methyl-ethoxy)-4-methyl-phenyl]-piperidine-1-carboxylic acid 2-(4-trifluoromethyl-phenyl)-ethyl ester and (R)-3-[3-(1-Carboxy-1-methyl-ethoxy)-4-methyl-phenyl]-piperidine-1-carboxylic acid 2-(4-trifluoromethyl-phenyl)-ethyl ester MS (LC-MS) 494.3 (M–H)$^+$.
rotation data for the R-isomer [α]$_D^{25}$ 50.7° (c 0.82, CH$_3$OH)
$^1$H NMR (400 MHz, CD$_3$OD) δ 7.57 (br s, 2H), 7.43 (br s, 2H), 7.07 (d, 1H), 6.75 (br s, 1H), 6.63 (s, 1H), 4.34 (br s, 2H), 4.05 (brm, 2H), 3.06 (t, 2H), 2.72 (brm, 1H), 2.43 (brm, 1H), 2.18 (s, 3H), 1.92 (d, 1H), 1.70 (m, 1H), 1.61 (t, 1H), 1.56 (m, 1H), 1.43 (br, 1H).

EXAMPLE 12

(S)-(2-methyl-5-{1-[4-methyl-2-(4-trifluoromethyl-phenyl)-thiazole-5-carbonyl]-piperidin-3-yl}-phenoxy)-acetic acid To a solution of 3-(3-hydroxy-4-methyl-phenyl)-piperidine-1-carboxylic acid benzyl ester (Example 11; 2.08 g, 6.39 mmol) in 15 mL dimethylformamide was added cesium carbonate (4.17 g, 12.78 mmol) and ethyl bromoacetate (1.42 mL, 12.78 mmol). The mixture was heated to 60° C. under N$_2$ with stirring for 3 h and cooled to ambient temperature. The resultant brown suspension was diluted with 300 mL water and extracted with diethyl ether (2×200 mL). The organic phases were combined and dried over anhydrous sodium sulfate, filtered and concentrated under reduced pressure. The resultant oil was flash chromatographed with 15% ethyl acetate/hexanes to yield 1.42 g (54%) of the desired 3-(3-ethoxycarbonylmethoxy-4-methyl-phenyl)-piperidine-1-carboxylic acid benzyl ester as a clear oil.

MS (LC-MS) 462.1(M+Na)$^+$.
$^1$H NMR (400 MHz, CDCl$_3$) δ 7.35 (m, 5H), 7.09 (d, 1H), 6.76 (d, 1H), 6.56 (s, 1H), 5.14 (m, 2H), 4.61 (s, 2H), 4.23 (m, 2H), 2.78 (q, 2H), 2.62 (m, 1H), 2.25 (s, 3H), 1.98 (m, 1H), 1.76 (m, 1H), 1.56 (m, 3H), 1.29 (t, 3H).

A 250 mL Parr bottle was charged with 0.14 g of 10% palladium on carbon (50% water) and covered with 20 mL ethanol. 3-(3-ethoxycarbonylmethoxy-4-methyl-phenyl)-piperidine-1-carboxylic acid benzyl ester (1.42 g, 3.45 mmol) was dissolved in 50 mL ethanol and added to the catalyst suspension. The reaction was hydrogenated at 50 psi for 2 h. The catalyst was filtered through a celite plug. The filter cake was washed with 150 mL ethanol and the filtrated concentrated under reduced pressure. The resultant oil was taken up in 20 mL hot ethanol to which was added L-tartaric acid (518 mg, 3.45 mmol) in 10 mL hot ethanol. The solution was allowed to stir 24 h at ambient temperature. The white crystalline precipitate was collected by filtration to yield 730 mg (50%) of (2-methyl-5-piperidin-3-yl-phenoxy)-acetic acid ethyl ester L-tartaric acid salt as a white crystalline solid.

MS (LC-MS) 278.3 (M+H)$^+$.
$^1$H NMR (400 MHz, DMSO$_{d6}$) δ 7.11 (d, 1H), 6.78 (d, 1H), 6.44 (s, 1H), 4.16 (q, 2H), 3.81 (s, 2H), 3.21 (t, 2H), 2.78 (m, 2H), 2.10 (s, 3H), 1.81 (m, 2H), 1.69 (m, 1H), 1.56 (m, 1H), 1.51 (s, 6H), 1.14 (t, 3H).

HPLC analysis: Chiralpak AD, 1 mL/min, 5% isopropanol/heptane 0.2% diethylamine, rt=4.01 min.
ee=99.3%.

(2-methyl-5-piperidin-3-yl-phenoxy)-acetic acid ethyl ester L-tartaric acid salt (147 mg, 0.34 mmol) was dissolved in 50 mL ethyl acetate and washed with 50 mL saturated aqueous NaHCO$_3$. The organic phase was dried over Na$_2$SO$_4$ and concentrated under reduced pressure. The resultant oil was taken up in 2 mL CH$_2$Cl$_2$ and 1-(3-dimethylaminopropyl)-3-ethyl carbodiimide (132 mg, 0.69 mmol) and 4-methyl-2-[4-(trifluoromethyl)phenyl]-1,3-thiazole-5-carboxylic acid (99 mg, 0.34 mmol) were added. The reaction was stirred at ambient temperature under nitrogen for 24 h. The reaction was diluted with 100 mL diethyl ether and washed with water (100 mL), 0.5 N HCl (2×100 mL), saturated aqueous NaHCO$_3$ (2×100 mL), dried over Na$_2$SO$_4$ and concentrated under reduced pressure to yield (2-methyl-5-{1-[4-methyl-2-(4-trifluoromethyl-phenyl)-thiazole-5-carbonyl]-piperidin-3-yl}-phenoxy)-acetic acid ethyl ester (146 mg, 76%) as a clear oil.

MS (LC-MS) 547.1 (M+H)$^+$.
$^1$H NMR (400 MHz, CDCl$_3$) δ 8.03 (d, 2H), 7.69 (d, 2H), 7.10 (d, 1H), 6.76 (brs, 1H), 6.57 (brs, 1H), 4.62 (brs, 2H), 4.25 (q, 2H), 2.97 (brm, 1H), 2.72 (m, 1H), 2.52 (s, 3H), 2.25 (s, 3H), 2.09 (m, 1H), 1.91 (m, 1H), 1.70 (m, 4H), 1.28 (t, 3H).

A mixture of (2-methyl-5-{1-[4-methyl-2-(4-trifluoromethyl-phenyl)-thiazole-5-carbonyl]-piperidin-3-yl}-phenoxy)-acetic acid ethyl ester (146 mg, 0.26 mmol), potassium carbonate (71 mg, 0.52 mmol), methanol (10 mL) and water (2 mL) was heated at reflux for 3 h, cooled to room temperature and concentrated under reduced pressure. The resulting residue was taken up in water (50 mL), acidified with 1N aqueous hydrochloric acid and extracted with ethyl acetate (2×50 mL). The combined organic extracts were washed with saturated aqueous sodium chloride, dried over anhydrous sodium sulfate, filtered, concentrated under reduced pressure to yield 130 mg (94%) of (S)-(2-methyl-5-{1-[4-methyl-2-(4-trifluoromethyl-phenyl)-thiazole-5-carbonyl]-piperidin-3-yl}-phenoxy)-acetic acid as a white solid.

MS (LC-MS) 450.1 (M–H)$^-$.
$^1$H NMR (400 MHz, CD$_3$OD) δ 8.13 (d, 2H), 7.78 (d, 2H), 7.06 (m, 1H), 6.75 (brm, 2H), 4.66 (brs, 2H), 2.76 (t, 1H), 2.48 (s, 3H), 2.20 (s, 3H), 2.04 (d, 1H), 1.83 (m, 2H), 1.67 (m, 1H).

EXAMPLE 12-1

(S)-3-(3-carboxymethoxy-4-methyl-phenyl)-piperidine-1-carboxylic acid 4-trifluoromethyl-benzyl ester (2-methyl-5-piperidin-3-yl-phenoxy)-acetic acid ethyl ester L-tartaric acid salt (Example 12; 147 mg, 0.34 mmol) was dissolved in 50 mL ethyl acetate and washed with 50 mL saturated aqueous NaHCO$_3$. The organic phase was dried over Na$_2$SO$_4$ and concentrated under reduced pressure. The resultant oil was taken up in 3 mL toluene and imidazole-1-carboxylic acid 4-trifluoromethyl-benzyl ester (93 mg, 0.34 mmol) was added. The reaction was stirred for 18 h at room temperature under nitrogen. The reaction was flash chromatographed with 15% ethyl acetate/hexanes to yield 118 mg (74%) of the desired 3-(3-ethoxycarbonylmethoxy-4-methyl-phenyl)-piperidine-1-carboxylic acid 4-trifluoromethyl-benzyl ester as a clear oil.

MS (LC-MS) 502.1 (M+Na)$^+$.

$^1$H NMR (400 MHz, CDCl$_3$) δ 7.61(d, 2H), 7.46 (d, 2H), 7.10 (d, 1H), 6.76 (d, 1H), 6.56 (s, 1H), 5.19 (m, 2H), 4.62 (s, 2H), 4.25 (m, 2H), 2.79 (brm, 2H), 2.63 (m, 1H), 2.26 (s, 3H), 2.02 (m, 1H), 1.80 (m, 2H), 1.56 (m, 4H), 1.28 (t, 3H).

A mixture of 3-(3-ethoxycarbonylmethoxy-4-methyl-phenyl)-piperidine-1-carboxylic acid 4-trifluoromethyl-benzyl ester (118 mg, 0.25 mmol), potassium carbonate (68 mg, 0.49 mmol) and water (2 mL) was heated at reflux for 3 h, cooled to room temperature and concentrated under reduced pressure. The resulting residue was taken up in water (50 mL), acidified with 1N aqueous hydrochloric acid and extracted with ethyl acetate (2×50 mL). The combined organic extracts were washed with saturated aqueous sodium chloride, dried over anhydrous sodium sulfate, filtered, concentrated under reduced pressure to yield 110 mg (97%) of (S)-3-(3-carboxymethoxy-4-methyl-phenyl)-piperidine-1-carboxylic acid 4-trifluoromethyl-benzyl ester as a white solid.

MS (LC-MS) 450.1 (M–H)$^-$.

$^1$H NMR (400 MHz, CD$_3$OD) δ 7.66 (d, 2H), 7.54 (m, 2H), 7.06 (d, 1H), 6.76 (d, 1H), 6.69 (s, 1H), 5.21 (s, 2H), 4.66 (s, 2H), 4.15 (m, 2H), 2.88 (brm, 2H), 2.62 (t, 1H), 2.21 (s, 3H), 1.96 (d, 1H), 1.79 (m, 1H), 1.69 (t, 1H), 1.58 (m, 1H).

EXAMPLE 12-2

(R)-(2-Methyl-5-{1-[4-methyl-2-(4-trifluoromethyl-phenyl)-thiazole-5-carbonyl]-piperidin-3-yl}-phenoxy)-acetic acid To a solution of 3-(3-hydroxy-4-methyl-phenyl)-piperidine-1-carboxylic acid benzyl ester (Example 11-2; 2.34 g, 7.19 mmol) in 15 mL dimethylformamide was added cesium carbonate (4.69 g, 14.38 mmol) and ethyl bromoacetate (1.60 mL, 14.38 mmol). The mixture was heated to 60° C. under N$_2$ with stirring for 3 h and cooled to ambient temperature. The resultant brown suspension was diluted with 300 mL water and extracted with diethyl ether (2×200 mL). The organic phases were combined and dried over anhydrous sodium sulfate, filtered and concentrated under reduced pressure. The resultant oil was flash chromatographed with 15% ethyl acetate/hexanes to yield 1.78 g (60%) of the desired 3-(3-ethoxycarbonylmethoxy-4-methyl-phenyl)-piperidine-1-carboxylic acid benzyl ester as a clear oil.

MS (LC-MS) 462.1(M+Na)$^+$.

$^1$H NMR (400 MHz, CDCl$_3$) δ 7.35 (m, 5H), 7.09 (d, 1H), 6.76 (d, 1H), 6.56 (s, 1H), 5.14 (m, 2H), 4.61 (s, 2H), 4.23 (m, 2H), 2.78 (q, 2H), 2.62 (m, 1H), 2.25 (s, 3H), 1.98 (m, 1H), 1.76 (m, 1H), 1.56 (m, 3H), 1.29 (t, 3H).

A 250 mL Parr bottle was charged with 0.18 g of 10% palladium on carbon (50% water) and covered with 20 mL ethanol. 3-(3-ethoxycarbonylmethoxy-4-methyl-phenyl)-piperidine-1-carboxylic acid benzyl ester (1.78 g, 4.33 mmol) was dissolved in 50 mL ethanol and added to the catalyst suspension. The reaction was hydrogenated at 50 psi for 2 h. The catalyst was filtered through a celite plug. The filter cake was washed with 150 mL ethanol and the filtrated concentrated under reduced pressure. The resultant oil was taken up in 20 mL hot ethanol to which was added D-tartaric acid (650 mg, 4.33 mmol) in 10 mL hot ethanol. The solution was allowed to stir 24 h at ambient temperature. The white crystalline precipitate was collected by filtration to yield 1.014 g (55%) of (2-methyl-5-piperidin-3-yl-phenoxy)-acetic acid ethyl ester D-tartaric acid salt as a white crystalline solid.

MS (LC-MS) 278.3 (M+H)$^+$.

$^1$HNMR (400 MHz, DMSO$_{d6}$) δ 7.11 (d, 1H), 6.78 (d, 1H), 6.44 (s, 1H), 4.16 (q, 2H), 3.81 (s, 2H), 3.21 (t, 2H), 2.78 (m, 2H), 2.10 (s, 3H), 1.81 (m, 2H), 1.69 (m, 1H), 1.56 (m, 1H), 1.51 (s, 6H), 1.14 (t, 3H).

HPLC analysis: Chiralpak AD, 1 mL/min, 5% isopropanol/heptane 0.2% diethylamine, rt=3.18.

ee=98.9.

(2-Methyl-5-piperidin-3-yl-phenoxy)-acetic acid ethyl ester D-tartaric acid salt was carried on using procedures analogous to those described in Example 12 to give the title compound, (R)-(2-methyl-5-{1-[4-methyl-2-(4-trifluoromethyl-phenyl)-thiazole-5-carbonyl]-piperidin-3-yl}-phenoxy)-acetic acid.

MS (LC-MS) 450.1 (M–H)$^-$.

$^1$H NMR (400 MHz, CD$_3$OD) δ 8.13 (d, 2H), 7.78 (d, 2H), 7.06 (m, 1H), 6.75 (brm, 2H), 4.66 (brs, 2H), 2.76 (t, 1H), 2.48 (s, 3H), 2.20 (s, 3H), 2.04 (d, 1H), 1.83 (m, 2H), 1.67 (m, 1H).

EXAMPLE 12-3

(R)-3-(3-Carboxymethoxy-4-methyl-phenyl)-piperidine-1-carboxylic acid 4-trifluoromethyl-benzyl ester The title compound was prepared using the starting material prepared in Example 12-2 and using procedures analogous to those described in Example 12-1.

MS (LC-MS) 450.1 (M–H)$^-$.

$^1$H NMR (400 MHz, CD$_3$OD) δ 7.66 (d, 2H), 7.54 (m, 2H), 7.06 (d, 1H), 6.76 (d, 1H), 6.69 (s, 1H), 5.21 (s, 2H), 4.66 (s, 2H), 4.15 (m, 2H), 2.88 (brm, 2H), 2.62 (t, 1H), 2.21 (s, 3H), 1.96 (d, 1H), 1.79 (m, 1H), 1.69 (t, 1H), 1.58 (m, 1H).

Examples 12-4 and 12-5 were prepared using methods analogous to those described in Example 12 and 12-1.

EXAMPLE 12-4

(2-Methyl-4-{1-[4-methyl-2-(4-trifluoromethyl-phenyl)-thiazole-5-carbonyl]-piperidin-3-yl}-phenoxy)-acetic acid

MS (LC-MS) 519.0 (M–H)$^-$.

$^1$H NMR (400 MHz, CD$_3$OD) δ 8.13 (d, 2H), 7.78 (d, 2H), 7.03 (br s, 2H), 6.74 (brm, 1H), 4.64 (brs, 2H), 2.74 (t, 1H), 2.48 (s, 3H), 2.22 (brs, 3H), 2.02 (d, 1H), 1.84 (m, 2H), 1.67 (m, 1H).

EXAMPLE 12-5

3-(4-Carboxymethoxy-3-methyl-phenyl)-piperidine-1-carboxylic acid 4-trifluoromethyl-benzyl ester

MS (LC-MS) 450.0 (M–H)$^-$.

$^1$H NMR (400 MHz, CD$_3$OD) δ 7.66 (d, 2H), 7.54 (m, 2H), 7.03 (s, 1H), 6.99 (d, 1H), 6.73 (d, 1H), 5.21 (s, 2H), 4.64 (s, 2H), 4.15 (m, 2H), 2.89 (brm, 2H), 2.58 (t, 1H), 2.23 (s, 3H), 1.94 (d, 1H), 1.79 (d, 1H), 1.69 (q, 1H), 1.58 (m, 1H).

EXAMPLE 13

C,C,C-Trifluoro-N-(2-methyl-5-{1-[4-methyl-2-(4-trifluoromethyl-phenyl)-thiazole-5-carbonyl]-piperidin-3-yl}-phenyl)-methanesulfonamide 2-Nitro-4-bromotoluene (8.74 g, 40.46 mmol) was dissolved in 75 mL dioxane and 25 mL water to which was added diethyl-(3-pyridyl)borane (5.95 g, 40.46 mmol), sodium carbonate (8.58 g, 80.91 mmol) and tetrakis(triphenylphosphine palladium(0) (0.94 g, 0.81 mmol). The mixture was heated at reflux for 18 h then cooled to ambient temperature. The mixture was diluted with 600 mL water and extracted with diethyl ether (2×300 mL). The organic phases were combined and extracted with 0.3 N HCl (3×200 mL). The acidic extractions were combined and made basic with 5N aqueous sodium hydroxide. This basic layer was extracted with diethyl ether (2×300 mL) and the extracts were combined and dried over anhydrous sodium sulfate, filtered and concentrated under reduced pressure to yield 6.39 g (74%) of 2-nitro-4-(3-pyridyl)toluene as a brown oil.

MS (LC-MS) 215.1 (M+H)$^+$.

$^1$H NMR (400 MHz, CDCl$_3$) δ 8.87 (d, 1H), 8.66 (d, 1H), 8.20 (d, 1H), 7.92 (d, 1H), 7.73 (dd, 1H), 7.44 (m, 2H), 2.66 (s, 3H).

A 500 mL hydrogenation vessel was charged with 0.64 g platinum(II)oxide and purged with nitrogen. 2-Nitro-4-(3-pyridyl)toluene (19.57 g, 81.10 mmol) was added as a solution in 150 mL acetic acid. The suspension was hydrogenated at 45 psi for 18 h. The catalyst was filtered through celite and the filter plug was washed with 300 mL ethyl acetate. The filtrate was concentrated under reduced pressure. The resultant oil was taken up in 300 mL water and made basic with 5N aqueous sodium hydroxide. This basic layer was extracted with ethyl acetate (2×300 mL) and the extracts were combined and dried over anhydrous sodium sulfate, filtered and concentrated under reduced pressure to yield 5.38 g (95%) of 2-amino-4-(3-piperidinyll)toluene as a brown oil.

MS (LC-MS) 191.2 (M+H)$^+$.

$^1$H NMR (400 MHz, CDCl$_3$) δ 6.97 (d, 1H), 6.56 (dd, 1H), 6.54 (d, 1H), 3.57 (brs, 1H), 3.12 (dd, 2H), 2.61 (m, 3H), 2.13 (s, 3H), 1.95 (brs, 2H), 1.75 (m, 1H), 1.57 (m, 2H).

2-Amino-4-(3-piperidinyl)toluene (1.25 g, 6.57 mmol) was dissolved in 25 mL tetrahydrofuran. 1 N sodium hydroxide (13.14 mL, 13.14 mmol) was added followed by dibenzyl-dicarbonate (1.88 g, 6.57 mmol). The reaction was stirred for 2 h at ambient temperature then diluted with 200 mL diethyl ether and washed with 200 mL water. The organic phase was dried over anhydrous sodium sulfate, filtered and concentrated under reduced pressure. The resultant oil was flash chromatographed with 20% ethyl acetate/hexanes to yield 1.414 g (66%) of the desired 3-(3-amino-4-methyl-phenyl)-piperidine-1-carboxylic acid benzyl ester as a clear oil.

MS (LC-MS) 325.2 (M+H)$^+$.

$^1$H NMR (400 MHz, DMSO-d$_6$) δ 7.34 (m, 5H), 6.81 (d, 1H), 6.45 (s, 1H), 6.32 (d, 1H), 5.06 (s, 2H), 4.02 (m, 2H), 2.76 (brm, 1H), 2.41 (t, 1H), 1.97 (s, 3H), 1.82 (d, 2H), 1.69 (d, 1H), 1.54 (q, 1H), 1.44 (t, 1H).

3-(3-Amino-4-methyl-phenyl)-piperidine-1-carboxylic acid benzyl ester (470 mg, 1.45 mmol) was dissolved in 10 mL CH$_2$Cl$_2$ and cooled to 0° C. Triethylamine (0.4 mL, 2.90 mmol) was added followed by dropwise addition of trifluoromethane sulfonic anhydride (0.24 mL, 1.45 mmol) and the reaction stirred for 0.5 h at 0° C. The mixture was concentrated under reduced pressure and taken up in 50 mL water. The aqueous suspension was made acidic with 1 N HCl and extracted with 50 mL ethyl acetate. The organic phase was dried over anhydrous sodium sulfate, filtered and concentrated under reduced pressure. The resultant oil was flash chromatographed with 15% methanol/chloroform (1% ammonium hydroxide modifier). The product fractions were combined and concentrated under reduced pressure. The resultant oil was taken up in 50 mL water, made acidic with 1 N HCl and extracted with 50 mL ethyl acetate. The organic phase was dried over anhydrous sodium sulfate, filtered and concentrated under reduced pressure to yield 403 mg (61%) of the desired 3-[4-methyl-3-(trifluoro-methanesulfonylamino)-phenyl]-piperidine-1-carboxylic acid benzyl ester as a clear oil.

MS (LC-MS) 455.1 (M−H)$^-$.

$^1$H NMR (400 MHz, CD$_3$OD) δ 7.35 (m, 5H), 7.22 (d, 1H), 7.18 (brs, 2H), 5.13 (s, 2H), 4.15 (d, 2H), 2.89 (brm, 2H), 2.65 (m, 1H), 2.32 (s, 3H), 2.00 (d, 1H), 1.76 (d, 1H), 1.69 (q, 1H), 1.58 (t, 1H).

A 250 mL Parr bottle was charged with 80 mg of 10% palladium on carbon (50% water) and covered with 10 mL ethanol. 3-[4-methyl-3-(trifluoromethanesulfonylamino)-phenyl]-piperidine-1-carboxylic acid benzyl ester (403 mg, 0.88 mmol) was dissolved in 20 mL ethanol and added to the catalyst suspension. The reaction was hydrogenated at 45 psi for 2 h. Water (50 mL) was added to dissolve the white precipitate and the catalyst was filtered through a celite plug. The filter cake was washed with 200 mL 25% water/ethanol and the filtrate concentrated under reduced pressure to yield 275 mg (97%) of c,c,c-trifluoro-N-(2-methyl-5-piperidin-3-yl-phenyl)-methanesulfonamide as a white crystalline solid.

MS (LC-MS) 323.2 (M+H)$^+$.

$^1$H NMR (400 MHz, DMSO-d$_6$) δ 8.58 (brs, 1H), 8.29 (brs, 1H), 6.97 (s, 1H), 6.92 (d, 1H), 6.56 (d, 1H), 3.24 (m, 2H), 2.87 (brm, 2H), 2.70 (t, 1H), 2.06 (s, 3H), 1.83 (t, 2H), 1.66 (m, 2H).

To a 10 mL round bottom flask was added c,c,c-trifluoro-N-(2-methyl-5-piperidin-3-yl-phenyl)-methanesulfonamide (64 mg, 0.20 mmol), 3 mL CH$_2$Cl$_2$, 1-(3-dimethylaminopropyl)-3-ethyl carbodiimide (76 mg, 0.40 mmol), and 4-methyl-2-[4-(trifluoromethyl)phenyl]-1,3-thiazole-5-carboxylic acid (57 mg, 0.20 mmol). The suspension was stirred at ambient temperature for 72 h. The reaction was filtered and the filtrate flash chromatographed with with 10% methanol/chloroform (1% ammonium hydroxide modifier). The product fractions were combined and concentrated under reduced pressure. The resultant oil was taken up in 50 mL water, made acidic with 1 N HCl and extracted with 50 mL ethyl acetate. The organic phase was dried over anhydrous sodium sulfate, filtered and concentrated under reduced pressure to yield 28 mg (24%) of c,c,c-trifluoro-N-(2-methyl-5-{1-[4-methyl-2-(4-trifluoromethyl-phenyl)-thiazole-5-carbonyl]-piperidin-3-yl}-phenyl)-methanesulfonamide as a white solid.

MS (LC-MS) 592.0 (M−H)$^-$.

$^1$H NMR (400 MHz, CD$_3$OD) δ 8.13 (d, 2H), 7.79 (d, 1H), 7.22 (brm, 3H), 2.81 (t, 1H), 2.48(s, 3H), 2.31 (s, 3H), 2.07 (d, 1H), 1.85 (m, 2H), 1.69 (m, 2H).

EXAMPLE 13-1

3-[3-(Carboxymethyl-amino)-4-methyl-phenyl]-piperidine-1-carboxylic acid 4-trifluoromethyl-benzyl ester 3-(3-Amino-4-methyl-phenyl)-piperidine-1-carboxylic acid benzyl ester (Example 13; 230 mg, 0.71 mmol) was dissolved in 5 mL dimethylformamide. Cesium carbonate (462 mg, 1.42 mol) and ethyl bromoacetate (86 μL, 0.78 mmol) were added and the mixture stirred at ambient temperature under a nitrogen atmosphere for 72 h. An additional 86 μL of ethyl bromoacetate were added and the reaction stirred an additional 24 h. The mixture was diluted with 100 mL water and extracted with diethyl ether (2×50 mL). The organic extracts were combined, dried over anhydrous sodium sulfate, filtered and concentrated under reduced pressure. The resultant oil was flash chromatographed with 20% ethyl acetate/hexanes to yield 152 mg (52%) of 3-[3-(ethoxycarbonylmethyl-amino)-4-methyl-phenyl]-piperidine-1-carboxylic acid benzyl ester as a clear oil.

MS (LC-MS) 411.2 (M+H)$^+$.

$^1$H NMR (400 MHz, CDCl$_3$) δ 7.37 (m, 5H), 7.03 (d, 1H), 6.84 (brm, 1H), 6.78 (brm, 1H), 5.14 (s, 2H), 4.22 (q, 2H), 3.98 (s, 2H), 2.79 (m, 2H), 2.63 (m, 1H), 2.25 (s, 3H), 1.99 (d, 1H), 1.83 (d, 1H), 1.58 (m, 2H), 1.28 (t, 3H).

A 100 mL Parr bottle was charged with 30 mg of 10% palladium on carbon (50% water) and covered with 10 mL ethanol. 3-[3-(ethoxycarbonylmethyl-amino)-4-methyl-phenyl]-piperidine-1-carboxylic acid benzyl ester (152 mg, 0.37 mmol) was dissolved in 10 mL ethanol and added to the catalyst suspension. The reaction was hydrogenated at 45 psi for 2 h. The catalyst was filtered through a celite plug. The filter cake was washed with 30 mL ethanol and the filtrate concentrated under reduced pressure to yield 126 mg (100%) of (2-methyl-5-piperidin-3-yl-phenylamino)-acetic acid ethyl ester as a clear oil.

MS (LC-MS) 277.2 (M+H)$^+$.

$^1$H NMR (400 MHz, CDCl$_3$) δ 9.80 (brs, 1H), 9.56 (brs, 1H), 7.02 (d, 1H), 6.55 (brm, 1H), 6.36 (brm, 1H), 4.22 (q, 2H), 3.93 (s, 2H), 3.52 (t, 2H), 3.13 (m, 1H), 2.87 (m, 2H), 2.02 (d, 1H), 1.98 (d, 1 h), 1.59 (m, 2H), 1.23 (t, 3H).

(2-Methyl-5-piperidin-3-yl-phenylamino)-acetic acid ethyl ester (63 mg, 0.23 mmol) was dissolved in 3 mL toluene and imidazole-1-carboxylic acid 4-trifluoromethyl-benzyl ester (93 mg, 0.34 mmol) was added. The reaction was stirred for 18 h at room temperature under nitrogen. The reaction was flash chromatographed with 15% ethyl acetate/hexanes to yield 40 mg (37%) of the desired 3-[3-(ethoxycarbonylmethyl-amino)-4-methyl-phenyl]-piperidine-1-carboxylic acid 4-trifluoromethyl-benzyl ester as a clear oil.

MS (LC-MS) 479.1 (M+H)$^+$.

$^1$H NMR (400 MHz, CD$_3$OD) δ 7.66 (d, 2H), 7.54 (m, 2H), 6.94 (d, 1H), 6.51 (d, 1H), 6.32 (m, 1H), 5.21 (s, 2H), 4.21 (m, 2H), 3.96 (s, 2H), 2.91 (m, 2H), 2.58 (t, 1H), 2.13 (s, 3H), 1.97 (d, 1H), 1.80 (d, 1H), 1.72 (m, 1H), 1.58 (m, 1H), 1.23 (m, 3H).

A mixture of 3-[3-(ethoxycarbonylmethyl-amino)-4-methyl-phenyl]-piperidine-1-carboxylic acid 4-trifluoromethyl-benzyl ester (40 mg, 0.0.084 mmol), potassium carbonate (23 mg, 0.167 mmol), methanol (5 mL) and water (1 mL) was heated at reflux for 3 h, cooled to room temperature and concentrated under reduced pressure. The resulting residue was taken up in water (50 mL), acidified with 1N aqueous hydrochloric acid and extracted with ethyl acetate (2×50 mL). The combined organic extracts were washed with saturated aqueous sodium chloride, dried over anhydrous sodium sulfate, filtered, concentrated under reduced pressure to yield 40 mg (99%) of 3-[3-(carboxymethyl-amino)-4-methyl-phenyl]-piperidine-1-carboxylic acid 4-trifluoromethyl-benzyl ester as a white solid.

MS (LC-MS) 451.0 (M+H)$^+$.

$^1$H NMR (400 MHz, CD$_3$OD) δ 7.67 (d, 2H), 7.54 (brs, 2H), 6.94 (d, 1H), 6.50 (d, 1H), 6.35 (brs, 1H), 5.21 (s, 2H), 4.15 (brm, 2H), 3.92 (s, 2H), 3.92 (m, 1H), 3.81 (m, 1H), 2.57 (t, 1H), 2.13 (s, 3H), 1.95 (d, 1H), 1.78 (d, 1H), 1.72 (q, 1H), 1.58 (t, 1H).

EXAMPLE 13-2

(2-Methyl-5-{1-[4-methyl-2-(4-trifluoromethyl-phenyl)-thiazole-5-carbonyl]-piperidin-3-yl}-phenylamino)-acetic acid (2-Methyl-5-piperidin-3-yl-phenylamino)-acetic acid ethyl ester (Example 13-1; 63 mg, 0.23 mmol) was dissolved in 2 mL CH$_2$Cl$_2$ and 1-(3-dimethylaminopropyl)-3-ethyl carbodiimide (87 mg, 0.46 mmol) and 4-methyl-2-[4-(trifluoromethyl)phenyl]-1,3-thiazole-5-carboxylic acid (65 mg, 0.23 mmol) were added. The reaction was stirred at ambient temperature under nitrogen for 24 h. The reaction was flash chromatographed with 30% ethyl acetate/hexanes to yield 19 mg (15%) of the desired (2-methyl-5-{1-[4-methyl-2-(4-trifluoromethyl-phenyl)-thiazole-5-carbonyl]-piperidin-3-yl}-phenylamino)-acetic acid ethyl ester as a clear oil.

MS (LC-MS) 546.0 (M+H)$^+$.

$^1$H NMR (400 MHz, CD$_3$OD) δ 8.14 (d, 2H), 7.79 (d, 2H), 6.91 (m, 1H), 6.51 (m, 1H), 6.34 (m, 1H), 4.19 (brm, 2H), 3.97 (brs, 2H), 2.69 (m, 1H), 2.47 (s, 3H), 2.13 (s, 3H), 2.02 (d, 1H), 1.85 (m, 2H), 1.64 (m 1H), 1.24 (brm, 3H).

A mixture of (2-methyl-5-{1-[4-methyl-2-(4-trifluoromethyl-phenyl)-thiazole-5-carbonyl]-piperidin-3-yl}-phenylamino)-acetic acid ethyl ester (19 mg, 0.035 mmol), potassium carbonate (10 mg, 0.07 mmol), methanol (5 mL) and water (1 mL) was heated at reflux for 3 h, cooled to room temperature and concentrated under reduced pressure. The resulting residue was taken up in water (50 mL), acidified with 1N aqueous hydrochloric acid and extracted with ethyl acetate (2×50 mL). The combined organic extracts were washed with saturated aqueous sodium chloride, dried over anhydrous sodium sulfate, filtered, concentrated under reduced pressure to yield 20 mg (99%) of (2-methyl-5-{1-[4-methyl-2-(4-trifluoromethyl-phenyl)-thiazole-5-carbonyl]-piperidin-3-yl}-phenylamino)-acetic acid as a white solid.

MS (LC-MS) 518.0 (M−H)$^−$.

$^1$H NMR (400 MHz, CD$_3$OD) δ 8.13 (d, 2H), 7.79 (d, 2H), 6.97 (m, 1H), 6.54 (m, 1H), 6.37 (m, 1H), 3.91 (brs, 2H), 2.71 (t, 1H), 2.69 (m, 1H), 2.47 (s, 3H), 2.12 (s, 3H), 2.03 (d, 1H), 1.87 (m, 2H), 1.65 (m 1H).

The invention claimed is:

1. A compound of Formula I

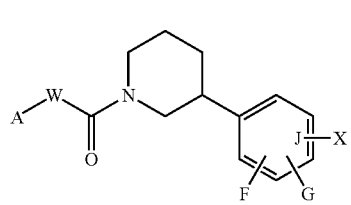

I or a pharmaceutically acceptable salt of said compound wherein

F and G are each independently a) hydrogen, b) halo, c) (C$_1$–C$_4$)alkyl or d) (C$_1$–C$_4$)alkoxy;

X is a)-Z or b) O—C(R$^1$R$^2$)-Z;

Z is a) —C(O)OH, b) —C(O)O—(C$_1$–C$_4$)alkyl, c) —C(O)—NH$_2$, or d) tetrazolyl;

R$^1$ is a) H, or b) methyl;

R² is a) H, b) methyl or c) —O—CH₂-phenyl;

W is a) a bond, b) oxy c) —N(H)—, d) —NH—(C₁–C₄)alkyl-, e) —(C₁–C₄f) —(C₁–C₄)alkyl-O—;

or g) CR⁷R⁸ wherein R⁷ and R⁸ are linked together to form a three membered fully saturated carbocyclic ring;

A is a) phenyl optionally independently substituted with one or two 1) —(C₁–C₆)alkyl, 2) —CF₃, 3)—OCF₃ 4) —(C₁–C₆)alkoxy, 5) (C₃–C₆)cycloalkyl, 6) halo or 7) hydroxy; or b) thiazolyl optionally independently substituted with 1) one or two methyl or 2) phenyl optionally independently substituted with one or two a) —(C₁–C₆)alkyl, b) —CF₃, c) —OCF₃, d) —(C₁–C₆)alkoxy, e) (C₃–C₇)cycloalkyl, f) halo, g) —(C₁–C₄)alkylthio or h) hydroxy;

provided that: and when, W is a bond, X is O—C(R¹R²)-Z, wherein R¹ and R² are each hydrogen, and Z is —C(O)OH or —C(O)O—(C₁–C₄)alkyl, then one of F or G must be a)—(C₁–C₄)alkyl, or b) (C₁–C₄)alkoxy.

2. A compound of claim 1 wherein
X is —O—C(R¹R²)-Z.

3. A compound of claim 2 of the formula I-A or formula I-C

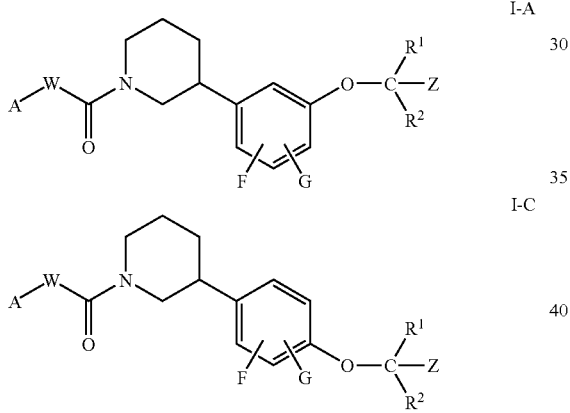

wherein R¹ and R² are each independently a) hydrogen or b) methyl;

F and G are each independently a) hydrogen or b) methyl; and

Z is —C(O)OH.

4. A compound of claim 3 wherein

W is a) oxy, b) —N(H)—, c) —N(H)—(C₁–C₄)alkyl, d) —(C₁–C₄)alkyl- or e) —(C₁–C₄)alkyl-O—; and A is phenyl optionally substituted with a) —(C₁–C₄)alkyl, b) —CF₃, c) —OCF₃ d) —(C₁–C₄)alkoxy, e) cyclopropyl, f) halo, or g) hydroxy; or W is a bond; and A is thiazolyl optionally substituted with a) one or two -methyl, or b)-phenyl optionally substituted with 1) —(C₁–C₄)alkyl, 2) —CF₃, 3) —OCF'4) —(C₁–C₄)alkoxy, 5) cyclopropyl, 6) halo or 7) —(C₁–C₄)alkylthio.

5. A compound of claim 1 wherein
X is -Z.

6. A compound of claim 5 of the formula I-B or formula I-D

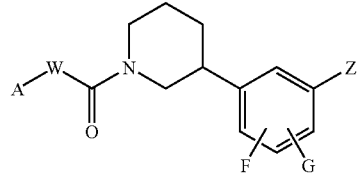

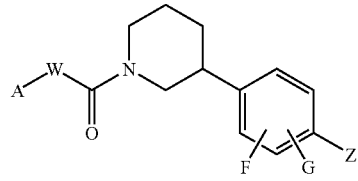

wherein F and G are each a) hydrogen, b) methyl, c) fluoro or d) methoxy; and

Z is a) —C(O)OH, b) —C(O)O—(C₁–C₄)alkyl or c) —C(O)NH₂.

7. A compound of claim 6 wherein

W is a) —(C₁–C₄)alkyl- or b) —(C₁–C₄)alkyl-O—; and A is phenyl optionally substituted with a) —(C₁–C₄)alkyl, b) —CF₃, c) —OCF₃, d) —(C₁–C₄)alkoxy, e) cyclopropyl, f) halo, or g) hydroxy; or W is a bond; and A is a) thiazolyl optionally substituted with 1) one or two -methyl or 2)-phenyl optionally substituted with i) —(C₁–C₄)alkyl, ii) —CF₃, iii) —OCF₃ iv) —(C₁–C₄)alkoxy, v) cyclopropyl or vi) halo; or b) phenyl optionally substituted with 1) —(C₁–C₄)alkyl, 2) —CF₃, 3) —OCF₃ 4) —(C₁–C₄)alkoxy, 5) cyclopropyl, 6) halo, or 7) —(C₁–C₄)alkylthio.

8. A compound of claim 4 selected from:

2-{3-[1-(4-Isopropyl-phenylcarbamoyl)-piperidin-3-yl]-phenoxy}-2-methyl-propionic acid;

(S)-2-{3-[1-(4-Isopropyl-phenylcarbamoyl)-piperidin-3-yl]-phenoxy}-2-methyl-propionic acid;

(R)-2-{3-[1-(4-Isopropyl-phenylcarbamoyl)-piperidin-3-yl]-phenoxy}-2-methyl-propionic acid;

2-Methyl-2-(3-{1-[(4-trifluoromethyl-phenyl)-acetyl]-piperidin-3-yl}-phenoxy)-propionic acid;

(S)-2-Methyl-2-(3-{1-[(4-trifluoromethyl-phenyl)-acetyl]-piperidin-3-yl}-phenoxy)-propionic acid;

(R)-2-Methyl-2-(3-{1-[(4-trifluoromethyl-phenyl)-acetyl]-piperidin-3-yl}-phenoxy)-propionic acid.

2-(3-{1-[(4-Isopropyl-phenyl)-acetyl]-piperidin-3-yl}-phenoxy)-2-methyl-propionic acid;

(S)-2-(3-{1-[(4-Isopropyl-phenyl)-acetyl]-piperidin-3-yl}-phenoxy)-2-methyl-propionic acid;

(R)-2-(3-{1-[(4-Isopropyl-phenyl)-acetyl]-piperidin-3-yl}-phenoxy)-2-methyl-propionic acid;

2-(3-{1-[3-(4-Isopropyl-phenyl)-propionyl]-piperidin-3-yl}-phenoxy)-2-methyl-propionic acid;

(S)-2-(3-{1-[3-(4-Isopropyl-phenyl)-propionyl]-piperidin-3-yl}-phenoxy)-2-methyl-propionic acid;

(R)-2-(3-{1-[3-(4-Isopropyl-phenyl)-propionyl]-piperidin-3-yl}-phenoxy)-2-methyl-propionic acid;

2-(3-{1-[(4-Isopropyl-phenoxy)-acetyl]-piperidin-3-yl}-phenoxy)-2-methyl-propionic acid;

(S)-2-(3-{1-[(4-Isopropyl-phenoxy)-acetyl]-piperidin-3-yl}-phenoxy)-2-methyl-propionic acid; and (R)-2-(3-{1-[(4-Isopropyl-phenoxy)-acetyl]-piperidin-3-yl}-phenoxy)-2-methyl-propionic acid;

2-(3-{1-[2-(4-Isopropyl-phenoxy)-2-methyl-propionyl]-piperidin-3-yl}-phenoxy)-2-methyl-propionic acid;
(S)-2-(3-{1-[2-(4-Isopropyl-phenoxy)-2-methyl-propionyl]-piperidin-3-yl}-phenoxy)-2-methyl-propionic acid;
(R)-2-(3-{1-[2-(4-Isopropyl-phenoxy)-2-methyl-propionyl]-piperidin-3-yl}-phenoxy)-2-methyl-propionic acid;
2-Methyl-2-(3-{1-[3-(4-trifluoromethyl-phenyl)-propionyl]-piperidin-3-yl}-phenoxy)-propionic acid;
(S)-2-Methyl-2-(3-{1-[3-(4-trifluoromethyl-phenyl)-propionyl]-piperidin-3-yl}-phenoxy)-propionic acid;
(R)-2-Methyl-2-(3-{1-[3-(4-trifluoromethyl-phenyl)-propionyl]-piperidin-3-yl}-phenoxy)-propionic acid;
2-Methyl-2-(3-{1-[(4-trifluoromethoxy-phenoxy)-acetyl]-piperidin-3-yl}-phenoxy)-propionic acid;
(S)-2-Methyl-2-(3-{1-[(4-trifluoromethoxy-phenoxy)-acetyl]-piperidin-3-yl}-phenoxy)-propionic acid;
(R)-2-Methyl-2-(3-{1-[(4-trifluoromethoxy-phenoxy)-acetyl]-piperidin-3-yl}-phenoxy)-propionic acid;
(3-{1-[(4-Isopropyl-phenyl)-acetyl]-piperidin-3-yl}-phenoxy)-acetic acid;
(S)-(3-{1-[(4-Isopropyl-phenyl)-acetyl]-piperidin-3-yl}-phenoxy)-acetic acid;
(R)-(3-{1-[(4-Isopropyl-phenyl)-acetyl]-piperidin-3-yl}-phenoxy)-acetic acid;
3-[3-(1-Carboxy-1-methyl-ethoxy)-phenyl]-piperidine-1-carboxylic acid 4-isopropyl-phenyl ester;
(S)-3-[3-(1-Carboxy-1-methyl-ethoxy)-phenyl]-piperidine-1-carboxylic acid 4-isopropyl-phenyl ester;
(R)-3-[3-(1-Carboxy-1-methyl-ethoxy)-phenyl]-piperidine-1-carboxylic acid 4-isopropyl-phenyl ester;
(S)-2-(3-{1-[(4-tert-Butyl-phenyl)-acetyl]-piperidin-3-yl}-phenoxy)-2-methyl-propionic acid;
(R)-2-(3-{1-[(4-tert-Butyl-phenyl)-acetyl]-piperidin-3-yl}-phenoxy)-2-methyl-propionic acid;
2-(3-{1-[(4-tert-Butyl-phenyl)-acetyl]-piperidin-3-yl}-phenoxy)-2-methyl-propionic acid;
(S)-2-Methyl-2-(3-{1-[(4-trifluoromethoxy-phenyl)-acetyl]-piperidin-3-yl}-phenoxy)-propionic acid;
(R)-2-Methyl-2-(3-{1-[(4-trifluoromethoxy-phenyl)-acetyl]-piperidin-3-yl}-phenoxy)-propionic acid;
2-Methyl-2-(3-{1-[(4-trifluoromethoxy-phenyl)-acetyl]-piperidin-3-yl}-phenoxy)-propionic acid;
(S)-3-[3-(1-Carboxy-1-methyl-ethoxy)-phenyl]-piperidine-1-carboxylic acid 4-isopropyl-benzyl ester;
(R)-3-[3-(1-Carboxy-1-methyl-ethoxy)-phenyl]-piperidine-1-carboxylic acid 4-isopropyl-benzyl ester;
3-[3-(1-Carboxy-1-methyl-ethoxy)-phenyl]-piperidine-1-carboxylic acid 4-isopropyl-benzyl ester;
(S)-3-[3-(1-Carboxy-1-methyl-ethoxy)-phenyl]-piperidine-1-carboxylic acid 4-isopropyl-phenyl ester;
(R)-3-[3-(1-Carboxy-1-methyl-ethoxy)-phenyl]-piperidine-1-carboxylic acid 4-isopropyl-phenyl ester;
3-[3-(1-Carboxy-1-methyl-ethoxy)-phenyl]-piperidine-1-carboxylic acid 4-isopropyl-phenyl ester;
2-{3-[1-(4-Isopropyl-benzylcarbamoyl)-piperidin-3-yl]-phenoxy}-2-methyl-propionic acid;
(S)-2-{3-[1-(4-Isopropyl-benzylcarbamoyl)-piperidin-3-yl]-phenoxy}-2-methyl-propionic acid;
(R)-2-{3-[1-(4-Isopropyl-benzylcarbamoyl)-piperidin-3-yl]-phenoxy}-2-methyl-propionic acid;
3-[3-(1-Carboxy-1-methyl-ethoxy)-phenyl]-piperidine-1-carboxylic acid 4-trifluoromethyl-benzyl ester;
(S)-3-[3-(1-Carboxy-1-methyl-ethoxy)-phenyl]-piperidine-1-carboxylic acid 4-trifluoromethyl-benzyl ester;
(R)-3-[3-(1-Carboxy-1-methyl-ethoxy)-phenyl]-piperidine-1-carboxylic acid 4-trifluoromethyl-benzyl ester;
(S)-2-Methyl-2-{3-[1-(4-trifluoromethoxy-benzylcarbamoyl)-piperidin-3-yl]-phenoxy}-propionic acid;
(R)-2-Methyl-2-{3-[1-(4-trifluoromethoxy-benzylcarbamoyl)-piperidin-3-yl]-phenoxy}-propionic acid;
2-Methyl-2-{3-[1-(4-trifluoromethoxy-benzylcarbamoyl)-piperidin-3-yl]-phenoxy}-propionic acid;
3-[3-(1-Carboxy-1-methyl-ethoxy)-phenyl]-piperidine-1-carboxylic acid 4-cyclopropyl-benzyl ester;
(S)-3-[3-(1-Carboxy-1-methyl-ethoxy)-phenyl]-piperidine-1-carboxylic acid 4-cyclopropyl-benzyl ester;
(R)-3-[3-(1-Carboxy-1-methyl-ethoxy)-phenyl]-piperidine-1-carboxylic acid 4-cyclopropyl-benzyl ester;
(S)-3-(3-carboxymethoxy-4-methyl-phenyl)-piperidine-1-carboxylic acid 4-trifluoromethyl-benzyl ester;
(R)-3-(3-carboxymethoxy-4-methyl-phenyl)-piperidine-1-carboxylic acid 4-trifluoromethyl-benzyl ester;
3-(3-carboxymethoxy-4-methyl-phenyl)-piperidine-1-carboxylic acid 4-trifluoromethyl-benzyl ester;
(S)-3-[3-(1-Carboxy-1-methyl-ethoxy)-4-methyl-phenyl]-piperidine-1-carboxylic acid 4-trifluoromethyl-benzyl ester;
(R)-3-[3-(1-Carboxy-1-methyl-ethoxy)-4-methyl-phenyl]-piperidine-1-carboxylic acid 4-trifluoromethyl-benzyl ester;
3-[3-(1-Carboxy-1-methyl-ethoxy)-4-methyl-phenyl]-piperidine-1-carboxylic acid 4-trifluoromethyl-benzyl ester;
(S)-2-Methyl-2-(3-{1-[4-methyl-2-(4-trifluoromethyl-phenyl)-thiazole-5-carbonyl]-piperidin-3-yl}-phenoxy)-propionic acid;
(R)-2-Methyl-2-(3-{1-[4-methyl-2-(4-trifluoromethyl-phenyl)-thiazole-5-carbonyl]-piperidin-3-yl}-phenoxy)-propionic acid;
2-Methyl-2-(3-{1-[4-methyl-2-(4-trifluoromethyl-phenyl)-thiazole-5-carbonyl]-piperidin-3-yl}-phenoxy)-propionic acid;
(S)-(2-methyl-5-{1-[4-methyl-2-(4-trifluoromethyl-phenyl)-thiazole-5-carbonyl]-piperidin-3-yl}-phenoxy)-acetic acid;
(R)-(2-methyl-5-{1-[4-methyl-2-(4-trifluoromethyl-phenyl)-thiazole-5-carbonyl]-piperidin-3-yl}-phenoxy)-acetic acid;
(2-methyl-5-{1-[4-methyl-2-(4-trifluoromethyl-phenyl)-thiazole-5-carbonyl]-piperidin-3-yl}-phenoxy)-acetic acid;
(S)-2-Methyl-2-(2-methyl-5-{1-[4-methyl-2-(4-trifluoromethyl-phenyl)-thiazole-5-carbonyl]-piperidin-3-yl}-phenoxy)-propionic acid;
(R)-2-Methyl-2-(2-methyl-5-{1-[4-methyl-2-(4-trifluoromethyl-phenyl)-thiazole-5-carbonyl]-piperidin-3-yl}-phenoxy)-propionic acid;
2-Methyl-2-(2-methyl-5-{1-[4-methyl-2-(4-trifluoromethyl-phenyl)-thiazole-5-carbonyl]-piperidin-3-yl}-phenoxy)-propionic acid;
(R)-3-[3-(1-Carboxy-1-methyl-ethoxy)-phenyl]-piperidine-1-carboxylic acid 3-trifluoromethyl-benzyl ester;
(S)-3-[3-(1-Carboxy-1-methyl-ethoxy)-phenyl]-piperidine-1-carboxylic acid 3-trifluoromethyl-benzyl ester;
3-[3-(1-Carboxy-1-methyl-ethoxy)-phenyl]-piperidine-1-carboxylic acid 3-trifluoromethyl-benzyl ester;
(S)-3-[3-(1-Carboxy-1-methyl-ethoxy)-4-methyl-phenyl]-piperidine-1-carboxylic acid 2-(4-trifluoromethyl-phenyl)-ethyl ester;

(R)-3-[3-(1-Carboxy-1-methyl-ethoxy)-4-methyl-phenyl]-piperidine-1-carboxylic acid 2-(4-trifluoromethyl-phenyl)-ethyl ester; and 3-[3-(1-Carboxy-1-methyl-ethoxy)-4-methyl-phenyl]-piperidine-1-carboxylic acid 2-(4-trifluoromethyl-phenyl)-ethyl ester.

9. A compound of claim 7 selected from:

2-methyl-5-{1-[4-methyl-2-(4-trifluoromethyl-phenyl)-thiazole-5-carbonyl]-piperidin-3-yl}-benzoic acid;

(S)-2-methyl-5-{1-[4-methyl-2-(4-trifluoromethyl-phenyl)-thiazole-5-carbonyl]-piperidin-3-yl}-benzoic acid;

(R)-2-methyl-5-{1-[4-methyl-2-(4-trifluoromethyl-phenyl)-thiazole-5-carbonyl]-piperidin-3-yl}-benzoic acid;

3-(3-carboxy-4-methyl-phenyl)-piperidine-1-carboxylic acid 4-trifluoromethyl-benzyl ester;

(S)-3-(3-carboxy-4-methyl-phenyl)-piperidine-1-carboxylic acid 4-trifluoromethyl-benzyl ester;

(R)-3-(3-carboxy-4-methyl-phenyl)-piperidine-1-carboxylic acid 4-trifluoromethyl-benzyl ester;

(R)-2-methyl-5-{1-[4-methyl-2-(4-trifluoromethyl-phenyl)-thiazole-5-carbonyl]-piperidin-3-yl}-benzoic acid;

(S)-2-methyl-5-{1-[4-methyl-2-(4-trifluoromethyl-phenyl)-thiazole-5-carbonyl]-piperidin-3-yl}-benzoic acid;

2-methyl-5-{1-[4-methyl-2-(4-trifluoromethyl-phenyl)-thiazole-5-carbonyl]-piperidin-3-yl}-benzoic acid;

(S)-2-methyl-5-{1-[4-methyl-2-(4-trifluoromethyl-phenyl)-thiazole-5-carbonyl]-piperidin-3-yl}-benzoic acid;

(R)-2-methyl-5-{1-[4-methyl-2-(4-trifluoromethyl-phenyl)-thiazole-5-carbonyl]-piperidin-3-yl}-benzoic acid;

2-methyl-5-{1-[4-methyl-2-(4-trifluoromethyl-phenyl)-thiazole-5-carbonyl]-piperidin-3-yl}-benzoic acid;

(R)-3-(3-carboxy-4-methyl-phenyl)-piperidine-1-carboxylic acid 4-trifluoromethyl-benzyl ester;

(S)-3-(3-carboxy-4-methyl-phenyl)-piperidine-1-carboxylic acid 4-trifluoromethyl-benzyl ester;

3-(3-carboxy-4-methyl-phenyl)-piperidine-1-carboxylic acid 4-trifluoromethyl-benzyl ester;

2-Methoxy-5-{1-[4-methyl-2-(4-trifluoromethyl-phenyl)-thiazole-5-carbonyl]-piperidin-3-yl}-benzoic acid;

(S)-2-Methoxy-5-{1-[4-methyl-2-(4-trifluoromethyl-phenyl)-thiazole-5-carbonyl]-piperidin-3-yl}-benzoic acid;

(R)-2-Methoxy-5-{1-[4-methyl-2-(4-trifluoromethyl-phenyl)-thiazole-5-carbonyl]-piperidin-3-yl}-benzoic acid;

2-Fluoro-5-{1-[4-methyl-2-(4-trifluoromethyl-phenyl)-thiazole-5-carbonyl]-piperidin-3-yl}-benzoic acid;

(S)-2-Fluoro-5-{1-[4-methyl-2-(4-trifluoromethyl-phenyl)-thiazole-5-carbonyl]-piperidin-3-yl}-benzoic acid;

(R)-2-Fluoro-5-{1-[4-methyl-2-(4-trifluoromethyl-phenyl)-thiazole-5-carbonyl]-piperidin-3-yl}-benzoic acid;

2-Methyl-5-{1-[4-methyl-2-(4-trifluoromethyl-phenyl)-thiazole-5-carbonyl]-piperidin-3-yl}-benzamide;

(S)-2-Methyl-5-{1-[4-methyl-2-(4-trifluoromethyl-phenyl)-thiazole-5-carbonyl]-piperidin-3-yl}-benzamide;

(R)-2-Methyl-5-{1-[4-methyl-2-(4-trifluoromethyl-phenyl)-thiazole-5-carbonyl]-piperidin-3-yl}-benzamide;

(R)-3-(3-Carboxy-4-methyl-phenyl)-piperidine-1-carboxylic acid 2-(4-trifluoromethyl-phenyl)-ethyl ester;

(S)-3-(3-Carboxy-4-methyl-phenyl)-piperidine-1-carboxylic acid 2-(4-trifluoromethyl-phenyl)-ethyl ester; and 3-(3-Carboxy-4-methyl-phenyl)-piperidine-1-carboxylic acid 2-(4-trifluoromethyl-phenyl)-ethyl ester.

10. A method for treating obesity, hypertriglyceridemia, hyperlipidemia, hypoalphalipoproteinemia, diabetes mellitus (Type I and/or Type II), hyperinsulinemia, atherosclerosis, or hypercholesterolemia, in a mammal by administering to a mammal in need of such treatment a therapeutically effective amount of a compound of claim 1, or a pharmaceutically acceptable salt of said compound.

11. A pharmaceutical composition which comprises a therapeutically effective amount of a compound of claim 1, or a pharmaceutically acceptable salt of said compound and a pharmaceutically acceptable carrier, vehicle or diluent.

12. A kit comprising:

a compound of claim 1, or a pharmaceutically acceptable salt of said compound and a pharmaceutically acceptable carrier, vehicle or diluent in a unit dosage form.

* * * * *